US008110656B2

(12) United States Patent
Benning et al.

(10) Patent No.: US 8,110,656 B2
(45) Date of Patent: Feb. 7, 2012

(54) COMPOSITIONS AND METHODS OF A PHOSPHATIDIC ACID BINDING PROTEIN

(75) Inventors: Christoph Benning, East Lansing, MI (US); Binbin Lu, Ann Arbor, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 12/506,633

(22) Filed: Jul. 21, 2009

(65) Prior Publication Data

US 2010/0105078 A1    Apr. 29, 2010

(51) Int. Cl.
*G01N 33/53* (2006.01)
*C07K 14/00* (2006.01)
(52) U.S. Cl. .................... 530/324; 436/501; 435/7.8
(58) Field of Classification Search .................. None
See application file for complete search history.

(56) References Cited

OTHER PUBLICATIONS

Awai et al., (2006) "A phosphatidic acid-binding protein of the chloroplast inner envelope membrane involved in lipid trafficking" Proc. Natl. Acad. Sci. USA, vol. 103, No. 28, pp. 10817-10822.*
A printout from the GenBank database for *Arabidopsis* Gene At3g20320.*
Testerink et al. "Phosphatidic acid: a multifunctional stress signaling lipid in plants," Trends in Plant Science, 2005, vol. 10, Issue 8, pp. 368-375.*

* cited by examiner

*Primary Examiner* — Shafiqul Haq
*Assistant Examiner* — Galina Yakovleva
(74) *Attorney, Agent, or Firm* — Medlen & Carroll, LLP

(57) ABSTRACT

TGD2 proteins of *Arabidopsis* are proposed to be a substrate binding component of a lipid transfer complex in the inner chloroplast envelope membrane. Loss of function of this protein or other components of this complex may disrupt the endoplasmic reticulum (ER)-pathway of thylakoid lipid biosynthesis. In one embodiment, the present invention contemplates a minimal binding domain capable of specifically binding phosphatidic acid. Alternatively, the minimal binding domain may further comprise accessory binding domains that, in combination, create a complete TGD2 phosphatidic acid binding domain. Consequently, phosphatidic acid may be quantitatively detected from samples as described in the methods herein.

14 Claims, 28 Drawing Sheets
(14 of 28 Drawing Sheet(s) Filed in Color)

SEQUENCE LISTING

<160> NUMBER OF SEQ ID NOS: 129

<210> SEQ ID NO 1
<211> LENGTH: 381
<212> TYPE: PRT
<213> ORGANISM: Arabidopsis thaliana

<400> SEQUENCE: 1

```
Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg Ala Ala Ser
        35                  40                  45

Asn Ser Asp Ala Ala His Gly Gln Pro Ser Ser Asp Gly Gly Lys Asn
    50                  55                  60

Pro Leu Thr Val Val Leu Asp Val Pro Arg Asn Ile Trp Arg Gln Thr
65                  70                  75                  80

Leu Lys Pro Leu Ser Asp Phe Gly Phe Gly Lys Arg Ser Ile Trp Glu
                85                  90                  95

Gly Gly Val Gly Leu Phe Ile Val Ser Gly Ala Thr Leu Leu Ala Leu
            100                 105                 110

Ser Trp Ala Trp Leu Arg Gly Phe Gln Met Arg Ser Lys Phe Arg Lys
        115                 120                 125

Tyr Gln Thr Val Phe Glu Leu Ser His Ala Ser Gly Ile Cys Thr Gly
```

```
                130                 135                 140
Thr Pro Val Arg Ile Arg Gly Val Thr Val Gly Thr Ile Ile Arg Val
145                 150                 155                 160

Asn Pro Ser Leu Lys Asn Ile Glu Ala Val Ala Glu Ile Glu Asp Asp
                165                 170                 175

Lys Ile Ile Ile Pro Arg Asn Ser Leu Val Glu Val Asn Gln Ser Gly
                180                 185                 190

Leu Leu Met Glu Thr Met Ile Asp Ile Met Pro Arg Asn Pro Ile Pro
                195                 200                 205

Glu Pro Ser Val Gly Pro Leu His Pro Glu Cys Gly Lys Glu Gly Leu
210                 215                 220

Ile Val Cys Asp Arg Gln Thr Ile Lys Gly Val Gln Gly Val Ser Leu
225                 230                 235                 240

Asp Glu Leu Val Gly Ile Phe Thr Arg Ile Gly Arg Glu Val Glu Ala
                245                 250                 255

Ile Gly Val Ala Asn Thr Tyr Ser Leu Ala Glu Arg Ala Ala Ser Val
                260                 265                 270

Ile Glu Glu Ala Arg Pro Leu Leu Lys Lys Ile Gln Ala Met Ala Glu
                275                 280                 285

Asp Ala Gln Pro Leu Leu Ser Glu Phe Arg Asp Ser Gly Leu Leu Lys
290                 295                 300

Glu Val Glu Cys Leu Thr Arg Ser Leu Thr Gln Ala Ser Asp Asp Leu
305                 310                 315                 320

Arg Lys Val Asn Ser Ser Ile Met Thr Pro Glu Asn Thr Glu Leu Ile
                325                 330                 335

Gln Lys Ser Ile Tyr Thr Leu Val Tyr Thr Leu Lys Asn Val Glu Ser
                340                 345                 350

Ile Ser Ser Asp Ile Leu Gly Phe Thr Gly Asp Glu Ala Thr Arg Lys
                355                 360                 365

Asn Leu Lys Leu Leu Ile Lys Ser Leu Ser Arg Leu Leu
                370                 375                 380

<210> SEQ ID NO 2
<211> LENGTH: 91
<212> TYPE: PRT
<213> ORGANISM: Arabidopsis thaliana

<400> SEQUENCE: 2

Arg Lys Tyr Gln Thr Val Phe Glu Leu Ser His Ala Ser Gly Ile Cys
1               5                   10                  15

Thr Gly Thr Pro Val Arg Ile Arg Gly Val Thr Val Gly Thr Ile Ile
                20                  25                  30

Arg Val Asn Pro Ser Leu Lys Asn Ile Glu Ala Val Ala Glu Ile Glu
                35                  40                  45

Asp Asp Lys Ile Ile Ile Arg Asn Pro Ile Pro Glu Pro Ser Val Gly
50                  55                  60

Pro Leu His Pro Glu Cys Gly Lys Glu Gly Leu Ile Val Cys Asp Arg
65                  70                  75                  80

Gln Thr Ile Lys Gly Val Gln Gly Val Ser Leu
                85                  90

<210> SEQ ID NO 3
<211> LENGTH: 23
<212> TYPE: PRT
<213> ORGANISM: Arabidopsis thaliana

<400> SEQUENCE: 3
```

```
Glu Gly Gly Val Gly Leu Phe Ile Val Ser Gly Ala Thr Leu Leu Ala
1               5                   10                  15

Leu Ser Trp Ala Trp Leu Arg
            20

<210> SEQ ID NO 4
<211> LENGTH: 45
<212> TYPE: PRT
<213> ORGANISM: Arabidopsis thaliana

<400> SEQUENCE: 4

Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg
            35                  40                  45

<210> SEQ ID NO 5
<211> LENGTH: 381
<212> TYPE: PRT
<213> ORGANISM: Arabidopsis thaliana

<400> SEQUENCE: 5

Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg Ala Ala Ser
            35                  40                  45

Asn Ser Asp Ala Ala His Gly Gln Pro Ser Ser Asp Gly Gly Lys Asn
50                  55                  60

Pro Leu Thr Val Val Leu Asp Val Pro Arg Asn Ile Trp Arg Gln Thr
65                  70                  75                  80

Leu Lys Pro Leu Ser Asp Phe Gly Phe Gly Lys Arg Ser Ile Trp Glu
                85                  90                  95

Gly Gly Val Gly Leu Phe Ile Val Ser Gly Ala Thr Leu Leu Ala Leu
                100                 105                 110

Ser Trp Ala Trp Leu Arg Gly Phe Gln Met Arg Ser Lys Phe Arg Lys
            115                 120                 125

Tyr Gln Thr Val Phe Glu Leu Ser His Ala Ser Gly Ile Cys Thr Gly
            130                 135                 140

Thr Pro Val Arg Ile Arg Gly Val Thr Val Gly Thr Ile Ile Arg Val
145                 150                 155                 160

Asn Pro Ser Leu Lys Asn Ile Glu Ala Val Ala Glu Ile Glu Asp Asp
                165                 170                 175

Lys Ile Ile Ile Pro Arg Asn Ser Leu Val Glu Val Asn Gln Ser Gly
                180                 185                 190

Leu Leu Met Glu Thr Met Ile Asp Ile Met Pro Arg Asn Pro Ile Pro
            195                 200                 205

Glu Pro Ser Val Gly Pro Leu His Pro Glu Cys Gly Lys Glu Gly Leu
210                 215                 220

Ile Val Cys Asp Arg Gln Thr Ile Lys Gly Val Gln Gly Val Ser Leu
225                 230                 235                 240

Asp Glu Leu Val Gly Ile Phe Thr Arg Ile Gly Arg Glu Val Glu Ala
                245                 250                 255
```

-continued

Ile Gly Val Ala Asn Thr Tyr Ser Leu Ala Glu Arg Ala Ala Ser Val
         260                 265                 270

Ile Glu Glu Ala Arg Pro Leu Leu Lys Lys Ile Gln Ala Met Ala Glu
         275                 280                 285

Asp Ala Gln Pro Leu Leu Ser Glu Phe Arg Asp Ser Gly Leu Leu Lys
290                 295                 300

Glu Val Glu Cys Leu Thr Arg Ser Leu Thr Gln Ala Ser Asp Asp Leu
305                 310                 315                 320

Arg Lys Val Asn Ser Ser Ile Met Thr Pro Glu Asn Thr Glu Leu Ile
                 325                 330                 335

Gln Lys Ser Ile Tyr Thr Leu Val Tyr Thr Leu Lys Asn Val Glu Ser
             340                 345                 350

Ile Ser Ser Asp Ile Leu Gly Phe Thr Gly Asp Glu Ala Thr Arg Lys
         355                 360                 365

Asn Leu Lys Leu Leu Ile Lys Ser Leu Ser Arg Leu Leu
             370                 375                 380

<210> SEQ ID NO 6
<211> LENGTH: 408
<212> TYPE: PRT
<213> ORGANISM: Vitis vinifera

<400> SEQUENCE: 6

Met Val Gly Asn Pro Ile Val Gln Val Pro Thr Cys Pro Ala Ala Leu
1               5                   10                  15

Ser Ser Ala Leu Ala Thr Leu Pro Trp Gly Ser Gly Asn Phe Met Pro
            20                  25                  30

Cys Leu Pro Pro Arg Ser Arg Lys Leu Leu Leu Val Arg Ala Asn
        35                  40                  45

Ser Ala Asp Ala Gly His Ser Gln Pro Pro Ser Pro Ser Lys Thr Lys
50                  55                  60

Asn Pro Leu Ala Val Ile Leu Asp Phe Pro Arg Asn Val Trp Lys Gln
65                  70                  75                  80

Thr Leu Arg Pro Leu Ser Asp Phe Gly Phe Gly Arg Arg Ser Ile Trp
                85                  90                  95

Glu Gly Gly Val Gly Leu Phe Leu Val Ser Gly Thr Val Leu Leu Val
            100                 105                 110

Leu Ser Leu Ala Trp Leu Arg Gly Phe Gln Leu Arg Ser Lys Phe Arg
        115                 120                 125

Lys Tyr Leu Ala Val Phe Glu Phe Thr Gln Ala Cys Gly Ile Cys Lys
130                 135                 140

Gly Thr Pro Val Arg Ile Arg Gly Val Thr Val Gly Asn Val Ile Gln
145                 150                 155                 160

Val Asn Pro Ser Leu Lys Ser Ile Glu Ala Val Val Glu Val Glu Asp
                165                 170                 175

Asp Lys Ile Ile Ile Pro Gln Asn Ser Leu Ile Glu Val Asn Gln Ser
            180                 185                 190

Gly Leu Leu Met Glu Thr Leu Ile Asp Ile Thr Pro Arg Asp Pro Leu
        195                 200                 205

Pro Thr Pro Ser Val Gly Pro Leu Asp Pro Asp Cys Thr Lys Glu Gly
210                 215                 220

Val Ile Val Cys Asp Arg Gln Lys Ile Arg Gly Tyr Gln Gly Val Ser
225                 230                 235                 240

Leu Asp Ala Leu Val Gly Ile Phe Thr Arg Leu Gly Arg Glu Val Glu
                245                 250                 255

```
Glu Ile Gly Ile Ala Gln Gly Tyr Ser Met Ala Glu Arg Ala Leu Ser
            260                 265                 270

Ile Ile Glu Glu Ala Arg Pro Leu Ala Lys Ile Asn Asn Gln Arg
            275                 280                 285

Gly Met Gln Asn Arg Val Gly Thr Ser Asp Val Leu Phe Leu Val Trp
            290                 295                 300

Asp Trp Thr Phe Pro Ile Lys Ala Met Ala Glu Asp Val Gln Pro Leu
305                 310                 315                 320

Val Thr Glu Phe Arg Asp Thr Gly Leu Leu Lys Glu Val Glu Ser Leu
                325                 330                 335

Thr Lys Ser Leu Ala Gln Ala Thr Glu Glu Leu Arg Arg Val His Ser
            340                 345                 350

Ser Ile Leu Thr Pro Glu Asn Thr Glu Leu Ile Gln Lys Ser Ile Tyr
            355                 360                 365

Thr Leu Ile Phe Thr Leu Lys Asn Ile Glu Asn Ile Ser Ser Asp Ile
            370                 375                 380

Leu Gly Phe Thr Gly Asp Glu Ala Thr Arg Arg Asn Leu Lys Leu Leu
385                 390                 395                 400

Ile Lys Ser Leu Ser Arg Leu Leu
                405

<210> SEQ ID NO 7
<211> LENGTH: 370
<212> TYPE: PRT
<213> ORGANISM: Oryza sativa

<400> SEQUENCE: 7

Met Ala Thr Thr Lys Ser Phe Leu Pro Pro Phe Ile Ala Leu Ser
1               5                   10                  15

Ser Asn Pro Arg Pro Thr Thr Leu Ala Pro Thr Pro Asn Pro Arg Pro
            20                  25                  30

Arg Arg Arg Asn Ser Leu Ala Ile Cys Ser Ala Ser Ala Ser Gly Asp
            35                  40                  45

Pro Ser Pro Pro Pro Glu Ala Glu Gly Gly Ser Asn Pro Leu Leu Ala
50                  55                  60

Leu Trp Arg Arg Thr Leu His Pro Leu Gly Asp Tyr Gly Phe Gly Lys
65                  70                  75                  80

Arg Ser Val Trp Glu Gly Gly Val Gly Leu Phe Met Val Ser Gly Ala
                85                  90                  95

Ala Leu Leu Ala Leu Ala Leu Ala Trp Leu Arg Gly Phe Gln Leu Arg
            100                 105                 110

Ala Arg Phe Arg Lys Tyr Gln Ala Val Phe Glu Phe Thr Gln Ala Cys
            115                 120                 125

Gly Ile Cys Val Gly Thr Pro Val Arg Ile Arg Gly Val Thr Val Gly
            130                 135                 140

Asn Val Arg Val Asp Ser Ser Leu Lys Ser Ile Asp Ala Tyr Val
145                 150                 155                 160

Glu Val Glu Asp Asp Lys Ile Ile Val Pro Arg Asn Ser Val Val Glu
                165                 170                 175

Val Asn Gln Ser Gly Leu Leu Met Glu Thr Leu Ile Asp Ile Thr Pro
            180                 185                 190

Lys Asp Pro Leu Pro Thr Pro Ser Val Gly Pro Leu Asp Pro Asp Cys
            195                 200                 205

Ser Lys Glu Gly Leu Ile Leu Cys Asp Lys Glu Arg Met Lys Gly Gln
210                 215                 220
```

```
Gln Gly Val Ser Leu Asp Ala Leu Val Gly Ile Phe Thr Arg Leu Gly
225                 230                 235                 240

Arg Glu Met Glu Ile Gly Val His Lys Ser Tyr Lys Leu Ala Glu
            245                 250                 255

Lys Val Ala Ser Ile Met Glu Glu Ala Gln Pro Leu Leu Ser Arg Ile
            260                 265                 270

Glu Ala Leu Ala Glu Glu Ile Gln Pro Leu Leu Ser Glu Val Arg Asp
            275                 280                 285

Ser Asp Leu Val Lys Asp Val Glu Ile Ile Ala Lys Gly Leu Ala Asp
290                 295                 300

Ala Ser Gly Asp Leu Arg Arg Leu Lys Ser Ser Met Leu Thr Pro Glu
305                 310                 315                 320

Asn Thr Asp Leu Ile Lys Gln Ser Ile Phe Thr Leu Ile Phe Thr Leu
                325                 330                 335

Lys Asn Ile Glu Ser Ile Ser Ser Asp Ile Ser Gly Phe Thr Gly Asp
            340                 345                 350

Asp Ala Thr Arg Arg Asn Ile Lys Leu Leu Ile Lys Ser Leu Ser Arg
            355                 360                 365

Leu Leu
    370

<210> SEQ ID NO 8
<211> LENGTH: 321
<212> TYPE: PRT
<213> ORGANISM: Physcomitrella patens

<400> SEQUENCE: 8

Met Ser Val Thr Glu Lys Leu Val Ser Leu Pro Gly Ala Ile Trp Lys
1               5                   10                  15

Gln Ile Leu Gly Pro Leu Ser Asn Phe Gly Phe Gly Lys Arg Ser Leu
            20                  25                  30

Trp Glu Gly Gly Val Gly Leu Phe Ile Met Ser Gly Val Leu Leu Leu
        35                  40                  45

Ala Ile Thr Leu Val Trp Val Lys Gly Lys Gln Ile Arg Ala Gln Thr
50                  55                  60

Arg Lys Tyr Glu Ala Val Phe Glu Phe Gln Leu Ala Gln Gly Ile Thr
65                  70                  75                  80

Val Gly Thr Pro Val Arg Ile Arg Gly Val Asp Val Gly Asn Val Val
                85                  90                  95

Gln Val Arg Pro Ser Leu Glu Lys Ile Asp Val Val Glu Leu Ser
            100                 105                 110

Asp Ala Gly Ile Val Val Pro Arg Asn Ala Leu Val Glu Val Asn Gln
            115                 120                 125

Ser Gly Leu Ile Ser Glu Thr Leu Ile Asp Val Thr Pro Arg Arg Pro
130                 135                 140

Ile Pro Lys Pro Thr Val Gly Pro Leu Asp Pro Lys Cys Pro Ser Glu
145                 150                 155                 160

Gly Leu Ile Val Cys Asp Arg Glu Arg Ile Lys Gly Glu Gln Gly Val
                165                 170                 175

Ser Leu Asp Glu Leu Val Gly Ile Cys Thr Lys Ile Ala Arg Gln Ile
            180                 185                 190

Asp Gly Leu Gly Val Glu Arg Met Ala Ser Met Ala Glu Arg Leu Gly
        195                 200                 205

Asp Ala Val Gln Glu Ala Arg Pro Leu Leu Leu Lys Val Gln Ser Met
210                 215                 220
```

```
Ala Glu Asp Val Glu Pro Leu Leu Lys Glu Val Arg Glu Gly Gly Leu
225                 230                 235                 240

Leu Lys Asp Phe Glu Lys Leu Thr Lys Val Ala Ala Glu Ala Gly Arg
            245                 250                 255

Asp Leu Ser Asn Leu Asn Lys Val Val Leu Thr Ser Asp Asn Thr Glu
            260                 265                 270

Leu Leu Arg Asp Ser Val Ser Thr Leu Thr Lys Thr Leu Lys His Val
            275                 280                 285

Glu Ser Ile Ser Lys Asp Val Ser Gly Val Thr Gly Asp Ala Lys Thr
            290                 295                 300

Arg Asn Asn Leu Arg Gln Leu Ile Glu Ser Leu Ser Arg Leu Val Thr
305                 310                 315                 320

Asp

<210> SEQ ID NO 9
<211> LENGTH: 449
<212> TYPE: PRT
<213> ORGANISM: Ostreococcus tauri

<400> SEQUENCE: 9

Met Ala Ala Pro Ser Ala Thr Cys Ala Arg Gly Cys Ala Arg Ser Thr
1               5                   10                  15

Thr Thr Ser Ala Ser Gly Ile Asn Gly Tyr Val Arg Ala Ser Arg Ala
            20                  25                  30

Arg Ala Thr Arg Ile Ala Cys Ser Ser Leu Gly Glu Gly Glu Arg Gly
        35                  40                  45

Arg Glu Gly Gly Asp Val Arg Gly Glu Ile Gly Leu Ala Arg Leu Pro
    50                  55                  60

Arg Pro Ser Val Arg Arg Ala Val Val Arg Arg Asp Ala Arg Thr Ser
65                  70                  75                  80

Gly Thr Ser Gly Arg Ile Gln Gly Asn Val Ala Gly Asp Asp Gly Arg
                85                  90                  95

Ala Trp Trp Arg Asn Val Thr Ala Lys Ala Ala Val Asp Gly Gly Ser
            100                 105                 110

Glu Ser Ala Asp Ala Ser Ala Ser Glu Asp Phe Gly Ser Glu Asp Glu
        115                 120                 125

Gly Thr Ala Gly Lys Pro Val Asn Val Leu Lys Thr Phe Leu Arg Arg
    130                 135                 140

Leu Val Lys Pro Leu Gln Asp Phe Gly Phe Gly Arg Thr Arg Leu Trp
145                 150                 155                 160

Glu Gly Gly Val Gly Leu Phe Ile Ile Ser Gly Val Ala Val Thr Phe
                165                 170                 175

Ile Ile Trp Gly Trp Ile Gln Gly Leu Leu Ser Phe Ala Arg Lys Asn
            180                 185                 190

Ser Tyr Gln Ala Phe Ile Glu Phe Pro Val Ala Cys Gly Ile Gln Val
        195                 200                 205

Gly Thr Asn Val Arg Val Arg Gly Val Lys Ala Gly Thr Val Leu Ser
    210                 215                 220

Val Gln Pro Ser Leu Glu Lys Val Asp Val Leu Val Glu Met Asp Asp
225                 230                 235                 240

Lys Asn Val Pro Ile Pro Arg Asn Ser Val Ile Glu Ala Asn Gln Ser
                245                 250                 255

Gly Leu Ile Ala Glu Thr Ile Ile Asp Ile Thr Pro Ala Leu Pro Ile
            260                 265                 270

Pro Asn Ala Gln Trp Gly Pro Leu Asp Ser Gly Cys Glu Gly Glu Gly
```

-continued

```
                275                 280                 285
Leu Ile Val Cys Asp Arg Gly Lys Ile Lys Gly Val Gln Gly Val Ser
290                 295                 300

Met Asp Glu Leu Val Gly Ile Cys Thr Lys Leu Ala Arg Glu Met Glu
305                 310                 315                 320

Arg Gln Asn Gly Val Gln Gln Met Phe Ala Thr Thr Glu Ser Ala Gln
                325                 330                 335

Arg Leu Met Thr Thr Leu Gln Pro Leu Leu Arg Glu Ala Ala Gln Ile
                340                 345                 350

Ala His Glu Leu Arg Pro Met Met Gln Asn Val Asn Glu Gln Gly Thr
                355                 360                 365

Leu Asp Thr Leu Glu Asp Leu Ala Gly Lys Thr Ser Ala Thr Val Glu
                370                 375                 380

Asp Ile Arg Arg Leu Lys Thr Thr Ile Leu Thr Asp Glu Asn Gln Glu
385                 390                 395                 400

Leu Leu Arg Gln Ser Ile Ser Thr Leu Thr Lys Thr Leu Gln His Val
                405                 410                 415

Glu Lys Val Ser Gly Asp Ile Ser Ser Val Ser Gly Asp Pro Ser Thr
                420                 425                 430

Arg Thr Asn Leu Arg His Leu Ile Gln Ser Leu Ser Arg Leu Val Asp
                435                 440                 445

Ala

<210> SEQ ID NO 10
<211> LENGTH: 278
<212> TYPE: PRT
<213> ORGANISM: Chlamydomonas reinhardtii

<400> SEQUENCE: 10

Met Val Ile His Ala Ser Ala Ser Gln Gly Asp Ala Glu Ser Gln Pro
1               5                   10                  15

Gly Phe Lys Gln Gly Leu Phe Gly Ser Ile Ala Lys Ser Leu Ser Asp
                20                  25                  30

Tyr Gly Ile Gly Lys Lys Ser Ile Trp Glu Gly Val Gly Leu Phe
                35                  40                  45

Val Leu Ala Gly Gly Ala Ala Val Ala Leu Val Ala Trp Ala Arg
50                  55                  60

Gly Asn Ala Leu Arg Thr Gly Thr Pro Tyr Gln Ala Thr Ile Glu Phe
65                  70                  75                  80

Pro Leu Ala Cys Gly Ile Gln Ile Gly Thr Pro Val Arg Ile Arg Gly
                85                  90                  95

Val Gln Val Asn Asp Val Ser Thr Val Ile Pro Arg Asn Ser Val Ile
                100                 105                 110

Glu Ala Asn Gln Ser Gly Leu Ile Ala Glu Pro Leu Val Pro Val Pro
                115                 120                 125

Asp Tyr Arg Ala Leu Pro His Glu Pro Arg Cys Gln Asp Glu Ser Leu
130                 135                 140

Ile Gly Val Ala Leu Asp Asp Leu Val Tyr Ile Met Thr Arg Cys Glu
145                 150                 155                 160

Leu Cys Glu Cys Ala Glu Asn Asp Gly Val Asp Lys Val Phe Ala Ala
                165                 170                 175

Ala Glu Ser Ala Thr Gln Leu Met Glu Lys Ala Ala Pro Leu Val Ser
                180                 185                 190

Ser Ala Ala Glu Leu Val Gly Asn Ile Glu Ala Leu Thr Arg Thr Ala
                195                 200                 205
```

```
Ala Asp Ala Ala Ala Asp Ile Arg Arg Leu Gln Gly Ser Val Leu Thr
    210                 215                 220

Glu Asp Asn Val Arg Ala Leu Arg Gln Ala Val Leu Thr Leu Cys Lys
225                 230                 235                 240

Thr Leu Asp His Val Glu Ser Ile Ser Ala Asp Val Ser Ile Leu Ala
                245                 250                 255

Arg Asp Ser Gly Val Gln Arg Asn Leu Lys Thr Leu Val Gln Ala Leu
            260                 265                 270

Ser Arg Leu Leu Asp Asp
        275

<210> SEQ ID NO 11
<211> LENGTH: 132
<212> TYPE: PRT
<213> ORGANISM: Arabidopsis thaliana

<400> SEQUENCE: 11

Gly Phe Gln Met Arg Ser Lys Phe Arg Lys Tyr Gln Thr Val Phe Glu
1               5                   10                  15

Leu Ser His Ala Ser Gly Ile Cys Thr Gly Thr Pro Val Arg Ile Arg
            20                  25                  30

Gly Val Thr Val Gly Thr Ile Ile Arg Val Asn Pro Ser Leu Lys Asn
        35                  40                  45

Ile Glu Ala Val Ala Glu Ile Glu Asp Asp Lys Ile Ile Pro Arg
    50                  55                  60

Asn Ser Leu Val Glu Val Asn Gln Ser Gly Leu Leu Met Glu Thr Met
65                  70                  75                  80

Ile Asp Ile Met Pro Arg Asn Pro Ile Pro Glu Pro Ser Val Gly Pro
                85                  90                  95

Leu His Pro Glu Cys Gly Lys Glu Gly Leu Ile Val Cys Asp Arg Gln
            100                 105                 110

Thr Ile Lys Gly Val Gln Gly Val Ser Leu Asp Glu Leu Val Gly Ile
        115                 120                 125

Phe Thr Arg Ile
    130

<210> SEQ ID NO 12
<211> LENGTH: 25
<212> TYPE: PRT
<213> ORGANISM: Arabidopsis thaliana

<400> SEQUENCE: 12

Ile Met Pro Arg Asn Pro Ile Pro Glu Pro Ser Val Gly Pro Leu His
1               5                   10                  15

Pro Glu Cys Gly Lys Glu Gly Leu Ile
            20                  25

<210> SEQ ID NO 13
<211> LENGTH: 263
<212> TYPE: PRT
<213> ORGANISM: Arabidopsis thaliana

<400> SEQUENCE: 13

Gly Phe Gln Met Arg Ser Lys Phe Arg Lys Tyr Gln Thr Val Phe Glu
1               5                   10                  15

Leu Ser His Ala Ser Gly Ile Cys Thr Gly Thr Pro Val Arg Ile Arg
            20                  25                  30

Gly Val Thr Val Gly Thr Ile Ile Arg Val Asn Pro Ser Leu Lys Asn
```

```
                    35                  40                  45
Ile Glu Ala Val Ala Glu Ile Glu Asp Lys Ile Ile Pro Arg
 50                  55                  60

Asn Ser Leu Val Glu Val Asn Gln Ser Gly Leu Leu Met Glu Thr Met
 65                  70                  75                  80

Ile Asp Ile Met Pro Arg Asn Pro Ile Pro Glu Pro Ser Val Gly Pro
                 85                  90                  95

Leu His Pro Glu Cys Gly Lys Glu Gly Leu Ile Val Cys Asp Arg Gln
            100                 105                 110

Thr Ile Lys Gly Val Gln Gly Val Ser Leu Asp Glu Leu Val Gly Ile
        115                 120                 125

Phe Thr Arg Ile Gly Arg Glu Val Glu Ala Ile Gly Val Ala Asn Thr
    130                 135                 140

Tyr Ser Leu Ala Glu Arg Ala Ala Ser Val Ile Glu Glu Ala Arg Pro
145                 150                 155                 160

Leu Leu Lys Lys Ile Gln Ala Met Ala Glu Asp Ala Gln Pro Leu Leu
                165                 170                 175

Ser Glu Phe Arg Asp Ser Gly Leu Leu Lys Glu Val Glu Cys Leu Thr
            180                 185                 190

Arg Ser Leu Thr Gln Ala Ser Asp Asp Leu Arg Lys Val Asn Ser Ser
        195                 200                 205

Ile Met Thr Pro Glu Asn Thr Glu Leu Ile Gln Lys Ser Ile Tyr Thr
    210                 215                 220

Leu Val Tyr Thr Leu Lys Asn Val Glu Ser Ile Ser Ser Asp Ile Leu
225                 230                 235                 240

Gly Phe Thr Gly Asp Glu Ala Thr Arg Lys Asn Leu Lys Leu Leu Ile
                245                 250                 255

Lys Ser Leu Ser Arg Leu Leu
            260

<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14
ccggagctcg gttttcaaat gcggtc                                          26

<210> SEQ ID NO 15
<211> LENGTH: 26
<212> TYPE: DNA
<213> ORGANISM: Artificial Sequence
<220> FEATURE:
<223> OTHER INFORMATION: Synthetic

<400> SEQUENCE: 15
cggctcgagt agtagcctgc ttaggg                                          26

<210> SEQ ID NO 16

<400> SEQUENCE: 16

000

<210> SEQ ID NO 17

<400> SEQUENCE: 17
```

000

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
gcgctcgaga atacgagtga aaattcc          27

<210> SEQ ID NO 19
<211> LENGTH: 130
<212> TYPE: PRT
<213> ORGANISM: Arabidopsis thaliana

<400> SEQUENCE: 19

Ala Glu Ile Glu Asp Asp Lys Ile Ile Ile Pro Arg Asn Ser Leu Val
1               5                   10                  15

Glu Val Asn Gln Ser Gly Leu Leu Met Glu Thr Met Ile Asp Ile Met
            20                  25                  30

Pro Arg Asn Pro Ile Pro Glu Pro Ser Val Gly Pro Leu His Pro Glu
        35                  40                  45

Cys Gly Lys Glu Gly Leu Ile Val Cys Asp Arg Gln Thr Ile Lys Gly
    50                  55                  60

Val Gln Gly Val Ser Leu Asp Glu Leu Val Gly Ile Phe Thr Arg Ile
65                  70                  75                  80

Gly Arg Glu Val Glu Ala Ile Gly Val Ala Asn Thr Tyr Ser Leu Ala
                85                  90                  95

Glu Arg Ala Ala Ser Val Ile Glu Glu Ala Arg Pro Leu Leu Lys Lys
            100                 105                 110

Ile Gln Ala Met Ala Glu Asp Ala Gln Pro Leu Leu Ser Glu Phe Arg
        115                 120                 125

Asp Ser
    130

<210> SEQ ID NO 20
<211> LENGTH: 25
<212> TYPE: DNA
<213> ORGANISM: Artificial Sequence
<220> FEATURE:
<223> OTHER INFORMATION: Synthetic

<400> SEQUENCE: 20
ccggagctcg ctgagataga agatg          25

<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21
cgactcgagg ctatcacgaa actcag          26

<210> SEQ ID NO 22
<211> LENGTH: 130
<212> TYPE: PRT
<213> ORGANISM: Arabidopsis thaliana

<400> SEQUENCE: 22

```
Lys Glu Gly Leu Ile Val Cys Asp Arg Gln Thr Ile Lys Gly Val Gln
1               5                   10                  15

Gly Val Ser Leu Asp Glu Leu Val Gly Ile Phe Thr Arg Ile Gly Arg
            20                  25                  30

Glu Val Glu Ala Ile Gly Val Ala Asn Thr Tyr Ser Leu Ala Glu Arg
            35                  40                  45

Ala Ala Ser Val Ile Glu Glu Ala Arg Pro Leu Leu Lys Lys Ile Gln
50                  55                  60

Ala Met Ala Glu Asp Ala Gln Pro Leu Leu Ser Glu Phe Arg Asp Ser
65                  70                  75                  80

Gly Leu Leu Lys Glu Val Glu Cys Leu Thr Arg Ser Leu Thr Gln Ala
                85                  90                  95

Ser Asp Asp Leu Arg Lys Val Asn Ser Ser Ile Met Thr Pro Glu Asn
            100                 105                 110

Thr Glu Leu Ile Gln Lys Ser Ile Tyr Thr Leu Val Tyr Thr Leu Lys
            115                 120                 125

Asn Val
    130

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
caggagctca aggaaggtct gatcg                                           25

<210> SEQ ID NO 24
<211> LENGTH: 26
<212> TYPE: DNA
<213> ORGANISM: Artificial Sequence
<220> FEATURE:
<223> OTHER INFORMATION: Synthetic

<400> SEQUENCE: 24
cggctcgagg acgttcttca aagtat                                          26

<210> SEQ ID NO 25
<211> LENGTH: 181
<212> TYPE: PRT
<213> ORGANISM: Arabidopsis thaliana

<400> SEQUENCE: 25

Ile Met Pro Arg Asn Pro Ile Pro Glu Pro Ser Val Gly Pro Leu His
1               5                   10                  15

Pro Glu Cys Gly Lys Glu Gly Leu Ile Val Cys Asp Arg Gln Thr Ile
            20                  25                  30

Lys Gly Val Gln Gly Val Ser Leu Asp Glu Leu Val Gly Ile Phe Thr
            35                  40                  45

Arg Ile Gly Arg Glu Val Glu Ala Ile Gly Val Ala Asn Thr Tyr Ser
50                  55                  60

Leu Ala Glu Arg Ala Ala Ser Val Ile Glu Glu Ala Arg Pro Leu Leu
65                  70                  75                  80

Lys Lys Ile Gln Ala Met Ala Glu Asp Ala Gln Pro Leu Leu Ser Glu
                85                  90                  95

Phe Arg Asp Ser Gly Leu Leu Lys Glu Val Glu Cys Leu Thr Arg Ser
            100                 105                 110
```

```
Leu Thr Gln Ala Ser Asp Asp Leu Arg Lys Val Asn Ser Ser Ile Met
            115                 120                 125

Thr Pro Glu Asn Thr Glu Leu Ile Gln Lys Ser Ile Tyr Thr Leu Val
130                 135                 140

Tyr Thr Leu Lys Asn Val Glu Ser Ile Ser Ser Asp Ile Leu Gly Phe
145                 150                 155                 160

Thr Gly Asp Glu Ala Thr Arg Lys Asn Leu Lys Leu Leu Ile Lys Ser
                165                 170                 175

Leu Ser Arg Leu Leu
            180

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
ccggagctca ttatgcctag gaatccg                                               27

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
cggctcgagt agtagcctgc ttaggg                                                26

<210> SEQ ID NO 28
<211> LENGTH: 182
<212> TYPE: PRT
<213> ORGANISM: Arabidopsis thaliana

<400> SEQUENCE: 28

Gly Phe Gln Met Arg Ser Lys Phe Arg Lys Tyr Gln Thr Val Phe Glu
1               5                   10                  15

Leu Ser His Ala Ser Gly Ile Cys Thr Gly Thr Pro Val Arg Ile Arg
            20                  25                  30

Gly Val Thr Val Gly Thr Ile Ile Arg Val Asn Pro Ser Leu Lys Asn
        35                  40                  45

Ile Glu Ala Val Ala Glu Ile Glu Asp Asp Lys Ile Ile Ile Pro Arg
50                  55                  60

Asn Ser Leu Val Glu Val Asn Gln Ser Gly Leu Leu Met Glu Thr Met
65                  70                  75                  80

Ile Asp Ile Met Pro Arg Asn Pro Ile Pro Glu Pro Ser Val Gly Pro
                85                  90                  95

Leu His Pro Glu Cys Gly Lys Glu Gly Leu Ile Val Cys Asp Arg Gln
            100                 105                 110

Thr Ile Lys Gly Val Gln Gly Val Ser Leu Asp Glu Leu Val Gly Ile
            115                 120                 125

Phe Thr Arg Ile Gly Arg Glu Val Glu Ala Ile Gly Val Ala Asn Thr
130                 135                 140

Tyr Ser Leu Ala Glu Arg Ala Ala Ser Val Ile Glu Glu Ala Arg Pro
145                 150                 155                 160

Leu Leu Lys Lys Ile Gln Ala Met Ala Glu Asp Ala Gln Pro Leu Leu
                165                 170                 175
```

Ser Glu Phe Arg Asp Ser
            180

<210> SEQ ID NO 29

<400> SEQUENCE: 29

000

<210> SEQ ID NO 30

<400> SEQUENCE: 30

000

<210> SEQ ID NO 31
<211> LENGTH: 107
<212> TYPE: PRT
<213> ORGANISM: Arabidopsis thaliana

<400> SEQUENCE: 31

Gly Phe Gln Met Arg Ser Lys Phe Arg Lys Tyr Gln Thr Val Phe Glu
1               5                   10                  15

Leu Ser His Ala Ser Gly Ile Cys Thr Gly Thr Pro Val Arg Ile Arg
            20                  25                  30

Gly Val Thr Val Gly Thr Ile Arg Val Asn Pro Ser Leu Lys Asn
        35                  40                  45

Ile Glu Ala Val Ala Glu Ile Glu Asp Lys Ile Ile Ile Pro Arg
    50                  55                  60

Asn Ser Leu Val Glu Val Asn Gln Ser Gly Leu Leu Met Glu Thr Met
65                  70                  75                  80

Ile Asp Ile Met Pro Arg Asn Pro Ile Pro Glu Pro Ser Val Gly Pro
                85                  90                  95

Leu His Pro Glu Cys Gly Lys Glu Gly Leu Ile
            100                 105

<210> SEQ ID NO 32

<400> SEQUENCE: 32

000

<210> SEQ ID NO 33
<211> LENGTH: 26
<212> TYPE: DNA
<213> ORGANISM: Artificial Sequence
<220> FEATURE:
<223> OTHER INFORMATION: Synthetic

<400> SEQUENCE: 33
cggctcgagg atcagacctt ccttac                                    26

<210> SEQ ID NO 34
<211> LENGTH: 55
<212> TYPE: PRT
<213> ORGANISM: Arabidopsis thaliana

<400> SEQUENCE: 34

Ala Glu Ile Glu Asp Asp Lys Ile Ile Ile Pro Arg Asn Ser Leu Val
1               5                   10                  15

Glu Val Asn Gln Ser Gly Leu Leu Met Glu Thr Met Ile Asp Ile Met
            20                  25                  30

```
Pro Arg Asn Pro Ile Pro Glu Pro Ser Val Gly Pro Leu His Pro Glu
        35                  40                  45

Cys Gly Lys Glu Gly Leu Ile
        50                  55

<210> SEQ ID NO 35
<211> LENGTH: 25
<212> TYPE: DNA
<213> ORGANISM: Artificial Sequence
<220> FEATURE:
<223> OTHER INFORMATION: Synthetic

<400> SEQUENCE: 35
ccggagctcg ctgagataga agatg                                          25

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40
<211> LENGTH: 30
<212> TYPE: PRT
<213> ORGANISM: Arabidopsis thaliana

<400> SEQUENCE: 40

Lys Glu Gly Leu Ile Val Cys Asp Arg Gln Thr Ile Lys Gly Val Gln
1               5                   10                  15

Gly Val Ser Leu Asp Glu Leu Val Gly Ile Phe Thr Arg Ile
            20                  25                  30

<210> SEQ ID NO 41

<400> SEQUENCE: 41

000

<210> SEQ ID NO 42

<400> SEQUENCE: 42

000

<210> SEQ ID NO 43
<211> LENGTH: 351
<212> TYPE: PRT
<213> ORGANISM: Artificial Sequence
<220> FEATURE:
```

<223> OTHER INFORMATION: Synthetic

<400> SEQUENCE: 43

```
Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg Ala Ala Ser
        35                  40                  45

Asn Ser Asp Ala Ala His Gly Gln Pro Ser Ser Asp Gly Gly Lys Asn
    50                  55                  60

Pro Leu Thr Val Val Leu Asp Val Pro Arg Asn Ile Trp Arg Gln Thr
65                  70                  75                  80

Leu Lys Pro Leu Ser Asp Phe Gly Phe Gly Lys Arg Ser Ile Trp Glu
                85                  90                  95

Gly Gly Val Gly Leu Phe Ile Val Ser Gly Ala Thr Leu Leu Ala Leu
            100                 105                 110

Ser Trp Ala Trp Leu Arg Gly Phe Gln Met Arg Ser Lys Phe Arg Lys
        115                 120                 125

Tyr Gln Thr Val Phe Glu Leu Ser His Ala Ser Gly Ile Cys Thr Gly
    130                 135                 140

Thr Pro Val Arg Ile Arg Gly Val Thr Val Gly Thr Ile Ile Arg Val
145                 150                 155                 160

Asn Pro Ser Leu Lys Asn Ile Glu Ala Val Ala Glu Ile Glu Asp Asp
                165                 170                 175

Lys Ile Ile Ile Pro Arg Asn Ser Leu Val Glu Val Asn Gln Ser Gly
            180                 185                 190

Leu Leu Met Glu Thr Met Ile Asp Ile Met Pro Arg Asn Pro Ile Pro
        195                 200                 205

Glu Pro Ser Val Gly Pro Leu His Pro Glu Cys Gly Gly Arg Glu Val
    210                 215                 220

Glu Ala Ile Gly Val Ala Asn Thr Tyr Ser Leu Ala Glu Arg Ala Ala
225                 230                 235                 240

Ser Val Ile Glu Glu Ala Arg Pro Leu Leu Lys Lys Ile Gln Ala Met
                245                 250                 255

Ala Glu Asp Ala Gln Pro Leu Leu Ser Glu Phe Arg Asp Ser Gly Leu
            260                 265                 270

Leu Lys Glu Val Glu Cys Leu Thr Arg Ser Leu Thr Gln Ala Ser Asp
        275                 280                 285

Asp Leu Arg Lys Val Asn Ser Ser Ile Met Thr Pro Glu Asn Thr Glu
    290                 295                 300

Leu Ile Gln Lys Ser Ile Tyr Thr Leu Val Tyr Thr Leu Lys Asn Val
305                 310                 315                 320

Glu Ser Ile Ser Ser Asp Ile Leu Gly Phe Thr Gly Asp Glu Ala Thr
                325                 330                 335

Arg Lys Asn Leu Lys Leu Leu Ile Lys Ser Leu Ser Arg Leu Leu
            340                 345                 350
```

<210> SEQ ID NO 44
<211> LENGTH: 36
<212> TYPE: DNA
<213> ORGANISM: Artificial Sequence
<220> FEATURE:
<223> OTHER INFORMATION: Synthetic

<400> SEQUENCE: 44

-continued ctgcatcctg aatgtggtgg acgcgaagtt gaggcc                                    36

<210> SEQ ID NO 45
<211> LENGTH: 36
<212> TYPE: DNA
<213> ORGANISM: Artificial Sequence
<220> FEATURE:
<223> OTHER INFORMATION: Synthetic

<400> SEQUENCE: 45
ggcctcaact tcgcgtccac cacattcagg atgcag                                    36

<210> SEQ ID NO 46
<211> LENGTH: 376
<212> TYPE: PRT
<213> ORGANISM: Artificial Sequence
<220> FEATURE:
<223> OTHER INFORMATION: Synthetic

<400> SEQUENCE: 46

```
Met Ile Gly Asn Pro Val Ile Gln Val Pro Ser Ser Leu Met Pro Ser
1               5                   10                  15

Ser Ser Met Ile Ala Cys Pro Arg Val Ser Pro Asn Gly Val Pro Tyr
            20                  25                  30

Leu Pro Pro Lys Pro Arg Thr Arg His Leu Val Val Arg Ala Ala Ser
        35                  40                  45

Asn Ser Asp Ala Ala His Gly Gln Pro Ser Ser Asp Gly Gly Lys Asn
    50                  55                  60

Pro Leu Thr Val Val Leu Asp Val Pro Arg Asn Ile Trp Arg Gln Thr
65                  70                  75                  80

Leu Lys Pro Leu Ser Asp Phe Gly Phe Gly Lys Arg Ser Ile Trp Glu
                85                  90                  95

Gly Gly Val Gly Leu Phe Ile Val Ser Gly Ala Thr Leu Leu Ala Leu
            100                 105                 110

Ser Trp Ala Trp Leu Arg Gly Phe Gln Met Arg Ser Lys Phe Arg Lys
        115                 120                 125

Tyr Gln Thr Val Phe Glu Leu Ser His Ala Ser Gly Ile Cys Thr Gly
    130                 135                 140

Thr Pro Val Arg Ile Arg Gly Val Thr Val Gly Thr Ile Ile Arg Val
145                 150                 155                 160

Asn Pro Ser Leu Lys Asn Ile Glu Ala Val Ala Glu Ile Glu Asp Asp
                165                 170                 175

Lys Ile Ile Ile Pro Arg Asn Ser Leu Val Glu Val Asn Gln Ser Gly
            180                 185                 190

Leu Leu Met Glu Thr Met Ile Asp Ile Met Pro Arg Asn Pro Ile Pro
        195                 200                 205

Glu Pro Ser Val Gly Pro Leu His Pro Glu Cys Gly Val Cys Asp Arg
    210                 215                 220

Gln Thr Ile Lys Gly Val Gln Gly Val Ser Leu Asp Glu Leu Val Gly
225                 230                 235                 240

Ile Phe Thr Arg Ile Gly Arg Glu Val Glu Ala Ile Gly Val Ala Asn
                245                 250                 255

Thr Tyr Ser Leu Ala Glu Arg Ala Ala Ser Val Ile Glu Glu Ala Arg
            260                 265                 270

Pro Leu Leu Lys Lys Ile Gln Ala Met Ala Glu Asp Ala Gln Pro Leu
        275                 280                 285

Leu Ser Glu Phe Arg Asp Ser Gly Leu Leu Lys Glu Val Glu Cys Leu
    290                 295                 300
```

```
Thr Arg Ser Leu Thr Gln Ala Ser Asp Asp Leu Arg Lys Val Asn Ser
305                 310                 315                 320

Ser Ile Met Thr Pro Glu Asn Thr Glu Leu Ile Gln Lys Ser Ile Tyr
                325                 330                 335

Thr Leu Val Tyr Thr Leu Lys Asn Val Glu Ser Ile Ser Asp Ile
            340                 345                 350

Leu Gly Phe Thr Gly Asp Glu Ala Thr Arg Lys Asn Leu Lys Leu Leu
        355                 360                 365

Ile Lys Ser Leu Ser Arg Leu Leu
    370                 375

<210> SEQ ID NO 47
<211> LENGTH: 36
<212> TYPE: DNA
<213> ORGANISM: Artificial Sequence
<220> FEATURE:
<223> OTHER INFORMATION: Synthetic

<400> SEQUENCE: 47
ctgcatcctg aatgtggtgt ttgtgatagg cagaca                         36

<210> SEQ ID NO 48
<211> LENGTH: 36
<212> TYPE: DNA
<213> ORGANISM: Artificial Sequence
<220> FEATURE:
<223> OTHER INFORMATION: Synthetic

<400> SEQUENCE: 48
tgtctgccta tcacaaacac cacattcagg atgcag                         36

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
gacagcccac aaattgatgg                                           20

<210> SEQ ID NO 50
<211> LENGTH: 19
<212> TYPE: DNA
<213> ORGANISM: Artificial Sequence
<220> FEATURE:
<223> OTHER INFORMATION: Synthetic

<400> SEQUENCE: 50
accaacgctc aatgcctac                                            19

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
ggggtcctta aaatagagac                                           20

<210> SEQ ID NO 52
<211> LENGTH: 21
<212> TYPE: DNA
```

```
<213> ORGANISM: Artificial Sequence
<220> FEATURE:
<223> OTHER INFORMATION: Synthetic

<400> SEQUENCE: 52
ggccttttga gttgggaaaa g                                              21

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gggggtgata tctatcgtag                                                20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gcaccctgga tattctttcg                                                20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
cggtcatatg ctggctgaag                                                20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
gacagcacac aagttccagg                                                20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
gtgctatggt tcaggagttc                                                20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
cttaccagcc atgacgattc                                                20
```

```
<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gagaagaaac accgattccg                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
gttgtgatac gaatggtggc                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
ggacctgcct ttcccatatc                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
gcccaagcct caagatgttg                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
ggaagaggga ggttttgttc                                               20

<210> SEQ ID NO 64
<211> LENGTH: 21
<212> TYPE: DNA
<213> ORGANISM: Artificial Sequence
<220> FEATURE:
<223> OTHER INFORMATION: Synthetic

<400> SEQUENCE: 64
ccaattcgtc tcctttcac c                                              21

<210> SEQ ID NO 65
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 65
gtgagaccaa cagtgtcaac                                                    20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
ccacaataca ccaccacttg                                                    20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
cctccgtctc atacatctac                                                    20

<210> SEQ ID NO 68
<211> LENGTH: 25
<212> TYPE: DNA
<213> ORGANISM: Artificial Sequence
<220> FEATURE:
<223> OTHER INFORMATION: Synthetic

<400> SEQUENCE: 68
ccaattcggt ttcatccaat cctct                                              25

<210> SEQ ID NO 69
<211> LENGTH: 28
<212> TYPE: DNA
<213> ORGANISM: Artificial Sequence
<220> FEATURE:
<223> OTHER INFORMATION: Synthetic

<400> SEQUENCE: 69
catatgcatt gatgataact gaaatcga                                           28

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
cttctagatc tcctcctttc                                                    20

<210> SEQ ID NO 71
<211> LENGTH: 29
<212> TYPE: DNA
<213> ORGANISM: Artificial Sequence
<220> FEATURE:
<223> OTHER INFORMATION: Synthetic

<400> SEQUENCE: 71
tgatcgtttg tgataggcag cctataaaa                                          29

<210> SEQ ID NO 72
<211> LENGTH: 20
<212> TYPE: DNA
```

<213> ORGANISM: Artificial Sequence
<220> FEATURE:
<223> OTHER INFORMATION: Synthetic

<400> SEQUENCE: 72
ccttgcttcc tcaataaccg                                         20

<210> SEQ ID NO 73
<211> LENGTH: 31
<212> TYPE: DNA
<213> ORGANISM: Artificial Sequence
<220> FEATURE:
<223> OTHER INFORMATION: Synthetic

<400> SEQUENCE: 73
gtcgacatga ttgggaatcc agtaattcaa g                            31

<210> SEQ ID NO 74
<211> LENGTH: 26
<212> TYPE: DNA
<213> ORGANISM: Artificial Sequence
<220> FEATURE:
<223> OTHER INFORMATION: Synthetic

<400> SEQUENCE: 74
gtcgactcat agtagcctgc ttaggg                                  26

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
cggcttgctc aaggaagttg                                         20

<210> SEQ ID NO 76
<211> LENGTH: 22
<212> TYPE: DNA
<213> ORGANISM: Artificial Sequence
<220> FEATURE:
<223> OTHER INFORMATION: Synthetic

<400> SEQUENCE: 76
ccagtctaaa atctacaggc tg                                      22

<210> SEQ ID NO 77
<211> LENGTH: 29
<212> TYPE: DNA
<213> ORGANISM: Artificial Sequence
<220> FEATURE:
<223> OTHER INFORMATION: Synthetic

<400> SEQUENCE: 77
tgatcgtttg tgataggcag cctataaaa                               29

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
ccttgcttcc tcaataaccg                                         20

<210> SEQ ID NO 79
<211> LENGTH: 29
<212> TYPE: DNA
<213> ORGANISM: Artificial Sequence
<220> FEATURE:
<223> OTHER INFORMATION: Synthetic

<400> SEQUENCE: 79
tcaattctct ctaccgtgat caagatgca                              29

<210> SEQ ID NO 80
<211> LENGTH: 27
<212> TYPE: DNA
<213> ORGANISM: Artificial Sequence
<220> FEATURE:
<223> OTHER INFORMATION: Synthetic

<400> SEQUENCE: 80
gtgtcagaac tctccacctc aagagta                                27

<210> SEQ ID NO 81
<211> LENGTH: 31
<212> TYPE: DNA
<213> ORGANISM: Artificial Sequence
<220> FEATURE:
<223> OTHER INFORMATION: Synthetic

<400> SEQUENCE: 81
gtcgacatga ttgggaatcc agtaattcaa g                           31

<210> SEQ ID NO 82
<211> LENGTH: 28
<212> TYPE: DNA
<213> ORGANISM: Artificial Sequence
<220> FEATURE:
<223> OTHER INFORMATION: Synthetic

<400> SEQUENCE: 82
gtcgactagt agcctgctta gggatttg                               28

<210> SEQ ID NO 83
<211> LENGTH: 27
<212> TYPE: DNA
<213> ORGANISM: Artificial Sequence
<220> FEATURE:
<223> OTHER INFORMATION: Synthetic

<400> SEQUENCE: 83
gtcgacggtt ttcaaatgcg gtcgaag                                27

<210> SEQ ID NO 84
<211> LENGTH: 26
<212> TYPE: DNA
<213> ORGANISM: Artificial Sequence
<220> FEATURE:
<223> OTHER INFORMATION: Synthetic

<400> SEQUENCE: 84
gtcgactcat agtagcctgc ttaggg                                 26

<210> SEQ ID NO 85
<211> LENGTH: 74
<212> TYPE: PRT
<213> ORGANISM: Arabidopsis thaliana

<400> SEQUENCE: 85

-continued

Asp Lys Ile Ile Pro Arg Asn Ser Leu Val Glu Val Asn Gln Ser
1               5                   10                  15

Gly Leu Leu Met Glu Thr Met Ile Asp Ile Met Pro Arg Asn Pro Ile
                20                  25                  30

Pro Glu Pro Ser Val Gly Pro Leu His Pro Glu Cys Gly Lys Glu Gly
            35                  40                  45

Leu Ile Val Cys Asp Arg Gln Thr Ile Lys Gly Val Gln Gly Val Ser
        50                  55                  60

Leu Asp Glu Leu Val Gly Ile Phe Thr Arg
65                  70

<210> SEQ ID NO 86
<211> LENGTH: 74
<212> TYPE: PRT
<213> ORGANISM: Nodularia spumigena

<400> SEQUENCE: 86

Ala Asp Leu Met Ile Ser Arg Asp Ala Val Ile Glu Ala Asn Gln Ser
1               5                   10                  15

Gly Leu Ile Ser Glu Ser Ile Ile Asp Ile Thr Pro Lys Thr Ser Ile
                20                  25                  30

Pro Val Gly Ala Ile Ala Lys Pro Leu Asp Asn Asn Cys Asp Asp Ser
            35                  40                  45

Leu Ile Val Cys Asn Gly Ser Arg Leu Thr Gly Glu Ile Gly Ile Ser
        50                  55                  60

Ile Asp Glu Leu Ile Arg Thr Ser Thr Asn
65                  70

<210> SEQ ID NO 87
<211> LENGTH: 75
<212> TYPE: PRT
<213> ORGANISM: Anabaena variabilis

<400> SEQUENCE: 87

Ser Asp Leu Ile Ile Pro Arg Asp Val Val Ile Glu Ala Asn Gln Thr
1               5                   10                  15

Gly Leu Ile Ser Glu Ser Ile Ile Asp Ile Thr Pro Lys Ser Ser Leu
                20                  25                  30

Pro Thr Gly Gln Asn Leu Thr Lys Pro Leu Asp Lys Asn Cys Asp Asn
            35                  40                  45

Ser Leu Ile Val Cys Asn Asn Ser Arg Leu Lys Gly Gln Ile Gly Ile
        50                  55                  60

Ser Val Asp Ala Leu Ile Arg Ser Ser Thr Asp
65                  70                  75

<210> SEQ ID NO 88
<211> LENGTH: 73
<212> TYPE: PRT
<213> ORGANISM: Cyanothece sp. PCC 8801

<400> SEQUENCE: 88

Arg Glu Leu Arg Ile Pro Ile Gly Ser Thr Ile Gln Ile Asn Arg Tyr
1               5                   10                  15

Gly Leu Ile Gly Glu Ala Ser Val Asp Ile Thr Pro Ser Glu Lys Leu
                20                  25                  30

Ser Asp Gln Ala Leu Ala Val Asp Pro Thr Ser Glu Glu Cys Pro Asp
            35                  40                  45

Lys Gln Leu Ile Ile Cys Asp Asn Asp Thr Leu Asp Gly Glu Thr Gly
        50                  55                  60

Ser Gln Leu Val Gln Ala Leu Thr Arg
65                  70

<210> SEQ ID NO 89
<211> LENGTH: 74
<212> TYPE: PRT
<213> ORGANISM: Crocosphaera watsonii

<400> SEQUENCE: 89

Ala Glu Leu Arg Ile Pro Lys Asp Ser Lys Val Arg Ile Asn Arg Ser
1               5                   10                  15

Gly Leu Ile Gly Glu Ala Ser Val Asp Ile Thr Pro Ser Arg Glu Leu
            20                  25                  30

Asp Glu Glu Ala Leu Ala Ile Asp Pro Val Gly Lys Asp Cys Ala Ser
        35                  40                  45

Ala Glu Gln Ile Leu Cys Asn Asn Asp Glu Gly Ile Lys Gly Glu Arg
    50                  55                  60

Gly Ser Gln Leu Val Glu Ala Leu Thr Arg
65                  70

<210> SEQ ID NO 90
<211> LENGTH: 72
<212> TYPE: PRT
<213> ORGANISM: Synechococcus sp. JA-2-3B's(213)

<400> SEQUENCE: 90

Pro Leu Val Ile Pro Arg Asp Ser Leu Phe Leu Thr Lys Gln Thr Gly
1               5                   10                  15

Leu Val Gly Glu Thr Val Met Asp Ile Leu Pro Gln Gly Arg Gly Gln
            20                  25                  30

Ala Ala Thr Gly Ser Pro Leu Ala Ala Asp Cys Asp Ser Ser Gln Ile
        35                  40                  45

Ile Cys Asp Gly Asp Val Val Glu Gly Lys Pro Gly Val Asp Phe Gly
    50                  55                  60

Gln Leu Leu Ile Arg Leu Asp Gln
65                  70

<210> SEQ ID NO 91
<211> LENGTH: 75
<212> TYPE: PRT
<213> ORGANISM: Microcystis aeruginosa

<400> SEQUENCE: 91

Ala Asp Arg Leu Ile Pro Ser Asn Ser Leu Ile Glu Ala Ile Gln Ser
1               5                   10                  15

Gly Leu Val Gly Glu Thr Thr Ile Asp Ile Thr Pro Leu Gln Ala Leu
            20                  25                  30

Pro Val Gly Gly Val Lys Glu Pro Pro Leu Ser Pro Asn Cys Asn Gly
        35                  40                  45

Glu Val Ile Ile Cys Asn Gly Ser Arg Leu Gln Gly Gln Ser Ala Leu
    50                  55                  60

Asn Val Asn Thr Leu Ile Arg Ser Leu Leu Arg
65                  70                  75

<210> SEQ ID NO 92
<211> LENGTH: 73
<212> TYPE: PRT
<213> ORGANISM: Thermosynechococcus elongatus

<400> SEQUENCE: 92

```
Val Leu Ile Pro Arg Arg Ala Val Pro Glu Ile Arg Gln Ser Gly Phe
1               5                   10                  15

Ile Gly Gln Ala Phe Leu Asp Phe Thr Pro Lys Glu Arg Val Pro Glu
            20                  25                  30

Ile Pro Glu Gly Val Thr Ala Phe Ala Pro Lys Cys Gln Pro Glu Leu
            35                  40                  45

Val Tyr Cys Asn Gly Asp Arg Val Thr Gly Val Arg Thr Ala Ser Leu
50                  55                  60

Glu Asp Leu Val Arg Ala Ala Thr Arg
65              70
```

<210> SEQ ID NO 93
<211> LENGTH: 77
<212> TYPE: PRT
<213> ORGANISM: Acaryochloris marina

<400> SEQUENCE: 93

```
Ser Thr Val Leu Ile Pro Arg Gln Thr Lys Val Glu Thr Ser Gln Ser
1               5                   10                  15

Gly Phe Val Gly Gln Ala Ala Leu Glu Phe Arg Pro Thr Glu Val Glu
            20                  25                  30

Phe Ser Asp Ala Ser Val Glu Asp Leu Ser Pro Phe Glu Pro Asp Cys
            35                  40                  45

Asp Pro Arg Met Ile Leu Cys Gln Gly Asp Arg Leu Glu Gly Asp Ser
50                  55                  60

Gly Asn Asn Leu Glu Glu Leu Ile Arg Ala Thr Met Gln
65              70                  75
```

<210> SEQ ID NO 94
<211> LENGTH: 75
<212> TYPE: PRT
<213> ORGANISM: Synechococcus sp. CC9902

<400> SEQUENCE: 94

```
Pro Asp Leu Arg Leu Pro Leu Pro Val Thr Ala Ser Val Gly Ala Ala
1               5                   10                  15

Ser Leu Leu Gly Gly Asp Ala Gln Val Asn Leu Ile Ser Gln Asn Lys
            20                  25                  30

Pro Leu Pro Ala Asp Ala Pro Arg Pro Lys Ser Lys Arg Cys Ser Gly
            35                  40                  45

Ser Ser Val Leu Cys Asp Gly Ala Gln Ile Ser Gly Val Glu Ala Pro
50                  55                  60

Ser Leu Asp Thr Val Thr Ala Ser Met Gln Arg
65              70                  75
```

<210> SEQ ID NO 95
<211> LENGTH: 75
<212> TYPE: PRT
<213> ORGANISM: Synechococcus sp. WH 5701

<400> SEQUENCE: 95

```
Pro Thr Leu Gln Leu Ala Arg Pro Thr Met Ala Gln Val Gln Thr Gly
1               5                   10                  15

Ser Leu Leu Gly Gly Asp Ala Gln Val Ala Leu Ile Ser Thr Gly Asn
            20                  25                  30

Pro Leu Pro Glu Ser Ala Pro Leu Pro Arg Ser Lys Asp Cys Asp Asn
            35                  40                  45

Thr Val Met Val Cys Ala Gly Ser Glu Leu Lys Gly Val Thr Ala Ala
```

```
                    50                  55                  60
Ser Leu Asn Ser Val Thr Glu Leu Met Gln Arg
 65                  70                  75

<210> SEQ ID NO 96
<211> LENGTH: 75
<212> TYPE: PRT
<213> ORGANISM: Prochlorococcus marinus str. MIT 9301

<400> SEQUENCE: 96

Pro Glu Ile Ile Leu Pro Lys Pro Ala Phe Ala Lys Val Val Thr Asn
  1               5                  10                  15

Ser Phe Leu Gly Gly Asp Val Gln Val Ser Leu Glu Thr Ser Gln Lys
                 20                  25                  30

Thr Ile Pro Lys Asp Ile Ala Lys Ala Ile Ser Glu Glu Cys Asp Ser
             35                  40                  45

Glu Leu Ile Val Cys Gln Gly Asp Thr Ile Thr Gly Lys Gln Leu Ser
         50                  55                  60

Ser Leu Ser Asn Ile Thr Asn Arg Ile Asn Gln
 65                  70                  75

<210> SEQ ID NO 97
<211> LENGTH: 75
<212> TYPE: PRT
<213> ORGANISM: Prochlorococcus marinus str. NATL2A

<400> SEQUENCE: 97

Asp Asn Leu Ile Leu Pro Lys Pro Val Ile Ala Lys Ile Val Thr Ser
  1               5                  10                  15

Ser Met Leu Gly Gly Asp Ala Gln Leu Ser Leu Ile Ser Leu Gly Lys
                 20                  25                  30

Ser Leu Asn Lys Asn Glu Leu Ile Thr Val Asn Lys Asp Cys Pro Gln
             35                  40                  45

Lys Arg Ile Leu Cys Ser Gly Asp Lys Ile Lys Gly Val Glu Met Val
         50                  55                  60

Ser Ile Ser Ser Leu Thr Glu Gly Ile Asn Gly
 65                  70                  75

<210> SEQ ID NO 98
<211> LENGTH: 74
<212> TYPE: PRT
<213> ORGANISM: Vitis vinifera

<400> SEQUENCE: 98

Asp Lys Ile Ile Ile Pro Gln Asn Ser Leu Ile Glu Val Asn Gln Ser
  1               5                  10                  15

Gly Leu Leu Met Glu Thr Leu Ile Asp Ile Thr Pro Arg Asp Pro Leu
                 20                  25                  30

Pro Thr Pro Ser Val Gly Pro Leu Asp Pro Asp Cys Thr Lys Glu Gly
             35                  40                  45

Val Ile Val Cys Asp Arg Gln Lys Ile Arg Gly Tyr Gln Gly Val Ser
         50                  55                  60

Leu Asp Ala Leu Val Gly Ile Phe Thr Arg
 65                  70

<210> SEQ ID NO 99
<211> LENGTH: 74
<212> TYPE: PRT
<213> ORGANISM: Oryza sativa
```

-continued

<400> SEQUENCE: 99

Asp Lys Ile Ile Val Pro Arg Asn Ser Val Glu Val Asn Gln Ser
1               5                   10                  15

Gly Leu Met Glu Thr Leu Ile Asp Ile Thr Pro Lys Asp Pro Leu
            20                  25                  30

Pro Thr Pro Ser Val Gly Pro Leu Asp Pro Asp Cys Ser Lys Glu Gly
        35                  40                  45

Leu Ile Leu Cys Asp Lys Glu Arg Met Lys Gly Gln Gln Gly Val Ser
    50                  55                  60

Leu Asp Ala Leu Val Gly Ile Phe Thr Arg
65                  70

<210> SEQ ID NO 100
<211> LENGTH: 74
<212> TYPE: PRT
<213> ORGANISM: Physcomitrella patens

<400> SEQUENCE: 100

Ala Gly Ile Val Val Pro Arg Asn Ala Leu Val Glu Val Asn Gln Ser
1               5                   10                  15

Gly Leu Ile Ser Glu Thr Leu Ile Asp Val Thr Pro Arg Pro Ile
            20                  25                  30

Pro Lys Pro Thr Val Gly Pro Leu Asp Pro Lys Cys Pro Ser Glu Gly
        35                  40                  45

Leu Ile Val Cys Asp Arg Glu Arg Ile Lys Gly Glu Gln Gly Val Ser
    50                  55                  60

Leu Asp Glu Leu Val Gly Ile Cys Thr Lys
65                  70

<210> SEQ ID NO 101
<211> LENGTH: 74
<212> TYPE: PRT
<213> ORGANISM: Ostreococcus tauri

<400> SEQUENCE: 101

Lys Asn Val Pro Ile Pro Arg Asn Ser Val Ile Glu Ala Asn Gln Ser
1               5                   10                  15

Gly Leu Ile Ala Glu Thr Ile Ile Asp Ile Thr Pro Ala Leu Pro Ile
            20                  25                  30

Pro Asn Ala Gln Trp Gly Pro Leu Asp Ser Gly Cys Glu Gly Glu Gly
        35                  40                  45

Leu Ile Val Cys Asp Arg Gly Thr Ile Lys Gly Val Gln Gly Val Ser
    50                  55                  60

Met Asp Glu Leu Val Gly Ile Cys Thr Lys
65                  70

<210> SEQ ID NO 102
<211> LENGTH: 57
<212> TYPE: PRT
<213> ORGANISM: Chlamydomonas reinhardtii

<400> SEQUENCE: 102

Val Ser Thr Val Ile Pro Arg Asn Ser Val Ile Glu Ala Asn Gln Ser
1               5                   10                  15

Gly Leu Ile Ala Glu Pro Leu Val Pro Val Pro Asp Tyr Arg Ala Leu
            20                  25                  30

Pro His Glu Pro Arg Cys Gln Asp Glu Ser Leu Ile Gly Val Ala Leu
        35                  40                  45

```
Asp Asp Leu Val Tyr Ile Met Thr Arg
    50                  55
```

<210> SEQ ID NO 103
<211> LENGTH: 50
<212> TYPE: PRT
<213> ORGANISM: Arabidopsis thaliana

<400> SEQUENCE: 103

```
Gly Arg Glu Val Glu Ala Ile Gly Val Ala Asn Thr Tyr Ser Leu Ala
1               5                   10                  15

Glu Arg Ala Ala Ser Val Ile Glu Gly Ala Arg Pro Leu Leu Lys Lys
            20                  25                  30

Ile Gln Ala Met Ala Glu Asp Ala Gln Pro Leu Leu Ser Glu Phe Arg
        35                  40                  45

Asp Ser
    50
```

<210> SEQ ID NO 104
<211> LENGTH: 54
<212> TYPE: PRT
<213> ORGANISM: Arabidopsis thaliana

<400> SEQUENCE: 104

```
Asn Pro Ser Leu Lys Asn Ile Glu Ala Val Ala Glu Ile Glu Asp Asp
1               5                   10                  15

Lys Ile Ile Ile Pro Arg Asn Ser Leu Val Glu Val Asn Gln Ser Gly
            20                  25                  30

Leu Leu Met Glu Thr Met Ile Asp Ile Met Pro Arg Asn Pro Ile Pro
        35                  40                  45

Glu Pro Ser Val Gly Pro
    50
```

<210> SEQ ID NO 105
<211> LENGTH: 50
<212> TYPE: PRT
<213> ORGANISM: Arabidopsis thaliana

<400> SEQUENCE: 105

```
Gln Pro Leu Leu Ser Glu Phe Arg Asp Ser Gly Leu Leu Lys Glu Val
1               5                   10                  15

Glu Cys Leu Thr Arg Ser Leu Thr Gln Ala Ser Asp Asp Leu Arg Lys
            20                  25                  30

Val Asn Ser Ser Ile Met Thr Pro Glu Asn Thr Glu Leu Ile Gln Lys
        35                  40                  45

Ser Ile
    50
```

<210> SEQ ID NO 106
<211> LENGTH: 51
<212> TYPE: PRT
<213> ORGANISM: Arabidopsis thaliana

<400> SEQUENCE: 106

```
Gln Thr Val Phe Glu Leu Ser His Ala Ser Gly Ile Cys Thr Gly Thr
1               5                   10                  15

Pro Val Arg Ile Arg Gly Val Thr Val Gly Thr Ile Ile Arg Val Asn
            20                  25                  30

Pro Ser Leu Lys Asn Ile Glu Ala Val Ala Glu Ile Glu Asp Asp Lys
        35                  40                  45
```

```
Ile Ile Ile
    50

<210> SEQ ID NO 107
<211> LENGTH: 261
<212> TYPE: PRT
<213> ORGANISM: Arabidopsis thaliana

<400> SEQUENCE: 107

Gln Met Arg Ser Lys Phe Arg Lys Tyr Gln Thr Val Phe Glu Leu Ser
1               5                   10                  15

His Ala Ser Gly Ile Cys Thr Gly Thr Pro Val Arg Ile Arg Gly Val
            20                  25                  30

Thr Val Gly Thr Ile Ile Arg Val Asn Pro Ser Leu Lys Asn Ile Glu
        35                  40                  45

Ala Val Ala Glu Ile Glu Asp Asp Lys Ile Ile Pro Arg Asn Ser
    50                  55                  60

Leu Val Glu Val Asn Gln Ser Gly Leu Leu Met Glu Thr Met Ile Asp
65                  70                  75                  80

Ile Met Pro Arg Asn Pro Ile Pro Glu Pro Ser Val Gly Pro Leu His
                85                  90                  95

Pro Glu Cys Gly Lys Glu Gly Leu Ile Val Cys Asp Arg Gln Thr Ile
            100                 105                 110

Lys Gly Val Gln Gly Val Ser Leu Asp Glu Leu Val Gly Ile Phe Thr
        115                 120                 125

Arg Ile Gly Arg Glu Val Glu Ala Ile Gly Val Ala Asn Thr Tyr Ser
    130                 135                 140

Leu Ala Glu Arg Ala Ala Ser Val Ile Glu Glu Ala Arg Pro Leu Leu
145                 150                 155                 160

Lys Lys Ile Gln Ala Met Ala Glu Asp Ala Gln Pro Leu Leu Ser Glu
                165                 170                 175

Phe Arg Asp Ser Gly Leu Leu Lys Glu Val Glu Cys Leu Thr Arg Ser
            180                 185                 190

Leu Thr Gln Ala Ser Asp Asp Leu Arg Lys Val Asn Ser Ser Ile Met
        195                 200                 205

Thr Pro Glu Asn Thr Glu Leu Ile Gln Lys Ser Ile Tyr Thr Leu Val
    210                 215                 220

Tyr Thr Leu Lys Asn Val Glu Ser Ile Ser Ser Asp Ile Leu Gly Phe
225                 230                 235                 240

Thr Gly Asp Glu Ala Thr Arg Lys Asn Leu Lys Leu Leu Ile Lys Ser
                245                 250                 255

Leu Ser Arg Leu Leu
            260

<210> SEQ ID NO 108
<211> LENGTH: 5
<212> TYPE: PRT
<213> ORGANISM: Arabidopsis thaliana

<400> SEQUENCE: 108

Lys Glu Gly Leu Ile
1               5

<210> SEQ ID NO 109
<211> LENGTH: 118
<212> TYPE: PRT
<213> ORGANISM: Arabidopsis thaliana

<400> SEQUENCE: 109
```

```
Val Gly Leu Phe Ile Val Ser Gly Ala Thr Leu Ala Leu Ser Trp
1               5                   10                  15

Ala Trp Leu Arg Gly Phe Gln Met Arg Ser Lys Phe Arg Lys Tyr Gln
            20                  25                  30

Thr Val Phe Glu Leu Ser His Ala Ser Gly Ile Cys Thr Gly Thr Pro
            35                  40                  45

Val Arg Ile Arg Gly Val Thr Val Gly Thr Ile Ile Arg Val Asn Pro
        50                  55                  60

Ser Leu Lys Asn Ile Glu Ala Val Ala Glu Ile Glu Asp Asp Lys Ile
65                  70                  75                  80

Ile Ile Pro Arg Asn Ser Leu Val Glu Val Asn Gln Ser Gly Leu Leu
                85                  90                  95

Met Glu Thr Met Ile Asp Ile Met Pro Arg Asn Pro Ile Pro Glu Pro
            100                 105                 110

Ser Val Gly Pro Leu His
            115
```

<210> SEQ ID NO 110
<211> LENGTH: 25
<212> TYPE: PRT
<213> ORGANISM: Artificial Sequence
<220> FEATURE:
<223> OTHER INFORMATION: Synthetic

<400> SEQUENCE: 110

```
Ile Thr Pro Arg Asp Pro Leu Pro Thr Pro Ser Val Gly Pro Leu Asp
1               5                   10                  15

Pro Asp Cys Thr Lys Glu Gly Val Ile
            20                  25
```

<210> SEQ ID NO 111
<211> LENGTH: 25
<212> TYPE: PRT
<213> ORGANISM: Artificial Sequence
<220> FEATURE:
<223> OTHER INFORMATION: Synthetic

<400> SEQUENCE: 111

```
Ile Thr Pro Lys Asp Pro Leu Pro Thr Pro Ser Val Gly Pro Leu Asp
1               5                   10                  15

Pro Asp Cys Ser Lys Glu Gly Leu Ile
            20                  25
```

<210> SEQ ID NO 112
<211> LENGTH: 25
<212> TYPE: PRT
<213> ORGANISM: Artificial Sequence
<220> FEATURE:
<223> OTHER INFORMATION: Synthetic

<400> SEQUENCE: 112

```
Val Thr Pro Arg Arg Pro Ile Pro Lys Pro Thr Val Gly Pro Leu Asp
1               5                   10                  15

Pro Lys Cys Pro Ser Glu Gly Leu Ile
            20                  25
```

<210> SEQ ID NO 113
<211> LENGTH: 25
<212> TYPE: PRT
<213> ORGANISM: Artificial Sequence
<220> FEATURE:
<223> OTHER INFORMATION: Synthetic

<400> SEQUENCE: 113

```
Ile Thr Pro Ala Leu Pro Ile Pro Asn Ala Gln Trp Gly Pro Leu Asp
1               5                   10                  15

Ser Gly Cys Glu Gly Glu Gly Leu Ile
            20                  25
```

<210> SEQ ID NO 114
<211> LENGTH: 20
<212> TYPE: PRT
<213> ORGANISM: Artificial Sequence
<220> FEATURE:
<223> OTHER INFORMATION: Synthetic

<400> SEQUENCE: 114

```
Pro Val Pro Asp Tyr Arg Ala Leu Pro His Glu Pro Arg Cys Gln Asp
1               5                   10                  15

Glu Ser Leu Ile
            20
```

<210> SEQ ID NO 115
<211> LENGTH: 281
<212> TYPE: PRT
<213> ORGANISM: Prochlorococcus marinus str. NATL2A

<400> SEQUENCE: 115

```
Met Arg Arg Ser Leu Arg Asp Ala Phe Val Gly Phe Ser Leu Leu Gly
1               5                   10                  15

Gly Leu Val Ile Phe Ser Gly Ala Met Leu Trp Leu Arg Asp Phe Arg
            20                  25                  30

Leu Gly Ser Lys Thr Trp Glu Ile Ser Ala Ser Phe Lys Asp Ala Ser
        35                  40                  45

Gly Leu Ala Lys Met Ser Pro Val Thr Tyr Arg Gly Ile Ile Val Gly
    50                  55                  60

Ser Val Gln Asn Ile Ser Phe Thr Pro Asn Thr Val Glu Thr Lys Ile
65                  70                  75                  80

Lys Ile Asn Asn Asp Asn Leu Ile Leu Pro Lys Pro Val Ile Ala Lys
                85                  90                  95

Ile Val Thr Ser Ser Met Leu Gly Gly Asp Ala Gln Leu Ser Leu Ile
            100                 105                 110

Ser Leu Gly Lys Ser Leu Asn Lys Asn Glu Leu Ile Thr Val Asn Lys
        115                 120                 125

Asp Cys Pro Gln Lys Arg Ile Leu Cys Ser Gly Asp Lys Ile Lys Gly
    130                 135                 140

Val Glu Met Val Ser Ile Ser Ser Leu Thr Glu Gly Ile Asn Gly Ile
145                 150                 155                 160

Ile Asp Glu Ala Asp Lys Gln Ala Ile Val Asn Lys Val Ser Glu Ser
                165                 170                 175

Ile Gln Gln Phe Asp Arg Thr Gln Ala Asn Leu Asp Glu Leu Val Leu
            180                 185                 190

Leu Ser Lys Ser Glu Leu Ile Arg Ala Lys Pro Ile Ile Ser Glu Leu
        195                 200                 205

Thr Lys Ala Ser Phe His Leu Asn Asn Ile Leu Glu Ser Leu Asp Asn
    210                 215                 220

Pro Glu Thr Leu Lys Asp Ile Gln Glu Leu Ala Ser Thr Ser Ser Ser
225                 230                 235                 240

Leu Thr Lys Lys Ile Asp Gln Met Ser Ser Asp Met Gly Asn Ile Met
                245                 250                 255
```

Glu Asp Lys Glu Leu Ile Asn Ala Leu Lys Lys Val Thr Ile Gly Leu
            260                 265                 270

Ser Lys Leu Phe Asp Asp Ile Tyr Pro
            275                 280

<210> SEQ ID NO 116
<211> LENGTH: 281
<212> TYPE: PRT
<213> ORGANISM: Prochlorococcus marinus str. MIT 9301

<400> SEQUENCE: 116

Met Arg Arg Ser Leu Arg Asp Ser Ile Val Gly Phe Ser Leu Leu Gly
1               5                   10                  15

Gly Ile Leu Ile Phe Thr Phe Phe Ser Phe Trp Leu Arg Gly Val Arg
            20                  25                  30

Leu Ser Ser Lys Asn Trp Tyr Leu Phe Ala Glu Phe Asn Asn Ala Ser
        35                  40                  45

Gly Leu Ser Lys Lys Ser Pro Val Thr Tyr Arg Gly Ile Leu Val Gly
    50                  55                  60

Ser Ile Glu Asp Ile Ile Phe Thr Asn Glu Ser Ile Lys Ala Lys Ile
65                  70                  75                  80

Val Leu Asn Asn Pro Glu Ile Ile Leu Pro Arg Pro Ala Phe Ala Arg
                85                  90                  95

Val Val Thr Asn Ser Phe Leu Gly Gly Asp Val Gln Val Ala Leu Glu
            100                 105                 110

Ala Ser Asp Lys Thr Ile Leu Lys Asn Ile Ala Lys Pro Ile Ser Glu
        115                 120                 125

Glu Cys Asp Ala Lys Leu Ile Val Cys Gln Gly Asn Thr Ile Thr Gly
    130                 135                 140

Lys Gln Leu Ser Ser Leu Ser Asn Ile Thr Asn Arg Ile Ser Gln Leu
145                 150                 155                 160

Leu Lys Glu Thr Asn Gln Glu Asn Leu Ile Glu Asn Ile Val Thr Ser
                165                 170                 175

Ile Asp Gln Phe Asp Arg Thr Gln Glu Asn Leu Asp Glu Leu Ile Phe
            180                 185                 190

Leu Ser Lys Gln Glu Leu Gln Arg Val Glu Pro Leu Ile Lys Glu Ile
        195                 200                 205

Thr Ile Ala Ala Asn His Leu Asn Asn Ile Leu Ser Thr Ile Asp Asp
    210                 215                 220

Lys Glu Thr Leu Asn Asp Ile Lys Leu Thr Ile Asn Ala Ala Arg Ser
225                 230                 235                 240

Ile Ser Thr Lys Ile Asp Asn Met Ser Asp Asp Phe Glu Lys Leu Thr
                245                 250                 255

Gln Asp Lys Glu Leu Thr Lys Ser Ile Arg Asp Leu Thr Ile Gly Leu
            260                 265                 270

Ser Lys Phe Leu Asn Glu Ile Tyr Pro
            275                 280

<210> SEQ ID NO 117
<211> LENGTH: 319
<212> TYPE: PRT
<213> ORGANISM: Synechococcus sp. WH 5701

<400> SEQUENCE: 117

Met Arg Arg Ser Val Arg Glu Ala Ile Val Gly Phe Ser Leu Leu Ala
1               5                   10                  15

Ala Val Val Gly Gly Ser Gly Phe Trp Ile Trp Leu Arg Gly Ile Ser
            20                  25                  30

Leu Ser Gln Asn Asn Trp Ile Leu Lys Val Ser Phe Gln Asp Ala Ala
                35                  40                  45

Gly Leu Ala Asp Arg Ser Ala Val Ile Phe Arg Gly Val Gln Val Gly
            50                  55                  60

Ser Val Arg Lys Val Gln Thr Thr Ser Ala Ala Val Leu Ala Glu Leu
65                  70                  75                  80

Glu Ile Ser Asp Pro Thr Leu Gln Leu Ala Arg Pro Thr Met Ala Gln
                85                  90                  95

Val Gln Thr Gly Ser Leu Leu Gly Asp Ala Gln Val Ala Leu Ile
            100                 105                 110

Ser Thr Gly Asn Pro Leu Pro Glu Ser Ala Pro Leu Pro Arg Ser Lys
            115                 120                 125

Asp Cys Asp Asn Thr Val Met Val Cys Ala Gly Ser Glu Leu Lys Gly
            130                 135                 140

Val Thr Ala Ala Ser Leu Asn Ser Val Thr Glu Leu Met Gln Arg Leu
145                 150                 155                 160

Leu Ser Gln Val Asp Glu Lys Gln Ile Val Glu Glu Met Ala Arg Thr
                165                 170                 175

Thr Arg Ser Phe Asp Ala Thr Ser Lys Glu Ala Thr Gln Phe Leu Lys
            180                 185                 190

Arg Ala Gln Val Leu Val Ala Glu Leu Lys Arg Ser Val Gly Lys Ala
            195                 200                 205

Asp Pro Ile Leu Ala Asn Leu Ser Thr Ala Thr Ala Glu Ala Ala Ala
            210                 215                 220

Ala Ser Arg His Val Arg Asn Val Thr Ala Ser Leu Asp Asn Pro Lys
225                 230                 235                 240

Thr Leu Ala Gln Leu Lys Thr Thr Val Gly Asn Ala Glu Arg Leu Thr
                245                 250                 255

Ala Arg Ile Asp Ala Val Gly Gly Asp Val Asn Lys Leu Thr Ser Asp
            260                 265                 270

Ala Glu Phe Met Asp Gly Val Arg Ser Val Ala Ile Gly Leu Gly Gln
            275                 280                 285

Leu Phe Asp Glu Leu Tyr Pro Ala Gln Thr Gly Leu Ala Lys Asp Lys
            290                 295                 300

Ala Glu Lys Glu Ala Gln Lys Lys Ala Ala Pro Lys Pro Pro Arg
305                 310                 315

<210> SEQ ID NO 118
<211> LENGTH: 286
<212> TYPE: PRT
<213> ORGANISM: Synechococcus sp. CC9902

<400> SEQUENCE: 118

Met Arg Arg Ser Val Arg Asp Ala Ile Val Gly Phe Thr Val Leu Gly
1               5                   10                  15

Gly Leu Val Gly Phe Ala Ala Thr Gly Met Trp Met Arg Gly Ile Arg
            20                  25                  30

Leu Gly Ser Ser Glu Trp Arg Leu Thr Ala Asn Phe Asn Asp Ala Ser
                35                  40                  45

Gly Leu Ala Glu Arg Ser Pro Val Thr Tyr Arg Gly Ile Leu Val Gly
            50                  55                  60

Ser Val Arg Ser Ile Lys Val Thr Ser Ser Ala Val Val Ala Glu Leu
65                  70                  75                  80

```
Glu Ile Thr Lys Gly Asp Leu Arg Leu Pro Leu Pro Val Thr Ala Thr
                85                  90                  95

Ile Gly Ser Ala Ser Leu Leu Gly Gly Asp Ala Gln Val Ser Leu Met
            100                 105                 110

Ser Arg Gly Lys Pro Leu Pro Glu Asn Ala Pro Leu Pro Lys Ala Val
        115                 120                 125

Thr Cys Gln Pro Lys Ala Gln Leu Cys Asp Gly Ala Thr Val Met Gly
    130                 135                 140

Gln Glu Ala Ser Ser Ile Thr Thr Val Thr Glu Thr Leu Gln Glu Leu
145                 150                 155                 160

Leu Thr Gln Ala Lys Ala Glu Lys Leu Ile Pro Asn Ala Ala Ala Ser
                165                 170                 175

Met Glu Gln Ile Asp Glu Thr Ala Lys Ser Phe Glu Ala Leu Thr Val
            180                 185                 190

Gln Leu Gln Ala Glu Leu Leu Lys Val Asp Pro Val Leu Arg Asn Leu
        195                 200                 205

Gln Ala Ala Thr Ala His Ala Asn Asn Ile Val Ala Ser Leu Asp Asn
    210                 215                 220

Pro Glu Thr Leu Thr Ser Leu Gln Gln Thr Ala Thr Asn Ala Ala Glu
225                 230                 235                 240

Leu Thr Ala Lys Leu Asp Ala Val Gly Gly Asp Val Glu Thr Leu Thr
                245                 250                 255

Ser Asp Pro Ala Phe Met Asp Gly Leu Arg Asn Val Thr Ile Gly Leu
            260                 265                 270

Gly Ala Leu Phe Ser Glu Val Tyr Pro Ala Gln Thr Ser Arg
        275                 280                 285

<210> SEQ ID NO 119
<211> LENGTH: 407
<212> TYPE: PRT
<213> ORGANISM: Synechococcus sp. JA-2-3B'a(2-13)

<400> SEQUENCE: 119

Met Arg Ser Arg Ala Val Arg Glu Gly Ala Val Gly Leu Leu Ile Leu
1               5                   10                  15

Ala Gly Ala Leu Gly Phe Ala Gly Leu Phe Leu Trp Ile Tyr Asn Leu
            20                  25                  30

Arg Phe Gly Ser Arg Gly Phe Gln Phe Thr Val Thr Tyr Thr Asn Val
        35                  40                  45

Val Gly Leu Thr Glu Gly Ser Ser Val Arg Leu Arg Gly Val Thr Ile
    50                  55                  60

Gly Arg Val Glu Arg Ile Val Pro Gln Pro Ser Gln Val Glu Val Gln
65                  70                  75                  80

Val Thr Ile Asp Gln Pro Leu Val Ile Pro Arg Asp Ser Leu Phe Leu
                85                  90                  95

Thr Lys Gln Thr Gly Leu Val Gly Glu Thr Val Met Asp Ile Leu Pro
            100                 105                 110

Gln Gly Arg Gly Gln Ala Ala Thr Gly Ser Pro Leu Ala Ala Asp Cys
        115                 120                 125

Asp Ser Ser Gln Ile Ile Cys Asp Gly Asp Val Val Glu Gly Lys Pro
    130                 135                 140

Gly Val Asp Phe Gly Gln Leu Leu Ile Arg Leu Asp Gln Leu Leu Thr
145                 150                 155                 160

Arg Ile Asn Asp Asp Glu Leu Phe Asp Thr Leu Asn Ala Thr Leu Glu
                165                 170                 175
```

```
Gly Leu Thr Arg Val Ala Asn Ser Val Ala Asp Leu Ser Glu Thr Val
                180                 185                 190

Glu Glu Arg Val Ala Ala Leu Arg Thr Glu Asp Leu Asp Leu Leu Gln
            195                 200                 205

Phe Thr Thr Ala Ala Thr Ala Ile Gln Asp Ala Ala Gly Ala Val Arg
210                 215                 220

Gly Thr Ala Arg Ser Leu Gln Ala Ala Ala Asp Gln Phe Thr Ala Leu
225                 230                 235                 240

Val Asp Gln Asn Arg Thr Ser Leu Asn Ala Ala Leu Glu Asn Ile Gln
                245                 250                 255

Gln Val Ser Ala Asp Leu Gln Ala Met Ser Ser Ala Val Arg Pro Leu
            260                 265                 270

Val Thr Asp Pro Gln Leu Gln Ala Asp Val Arg Gln Ile Leu Ala Glu
        275                 280                 285

Val Arg Ala Ala Ala Glu Asn Val Ala Gln Ala Thr Glu Asp Leu Gln
    290                 295                 300

Gln Ile Ala Ala Ser Leu Asn Asp Pro Gly Thr Leu Ala Thr Leu Arg
305                 310                 315                 320

Gln Thr Leu Asp Ser Ala Arg Ile Thr Phe Gln Asn Met Gln Lys Ile
                325                 330                 335

Thr Ala Asp Ile Asp Glu Leu Thr Gly Asp Pro Gln Phe Arg Arg Gly
            340                 345                 350

Ile Arg Glu Leu Val Leu Gly Leu Ser Asn Leu Val Ser Ser Val Pro
        355                 360                 365

Gly Glu Asp Gly Ile Gln Pro Ala Val Ala Glu Gly Tyr His Phe Arg
    370                 375                 380

Phe Ala Pro Val Ser Phe Ala Gln Gly Ile Val Ser Gly Ser Gln Gly
385                 390                 395                 400

Trp Gln Pro Gln Thr Ser Pro
                405

<210> SEQ ID NO 120
<211> LENGTH: 470
<212> TYPE: PRT
<213> ORGANISM: Anabaena variabilis

<400> SEQUENCE: 120

Met Arg Asp Leu Ile Thr Asn Arg Phe Thr Ser Gln Arg Thr Leu Arg
1               5                   10                  15

Glu Gly Ser Val Gly Leu Leu Phe Leu Leu Gly Leu Gly Ala Phe Gly
            20                  25                  30

Val Ile Leu Leu Trp Leu Asn Arg Tyr Thr Ala Ala Gly Ser Ser Tyr
        35                  40                  45

Lys Ala Val Val Glu Phe Ala Asn Ala Gly Gly Met Gln Arg Gly Ala
    50                  55                  60

Thr Val Arg Tyr Arg Gly Val Lys Val Gly Arg Ile Ser Gln Ile Gln
65                  70                  75                  80

Pro Gly Pro Asn Ala Val Glu Val Glu Ile Glu Phe Ala Gln Ser Asp
                85                  90                  95

Leu Ile Ile Pro Arg Asp Val Val Ile Glu Ala Asn Gln Thr Gly Leu
            100                 105                 110

Ile Ser Glu Ser Ile Ile Asp Ile Thr Pro Lys Ser Ser Leu Pro Thr
        115                 120                 125

Gly Gln Asn Leu Thr Lys Pro Leu Asp Lys Asn Cys Asp Asn Ser Leu
    130                 135                 140
```

```
Ile Val Cys Asn Asn Ser Arg Leu Lys Gly Gln Ile Gly Ile Ser Val
145                 150                 155                 160

Asp Ala Leu Ile Arg Ser Ser Thr Asp Phe Ala Asn Thr Tyr Asn Asn
                165                 170                 175

Pro Glu Phe Tyr Gln Arg Val Asn Arg Leu Leu Glu Thr Ser Ala Gln
            180                 185                 190

Ala Ala Thr Gly Val Ala Ala Leu Thr Gln Asp Phe Arg Gly Leu Thr
        195                 200                 205

Lys Ser Phe Gln Gly Gln Leu Gly Thr Phe Ala Ser Thr Ala Asn Thr
    210                 215                 220

Val Gln Arg Ala Thr Asn Glu Leu Thr Val Ser Thr Thr Lys Thr Val
225                 230                 235                 240

Asn Gln Phe Gly Ile Thr Ala Asp Lys Phe Gly Thr Thr Ala Thr Gln
                245                 250                 255

Ala Ser Arg Leu Leu Ser Asp Leu Asn Ser Leu Leu Asn Thr Asn Arg
            260                 265                 270

Ser Ser Leu Val Gly Ala Leu Asn Asn Ile Thr Glu Thr Ser Asn Gln
        275                 280                 285

Leu Arg Leu Thr Val Thr Asn Leu Ser Pro Ser Leu Asn Arg Leu Thr
    290                 295                 300

Gln Gly Glu Leu Ile Lys Asn Leu Glu Thr Leu Ser Ala Asn Ala Ala
305                 310                 315                 320

Gln Ala Ser Ala Asn Leu Arg Asn Ala Thr Glu Ser Leu Asn Asp Pro
                325                 330                 335

Lys Asn Ala Val Leu Leu Gln Gln Thr Leu Asp Ser Ala Arg Leu Thr
            340                 345                 350

Phe Glu Asn Thr Gln Lys Ile Thr Ser Asp Leu Asp Glu Leu Thr Gly
        355                 360                 365

Asp Pro Ser Phe Arg Gln Asn Leu Arg Gln Leu Val Asn Gly Leu Ser
    370                 375                 380

Gly Leu Val Ser Ser Thr Asp Gln Met Glu Gln Gln Ala Lys Leu Ala
385                 390                 395                 400

Thr Val Leu Glu Ser Met Lys Ala Ala Asp Lys Pro Asn Ile Thr
                405                 410                 415

Ile Pro Ser Leu Ala Thr Asn Pro Leu Pro Asn Ala Val Thr Ile Ala
            420                 425                 430

Asn Asn Gln Pro Gln Leu Ser Ser Gln Glu Lys Leu Leu Gln Gln Leu
        435                 440                 445

Arg Asp Tyr Ala Glu Gln Gly Asn Ser Glu Glu Lys Gln Gly Lys Glu
    450                 455                 460

Lys Lys Thr Asn Glu Asn
465                 470

<210> SEQ ID NO 121
<211> LENGTH: 494
<212> TYPE: PRT
<213> ORGANISM: Nodularia spumigena

<400> SEQUENCE: 121

Met Arg Asp Ile Ile Thr Asn Ser Phe Ala Ser Lys Arg Thr Leu Arg
1               5                   10                  15

Glu Gly Ser Val Gly Leu Leu Ile Leu Val Gly Leu Gly Ala Phe Val
            20                  25                  30

Met Ile Val Leu Trp Leu Asn Arg Phe Thr Ala Gly Thr Asn Ser Tyr
        35                  40                  45
```

```
Lys Phe Ile Val Glu Phe Ala Asn Ala Gly Met Gln Arg Gly Ala
 50                  55                  60

Pro Val Arg Tyr Arg Gly Val Lys Val Gly Asn Ile Ser Lys Leu Lys
 65                  70                  75                  80

Ala Gly Ser Asn Ala Val Glu Val Glu Ile Glu Ile Ala Pro Ala Asp
                 85                  90                  95

Leu Met Ile Ser Arg Asp Ala Val Ile Glu Ala Asn Gln Ser Gly Leu
                100                 105                 110

Ile Ser Glu Ser Ile Ile Asp Ile Thr Pro Lys Thr Ser Ile Pro Val
            115                 120                 125

Gly Ala Ile Ala Lys Pro Leu Asp Asn Asn Cys Asp Asp Ser Leu Ile
130                 135                 140

Val Cys Asn Gly Ser Arg Leu Thr Gly Glu Ile Gly Ile Ser Ile Asp
145                 150                 155                 160

Glu Leu Ile Arg Thr Ser Thr Asn Leu Ala Thr Thr Tyr Asn Asp Pro
                165                 170                 175

Ala Phe Tyr Gln Asn Leu Asn Arg Leu Leu Glu Ser Ser Thr Ala Ala
                180                 185                 190

Ala Thr Gly Val Ala Ser Leu Thr Gln Asp Phe Gln Val Leu Ser Lys
                195                 200                 205

Ser Phe Gln Gln Gln Leu Gly Thr Phe Ser Thr Thr Ala Asn Ser Val
210                 215                 220

Gln Gln Ser Thr Asn Lys Leu Thr Val Ser Ala Thr Lys Thr Val Asp
225                 230                 235                 240

Gln Leu Gly Ala Thr Ala Ser Glu Phe Ser Ala Thr Ala Asn Gln Ala
                245                 250                 255

Ser Arg Leu Leu Ser Asn Leu Asp Glu Leu Val Thr Ser Asn Arg Ser
                260                 265                 270

Ser Leu Val Gly Ala Leu Asn Asn Ile Thr Glu Thr Ser Asn Gln Leu
                275                 280                 285

Arg Val Thr Val Ser Ser Leu Ser Pro Ala Val Asn Gln Leu Thr Gln
                290                 295                 300

Gly Glu Leu Leu Asn Asn Leu Glu Ser Leu Ser Ala Asn Ala Ala Gln
305                 310                 315                 320

Ala Ser Ala Asn Leu Arg Asp Ala Ser Lys Thr Leu Asn Asp Pro Gln
                325                 330                 335

Asn Leu Val Leu Met Gln Gln Thr Leu Asp Ser Ala Arg Val Thr Phe
                340                 345                 350

Glu Asn Thr Gln Lys Ile Thr Ser Asp Leu Asp Glu Leu Thr Gly Asp
                355                 360                 365

Pro Ala Phe Arg Gln Asn Leu Leu Gln Leu Val Asn Gly Leu Ser Gly
370                 375                 380

Leu Val Ser Ser Thr Glu Gln Met Gln Gln Asp Val Lys Val Ala Ala
385                 390                 395                 400

Thr Leu Asp Ser Leu Lys Ile Ala Val Ser Lys Pro Gly Val Lys Gln
                405                 410                 415

Leu Pro Val Lys Lys Pro Phe Val Lys Gln Pro Val Ser Thr Pro
                420                 425                 430

Lys Ile Glu Leu Pro Thr Pro Asn Pro Lys Gln Gln Ala Leu Asn
                435                 440                 445

Ile Lys Pro Thr Pro Ala Ala Val Ala Ile Phe Glu Pro Asn Pro Gln
                450                 455                 460

Pro Ile Val Asn Pro Ala Ile Pro Asp Ser Ser Gln Asp Lys Leu Leu
465                 470                 475                 480
```

```
Gln Gln Leu Arg Lys Tyr Gly Glu Glu Arg Lys Val Asn Glu
            485                 490
```

<210> SEQ ID NO 122
<211> LENGTH: 465
<212> TYPE: PRT
<213> ORGANISM: Crocosphaera watsonii

<400> SEQUENCE: 122

```
Met Leu Arg Met Arg Thr Leu Gln Glu Gly Ser Val Gly Leu Phe Ala
1               5                   10                  15

Leu Phe Gly Leu Ile Ile Phe Gly Ser Ile Val Val Trp Leu Arg Gly
            20                  25                  30

Gly Ile Leu Gly Gln Gln Thr Tyr Gln Phe Phe Ala Asp Phe Glu Asn
        35                  40                  45

Val Asp Gly Leu Gln Ile Gly Ala Pro Val Arg Tyr Arg Gly Val Ala
    50                  55                  60

Val Gly Lys Ile Leu Gly Leu Gln Pro Ser Ser Asn Gly Val Thr Val
65                  70                  75                  80

Ala Val Glu Ile Ser Ser Ala Glu Leu Arg Ile Pro Lys Asp Ser Lys
                85                  90                  95

Val Arg Ile Asn Arg Ser Gly Leu Ile Gly Glu Ala Ser Val Asp Ile
            100                 105                 110

Thr Pro Ser Arg Glu Leu Asp Glu Glu Ala Leu Ala Ile Asp Pro Val
        115                 120                 125

Gly Lys Asp Cys Ala Ser Ala Glu Gln Ile Leu Cys Asn Asn Asp Glu
    130                 135                 140

Gly Ile Lys Gly Glu Arg Gly Ser Gln Leu Val Glu Ala Leu Thr Arg
145                 150                 155                 160

Leu Ser Arg Ala Tyr Ser Asp Pro Glu Phe Val Gly Asn Leu Asn Ala
                165                 170                 175

Ala Ala Arg Asn Val Ala Lys Ala Gly Asp Lys Ile Ala Thr Leu Ser
            180                 185                 190

Gln Glu Val Thr Glu Leu Ser Lys Ala Ala Arg Gly Glu Ile Gly Gly
        195                 200                 205

Val Ser Asp Leu Ile Ser Ser Ala Asp Gln Ala Ala Lys Asp Ala Ser
    210                 215                 220

Gln Leu Met Leu Asn Val Asn Thr Val Val Ala Glu Asn Arg Thr Asp
225                 230                 235                 240

Phe Asn Arg Thr Val Ser Ser Ala Ala Asn Leu Val Ser Asn Leu Asp
                245                 250                 255

Gly Leu Val Ser Glu Asn Arg Gly Asn Ile Val Asn Thr Leu Ser Ser
            260                 265                 270

Ile Glu Arg Thr Ser Asp Gln Val Arg Leu Leu Ala Met Asn Phe Asn
        275                 280                 285

Thr Thr Val Asp Arg Val Asn Glu Gly Ile Asp Glu Ile Asp Met Ala
    290                 295                 300

Gln Leu Ala Asn Asp Leu Glu Val Leu Met Ala Asn Ala Ala Gln Thr
305                 310                 315                 320

Ala Gln Asn Leu Gln Asn Leu Ser Gln Ser Leu Asn Asp Pro Glu Val
                325                 330                 335

Leu Val Thr Ile Gln Lys Thr Leu Asp Ser Ala Arg Val Thr Phe Glu
            340                 345                 350

Asn Thr Gln Lys Ile Thr Ser Asp Val Glu Glu Leu Thr Gly Asp Pro
        355                 360                 365
```

```
Thr Phe Arg Gln Asn Ile Arg Lys Leu Ile Asp Gly Leu Gly Asn Leu
    370                 375                 380

Val Ala Tyr Thr Glu Gln Leu Glu Gln Gln Val Tyr Val Gly Gln Val
385                 390                 395                 400

Ile Glu Ser Val Thr Ala Gln Val Glu Tyr Ser Leu Leu Pro Gln Gln
                405                 410                 415

His Leu Lys Ser Phe Ser Pro Glu Gln Lys Val Pro Ala Arg Leu Pro
            420                 425                 430

Lys Arg Leu Ser Pro Ile Asn Lys Pro Val Pro Thr Thr Glu Thr Lys
        435                 440                 445

Ala Ala Pro Thr Pro Val Glu Lys Asp Glu Glu Lys Gln Glu Ser Ser
    450                 455                 460

Arg
465

<210> SEQ ID NO 123
<211> LENGTH: 465
<212> TYPE: PRT
<213> ORGANISM: Cyanothece sp. PCC 8801

<400> SEQUENCE: 123

Met Leu Arg Ser Arg Thr Leu Gln Glu Gly Thr Val Gly Leu Phe Ala
1               5                   10                  15

Leu Ile Gly Leu Val Leu Phe Gly Gly Leu Val Ile Trp Leu Arg Gly
                20                  25                  30

Gly Val Leu Gly Gln Lys Pro Tyr Gln Ile Gln Ala Asn Phe Gln Asp
            35                  40                  45

Val Ser Gly Leu Gln Ile Gly Ala Pro Val Asn Phe Arg Gly Val Ala
        50                  55                  60

Val Gly Lys Ile Thr Ala Leu Gln Ala Ser Ser Asn Gly Val Thr Val
65                  70                  75                  80

Leu Ile Glu Val Ser Ser Arg Glu Leu Arg Ile Pro Ile Gly Ser Thr
                85                  90                  95

Ile Gln Ile Asn Arg Tyr Gly Leu Ile Gly Glu Ala Ser Val Asp Ile
            100                 105                 110

Thr Pro Ser Glu Lys Leu Ser Asp Gln Ala Leu Ala Val Asp Pro Thr
        115                 120                 125

Ser Glu Glu Cys Pro Asp Lys Gln Leu Ile Ile Cys Asp Asn Asp Thr
130                 135                 140

Leu Asp Gly Glu Thr Gly Ser Gln Leu Val Gln Ala Leu Thr Arg Leu
145                 150                 155                 160

Ser Asn Ala Tyr Ser Asp Pro Glu Phe Val Lys Glu Leu Lys Gly Ala
                165                 170                 175

Phe Thr Ser Val Ala Gln Ala Gly Thr Lys Ile Gly Lys Leu Ser Asp
            180                 185                 190

Glu Ala Ala Ile Phe Ser Lys Thr Ala Arg Arg Glu Ile Gln Gly Thr
        195                 200                 205

Ser Gln Thr Ile Ala Gln Ile Asn Gln Ala Ala Arg Asp Ala Ser Gln
    210                 215                 220

Leu Met Arg Asn Val Asn Thr Val Val Ser Glu Asn Arg Glu Ser Leu
225                 230                 235                 240

Asn Arg Ala Val Asn Asn Ala Ala Ser Leu Val Asn Leu Asn Gly
                245                 250                 255

Leu Val Ser Glu Asn Arg Gly Asn Val Ile Asn Thr Leu Asn Ser Leu
            260                 265                 270
```

```
Glu Arg Thr Ser Asp Glu Val Arg Met Val Ala Ile Gly Leu Gly Lys
            275                 280                 285
Thr Val Asn Lys Val Asn Ser Gly Ile Asp Glu Val Asn Ile Lys Lys
            290                 295                 300
Ile Ala Arg Asp Leu Glu Ile Leu Met Ala Asn Ala Glu Thr Ser
305                 310                 315                 320
Ala Asn Leu Arg Asp Ile Ser Gln Ser Phe Asn Asp Pro Thr Val Ile
            325                 330                 335
Leu Thr Val Gln Lys Thr Leu Asp Ser Ala Arg Ala Thr Phe Glu Asn
            340                 345                 350
Ala Gln Lys Ile Thr Ser Asp Val Glu Leu Thr Gly Asp Pro Ala
            355                 360                 365
Phe Arg Asp Asn Val Arg Lys Leu Ile Asn Gly Leu Ser Asn Leu Leu
            370                 375                 380
Ser Tyr Thr Asn Gln Leu Glu Gln Gln Ile Tyr Thr Ala Gln Leu Met
385                 390                 395                 400
Glu Ser Val Thr Glu Gln Leu Glu Tyr Gln Val Ala Val Gln Arg
            405                 410                 415
Phe Leu Glu Gln Glu Asn Ala Asn Gln Thr Thr Leu Ser Arg Asp Ser
            420                 425                 430
Ser Ile Pro Pro Gln Val Pro Val Lys Glu Thr Pro Lys Pro Val Arg
            435                 440                 445
Val Ile Ala Pro Glu Trp Val Leu Glu Ser Glu Lys Asn Asn Gln Ile
            450                 455                 460
Arg
465

<210> SEQ ID NO 124
<211> LENGTH: 458
<212> TYPE: PRT
<213> ORGANISM: Microcystis aeruginosa

<400> SEQUENCE: 124

Met Glu Ala Gly Gly Ser Gln Arg Gly Ile Ser Pro Thr Leu Arg Gln
1               5                   10                  15
Ser Gly Ile Gly Leu Met Leu Leu Ala Ser Gly Gly Ile Leu Ile Trp
            20                  25                  30
Phe Val Thr Trp Leu Ser Asn Phe Ser Phe Gly Gly Arg Ser Tyr Arg
            35                  40                  45
Ala Ser Phe Leu Phe Pro Asn Val Gly Met Met Val Gly Thr Arg
50                  55                  60
Val Gly Tyr Arg Gly Val Arg Ile Gly Gln Val Thr Ala Ile Thr Pro
65                  70                  75                  80
Glu Pro Glu Gly Val Ala Val Glu Val Glu Ile Ser Pro Ala Asp Arg
            85                  90                  95
Leu Ile Pro Ser Asn Ser Leu Ile Glu Ala Ile Gln Ser Gly Leu Val
            100                 105                 110
Gly Glu Thr Thr Ile Asp Ile Thr Pro Leu Gln Ala Leu Pro Val Gly
            115                 120                 125
Gly Val Lys Glu Pro Pro Leu Ser Pro Asn Cys Asn Gly Glu Val Ile
            130                 135                 140
Ile Cys Asn Gly Ser Arg Leu Gln Gly Gln Ser Ala Leu Asn Val Asn
145                 150                 155                 160
Thr Leu Ile Arg Ser Leu Leu Arg Ile Ser Asn Leu Val Ser Asp Pro
            165                 170                 175
```

```
Asp Met Val Ala Gly Phe Arg Ser Phe Thr Gln Arg Ala Ala Asn Ala
                180                 185                 190

Leu Gly Gly Leu Asp Arg Phe Ser Gly Glu Ala Thr Thr Ala Leu Ser
            195                 200                 205

Glu Val Arg Arg Ser Gly Thr Leu Gly Lys Val Asn Ser Gly Met Arg
    210                 215                 220

Ser Leu Glu Ser Leu Pro Gln Val Ser Gly Ser Leu Asp Arg Leu Ser
225                 230                 235                 240

Ser Asp Leu Ser Gly Val Gly Leu Ser Gln Glu Ala Thr Thr Leu
            245                 250                 255

Leu Arg Ser Leu Gln Gly Ser Gly Gly Leu Arg Asn Leu Asp Ala Thr
            260                 265                 270

Leu Val Glu Ala Arg Lys Thr Leu Leu Val Gly Glu Thr Thr Glu
            275                 280                 285

Glu Leu Arg Val Phe Leu Gly Ala Asn Gln Asn Arg Leu Ile Ala Thr
    290                 295                 300

Leu Asp Ser Ile Lys Thr Thr Ser Asp Arg Leu Gln Thr Thr Leu Ala
305                 310                 315                 320

Ala Leu Asp Pro Ile Leu Thr Gln Val Gln Lys Ser Gln Ile Ile Asp
            325                 330                 335

Asn Leu Asn Thr Ile Ser Ala Asn Ala Val Lys Leu Ser Glu Asn Leu
            340                 345                 350

Gly Asn Phe Thr Ala Tyr Leu Ser Asp Pro Ala Thr Val Val Thr Leu
            355                 360                 365

Gln Gln Leu Leu Asp Ser Ser Arg Ala Ala Phe Ala Asn Leu Gln Lys
    370                 375                 380

Ile Thr Ser Asp Val Asp Glu Ile Thr Gly Asn Pro Gln Leu Arg Gln
385                 390                 395                 400

Glu Ile Ile Arg Leu Ile Gln Gly Leu Ser Arg Leu Val Ser Ser Ser
            405                 410                 415

Glu Gln Leu Gln Gln Glu Phe Ala Gly Gln Ala Met Thr Arg Met
    420                 425                 430

Ala Ala Gln Ile Ala Thr Ile Ala Pro Asn Pro Ala Pro Asn Thr Pro
            435                 440                 445

Glu Lys Asp Pro Lys Lys Pro Glu Ser Glu
    450                 455

<210> SEQ ID NO 125
<211> LENGTH: 399
<212> TYPE: PRT
<213> ORGANISM: Acaryochloris marina

<400> SEQUENCE: 125

Met Arg Thr Arg Ala Val Arg Glu Gly Thr Val Gly Leu Leu Val Ile
1               5                   10                  15

Phe Gly Leu Gly Leu Val Thr Ser Leu Ile Phe Trp Val Arg Gly Phe
            20                  25                  30

Asn Phe Gly Gly Arg Ala Tyr Thr Leu Gln Val Glu Leu Ala Asp Ala
        35                  40                  45

Leu Gly Leu Ser Ile Gly Ser Pro Ala Lys Phe Arg Gly Val Lys Val
    50                  55                  60

Gly His Ile Thr Gln Met Arg Pro Gln Ala Asn Arg Val Val Glu
65                  70                  75                  80

Val Glu Ile Thr Ser Ser Thr Val Leu Ile Pro Arg Gln Thr Lys Val
            85                  90                  95
```

```
Glu Thr Ser Gln Ser Gly Phe Val Gly Gln Ala Ala Leu Glu Phe Arg
            100                 105                 110

Pro Thr Glu Val Glu Phe Ser Asp Ala Ser Val Glu Asp Leu Ser Pro
            115                 120                 125

Phe Glu Pro Asp Cys Asp Pro Arg Met Ile Leu Cys Gln Gly Asp Arg
130                 135                 140

Leu Glu Gly Asp Ser Gly Asn Asn Leu Glu Glu Leu Ile Arg Ala Thr
145                 150                 155                 160

Met Gln Ile Ala Thr Gln Leu Gly Gly Thr Asp Leu Lys Ala Thr Leu
                165                 170                 175

Asn Asn Leu Ser Gln Ala Ser Lys Asp Ile Ser Lys Leu Ser Lys Asp
            180                 185                 190

Thr Lys Val Ala Leu Lys Asp Val Ser Arg Ala Ala Arg Ser Val Thr
            195                 200                 205

Gln Leu Ser Leu Asp Thr Arg Lys Gln Leu Arg Gln Phe Gly Val Ala
            210                 215                 220

Ala Glu Ser Val Thr Ala Ala Ala Gln Gln Phe Asp Gln Leu Gly Gly
225                 230                 235                 240

Glu Val Asn Thr Leu Val Lys Gly Asn Lys Gly Thr Leu Val Thr Ser
                245                 250                 255

Leu Gln Asn Leu Gln Glu Thr Ser Gln Glu Leu Lys Val Val Val Thr
            260                 265                 270

Arg Leu Ser Pro Leu Leu Ser Arg Val Glu Gln Gly Lys Leu Leu Asp
            275                 280                 285

Asn Leu Glu Thr Leu Ala Ala Asn Gly Ala Gln Ala Ser Glu Thr Leu
            290                 295                 300

Lys Leu Leu Thr Thr Asp Val Asn Asn Pro Ala Thr Ala Ser Glu Leu
305                 310                 315                 320

Arg Gln Thr Leu Lys Ser Ala Arg Glu Thr Leu Asp Asn Ala Ser Gln
                325                 330                 335

Ile Thr Ser Asp Leu Lys Asp Ile Thr Gly Asn Glu Glu Val Arg Gln
            340                 345                 350

Asn Leu Ile Arg Leu Ile Asn Gly Leu Gly Lys Leu Leu Ser Ser Ser
            355                 360                 365

Gln Asp Leu Glu Gln Gln Met Gln Gly Val Gln Lys Ala Pro Leu Thr
            370                 375                 380

Ser Ala Phe Ser Gln Ser Asp Ala Pro Ser Thr Pro Ser Gln Asn
385                 390                 395

<210> SEQ ID NO 126
<211> LENGTH: 397
<212> TYPE: PRT
<213> ORGANISM: Thermosynechococcus elongatus

<400> SEQUENCE: 126

Met Met Gln Ser Arg Arg Val Gln Glu Ser Leu Val Gly Leu Val Ile
1               5                   10                  15

Leu Ala Gly Leu Ala Thr Leu Gly Val Gly Leu Leu Trp Leu Arg Gly
            20                  25                  30

Asn Leu Ala Gly Ala Asn Ser Tyr Thr Leu Glu Val Glu Leu Asp Thr
            35                  40                  45

Ala Pro Gly Leu Ala Val Gly Thr Gln Val Arg Tyr Arg Gly Val Gln
        50                  55                  60

Val Gly Arg Val Thr Ala Ile Gly Phe Asp Ala Asn Gly Val Gln Val
65                  70                  75                  80
```

```
Ser Val Arg Ile Asn Asn Val Leu Ile Pro Arg Arg Ala Val Pro Glu
                 85                  90                  95
Ile Arg Gln Ser Gly Phe Ile Gly Gln Ala Phe Leu Asp Phe Thr Pro
            100                 105                 110
Lys Glu Arg Val Pro Glu Ile Pro Glu Gly Val Thr Ala Phe Ala Pro
            115                 120                 125
Lys Cys Gln Pro Glu Leu Val Tyr Cys Asn Gly Asp Arg Val Thr Gly
            130                 135                 140
Val Arg Thr Ala Ser Leu Glu Asp Leu Val Arg Ala Ala Thr Arg Phe
145                 150                 155                 160
Thr Thr Ala Leu Glu Glu Ser Gly Leu Ile Asn Asn Ala Asn Thr Leu
                165                 170                 175
Ile Leu Gly Ala Thr Arg Ile Val Asn Arg Ala Asp Gln Ser Leu Thr
            180                 185                 190
Lys Val Thr Thr Ala Leu Asp Ser Phe Asn Ala Leu Ser Asn Gln Ala
            195                 200                 205
Arg Ala Glu Leu Arg Asn Phe Gly Ile Ala Ala Gln Ala Val Thr Arg
        210                 215                 220
Ala Ala Asn Gln Ile Ser Glu Ile Val Glu Val Asn Arg Asn Thr Ile
225                 230                 235                 240
Asn Ser Ser Leu Arg Asn Ile Asp Ser Ala Ala Arg Glu Leu Arg Thr
                245                 250                 255
Thr Leu Lys Ala Leu His Pro Leu Thr Asn Gln Leu Glu Gln Gly Glu
            260                 265                 270
Leu Leu Ala Asn Leu Asp Ala Leu Ile Lys Asn Gly Ala Glu Ala Ala
        275                 280                 285
Ala Asn Leu Asn Lys Val Ser Gly Ala Leu Ser Ser Pro Leu Ile Met
290                 295                 300
Leu Ser Ile Ala Gln Thr Leu Asp Ala Ala Arg Ala Thr Phe Ile Asn
305                 310                 315                 320
Ala Gln Lys Leu Thr Asn Asp Leu Leu Lys Leu Thr Ser Asp Pro Ser
                325                 330                 335
Phe Gln Ser Asp Leu Arg Arg Leu Ile Gln Ile Leu Arg Arg Leu Leu
            340                 345                 350
Ala Ser Ser Gln Asp Leu Glu Gln Gln Phe Leu Ala Leu His Ala Thr
        355                 360                 365
Ser Leu Gly Glu Ala His Glu Pro Met Pro Ala Ile Ser Ala Pro Thr
370                 375                 380
Ala Ala Ala Lys Pro Thr Lys Glu Glu Glu Pro Glu Pro
385                 390                 395

<210> SEQ ID NO 127
<211> LENGTH: 265
<212> TYPE: PRT
<213> ORGANISM: Pseudomonas putida

<400> SEQUENCE: 127

Met Arg Arg Lys Ser Leu Leu Glu Arg Val Arg Leu Leu Gly Arg Ser
1                 5                  10                  15
Ala Ile Asp Val Leu Ala Val Leu Gly Arg Ser Cys Leu Phe Leu Phe
            20                  25                  30
His Ala Leu Ile Gly Arg Gly Gly Ile Gly Gly Gly Phe Gln Leu Leu
        35                  40                  45
Thr Lys Gln Leu Tyr Ser Val Gly Val Leu Ser Leu Ala Ile Ile Val
    50                  55                  60
```

```
Val Ser Gly Val Phe Ile Gly Met Val Leu Ala Leu Gln Gly Phe Ser
 65                  70                  75                  80

Ile Leu Thr Lys Tyr Gly Ser Glu Gln Ala Val Gly Gln Met Val Ala
                 85                  90                  95

Leu Thr Leu Leu Arg Glu Leu Gly Pro Val Val Thr Ala Leu Leu Phe
            100                 105                 110

Ala Gly Arg Ala Gly Ser Ala Leu Thr Ala Glu Ile Gly Asn Met Lys
        115                 120                 125

Ser Thr Glu Gln Leu Ser Ser Leu Glu Met Ile Gly Val Asp Pro Leu
    130                 135                 140

Lys Tyr Ile Val Ala Pro Arg Leu Trp Ala Gly Phe Ile Ser Leu Pro
145                 150                 155                 160

Leu Leu Ala Leu Ile Phe Ser Val Val Gly Ile Trp Gly Gly Ser Trp
                165                 170                 175

Val Ala Val Asp Trp Leu Gly Val Tyr Glu Gly Ser Phe Trp Ala Asn
            180                 185                 190

Met Gln Asn Ser Val Ser Phe Thr Asp Asp Val Leu Asn Gly Leu Ile
        195                 200                 205

Lys Ser Leu Val Phe Ala Phe Val Thr Thr Trp Ile Ala Val Phe Gln
210                 215                 220

Gly Tyr Asp Cys Glu Pro Thr Ser Glu Gly Ile Ser Arg Ala Thr Thr
225                 230                 235                 240

Lys Thr Val Val Tyr Ala Ser Leu Ala Val Leu Gly Leu Asp Phe Ile
                245                 250                 255

Leu Thr Ala Leu Met Phe Gly Asp Phe
                260                 265

<210> SEQ ID NO 128
<211> LENGTH: 161
<212> TYPE: PRT
<213> ORGANISM: Pseudomonas putida

<400> SEQUENCE: 128

Met Gln Asn Arg Thr Leu Glu Ile Gly Val Gly Leu Phe Leu Leu Ala
  1               5                  10                  15

Gly Ile Leu Ala Leu Leu Leu Ala Leu Arg Val Ser Gly Leu Ser
             20                  25                  30

Ala Ser Pro Ser Ser Asp Thr Tyr Lys Val Tyr Ala Tyr Phe Asp Asn
         35                  40                  45

Ile Ala Gly Leu Thr Val Arg Ala Lys Val Thr Met Ala Gly Val Thr
 50                  55                  60

Ile Gly Lys Val Thr Ala Ile Asp Leu Asp Arg Asp Ser Tyr Thr Gly
 65                  70                  75                  80

Arg Val Thr Leu Gln Leu Asp Lys Ser Val Asp Asn Leu Pro Thr Asp
                 85                  90                  95

Ser Thr Ala Ser Ile Leu Thr Ala Gly Leu Leu Gly Glu Lys Tyr Ile
            100                 105                 110

Gly Ile Ser Val Gly Gly Glu Asp Gln Val Leu Lys Asp Gly Gly Thr
        115                 120                 125

Ile His Asp Thr Gln Ser Ala Leu Val Leu Glu Asp Leu Ile Gly Lys
    130                 135                 140

Phe Leu Leu Asn Ser Val Gly Lys Glu Pro Lys Glu Ala Gln Pro Ala
145                 150                 155                 160

Asn
```

<210> SEQ ID NO 129
<211> LENGTH: 87799
<212> TYPE: DNA
<213> ORGANISM: Arabidopsis thaliana

<400> SEQUENCE: 129

```
gatcaaaatt aaacaaaaga cttaaacttt atcattttct attcataaac tagttccttg      60
catgacttgt agaagaaaaa aaagtagata cagagaggaa gagggaagaa gaggcagagt     120
taagtacctg atggtgatat tcaagcttcc atgaaagtgt tttctcaaag gcttgaaat     180
aaaatgtttg aagagagaag agacccagag aaaaagagag atagagaaat taaaactaaa     240
cccctttgaaa agtttgcttc aaggggcttc gtcgagtcac caagtcaaga ctaatcttaa    300
cactttttg tttctcggca attattgtaa ggttttagtc tttaatttaa tacacaaaat      360
tttatttaaa gagttttcg atatcgcatt tttaacaaca ttacaatatt cagcatcacg      420
acggattcgc acacgaagag gtcgtcgtct ccttataatg actaaactac ccctcagcat    480
gttcttaac ggtggtggtg aagcaagccc ttttggtca ttcaagcttt ggctccaaat       540
tggtgactag gttgccacg tgttgacact tctagttgaa agagatacgt tcacgtggca     600
ttgtctctgt tgcctgttac tacgccacca ccaaaacaca ctttaagttt tttgttttg     660
tttcttcttc tttttggatt aagaaattct aattgtttgt tttaagaacc tgaacactgt     720
tcaacagttt tatagttata gttcttagga ttttgttaa ataggaaagt gtggaaaaga     780
aataaaaaga ctttggccaa aaacaatgaa agtgatagaa gaataagact tttctatcac    840
catcatgatc atgatcatgg atttagttc ccatcaacaa gacaacattg gattctttca     900
tatgtgctaa atccaaacga caacaatgaa aatggtccct taatagtgaa tctatgacca    960
aaccaagtgt gttcttggaa ttggactctt attgccaaga gaatgaatga aagcaaatgg   1020
aacaacacac acaatttctt ctttgatttg tctgcaaaag aaaaatcccc aaaccggatc   1080
ttaaagatcg tataaaaagg gaacagttga tgctacagta tttgaaatca ttgtgtgttc   1140
atcactttat tatatcaaca agggaaaaga attggagatg ggtgtctttg aagcttccca   1200
gctgaaaagt tgagcttttt catcttttct tcacaccata gaagttgctc tttactgatt   1260
ttcgacatcc tcaaaacccg tgttgcgagt ttgatgtcaa tggctgcaaa caagagttga   1320
acaccttccc atgtttgagg ccatgatttc tttctcagcc ctttttgtctt ctttgaaagc   1380
tcctttgctt tcacccttt ctgcaaaagt tcctctctta tgagacacca aagaagcata    1440
cgatagtaat aacatttgag tacagagaaa tcgtacctta tcaatggatg actgaaccag   1500
tagtaaagga gttgtagaat tcacatggtt gttgttgtgg ttcccaaaca agtgaatacc   1560
cccatttggt ttcttcttat ccattttcaa gaagacgttg aaagtaagga tcgagctctc   1620
tatgactttg atgagatcat cagcgaggac catgaagcct gtatctttct ccatctcctt   1680
tttatctgac cctgatatgt tttgaacata accaacttca agtgttacta ctacacataa   1740
ggttttaagt cgcgcaatgt atgagagctg agaaatcacc ttgaatctta ggagcttgaa   1800
gtagcttagg cattgcattt ctagcacgag cataaagttc cgatcttgag ccttgctcaa   1860
acggttcatt ctctatatac ctctgcaaca agactaggaa ttgctgaaac agttgggcag   1920
tatggttgta gcaagtcggg gtttcgggtt ggcatgagat taagtggctc agctgcgtgt   1980
attgacagtg aagtgcctcc caagtgaggc agagttgagc aacataggcc gtctctagat   2040
cttgataagg gtcgtcaact tctgtcggct gcaaatgctc gatatcttcc tccggaacat   2100
caaactttt gagagaaaga catcggaaag gcgatgacag cttcttagat gcagatcttg   2160
```

```
gcgatggagt tgaaggactt ggagcaattc caatgcctaa gagattgaaa agtaaccaac    2220
aaatccatga tcagtccaat ctatcacaat gaaaaacagt tcaaagcaag aagcttttac    2280
cagtttcctt gagctgctga gagcttaaac gatcaaagaa gagcatacgc tcgcaatact    2340
tttcatagac agcatcaaaa cctccccacc attgaagtcc ttcagcaacc acatctctcc    2400
actcacttga acacttgtct tctccgtcat catcatcttc atctagatac gattcctctt    2460
cttcttcttc ttcttcctca ggtatcaaca ccatgaaact gtttctcctc aactccttga    2520
gccttctctt aacctcattg gtaatgaaat catcatcgtc atcttcgatc tcatctcctt    2580
tccccgaatc tatcacacca gcttcagtgt tctcactcct tgcctgttct tgctgagcca    2640
atatcttgtc ttctttctcc ttttcaaggt ttggcttccg agactttcga aattttctaa    2700
ctttcaagaa atccattgcc tcctcaaaca cacttaggag agtgagtgtt ttttgttaaa    2760
tcataagatc taaactgaga ctagtctctt tgcatgagta aaagcgtttc tcttctgcca    2820
caacgaactt aatcaaagaa tcaaccaaac cagagaatga ggaaaatgca tgaatctagt    2880
aagatctcag agaatcatga gcaaacccta gagaattagg aacaccgaca gaagattaag    2940
aatgcataag tagatcagta gcaacaacag catttgtctg aaactttaga ttcgattcac    3000
taatctctag ctgataagaa cactagcatt ccctgataaa tcaacactcc actgaaacta    3060
ctactacact gagcaaagag tgtgagaaaa aaacaaaaa gaaagaaaaa gattcaaaat    3120
ttaagaaaga aagagaaacc caaataaaag caaaacaaaa tcgaaagaca aagacaggag    3180
gaggaggaga ttaaagaagg agaaatgttt ctaaccactt gcaagagaga gagagagaaa    3240
gcaaagtata ataatgtctc aattcaagtt ttttcagtaa atggacagag agagcacaat    3300
ataaatgtga gagaggaaag gagagcaagt attattgatt cttaaacaga tgtcattaaa    3360
ttcaataatt aaactttgtg atttcaaatt ccaaaaaaaa actagaaatt ttcttccttt    3420
cttaaaaccc tttcctcaaa aatttccatt tgcagtcaaa accctcacaa agaggtttct    3480
gagtcaattt gacttttgt ttatttccta atgggtcgaa attgtctttt actgtttggt    3540
ttcttacttt acttttctg atacttcatt ttctattggt taattttgg tttttgtttg    3600 gtgtttgatt agagaaggag agagatgtat gaatgaatga aaaggagaag aagcagtaac    3660
aagtaacaac tggtaggtag gtcagtgggg ggagagatag aaagaaaagc atcgtacaga    3720
gaatattgtc agaaaagccg cgctatctgt tctccttcca tttgctcact tctctctttt    3780
aaaattacat ctttacccctc ctccgtctca tacatctacg ggtcttatct ttgtttctga    3840
tgacaatttg ggcttctctt aaaatgggct tttctttac caaatttatg tatactgcta    3900
tgaaacgacg tcgtctttta ctttggttat attggtatgg ttttgaatt tactttggtt    3960 acgattccgg tctagtggat tggatgaaac cgaattggag agcttgaggt tatgatccat    4020
ggcttcattt ggcatgtctc tcacaccagt tcttcttctc agggattact tactacctct    4080
tgtaagttct cattcgattc tattttgct tgaattctgt ttcagctgat gaaacgcttg    4140
ttatcatctt agccgtttcg ttttctactc tttctagtta taaaattttg acttcttcaa    4200
gagaattttt tttgggttcc aatcaatcag attgctatga tcctctgaat agaatttcct    4260
tgttgatata gggacttgtg ttgttgagtt tgagcctata gtgatcaaat gggattctca    4320
tatgaatttt actcaaattt tgttactttt ttaatcttat aactgtagac aaaagcttat    4380 cctttattg gttacaaatc gtatgaacat ttgattctat gcttttgct ttgccattaa    4440 gcaattgatt ttttttagtt tgcttgtttc cggattatgg gaatgaagct tcactgggat    4500
taagaatctg taagtaatat gttttgttt aataagcttt aggcttatag atatgttttt    4560
```

```
ttaaagttct aagttagtgt tgtgtttgtt actcttaaac atacttaaaa agctactaaa    4620
tgagtgctat tcaataatgt tctgtttgat ttcgatggaa taatttagtg tgactgatgt    4680
tgcttttatg tcgcttatgt attattggtg atctatgtgt aaaacatgtg ttgcaggata    4740
gtaatgaacc gaagtaaaga agagaacgtt gctccgacaa tgaaagatga tagtccattt    4800
ggaaagctta cagaggatct cttgatagag atatttatca gaattccaat aacaaattgg    4860
gaacaagtat cgtgtgttag aaagcagtgg gctaatttat tccgcggaga atgcttatgg    4920
ctggctgctc ttaatcgggc gtatccactt gctagcaaaa ctaagagctg gattggacca    4980
attcgtcaag gattaagcaa acggtgactg gaaacacact tgatttctat gaaaaaagct    5040
agcttaataa tgtcttagtt agattcaagg aacttaacag ccttttagct gcaggagata    5100
tgtggcttta tacatcagca gaaacatatt aggtgtggat gatacagaca tagatgagat    5160
gcttggacat atttacgtgt tcttgaatga tcagcttcaa cttccacta tgcctgcttc     5220
aggcattttg catggaaccc ttatcggtaa gctagtttgg tatatgcatt tgactctgct    5280
taatgaatca ttgctaatga cggcattcat cttatattct ggtggcagac caattgattg    5340
tttgtggcca atcgaaagaa gaagctggtg agcttgcaac aaagatttgg ctggctcttc    5400
ttgacaattt agaggacaca aaacatacat ttaccgtgct gaaatcaatc gcacaagaat    5460
atgatgtaag aaaggataac agtgtccata aagttttcaa attctttct agtagaaact     5520
aactatctaa gagatgcagg gctttcttcc atatccatat tcaagaccaa tcaaagtgca    5580
gtggaaggtg ttcgagaaac tgtttgtaga tttccgtgac ttgcttgatc attcagagta    5640
ctgcgactta ataggaattg ccaaaaataa gtttcaaacc ataccttatg tttggttagg    5700
ctactaaact tagcctgctt cttccagttt ccacagccct gtaaagtaat ttgaggtcca    5760
attctacaac atacttgtac ataagacatt caaagtctgc atcttgtaag aaagaaagac    5820
gtgtaaaatg cagattcttg gccatgtata attcgtggtt cgttttaaag caaaagtcaa    5880
acattttgtt gactatttta acttcttcgt tacttgctaa gttcagttat ccatccactt    5940
tattcttctt cttggaaatg gctctcatga aagtaatgac gattctggtt ctcttcgtct    6000
cggtgtcatc gaccttggcg caatccaaca atggcggtca catttcgata atcgtctcgg    6060
aaacaggtct tgaatttgct aaagattacc tcatcaagaa agtgatcact acgacgcttc    6120
cacttcagct accagacatt gagaataagg ttaagatccc tctaatcggg aaagttcgaa    6180
tgggtctatc gaatattcag attgatgcag ttcatgtcca gtcttcgaag atggagactc    6240
gaaaagatgg aatcattttg agtgttttag gtgctacagc aaatttgagt atggactggt    6300
cttatactta cagagcttcc ttctttgaga tttctgatca tggagatgct tctgttgagg    6360
taaaactctg aaattatcga aaccaaatt gggtcttttt agttttgttg tttgtgttca     6420
gaacattgtt tcatcatcag aagaaaaagc ttaacaggtg aatgattatg acgatgaagg    6480
ttaaaggaat gaatgtgaga atcactgcca ctttggttaa tgataatgga agtctaaaga    6540
ttgcctcacg ggaaaatgat tgtacagtaa agaacattga tattcatatc aatggtggtg    6600
cttcttggct atatcaaggg tattattaaa tgttccataa gttttcgtat ctctaaaatc    6660
tcttattcca agattataat atttgttttc cttttttgcag ggtggttgat gcatttcaaa   6720
aaatgattat atctactgtt gaaaaaactg tctctactaa aattgtagaa aaaatgaaga    6780
agcttgattc tttcttgcaa tcacttccaa aacagagaaa gattgatgac tctgctgcag    6840
tgaatctcac ttttacaggc aaccctgtct tagggaattc gtcggttgaa gttgacatca    6900
atggtttatt catgccaaag ggtgatgata ttaaagttgc agggtctcgt tcttcttcct    6960
```

-continued

```
tctttggtgg ggttaataag agaatggtga caatttcagt agaagaagga gttttcaact    7020
ctgcaacact tgtctacttc aacgtaagtt ctcaaatctt gattagagta tggtggaaca    7080
aaacaatttg taagcttatt ggattggttt tgattcaggc taaggtgatg catttagtta    7140
tggaggaaac aaagaacggg tccattctaa gcacatctga ctggaaactc atccttccag    7200
agctgtacaa acattatcca gataataaaa tggtgcttaa catgtcagta acatctcctc    7260
ctgctgttaa aatcacagag aatggaattg atgcgacgat tcagctagat atagcgttcg    7320
atgttcaaga ctctggagaa aatctatctg tagcacgcct atcaacagta agactaatag    7380
taatccacca aacaatctaa cttaagaagc atcttttgat cactaaagtt agaatcttgt    7440
tcttgtttgc agattctgag tgttgcgtgt tctacagaaa tcgtaaagaa taatctaatc    7500
ggtagcctca gattaaatga tttcaatgca acaatgaagt ggagtaaaat tggagagttt    7560
caaacaaact atgttcaggt aagtcaagtt aattatcttg agtttaagat ttatcttgat    7620
tagcatcaaa ctggtggata tgtgttcttg ttgttaggct gctacgtcta ggattcttga    7680
agccttgttt ttgccgtacg taaacacacg tctcaagaga ggattccctt tgccgattcc    7740
cggcgatttc acgatcaaaa acataaagat tgtttatgtt aatagtggca ttttggtatg    7800
taccgatatc ggcactagca caaaccagta agcaagtatt atatagcttc ttagattgca    7860
tgtacgtaag cctgaagaaa tataatgaca accataattg tgatttgaac cgtttggaac    7920
ttcccctcta agaagcgttt tgacgagatc tctttatttc tttggctact tgcattatat    7980
ctggaacttc cccccctaag accaatgcat ctttctgaga ggttaaggaa aacttccatt    8040
aggcaattgc aagacacggc ccaatgattt atattacagg cctgttaaat atgggcccaa    8100
cttcgtaaac aatcaaaata ttattcatat gtacgcaaaa caacaataga aaaggataaa    8160
attgttattc tattatatct ctctaggaca aaaaaaagta aagtcaaaag atcctctctc    8220
atcgatctct ctctaacatc tccgtcttct gcttcgtgta atttgggtat tgttggctcc    8280
ctactctgat tcctcaaatt ccttattttt attaacccgc gaaaataaat tataaagagg    8340
gctttcaaaa ttttgaacct ttctctaaca atggagatct ccctccttcc cttttttcttc    8400 tttcgcgttt aaggtttctc ctcgtctctt ctcttttcaa tggatatagc gaccagtaat    8460
gctccaatga atcttgaatc cgtcgcaatg gttgatggca acggagcaga accggtgtct    8520
ccgcctgcga aaaagccacg ttttgacgag gagatgaata gagtggcgga gattgttctg    8580
gttctatcgg cgttagggag gatgcgtggt ggggaaactc cgacggcgtt ggaactcgag    8640
ctgatgtttg aagctaggtc caaattagct gggatgtgtc tggaatttga ccctaaggat    8700
attattcgta aggatgatgt taaatctgtg attgaggatt tgggtttcaa tggtaagctt    8760
aaagaccaga gattaggttt tcgagctcct acggtgacta tctctgagaa gctttctctt    8820
ggtaaacgaa aggtaatgcc ttttgtttct cagatcacaa ttgtgttttc tctttgatat    8880
tgctcacttc aattgggtat agttttgtca gcattttgag agatgcaatt ttctctgtgg    8940
cgttttcatc attgttttga ttttgtccag atggaagaag cagaaaagta tcctaccact    9000
tcgacagtat ccactggata tacattgtca cagccaaacg gtagtcttgc atctcctggt    9060
ggtcttggta aggctacaca ttttgacaaa ccatcaaagc tttatcttca ggcttcctga    9120
cagtttcttc accccttttgt ttctgcagcg aataaagctt ctgtggctca tcagtggcct    9180
agtagtgaag ttgctactgc taacactagt ggaagccatt tcaaattgga cagacctcag    9240
atggtactta acggtgcttc tcaagggact cgtaagtcct catatccccc tttgttttgt    9300
atagatgcag ttgtagtgat aagattcttt tagtctttga tttggaaatt acaacacttt    9360
```

```
tagtatgggt agggtattct ggttggtttg ctgttttgct ttatacgata ggacttgtaa    9420
atttagtga aggtaatcat aacagccaaa tacagataat tggctaatca ctaggcttgt    9480
agctgagtaa ctagccctca tgcttagaat aagtatacct tttgtgaata ctatcgtttt    9540
cttttgcaaa tcttactggt catggtagcc tttcttttg gttaggtttc tatcctgagt    9600
tgctaaattt atatgttatg tttctagttc tttaatagct ttttcatagt tgattttgag    9660
tttgtttcat atattacttg tttcagcagt tcttccgcg aattattatg ctgaaccctg     9720
gtctgcccaa cttccatcca ccatatcttt cagtactgca ccagataaga aggttccaat    9780
tcaaagttct gtcaggacag cagatccaag ctttaggcca ttcaggcacg gtacattcac   9840
tggcacaaat cagccaatgc attacagtca aacttcttcg ttcggaggca accatactga   9900
aattgctaag ataatccata aatttctgca accacgggtt aaacaatatc ctttgtggaa   9960
tccaccttca agagagtata tgagcagggc aatggcatgc cagatatgtg aagttaccat  10020
caatgaaatg gacactctac tgatttgtga tgcctgtgaa aaagcatacc acttgaaatg  10080
tctgcaagga acaatatga aaggggttcc aaaatctgaa tggcattgct caagatgtgt    10140
gcaagcattc aatgggaagc catttcctcc tacatatggg cgtgcgactc gtgccgtagc   10200
gacgactaca gcaaaaatgc cttttagggc agccggagtt ctatcatcct cagcaaagaa   10260
gattggaccg atggatataa aggctaatca acaaaaacca attgtatcta cgttttcaag   10320
attgcaaaat actggcttgg tttctggagc agcaactaca tctcagtttg agtctgctag   10380
tgtaaatgca aagacaactg caagcgcagc aaagactact aacattggat cacagggctc   10440
taaggaaaat gttgcctgtg gtgctaattc tccagcaccg gtatcgctta ccgagactcc   10500
aaatcgtaca ggaatcgcaa gtacaatttc tgtgataaac aatggcctca tttcaaaacc   10560
tttaacacca gttggtacta tgagcagcac ttctccattg cctgttgtta accaacttcc   10620
cgtgaatgca acctcaaacg caagtccgag tacaccaata actgctagcc ttgtagcaca   10680
agccccgaca gttacccaaa atggagatgg cagctcaacg gcctctggga ctgctgacca   10740
ttctatattg aatgctgaca ttaccactca agttcataca ttgactgtta cttccagtag   10800
taattctcaa caggcagtgt cacattctga ggttgcaaaa gcaactgaag atgcagctcc   10860
tttggaaaat gtttccgagt gtgagaaacc atcagaatct acatctcacc cagactctct   10920
gaatgataaa acaatatcag agaacgttca agaatcaagt aaggatgcta aagttgattc   10980
tgaagcttgc cagaaccacc caacagcatc cccagccact gttgtaccag atcaagactc   11040
gacgatcact gctgcaccat ccgtgacaca agaggattca gctttcaata cagagaaaac   11100
accacctcag ccactttcgg tgtcatctaa ctatgattca caaaccgaga aggaaacacc   11160
aaatgtccaa gattctgtac ataatgttcc gggagattca gagaagggta aagggttaaa   11220
tggtttagat gatagacatc aggaacagcc ttctgagccg gagttctata agtcagattc   11280
ggtaaaggaa gaaaatgctg cctaaaattt ttgagtaatc acctgggatt acttcaccag   11340
caattatcgt cttctctccc ctttggctct caaaggttta tatatctcag ttgttaacag   11400
aaaccaggaa tattcaaaac attgaagctg tggatgaact tgtcaaagca attagaataa   11460
tgtgagttga cacgctgacg gtttgatata acatggtttt aaggcatctt tgatctaact   11520
ctgtgatagc cgaagggaac tgtaatagaa tcttgattca ggttttgcaa cttatgaaat   11580
ataatgattt ttctcattga gtttaaactg ttttggatcc tacaaaatga ttcaatgaaa   11640
cgattgaaat gttacatagc acttgaatca ttttgttcct tttccttata acaaatccta   11700
tagatcggag attaattcaa gggttatacc caacaccata aaccaaacaa gcaaagaaat   11760
```

```
attaatttga tgcttacaat tatagaaaca gattattata tcgaaaagtt atcatgttag   11820
acttgatatt aacagtaata cttttggttt gtgatataag ccaattatca agtcagcact   11880
ctttatgttt gtctctattg tctacaaggc ttgtaagata caaatatgca ttaacgctca   11940
caagtcacaa gggctaggcc aaaagtgaat gtatagtttt ggattataca gcaaccgcag   12000
aagataagag ggatagaaat attaatcata agggttttg aaattttca agagctctgg    12060
gatgtcatac cccaacatat catcaacagt ctgcaacatt tcggctttta gcttctcaaa   12120
cttgtcgatg ttgtaaccac ttagcacctc cctgaaatga tccacatttg ggaaatctcc   12180
tttaggtaag tgatgctctc tttgtacctg ttttcatgtc ccccacaaca ttgaaacaca   12240
tattagcatg aaatatgatc ggaatcagaa ccggcgtatt gaaaagatcc gcagaatcaa   12300
accaattacc aaccttcca aactcgtctt ccaagttatc tatcagtttc tgttgagctt    12360
tggctttccc cattatcgct ggcatctcct tcttcaaatg gctgatgatg tacgcatgta   12420
tctttgctgc tcttgcccgt ttcacaaact catttatcta ttagacagaa aacaaatatg   12480
gttaaatcca atgagaggag ggagtgaaag aagaaatgtg cacactcact cgacgatcac   12540
aagctttctt aggaatgtct ttcaaatcag caagaaggtc atcttgctcc ttttcaaaca   12600
actctctccc aattggacca gttgcagctt cgtttatggg tttatcactg aaggaactgt   12660
tcaaagcaag taacaagga catcaaaaca tacattttag tttcaaaccg cttttatata    12720
agcaaaacac tgtcactagt tgaagaaaca ggtatgttta cccaatgtag acacgagaga   12780
cctcaggagt attgagaact ttcccaagtg accacatgag agctccatat accctcatta   12840
gctatacaag ataaggagaa agacggtgta aaatgtata agaacatgta aaacaatgaa    12900
agaagtgtga aagaaggaac gaaataagaa tcgataaccg atcagggcgt caatggtcaa   12960
cctgctgagt gtccacttgg tcagcettat tcagaacaac gcggatcttg tcatcatgac   13020
cgcgtaaaga tgaaattaca cgcttgaact catcacttac atccagcttg tgtgggtcaa   13080
ataggaggag gataagatca cacttagagg caaaccatga tgtaacacca gtgaaatcat   13140
atgctcgctg tgttctttgt tttccctg ataaactcc aggggtgtcg acaaatgtta     13200
catgctccag cagcttaaac aaagatgaat ggatcaacaa ttatcagcaa atcaatacag   13260
gcaaaagtaa tgaacgatct cctgtcagaa gcatgaggtt gttaaacata cagggtgagg   13320
catctgagag cattcaaact ttgacaaaaa ggcagtccca aaagttgtaa gaccactgaa    13380
tggcatatct gcttgaactg ctactgtgtt cccggaatg cttctttcat caggtccaga    13440
ctgtgaaaca cattgaacat atagaagtca ccttcaagag aggtgcaaat gaagtaatct   13500
agctaccatt gtcaactaaa taattgacac ttaaatatg tattccatta tccaacaaaa    13560
caagcaaatg aatagcagta catgatggat caacgtttg aaggactaat gcattctcac    13620
aaaaatgaaa ccttagaaaa ttacaaacta acataccatg acaacaacaa atctgtcagt   13680
agtcggctct ggtccaatat gagctcctga aaaaatatga caattgaagt tatataaagc   13740
tgttttacgg ttaatcattg acctgttccc atactttta aatatcgaa actagttagg     13800
tcacagaagg agaagaagat aggataagat ggataacttg cctggataag tagatttaag   13860
caaatgctta atgaatgttg tttttcctgt ggagtattga cccagaagca ttaccatagg   13920
ttttgcatcg aaatcactgt tagtctaaga aaaaaacaa gtaactagtt caatggtcaa    13980
atatagttta gaattcaata gtatttggaa cttaaataac gccataggag caccaataag   14040
caatgcccaa ctcaccaaca aaggggatac aaaatcgtta aaccgatatg ctacttcaag   14100
tggcttcagc ttctgaatgt acaacctctt caggccatcc actatagatg ttacggagga   14160
```

```
cagagaaatc tgagaacaag agtcttagtt ttcagaaacg atagatgtaa actagctata   14220
tcttagcagc tgagaaaatc ttgacagaaa caatgccaat gaactttgtg gatacataat   14280
agagatattg gtaagaacga ccaaaaagga atctttactt aaaatgacaa tatatggttg   14340
gtggttaaat agactgcttg aggcaaaaca aaccttttt gaagattttg aagagaacca    14400
gtgagctgta agtgaggtgt ctgcggcagg gctacctgaa taattgaatc aaatgagata   14460
tataattaaa aaggtaaacc attggctcta gagtatgaag agattctttg taccattcat   14520
attaggatca ctcgactttg atgaatgctt cttttctgt gataaatgaa cagttgtaag    14580
taatatttct ttgaactcga aagatataaa tcaaaattac aggcccaata ctaaccgcca   14640
ttaatacacc cagaccttcc atggtaggag gattgatatt tttgaaatca actgcagtca   14700
gccataaatg ttgcagaaag aagaacaata cattaacagg tattatttat acagtgggca   14760
tattaagatg aagacagccc ttaagcaaaa gatggaagac taaaagaaca cggattcaag   14820
atttattcac cataccatcg ctaataagaa cttcatgcga tatttcatgt ccagtttgag   14880
ccaacgaaac aagctataat gttggaaaat aacaacacat tagattcaca gcgagacatg   14940
gacatataaa tgtgagatat aaactggatc taaacctgca tggcaacaat aaactctttg   15000
aaaccaagat acccttgtct cttgaatct gcaatagccc agatctatca acaaaccaga    15060
agagaaacag cataagcttc tcacagttag cacctcttag acaacttaaa tgaatcaaca   15120
aaaggcttca aatgctttgc caagtgagca attaagcatg atcgcaaggg cttgttattt   15180
gtaactccat taaacctaga actcaaaacc attcaagcat tcacctatgt gtttcctctt   15240
aactcattaa tacaactcca tccccaaatg aacttggtca atcattataa tggccattaa   15300
taaaggttcc acaagtaagc aacgtaataa atttcaacac aaaatcctta cctgcttcaa   15360
ttccggacga ggcaaattcg acatagtgaa gaacttgatc gcatcgttac cagtaatacg   15420
gccatcgccg tctgctcatt tacaccaaac agagaataag cttttagcgc atatagtgaa   15480
gacgagaatc gaagactgaa gaacacaaga caacaaaatg aacatgaaac gagacctgaa   15540
tcggagaatt cgaaccattc cttgtagatc atttgattct ccttggaaca agaaccagct   15600
gcgacggatt cgatctccat ctccgattgc aaaaatctag agatgtaccg attaacaaac   15660
ttctcaggtg tgaatccaga tttgtggatt cgcagatatt gaacttatac ggagaagaac   15720
aaaaggtaag ctaaacaaca acaattacaa aaaaaaaaa aaaaaaaaaa aaagttggtt   15780
gatgtatacg tgagattacg gtttcagaga aagcgggttc ttcgtctcga cggcaaggga   15840
gaggaaaaag aattaccaat gcaagaaatt gccctttatt ttcaaaatct tacacatatg   15900
ccccagaact gttgagttgt tgaagtaacc cctattaaaa atctatgtga tagattttgc   15960
tgcgtcgtct caattattgg tagaagattt tgatagctac ttgtcaagga gcattaaaga   16020
ggtttgaata acagattggt ttcttggata agtgatgaac ttatttttg tgaaatttgg    16080 taaatgtact tttatgtctc aacatggtaa aaaaattttt tgtcaacaag gtaaaagact   16140
ttagatttta ataactttag atttaataa tttgattgat agattctaca ttaaaatgaa    16200
atctgttgac aaaaaaaggt tagactaatt aagtaaggct atggacaaaa aagggaaaaa   16260
aaaacagatg aatggcaaaa agcaaattat aactagtatg gacgattgtt tttagtaata   16320 tgttttttt tttttgtat cttgactggg atgtcctagg aatagcggta agtgtaacgg     16380
aaaaacattc atcccttata ttggactttg gaaccatat ttaaatagaa tagcttttgc    16440
aagtttgaac tgtcggctgc caaaagttac aaaccagagt tatcatgaat ttctgttggg   16500
gaaaattcaa ctataacaac tgcaaaatca caacacaaag atggaacaag agtggaaatc   16560
```

```
tcaaagacag taggagattt tacaaggcca atctaattta ctgtaagatc atttgttgaa   16620
cacatgaatt ctattacaaa tcgacatgtt aaagaaaaaa taagatgatt tacagtgata   16680
aaaaaacgag aaaacgttat tttacataga gcctctgtgt atacatacat gcatatacca   16740
acatcatcca acaagggagc caaaactttg agaactttaa tgatccaaag aatgattcaa   16800
gaaattccaa tggtcttacc aagtaaccag agaacaagcg acatttcgat accgaagatt   16860
gtatggagag tgcttctatc aagtgtaaac ccaaacaccg tgattcctga tctattgttc   16920
tcaaagtaat tcactacaaa acaaaaaatg tgaagatgaa taaacataac taaagatgtg   16980
aaggtatgag atttagtgtg gatgcagagg aatatatttt acatacctag agcttgccgt   17040
ttttggaatg atatggtgct ataagcataa gcaggaatga gattgttgtt atcgaaatca   17100
tcttcttcgt ctccataatc ttcactatct gattctccat tatcatcatc tgttggatag   17160
tatccgtgtc cgcttgctct atcaactaac cttggagtct ctccatccac agtctcaaag   17220
gattctatcg tcgcacatac atgccacttg gctgcaagac aagtcaccgc ctgagccttg   17280
tgtgtgatct ttgatgcact tcgtagtaaa atgagcagtg cagtgaccag cgtcattgaa   17340
catagctgag ataatcacaa gaaaaaacaa agactaagca aaatatttca tcaagaacca   17400
atagtatgta gaaacagaac ttactgctag ttctccagct ctgtagatat tcaattcagc   17460
gtaggcctta gtggtaataa gcagagagta aaactgactt ccagtgacta atatcaagga   17520
caacaatata aaggttcggt atcggtggct gatgattctc agatgacgtc tgatacggag   17580
atgttcagac aagatagaac caacatctga atccatctgg aaaacctggg caaagtcttg   17640
cagcctaaga atctggagat ggcagatgag acggaagagg acacaaacca gaaagatcac   17700
ggtagtacgg tacaaccacg agcagagctc catcaaacaa gcaactgtat cactcaagat   17760
aacattacca aggaaaggaa tctgagaagc tcctgaagca taccaccata tcttataaga   17820
gctcatcgct aagaaacaag gagacacgaa gtaggagaga atcttaagcg atctctgcat   17880
aacaaaaagt tgtgatttca aatcattgtt atgcttgtgt agcaagtaag aagacgattg   17940
tcaagattat aagtacttca tcgttaacac caccacctaa tatttatgta aaccctaaga   18000 ttttcttgc ttctggattg agattcaatg gtgggctttt aagttcttaa gtttcatatt   18060
gttaatttga tctactcata atgcgacaag atctggaatg atccaaaatt cgacagaac    18120 acgacagatt caaatactgt attgtcggaa aaagccaaag tcatttcaat caaaggccct   18180
caaaatcccc aaaatctaag gattccaccg aaaaatcgag aacccaaaat tcatattgga   18240
aacgacaaac gaagcaagag taaaccaaat taagaatgcg aaattcgaaa cggaattagg   18300
aaaagaaaaa caaaaactca cattgagctg attggtgtag cctagacgaa cggtctcgct   18360
ctcatcccaa agcttatcaa agaataggaa ccgtcggaga ccatacttgc taacgaatct   18420
ggagagacaa agaaacgaaa gagcagcgaa actgctaaga gaaagctgaa caacggaatc   18480
gtacggccta gagtgatggc tatcgcagtc agagcaagcg agcatgaagt gagacgtggc   18540
aggaacaacg agcgtgaaaa caacgaacat agaccatgat agaaccgccg tccaaggact   18600
cgactgatct acgcacatcc atcggagata tttccggaaa ctgtggagct cgtcttgtgc   18660
gtgagatacg ctacgtgtga acttgttttc tcggtttatt agacgttctc gtgtgcctcc   18720
tcttccttcg tttcctcctg ttgttgctgc ggttccgatg tcgatgtccg ccatggacga   18780
tcgctcggga aaatgagaaa ttaccggaga ggctctggct ttttttttt ttgttgtcta    18840 aatataaatt gatgacgcgg ttggaagaag gagaagacag aatcaggaat ggctaaaatt   18900
gtcttatggt tatttataaa ggatcgatgt ttaggtggat ttgacaaccg tatttaaatt   18960
```

```
gtaatttagt atcgtaaaac aaattactac aatatttcgt attaagatgt acatgttttg   19020
tatcttattg gctctgtttt attcgaatat ttacattttc aataatacta gtgacttggg   19080 gttttttctgc tctatgattc atgaggggat atttgaacaa acagtttaga atttggggat   19140
taagtagaga cgaaattgtg cacttccatt gtaagaaaga ttttttctga ttcacgataa   19200
aaacgaaaaa ggaaagtaga ttttgtgttc atgcgacaac catgatttca caatcacggg   19260
gtctatctac ttgctaataa agtattatca tcattagatc atagattttt atttctgttt   19320
ataaccttta gtactgtaac atgtaaatta gtgtatctcg gatgaatttt ttttttttagt   19380 ttgaaattca tggaatttat ctattaaaaa ggttttacta agtatattac agattaaata   19440
cactaaatac taattattct tttctttaaa aaaacaaaat ttgcatattg atatatttcc   19500
atatttcggc ggaaataggt ttacgtggca gtgacaaaat attatactgt aaacactgaa   19560
agaggcaaaa ataaaaacaa atgaaaagat gctggtgaag tgaacacagg ctgtagaatg   19620
ggtcccacgt tgacatgtga tgtgtaaaat ttaggccgta gattacgcat atctccgtac   19680
ttacggcgcc acgtatgttg ctaatataat tataagtacc attattttga ttttgatgtc   19740
ttcttataaa aaaacaaaaa cataagatat tatttagatc agctaaacta gtaaaggatt   19800
acttagaatt ttaaataccc ggcggcatgt cttgagttta ttggaaggat gagtatataa   19860
agtttaaagg ttttgaagat taatcgaatt atcaaaatga ggaatatcat atactttata   19920
gtataaagta tattaattgt caattattcg aatgaatcat gggtttggtt ttattacttg   19980
tgatcttatg agtggctgtc tatgcattcg ttttatatg ccctcatgac tttgagaata   20040
tttcattatt ccaattacta tacgataaat gttgttacat ctcttaatca aatgttgagt   20100
cgtttgatta ttttttttatt ttattttatt ttttgtttgt ttgtttgttg aagaatcgaa   20160
accgcagacc aaaaatattt tctgttgttt gctgtattta aatttacacg caactatact   20220
tttgatttaa accttctttc ttgtgattta atactccttc ttttagttttt ttgaagattt   20280 tcaatctcta tgttatacaa atacgtgaaa aatatgcatt ttacccttag aaagttagaa   20340
gtagaaacga acatctcaca atgcttgatt ttctttgcta aagagtatag accacataag   20400
ataaagaaaa aaaatatca tttaaagagc aacattatgt ttaatcgtgt aaaagtttc    20460 atagtaaaat ggtattcagg attcatcata gttgatagta gtaattggtt tgcaacattt   20520
gattgatttt gcttatttct aatgtatgta gcctttgaat ttagtagtag tacataaaaa   20580
gtgattcacg tctttacacg tttaagtatc agcaacgtgt attcacccag tttgaaattc   20640
aagattttga tcattctttta ttagccccca catatataaa gagtttcaag aactatagaa   20700
ccacagcttt cctgatttgg tcaaacctgg aaatatattc tttcgttatc tttctttttc    20760 ttaactttt atttaaatcc catatgtaaa atgtaaatta gattgctata attaacttga   20820
tggatcagaa attttgaaaa gctgtgataa ataatagag aatgtataat gagataacaa   20880
atcaaaaact ttaacgatta catttcaaat aatctctaaa aataaacaat atagtaaatt   20940
ttagaataaa ttcactcggc gtacgtgtct ccaaatctca aaacgtttat agacacacaa   21000
gattcataac ttatactcta taagaaaaa caaaatgcaa agtgaggggt ttggttgaag   21060
tggttgtctt gtgaatattg aattgttgta ttaaattcgt agaaaattag taaccagtac   21120
aagcttttgt gggctgataa agataaacac gttgagttag taatacgcaa accggtaatc   21180
tacttctaat caattaattt aaatgagttt tccaggcgtc tattataact tcaaagtctc   21240
gttttccgac aattaatata ttgtgtgatt aagatgaaaa taagcacaact acgacgacaa   21300 gctagccaaa ctctttttgga agcgaataaa acaagactag ctatttgtga acttattatt   21360
```

-continued

```
ttcttcttag actgatgatt ttacaattgt aacaatgcac tcctatttag accagtgatt      21420
ggctgatggc caggttattt tgtataatac tctctaacct ttctccattt gtctagttaa      21480
cctttagcca tttgccttgt taattgctca tacacttctt tttctcctta gttcaagtgt      21540
aatgtccaag ccattcatta tccattgtct tgttaatgaa tccatttgtc tcaacagttt      21600
tttatattaa ttttctcctt aattctagaa ttatcttcaa taactaaaga ttagaccaag      21660
ttgttctcat ttaatagcaa tgtagaatca tttggagaga aactatcatt tcaaagccga      21720
acaaccgaat tctcgaaagg ttgtaaaagt aaaaagtaac attgtggatt aatctcaact      21780
ccagaataat agaagattat taagagtacg aaccgaaaca ggaaaagcga cttgagatca      21840
gttgtcttaa atcgttacag tgaaaataac aagacattgc ttttgacttc cactttaagt      21900
taagaagaag cctaccccaa aacggtaaaa aaatactcgg tttttgcttc agacacaaag      21960
attcactgtc tgaatccgtg gcatagaagc aaagtagata ccaaaattgg gaaaactctc      22020
taccagcaaa ttcaaatcaa aaaggtcaaa cacacaacga attctgccac ctcaacccac      22080
agctcttaaa gatcaaaaca atcatctcag ccaccaaact ttaacctaaa gatttggcct      22140
gtgctcattg agctttatcg atcacaacaa aaccactcac cgcccattga ccatgccctt      22200
aatctctatg ttcttcacca tccaaaatat tcattgggta cacaaaaggg aaagcctttc      22260
ttgtctcctc gctgatgaat gaaaacttga ggcttaacaa tgacaatgag tattctaact      22320
tcctcttcga atcacccaat tagatagcaa aggagcttca ccgtctttct tcctttcatc      22380
tttttattgc ttccatctca gagaaccact aagcttact tgttgaatag aagaaaccct      22440
gaattgatca agatcaagcc aagagacaaa acacaaacaa atacttgtgc cctgtgtggt      22500
tctgttacat actatgtaaa tgcagcttcc tacttacatc aggggacact ctatgaataa      22560
gtagaaatct aaagataatg gatttgaatc attcagaaat catcaccagc ttcagaatgt      22620
tatatatatg taacaaaggg ttgttggatc ttttataaga agaaacagat aaaaatgaaa      22680
cccagatctg gttcttacag taacagatct taacacaatc tctctctctt tttaatcgtc      22740
atcatcttcg ttgatgataa aatcatcacg ctcaatcttt ttttttttgtt cttccttttt      22800 ttctcttttca atatgatatc aaaggaaaat ggaaaaacaa aagagcataa agttatcatt      22860
ttgtaaaatt tgagaatttt ttttgtgtgt aatcaacgga ttttttttgt aaagcagcaa      22920
atcagagacg tagatcggta cagtggagat catctatccc gccagcgaat aagtcaacgc      22980
catccaacgg cgggaaatta agatcaaact gaaacggcgt tttccggcgg gaagacgaag      23040
atgcgatatc atctccgtcg tcaataacag acgacgaaga atcgcagtcg ctatgacaat      23100
cctccggagc taccggtgga gttctcggat atctcttaat cgcatgtaac ggtttcgcca      23160
ccgacgaaga cgccgccgcg gcttccatcg gtctcggtcc gctacaagat ttaacggtgc      23220
tgctcatgct gctactcgcc ggccgactaa taatctgctg ctgctgctgc tcctggaaat      23280
tacctccgcc gtataaccga tggtccataa acggatcgat ctggttctga atcaccggag      23340
gagaacagag gttttgattg tggaggtagg tgagaggttg gagaggagaa gaaggagaac      23400
aatcgatcgg gaaattggtc ttggcctttg gaccacggag gttacgtgcg gcggtatcgt      23460
aagcgcgtgc agcatctacg gcggaatcga aagtaccgag ccagacacga gattttttta      23520
atggatcacg gatctcagct gcgaatcgac cccaaggtct cttcctaacg cctctatacc      23580
tcggctcctt cacagatcca ccggcggtta ctggaagggc gggtccaacg acggaagagc      23640
ctctcccttt cctcatggag aagaaaaaag atgtaaagcc agaagtaatg tgatgaagaa      23700
gagatctgtg tgtgtttgtg tgaagaagag aagaaaatgt tgaagagaga agaaagatga      23760
```

```
ggaagaagat gaaggaacaa agggtagaga ttggaaatta ttattataat tctcttttt   23820
tttttctaaa taatttactc aaagaatttt catttaataa attaattaaa ataataattt   23880
atggttggaa tagcttttc ttttcttttt tttttggtt gttaatttcg atttttctc     23940
taccttcacg cccgacccac aagaccgacc aattcgttc tttaaaatt taattatgga    24000
gtaacatttt tcctaacttg gattctttt ttcttttgct ttaaactttt tattcgatat  24060
attgtgtgga gaaaaaaaa caaaaaatta aaaagagtt cacaagagat gtctcgaaat   24120
gcgaagaaag taaagaggg taagcacttg cactctctgt cctgaccctg accacaatct  24180
atataataaa atcttatgtc ttactgtttg tttgttatca aattgatgca cctagagacc  24240
aaatagtcca cttgtaatga ccaaaaacac cctccagatt ttattttatt ttatttaata  24300
atacacccct cttcgaaatt attattagtt tcttctcctt cctttgggac cctacaagag  24360
acgagacgcg cttatcggca tcgtcgtcgt ctcccgtgtt aaaagtaaat gccgtgttga  24420
ggatacgcat taatgtggag aaacaaacat ttttgttctt ataaaaactg aattatgtct  24480
ctccattaaa ccccaatctc agaacacaaa acgaaaacaa aataactct aaagaagaaa   24540
caacacattt ttcgaatttt taaaacttgc ttaccataaa attctggatt ttatttatcc  24600
agtctaaaat ctacaggctg atcatagtag cctgcttagg gatttgatga gtagtttaag  24660
gtttttctt gtggcttcat ctcctgtgaa tcccagaata tctgagctta tactctacaa   24720
tcaagaaaat caaaaaccaa gtctttgtta acattgtttc ttccaacttg tcaaagctgg  24780
tattgataga ataagaagaa aaaaaagttt acctcgacgt tcttcaaagt ataaaccaga  24840
gtgtagattg acttctgtat gagttctgta ttctcaggag tcataattga cgaattaacc  24900
tttctgcaat gtaaccaaaa tgaaaattat atttttgctg tctactgcaa gaatataggt  24960
tctcataatc acagttatca ctcagttgat catacgtatg taagtaaacg agcttttgca  25020
tatatgtggt ccaggaacat acattaagtg acagaaacag taggctagca gaagataagt  25080
agaggcaaca caagataaat tattgaaatt ttaagacaat agaggaaaga ttgaaaagca  25140
ctgatgagca aagcagttaa tttaacatgg aacccataag ataagacaca tttatgcata  25200
gatatgtatg tgttttaact ttttaaccat catctcttgt tcagaaactt aatccacaaa  25260
tagagtgttg aagccacata cgagaaattg aagctagtgt gcttatatct atcgtaaggt  25320
ctgctttcat catgatgcag aaagagtttt gcatttgcac tatggaattc aaaatattca  25380
taatgatata cagtcgatat gccaagattg ttccactaag agctattacc tcaaatcgtc  25440
agaagcttgg gtaaggcttc gagtaagaca ctcaacttcc ttgagcaagc cgctatcacg  25500
aaactcagag agcaaaggtt gagcatcttc agccatggct tgaatctgtg acatcactac  25560
atcaaaaccc aacgcataag caggagaata cattttttc caatcttgaa attcacctat   25620
cgattctttt tgaatactgt aaacaagatc taaacaaaga ccaccaaaat tactcatatc  25680
accttttga gcaatggcct tgcttcctca ataaccgaag cagctctctc agcaagcgaa   25740
tacgtattgg caacaccaat ggcctcaact tcgcgtccaa tacgagtgaa aattccaact  25800
aattcatcta aactaactcc ttgcactcct tttattgtct gcctatcaca aacgatcaga  25860
ccttccttac cacattcagg atgcagaggt cctactgaag gttctggtat cggattccta  25920
ggcataatgt cgatcatagt ttccattaga agaccagact gattcacctc aaccaatgaa  25980
ttcctcggga taataatctt atcatcttct atctgcaaaa cataacacac gaccctcatt  26040
tcaaaaacaa atgtactatc aaaaccagat tcaaagtacc agatcatacc tcagcaacag  26100
cttcaatatt cttcaaggaa ggattaacac ggataatcgt accaacagta accccacgga  26160
```

```
tcctaaccgg tgttcccgtg caaataccag aagcatgact aagctcaaac acagtctgat   26220
atttcctaaa cttcgaccgc atttgaaaac ctcgcaacca agcccagcta agagcaagaa   26280
gagtagctcc agagacaata aacaaaccaa caccaccttc ccaaatactt ctcttaccaa   26340
acccaaaatc actcaaaggt tttaaagtct gtctccatat attcctgggc acatccaaaa   26400
caacggtgag aggattcttc cccccatcag acgatggttg accatgagca gcatcggaat   26460
tggatgcagc tctgaccact aaatgcctag ttctaggttt tggtggaaga taaggaaccc   26520
cattgggtga aactcgagga caagcaatca tggaggatga tggcattagt gatgatggaa   26580
cttgaattac tggattccca atcatccttc caaattcaat aaaaaaacta actttatgc    26640 agcaagttcc aattttgttt tccgagctgt agttagaaag aagatagaga acatgtgaat   26700
tgcgtgaagc ttctacttta tcgatcgaat tataagtcga gattagggtt tttgagcgaa   26760
agagagaata cctgggctcg aagcttgtga cgaactggtg tcgtgaatct gagaatagct   26820
tctccaaagg ctttgttgtt gggatttaga cggtaaagag aaaagacgga aaatcccatg   26880
tgattatcat taatcataat taattaagta atttattaat cacctaattt cgaaaatgta   26940
aaggcttaat cagttaatct taagccaatt tggaaggaag caagggcatt tccgtgataa   27000
tcagaaaaat atacagcgaa agtgaacttt tctctgttca ctgtaatgtt tcgtcctttg   27060
gagaagtggt aggccaaact gtgaaaaata gctcaaatca atttattcat taagttcaac   27120
aactcttcct catatcagtc ttttaaccaa caaaccaaca gatccttctt ttaattaaca   27180
tcaagatcac agcttttgtg cttaacactc aaaaatcact aaagcttcgg attttattat   27240
tgcagattcc ttgagctcat ggtaggcttg agaatcagtc cattaaagga tttaacttaa   27300
cgaccatgaa ctatccaatc accaaccgac aagcagtagc tttagaagag ccattctaat   27360
gaacaaaccg ttctttgctt gtctgaagta ggcagctctt ggatcagcat caacatctgc   27420
ggtgatctac acaataagaa atacaaagag tgaggattgt gtcacggtac atatatgaaa   27480
aatagaggtt ttcttaactt acttcatcca atctcggtaa aggatgcatg ataatagctt   27540 tttctgcat cactcctaac agatccttgt ctacgatata cttcccacga gctgcttcgt    27600
aaaggtccag ccttttctcca aacctctctc tttggattcg tgtttgataa actacatcac   27660
acttggatgc tacttccatt aaatctgaac tttcttccca ttcaaccccg cttgatgtca   27720
aatagtcttt tatatcatcc taccattaaa agaaacacact gaaaatggta aggaacatac   27780
acaatgatgt tctcgagtaa accaaaccat cttcttcagg ttctctcatg gagggtggca   27840
agtttagtgc tactaacctt cattttcaca atttcagggg aaacaaagta gatcttcacg   27900 tcttgaact tggcaagcaa gtatgcaaga gaccgcacag tccttccgtt ggcaaggtct    27960
ccaactaagg ctacactgat gccatctaat tttccaattt cactttggat ggtatagacg   28020
tccaatagag ccttcacaac agtaacagaa ccagaaataa gaaacaagga tgtaaagtaa   28080
tgtttgttta agacaattga aaaaaactaa aggttaagaa cacaacatac ctgagtagga   28140
tgctctccag gaccatcacc tgcattaatg acaggtatat tggcagtagc tgcagctttt   28200
cttgcagcac cgcttttcaaa atgtcgcatc acaattatat ctgaataacc ctccactgtt   28260
cttattgtgt ctgaaaaatg ccccaaaaat ttccgtaaat aatctaacac tcaacatgtt   28320
tcacagcaat aatgagatac tagctaagat ggtaccttca agtgtttccc ctttcgcggc   28380
agacgaaaac tctctagcgt tctcagtagt taagacttca cctccaaggc gtttcatagc   28440
agattcaaat gaaagcctgg tacgggtaga aggctcataa aagagggtag ccattaaata   28500
acccttgagg atttcacttt gtgaagagct cttttctatc ttttccattt cgcgtgcaac   28560
```

```
atcgaatata gcgcttagca tctctctatc aaactgtttc ccttcaatca catcactaag  28620
ttcaaatttc ttcaactccc tcgtcccagc ttgcatagca tgacacctga ctggaccaac  28680
atttcgagtc agattcaaag tagcattttt cttgagatcc ctagaggcag gaaacgaagt  28740
caaacaaatc tttgaacttt caaaagggct gggaagattg atagggaact cagagctgca  28800
ggctaatgct ttaggaaaaa ctgaggcgcc gcaaagtgtg gctgaagtaa gtgatgatgc  28860
aatagacatt cttgcgcagg atgctaattc gttgaagggg agatactgag tcacaacttc  28920
cagaatctgc taaaataaca gacaacaata tatgatgccg ttagtttaag aataatcgaa  28980
agcaactaag ttttcgagac tatgagaaaa aaactgcaaa ttttataaac tctaaagatg  29040
attacaagta tccacactcc atcaagctag tgccaacgat acttgttgcg gattatattg  29100
gtaacctctc ttacatatcc acttgctttc atataagaat ctaaacatta cttgaatcct  29160
gaattcaatt gtcttagatg gatagaggga gaatcaaaac cttgggtact ctatggaaat  29220
gatccttaat ctcaattata ataaaattat gagaaagtag ttaccataat ccgaaactat  29280
aacaaatttc aatttcaatc aatcgtaaat caaaaatcga aaagaaaaa  aattcagaat  29340 ctgatccgca gaatttcaaa acctacacag acctaaaaga gcgattgaat cagtaaagca  29400
gtcaaatggg gaagagtctg gctggtcgat gtaacgccgg tagagaatcc gacagcaatg  29460
agcacaaaaa gaaggaatta gactcaatcc tggttaaatc ggagaccggc ggcgggaacg  29520
gccggggaga aatcaaaggc gggcggagaa atgtagggtt ttactaagga aaggaaacta  29580
gtaatgatga attcaagacg ttttggaata ttaggggagg gaaaaaacga aacgcattgg  29640
gatgataatt aataaatcat atttaatgtc ttgtttcttt ttcgttggac gagtaaagtg  29700
aatttgggct tctaaagccc ataatatgtc ttcttttcct cccgcgaagc ccaaacagaa  29760
acagaaagct ccggcggata gtcaaagaga gagaggatca acaacggaga agagaggttt  29820
catgtcatga caagtttcag ctaaatcaag taagtcctgg tattaacaac aagcttttg   29880 attctgcttt tatgctttt  tatttacatt ctaacaaaca aaaacagaag cgtcatgtgt  29940
ccaaaccaaa atttcatca  aaactcttac cctaacacat atcaagaaag tgaagaaacc  30000
ctaagcatat acaaacatgg ccatctctga aaacaaaact cagttaactt ctggtatgct  30060
ctgtagaacc ggtctccata accgttgttg attggcttct tcgtacccgc gattgttcag  30120
gattggacat gagaaggttt gttgctggaa ggtcaagtca tggacgttga ctttactcag  30180
taaatcatgg agttgcttct tcgtgagcct gatcttgatc tcatgagatg gaacagagga  30240
tttactgtca cgtgttacaa ttactggttt gccatctctt gtggttttag agctataatg  30300
atgatcttct tcatcttctg tgatgaattc atcccagtct tcaccagccc aatgcatttc  30360
tgattcatgc cttaaacaat tccccatttt ttgtttctat ttttctttgg aggtaacccg  30420
taaaagagct tatatatata taacgtaggt agaagctggt gagatattat aatcataaaa  30480
ggagataaag atcaggagca gtgaatatat taaaaaaaaa ttaggatcaa tgataagaac  30540
atatacaata tgccacgtca gatttcagag tactttagtc ctacgtggac atgtgtttgt  30600
tgaactcacc gtcaccagct tttgtccttt tcaatttcca acgttccacg tgtccttatt  30660
ggctcgtcag ctcggcttgg atattttgc  tgattataat attttttatc tttgttttcc  30720
ggtggaaata aaatgcccat gaaataagag aaaaaaaaag aagaagaagt ataataattg  30780
cctaacgtga cgtctaacga aaacagaact cagcacgaaa gattctagtt catatgtggc  30840
taaaggaaaa catgtgaaat atgaataatg agaaggaagt ctcaaaggtc caatactctg  30900
atgctatgtt ttgttgtaga caaataaaac gtataacgtt gaggtacgta aacgtatacc  30960
```

```
aaaaaagaag tcatttatct tgtgcgtgta ataatacctt tgataatgag atgtcccatt   31020
ttttcttctt cttttcttt taagaaatac acatttatta gctagactat ctaccactga   31080
aaattaatat atatttacca attttaaag tgttatacaa caaatgttta acgtgtaaat   31140
ctacgaaatg gtcattgaca acaaattatg atcaatttca agatatatcg atcataacct   31200
taacagtaaa aaaatatatt ttctcagctt atgtaagtaa ataaaacgta aagtagaaca   31260
attagaaatg tatataacca aaaaaaaaaa gtgtggatgg agccgagcta ggcagaagaa   31320
gccgagtgaa gtgaagtagt gtgaacacgg cattgggaa gggatcttca aagtgtgaac    31380
gcaaccaaag ggaacagaat ctctgaacca aagatgccct acccaatttt caattactcg   31440
tttaggccat ctcatgttac acacactcac gtctcccacc tttccataat tttccattgc   31500
catcaccttt tttttttttt ttttttaaa gttttaaata tttctaaggt ttttgttttc    31560
ctgttaaaaa tagttacaag gttttgggta tttggaattt aagtaaatat tttgaatttg   31620
ttagttatta taccattaaa aatcactatt caaactcatg ttctacatta atcacttttt   31680
ttttatctgt ccatttgccg ttgtttgcat agtttgttct actatcatca tctgatctta   31740
ttaacatcaa ttacccaatt tactctacaa atgctttata tgatatattc aaatgcaatt   31800
caacaaccaa tataccatta ttattcatat aagtcaaaag cctgaggttg gtgttacatc   31860
gaattattcc actactagta tatagcattt ttatttaagt agtatcgatc acttgaccca   31920 catacccccga actttatttt tataaatgaa actgatctgt ataacattgg ttgatctatc   31980
gatctctctc acctattgct ctcattattt gttaattcga accgattagt aaataagtaa    32040
aagttataga atcttggtgt tcataccact gtagagacga aaaatctaat catctcatca   32100
taattaagtt aaatatgctt tatataccta tctctttatt cattttttat agttgaatat   32160
tatacattaa cgaatcaata caatgggtcg atcaataaaa tgtgtctatt atcaacttt    32220 tgtgttacat gttacacaaa catatattaa ttattaatta ttttcggctg ctatgtgata   32280
caacactcac cattttgtac aattttttttt ttgtttttttt ttctcttttt tttttcattt  32340
tgtacaattg ttcaatcatt atattgaaac gaaattaaac tgagattctt ttgttattaa   32400
tgagctctat tgagtttgtg tttaagtacc acccgaagac ttttttgttaa attgcgtagg   32460 ttaagacttt agaccgtcaa gaagttttgc ctaataaaaa tgacagtcaa agaataaaaa   32520
agaccacttc ctggttcctg ctactcgata tgcgtagcgt aaatataata atttaaagta   32580
atcaacaaca tttgttttttg tttttttgaca tttaatcaac aagttttga agttccacgc   32640 ataaacacag acgcataact ataagaaaca ttaaggaaa aaaaaagcag agctaagaag   32700 atgcaaaaa aaagatctaaa agaagatgc cattgagaca cctatatata gtgattattt   32760
caaagacaaa gagttaacgc aatcaagatc aggtgtttaa aacacaaatg atacaaaatt   32820
atatactcgt atattggaaa ccatgatctt tgagctttcc atccaatttt cttctgtaat   32880
taaacaaacc agaagacat taaataaaaa aaataaaca tgcatagcat atagtacaca    32940
tttagatagt aagatcgtat tgtatacatc ttttttttta ttcactgaga agtgagatca   33000
ttatcacaat aacaagaaac aaactaacga atcaaataaa atatgatgta acagtttcta   33060
tgtaataaaa tataaatga gaaaaagac aaagaatgca gaatccatgt gaagggaatg    33120
ggagtggaag aagcccatct atattaaaac ttactaaaag tactaatgat cgactacaat   33180
ctcataatta aggttttgac cacctctaat ctagccctta ataatttat ccttgtatgt    33240 atatgggctt tatttgtata tttgttgttg ggcttcgatg atacttaaag aatctgaagc   33300
acccaaaaag aaaaaaagag atttggtgaa actaatcaaa ttagtcagag acaccccagt   33360
```

```
acctccttca tcatcactct ctctctttcg ttacagttcc ctaatcaagc aagttgcata   33420
tcacgagctc tctcaactct caatccaatc catctctctc tcacgcattt tcgtttgttt   33480
cttcgttttc ctcttttcag attcttctct tcgattcttc acattgataa aacttgtcta   33540
tggtggttgt tacgtcgatt gagtagatga agttcaccgg aaaatcaaat ttgacggcta   33600
cattacccgc aactgtccca aatatcaggg atattcatag aaggagagcg cgaaaaccga   33660
gcttcactcg tcaacgaaga tctggcgtgt ctgtcaggag gctaagcagg ccggagactc   33720
ctcaattgaa atcgaaggtg gaggatcaaa acattgagcg atgcggcggg gttgaagatg   33780
gtgataacga ggatgatgat tgtaataaga tgcgttgtca ggaacggagt aggagtgtac   33840
ggcctgatac tgttaggaaa cttgctgccg gagtgtggcg attgcgagtc ccggatgcgg   33900
tttctagcgg cggagataag aggagcaagg atcggttacg gtttcaggta cagctttgct   33960
tttgaaaaaa tgagacattt ataggatccg cattgtgatg aagtgaattg tatgaaagca   34020
atcaaaagat tataggattg ctgattttgc cttagctttg aatctaaagt atgagagcac   34080
tggattgatt ttagctggtt gttttaatag taatgtcaaa gtaatctgaa atagaaatga   34140
ctgttgattc caggatcttc acactagttc ataactgttt gctcatgtct ctggaatctg   34200
tacactctgt ttcttgtgtg atggatctga attagttggc tttagctact atctcagagg   34260
agttcatatg tcaaataaat ttctctttat tttctttggt gttttctcc aggaaactgc   34320 tggtcctgct ggaaacttgg gtcctctgtt ttattatcac caccatgatg acaaacattc   34380 tggcttcaa agcaacaatt caagaaacaa gcatagtaga ttcttgtgta aggtttgttg   34440
ataatctcaa acttctaggt gaagattata ttatgtcaat tcaattagat gtggatatgc   34500 ttcaaaagt cttatacatg ttacttgagg tgctttatta agaaccataa ctaaatgttg   34560
tggttgagat gaaggttcta tgagtttaga gttgttactt gagctagtaa atctgacctc   34620
ggtcggttta accgtctggt cggagtatga aaatactgcc ttagcttcac tatagttgtt   34680
aacttgaaca ctttaagaca ttgacacgct gcacatttct tggttggcta ttcctttgtc   34740
tgagtcctct taaggttctt tatttatgtg acagtttccg ttaatcatta cttttttctt   34800
tttcttttgc tgttagcatg agccttcagt tccatttccc cactgcgcga tggagggagc   34860
aacaaaatgg gatcccatct gcttggatac aagggatgat gtacaccaaa tctataccaa   34920
cgtgaagtgg aataatcaac aagtgaatga tgtttcatta gcttcttcta ttgaattgaa   34980
acttcaggaa gctcgtgctt gcattaagga tcttgagagt gagaagcgat ctcagaaaaa   35040
gaagcttgag cagttcctga agaaagttag cgaggagagg gcagcttggc ggagcagaga   35100
gcatgagaag gtccgagcaa ttattgatga catgaaagct gacatgaacc aggaaaagaa   35160
gactcgtcag agattagaaa tcgtcaattc aaaattagtc aatgagcttg cagattcaaa   35220
gttagcagta aagcgttaca tgcatgatta ccaacaggaa aggaaggcaa gagaattgat   35280
cgaagaagtt tgtgatgaac tggcaaagga aatagaagaa gataaagctg agattgaagc   35340
attgaagagc gaatccatga atctcagaga ggaagtagac gatgaaagaa gaatgctgca   35400
gatggctgag gtttggcgtg aggaacgtgt ccagatgaag cttattgatg ccaaagtaac   35460
actcgaggaa aagtattcac aaatgaacaa actcgtagga gatatggaag ccttcctcag   35520
ttcaagaaat actacaggtg tgaaagaggt gagagttgcg gaattgttaa gagaaactgc   35580
tgcatcagtt gataatatcc aagaaatcaa ggaatttacg tatgaacccg caaagccgga   35640
cgatatcctc atgttgtttg aacaaatgaa catgggtgaa aaccaggata gagaaagcga   35700
gcaatatgtt gcctacagtc cggtcagcca cgcttcaaaa gctcacacgg taagtccaga   35760
```

```
tgtcaatttg attaacaaag ggagacactc gaatgctttc actgatcaga atggtgaatt     35820
tgaagaagat gacagtggct gggaaactgt gagccattct gaagaacacg gatccagtta     35880
ctctccagat gagagcatcc ctaatattag caacactcat caccgtaaca gcaatgtatc     35940
gatgaatgga acagagtatg aaaagactct attgagagaa ataaaagaag tgtgctcggt     36000
tccaagacga caatccaaaa agttaccgtc aatggcaaag ctctggagtt cattagaagg     36060
tatgaatgga agggtttcaa acgcgagaaa atcaaccgtg gagatggttt caccagaaac     36120
aggctcaaac aaaggcggat tcaacacatt ggacctggtt ggtcaatgga gctcatcacc     36180
agactcggct aatgctaatt taaatcgagg agggaggaaa gggtgcatag agtggccaag     36240
aggggcacat aagaacagct tgaagacaaa gctcatagaa gcacaaatcg agagccaaaa     36300
ggttcagctg aagcatgtcc ttgagcataa gatctaggcc acaacatatt ccaaaactac     36360
cagtcctagg ccattctact aatctttgtg gctgagcagc agaactggat ttttgatccc     36420
gttctcctgc tattgccatt gtcgcatgat ctagcgctgg tcaaaccaat caacgtggta     36480
tattttcgtt agctaaaagc aaaatgatct ttgtgattga ttactgtcat agcttggctg     36540
ggctagcttc agccacgtcc cagcaacccc ttggaacaga ggcacaatgg tgttttcctt     36600
tactgaattt tgttcctctt cagtccaact tgtgatgcta ggtcattaat atcttctttt     36660
attacattgt gtatatactt cgaaactgta ggatgcattc ttctatatgt aagttaaaga     36720
tatgataaac agaagaattt aaatgatata tccatttatt ttagaccaag tgggagaaag     36780
aaataaggtt ttccattcga aagaacgaac acttgaaaca caaagcataa gaaacatgat     36840
attaagttaa agcacaaaag ataagactat ataacacata tattatagat gccacggttt     36900
aagcttctaa acaagtctat ttgggaaggt aatttgtaga agaaatttcc tccatagcga     36960
cttgaacaac caacatatca ttcacaagaa aacccttga tgaatttctc agatcagaaa     37020
gaggcatgaa gtcagcgtat ccccacccga ttgtttgggg actgaaccag ttatcaactg     37080
ccagaaaaga aaagaaaaaa cacatattag tcatcgtagt gattgaagat gttatgaatt     37140
tcacattaaa taacagtcat aatcacatat ctagtatcca cttacgtggc ctttccaaaa     37200
cgagattgga ttgggatccg aattggttag gaacacgaag cttggctcgt acgtaaacct     37260
tgtcataagg ttttgctttt agtagctctt gtggcccaag gttaagataa agcgacaaat     37320
ttttgccttc aaaagcgcca aaaccatttt taaagattcg taaattcctg attcagcatt     37380
tgaaaaactt gttaaacact taatagtagt atactactac gtacccacca cacttgcact     37440
acaactaatt atattgagaa actcaccagc ttttcctcc gatgatgaac tcctctgata     37500
ggtaatcagt aggcagtgtc gagtatcctt gaatatacca ggtgaatctc gggctcggaa     37560
aactcttggt gacagagaaa acttccgatt tttcgtagaa tggtggaatg ataacgtcaa     37620
cgccaaactc acaatggtca acgtcataaa ggtatccatt ttttaggttg ttaaacgtaa     37680
tcagaggaag aaccttagaa aatccccaca ttcttttgat tgcactgaat cgccatacat     37740
cagtatctgg taacaccgca tagacataat aatagacaga tagatgttac tataaatata     37800
gaaacaatga catatttatt tgagtattac cgcataaagt tacttatata ttaaccttgg     37860
atcgtaaagt acttcgtctc tttcttgttg aatacgtaaa atctgagatc tacatgaacc     37920
tcttcacttt gagaggtgag agttgagttg tctaagacga cgtatagcga aatgtgccct     37980
gtaccgttat cgttcttgtt tcccttcgga tacacaacaa gcgtcctgtt tcaatttgtt     38040
caacacgatt cagcaaacaa ctatagtaca taatgaagtg gcttgaacaa agataggcca     38100
aggtcctcca ttaggaatat agggattgat caacgttttg tagtccagtc acaaacaata     38160
```

-continued

```
gtttttatca tggagctaga tagattttgg gacaaaggtt cctaatcttt tagctaataa   38220
aatagaagaa aaaacaaaga tggtacgtaa cgtaccagtt gtatctaccg accctaaaag   38280
gacgagattc gtatctctca gtgtaaacag acttcatgag tgtgttgaaa gactccatct   38340
tgagagagta agacgatgga ggacgttctc tcagacccct caccgtgctc gatagagaaa   38400
ccttactatc acgtgatgat atctgagtgg ggaaaatttt ctgagatcca ttttcctggt   38460
ttggaactgg tcctgcaaaa gaagaggtga tgaagagaca agacaagaga gaaattacaa   38520
tgcataaggt gtttatgtag tgatagctca tcatttcaaa gatctatgaa tgaagtttag   38580
agagtcactg tgagacttgt taacgataat ggcatgtgtg tgtgtatata tatagaaggg   38640
gagattggtt aactagatgc ttactggggc taaaaatagt gagattttgg catgataatg   38700
tttttcttct gcctagtgta ccagttggtt cattaatatt tgaaatacca atctcgtttg   38760
ataatgcgtt tacttttacc attgacttag gttatatatt atatttcctc catatttgga   38820
ttggatcagt cttttcgaat cggggatctt tttttaaata attgcaaatt catagaaata   38880
caccattcgt tcacaattgt agtagtattg aactcgaatc tgataactaa aacaatgcct   38940
ctctaactag ctagctacta tctaatttaa ttaatgccca taaactcgca aaatcaatta   39000
tctatgtaaa cgttgaattg ttttaacatt atagagtgta gactaaactt caaagcgaaa   39060
cttttttctt tgtctccttg ttcaacgaaa cgaaacctta taaatagcat acgtactttt   39120
gaaatcggag aactaaaaac taaagtgatg caaaatgaaa ggacataata tttgtctata   39180
acctaaactt tcttaattta tttctacttt aggggtttcg agttaaaatc agatttccta   39240
gttcctacta tatgcctctg cctcaagtcc aagatgccga caaaaaatag tcacaaagat   39300
tagataattg cagtgccaga tcaaaactca ctcacgtgtt ctcatctccc tccgcaacta   39360
gcgtcgatat cagtggtagg ttcacgtgga ccaaacaaac cttctcatct tccctattaa   39420
tttggtccat ctttagagac gtatgctatg acggagccac gaatttcatt tataagagtc   39480 acaaacatt tattttcta aacctaaaat aaaactaaat attttatttt cttatatata   39540 tacatttaa cctaaaatgt ttcatatttc atctttcaaa ataaacatac tctcaactta   39600
tcttttttta gttgtatcat caaattccct ttctcatcaa cactcttttt gttaatatat   39660
tgtggagatt gagtagttgt tgtgtttatc ttgattcatg attttagaa tatatatttt   39720 agattttttt tttgaaaaga atgtagaaac taaaactgga tatctaaaaa gaagaaaaaa   39780
gtattgattt gttaatgaat attacagggt ttaataag atattatagt tttataatt   39840 agccaaacaa aaatgcaaaa aggcattaag attaaatgac aaaatgaata tgcatggggt   39900
caaagacaag cataaatcac ataacatgag gtcattgtga gtactttaac ccaaaacata   39960
taattatctt agaagatata ccctatattt tttttttaaa ctataaattt tatgggggtc   40020
gactgagccc ccttcttgta tgttgcctcc ggcacacgta tgattggatt ttatcatctc   40080
catgatactt cagagttctg acaatctcga atataatgcc actttgtttt tttgctttgt   40140
aatggacatc atcgatgctt caatcttcga aaactgaaaa taacgtccgt ctgttttctt   40200
ccaaggtcgt gtggtagaca tgacatcttt tcggattatg aacatgagaa cagcccttat   40260
caattgtttg aaaacaaatc gaagatactc atatttcgga tgatgtctat tgatcgtcca   40320
gaatagattc taaacctctg cttccaatac gacgagaagg atctccgatc gaatatggaa   40380
acgtactacc aacgatgatc ccgaataatt catgttgcac cacaaagcat gaaacatctt   40440
ctttatttaa ttcgtacgac aacattctat tagtgacaga aaacaacaat taactttgta   40500
gctgttaaaa atactggtaa aagataaaaa aaagattgag ccgagtttat ctgttgtata   40560
```

```
tactattctt tttgatagat acatacaccc aagatatttt atcttgacat gtgatgaaga   40620
gatacggatt atcctctgaa caataatttt ctaaaaaaaa agaagcaaat ttttgataac   40680
ttaacttata aatccacctt tttccctaat tagaagatgg attctggctg attttcttgg   40740
attagtgtta gacagggata ctactatttc ttaacaatga gatgaggcaa tctatcaagg   40800
aaagtaaaaa aaaaacgaaa cttaaccctc tttttttctt tttttttta tgttagacca   40860 atcacttctt gaaaagattc cgtaactaga cgatttttat atatatttt ttatttttta   40920 attttaata tttccacttc aaatataaaa agaaagtata tttatttgtt atagaattat   40980
gattagaata tgaatacaaa tgtaaaaaaa aaatgatata gaattctata gaaaaaagaa   41040
aaaaccttat aagctagtca taccatttca tttcattata ttgacaatta aaaaaaactg   41100
atcatactat gatcatagta tgatggcggt tgagcaagta tgcccccatc gtctagtggt   41160
tcaggacatc tctctttcaa ggaggcagca gggattcgac ttcccctggg ggtagggtac   41220
tacgaaagga agttgatcat ggattatcca taaagttaga atagattctt cctgggtcga   41280
tgcccgagcg gttaatgggg acggactgta aattcgttgg caatatgtct acgctggttc   41340
aaatccagct cggcccaata attagctgtc tacataacca ttttttttttt ttgcataaat   41400 gacagagaag gggtaagaaa aaaaggtcaa atttcagggt atagggtata gttcgacttt   41460 acttttttt ttatttctta tgtttagtta ctttttttttc cataaaaaat tccgatcttg   41520
atcttgctaa ggattccgat atggatcctt taaagagaaa ctttaatgaa cagagtcgat   41580
aaaataatct atttgcttct gttcaatata taatgactga agctaacttt ggttggttaa   41640
tccgatcagt tcatcgatgg tcgtatagtt tagttattta ggcaataaaa ggtagggtt   41700 agaaattcag atgatggtac aaaaattaaa aatagatgcc aatacgtata ttttcttat   41760 taaaatatt atatcaaata ataattaaaa aaaaatatat atatatatat ataaatatac   41820
atagcacgca aataagaaaa tgcattattg aatattgaag aaactatgat tactctttga   41880
caacaaagag aaactataat caattaaaaa ctttaattag aataaacttg aaagaaaata   41940
tgagtaatac gttttcttag cagaaaaatt cgttttggaa gagttgagtg tgaatatgag   42000 gtttttttg ggtgtatttta ctatttacag taattgttag aagtcatgct tatctttga   42060 gaatttgtat atacataatt cattcataaa cgttaaaaaa aatgtgttta tatgatagct   42120
tttaatcaat tgatgtacaa tgaggtaatg aaactcagat gagtcaccaa ctaagttgag   42180
aacttgagat ggattcaata gtcaatgatg ctaggtgaaa taacgtaatc aaccaaaaat   42240
attattcaat ttttaattcg cattcgcaaa cacgaggcac ataaataat attatcagtc   42300 tcaataaaat cttgattctt gatcttgagc atcccaaagc attattaact aagcatgtat   42360
ctcccactaa ggcacaaatt actaaccata taagtctcag tactctctgt tctgcaaact   42420
tcatacacaa aaccaacatt aagagatggc gagccactac agaaacacaa gcgctattgc   42480
ttatctattg ctttgtctct tcattacatc tgccactgca cattccttca tacgacaaat   42540
cactgatgac ctcaaaacaa atctgcagcg tatgccaatt ttctatgttc ttttagttgt   42600
tataaatgga aaacagatcc tttgtttta tttctcaaat gctctgtttt tgtctggaaa   42660
cagaggaggt aggagcagaa ccaatccaaa acctggacgt aggacattac ttacaagaaa   42720
ataaggagat ctcatcacgt gattataaag tatcagcttc aaacgcagtg aaaggtttga   42780
gagatcgtcc tccatcgtct tactctctca agatggagtc tttcaacacg ctccttaagt   42840
caacttacac ggagaaatat gtatctcgtc ccttttcagt tggtggatac aactggtatg   42900
ttggtcatct gatctttatt tgcttgaatc tataatctta cataccaaat atattttgat   42960
```

```
gaatctcaat atatacagga cacttgttgt gttcccaaat ggtaacaaga aggatagtgg    43020
ttcagggtac cttctctctt acgtagccat agacaactca actctcggac agcaagagat    43080
ttacgcagat ctaaggtttt acatctttaa caagaatgag aggaagtact tcactatcca    43140
aggttcttat aattttcaat caagaaatgt agtgttttag caagaaagat actttgtgca    43200
tgatagtaat atgtatctat atatcgactg gtctttgtta tataatctgt agataccgat    43260
gtgtggaagt ttagtgtctt caaaacgatg tggggattct ctcaggtcct ccccattgat    43320
acattcaaag atccgacaaa aggatatctc tacgatggag atcactgcga gtttggtgtt    43380
gatgtaacca tgccttctct ctacgaaaaa tcggaacttt tctctgtcac agagaatttt    43440
ctaaatccga gattcacctg gaccattcgg ggattctcta cgctgctaaa aaacagttac    43500
ctatcagaag tgttctccat cggaggaaga agttggtgag tcaacattat ttcaaaataa    43560
aaactctggt ggagtagtaa aatggtggta agtagtaaca agtattttat atgttgatta    43620
ggaatataca aatcaatcca agtggtcttg gtacgggaga gggaaaagct tgtcgatgt    43680 atcttggcct taatgtgaat gagatattca gaccatatga gaagatttat gttcgagcca    43740
agcttcgagc tcttaaccaa ctcaatctca gtaacatcga aagggaacgt aagtaaatga    43800
tatgtgttca ttgatgggta tacataacat ctcatcgcaa tgactaatga gatttacttc    43860
tttttttggg gcagtcgata tttggtacaa tggtccggga tatggagaat atagctgggg    43920
tttccctgag tttatctatt tcccttatct cacagattca tcaaagggtt tcgttaagaa    43980
cgatgtgttg atggttcaag ttgaaatgga ggccatttct tcaaccaagt acttcccgag    44040
ttagattttc tctaagcaaa gaacttgtac ctacctccat gtgtttgatt tgttatcaaa    44100
tactaataag aatttgatta tgcatttcaa atacaattgt ttcttttttct tcagcatatc    44160 attatcaaat tatcatatat cttcttgaaa gatcaaatag tcttcaccca aaaaaaaatc    44220
cgccaatcca acattcggct cagttttgtt tgttttgata cctaagaatt aaagaattaa    44280
tggataattt atgatggagg ttagagtcta ctgctaaatt actatcacta atgtattgcc    44340
ataaacaata aaataatata attgctaatc ttaaatctca acttgactat aaagataaag    44400
actaaatcga tcaaaaacca atacactaga tgaagcctgg cttttggtgg gggattttaa    44460
tgaaattcaa tgtgaaaatt taataagaac ttttgtgaaa agaaaattgg aaaatataag    44520 taaagaaaa aggttaaata aaactatcta acatcataaa aagttaaaga atagagcaat    44580
tggatctagt gtattggttt ttgatcgatt tagtctttat ctttataatc aagtggagat    44640
ttaagattag caattataat attgtttatt gtttatggca atacattaat gatagtactt    44700
tagcagtaga ctccaaccctc catagaaaaa aatccattga ttctttttatt cataggtatc    44760 aaaacttaca atgcatttga acctattta aatttaatt caaactactg tattcagttc    44820
caatcatatg ttttgaatg ttttttaag aaaattgaag ttcatatagg atttataaaa    44880
atttattcat ctgatgtaga attattttat ggtcaagtta atgaaaactt caagtgaggg    44940
cactcccaaa cttgagatgg attcaaaagt caacgatgct aaatgaaacc atcgaatcat    45000
gttttgtttt tgaaacaaca ttattacgta agaatctaac taatattcga agactccatc    45060
ctaaagcatt tctctatctc tttaatatat aagttccact aacctctctt ctcttcactt    45120
cattcacata agtcataacc ttgaaagatg acgagtctct acagaaacac atcctctttt    45180
gtttatctcc tgttttgtct cttcatcaca tcttcgtctg cgggttcctt tatacgacaa    45240
ttcagtgatg acttcaacac aattcaacag cgtataaaat ctctttcact cttagattca    45300
tctatgtaac ttagattttg tgtgtggaca taatcctctg ttttttttc ttttttcaaa    45360
```

```
tgctctgtat ttttgtctga acagagaag ggaaaagatg gaccaacacc aaacctggaa    45420
aaaggaaatt acttgcataa acataatgag atctcatcat cacttgatta taaagtatca    45480
gcttcaaaca tagtgaaagg tctaacagaa gttcctccct cgtcttactc tttcaagata    45540
gagtcttata actcgttcct taaaatcccc tacttgggat tcgaatctcg tcccttttgca   45600 gctggtggat acaactggta tgttggtatt ctgatcttca ttttcatgaa tcgaatctta    45660
tgtaccaaaa atcttttgat gggtcttaaa agacatgata tataatacag ggtacttaag    45720
gtacacccta acgggctcac gtgggatggt acttcaggat acgtttcgct ttacgtactc    45780
ttacacgaat cgaccccat cactgcagat caagtcgttt acgcggatct aaggttttac     45840
atcttcaata acaacgagaa gaagtacttt accgtccaag gttttttgcta aatttttca    45900 atatgtataa caagcaagaa taattatcta tgcgtgcatg atatatagta acattttgt     45960 tataatctat agataccaac gtatggaaat ttactgcacc caaaaggctt ttgggattcc    46020
ctaaggtcat gtctgcagat caattcgaag acctgcgaaa cggatacatc tacgataatc    46080
actgtgagtt tggtgttgat gtgaccgttg cttctcacta ccaaaaatct gaatctttat    46140
ttgtcactga gaaattcgat aacccaatat tcacttatgc actcctgaga ttctcgacgc    46200
tgctcaaaga aagttaccaa tccgatgtgt tctccattgg aggaagaagc atgtgagtac    46260
cacatcatta cagaagtaaa aactttgcgc tataagagta tagtggtagt aattaacaat    46320
tattgtttta tatgatgatc aggtatttac aagtgtttcc gaatggtcgt aatctttcaa    46380
agggaaaagc catgtcgctg tatcttaaca ttaacgataa attcaaaccc tttgagatga   46440
tttatgttcg agccaagctt cgagttctta accaacgcaa actcaataac gtcgaaatac    46500
aaggtacgta agaaaatgga tatataacat ctcatcgcca ttgactaatg ggattttact    46560 ttctttttc gcagttagta attggtacac ttcttggttt tattactcgg gcgactttca     46620
gattatccct ctagctgatc tcagagattc atcaaagggt tttgttgtga atgatatgtt    46680
gaaggttgaa gttcaactcg agggcatttc ctcaaccaag tggtaccota gttagatttc    46740 tcaaactata ggaacttgaa gctccatgtt tttcctttgt taccaaacca cctaataata    46800 ataagggta atttgtgttt gcattttttt ttacatatat tttctttctc tagcaatatt    46860
aaattatcat tcctcttcta acgaccatat taagttatta actcttgtct cttcaagcat    46920
aatggttttc actcaaataa aataatgtat acaatcaata catacgtc aacagcaaat      46980 gagggtggac aagacactaa ataacttatt cttgattaga ggcttttgat ttgtaaccaa    47040
cctaatggtt gataatccgc aacattttc gtagtgcagc aaaatgaaaa gtaggttaaa    47100
tatgggttaa gccccaaaaa ccattgtttc tcttatttgt tttgacatct tccggaccaa    47160
aatacccttc gtagagattg atttgagtgt tctagagtgt tgcaatacat tcaatctcga    47220
tcttggcgtt tagaggcaaa gctgcaactt gatacgtcga tcgtgctgga gaaggagctg    47280
ggaagtctgc aacagagaca aatgtttcat gcccttaacg actccactaa taattatgca   47340
tctcaaacaa agtaggaaca caaacaatct tgttaaagaa ctcacatttg gcatatatct    47400
cgttcactgt cttgaagtca gccaaatcag ccaacctttg agagaaaacc agaagagatt   47460
gttttctttt ctatttagat tcagaattca aatggacaat ggtactgttg aaaaaaacaa    47520
gatcccttac atgattgttg tcttcaccac cgaggaataa tcagcaccac tagctttcaa    47580
tatctccccc atgttttttga gtacctttga tattccataa gataatagaa gcaagtagat    47640
aaaatcagga aggaaaaaca gagcaactca accttgctac aactcactg gaacaagtta     47700 atttgaagac taataccaac caaatcaaga attttaaagc aaacccaaa agtttcaaag    47760
```

```
gcttagtttt gtatcatgaa agtttatatc ccaataaact cagctagaat aaggcacatt    47820
aagttgtcat ccctcactac attttcacca acaaacaaca tcatgacgac ctagaggcta    47880
gacctccttt tctgtggata atcatccacc aaaacagaga agcaagtgga aagtactcta    47940
aacaaaacca atttttatag agactacggt gacagtttga aagctaacct gctcagtctg    48000
atcttcgacg ctctccgaaa caaactttcc agtctatata cacaaaacaa aaagagcaaa    48060
tcttgtaatc ttagaacaca gaaaagagaa acaaatggt gattacacag tttcatatct     48120
tatatatacg gacctcaggt ataagtccaa gaacacctga agaaaaacc agattattgg     48180 ctttaatggc ctgagagtaa ggtcccaaag cagctggtgc tttctcagta gacacaactt    48240
ccttcttcac tgcacaccac acacaacatc acatttcttt agtaaaaacc ctattctcaa    48300
acccttgatc attcaatacg gaagatgaaa gaaactaaaa cccaatacta acaaacatat    48360
gcattgatga taactgaaat caatttcaac ttttgacac tgacattcat aaaaatcgca     48420
tctttagaaa gtactaatat cggtccaaat tggagaaaat tgagtaaaat cgtcaccaga    48480
agaagcagag acagagaggg aagcgaaagg aggagatcta gaagacattc tgaagagaga    48540
aacaccagcg aatgttgcgc agccgacacc agcagcgacc aatggggtac gagtggagcg    48600
aagtgcggtg gagaggtcga gtgttggagt atttatggat ctgaaaaccg accaagtcat    48660
ctcactctct ccggcgccga caagaagtat agaatagcga atggaccacg agagagagag    48720
agaaaggtag gtgaagaaga agaagaagac tgagtcgatg cgattggatt ttaagcagat    48780
gattctcgtg cttcttcttt tgtcttcttc cttctcttcg aaatgttttt ttgtatttcc    48840
cactttaccc ttagttaggt acatatatta ctgagaattt aattttattt tttgtgtagt    48900
ttagttggat tgcaaatttt aaaaatttgg acccgttggg tcatgtcggt ccatagcttt    48960
gtgaagttta tccacaacat attgttatgt agaagttgtg ttatgtgaaa gatggtctct    49020
acaaatgggg caagtttctt gtctaagcaa ccactcatct atgcaattca tatgaaatgt    49080
gtggccacat cttgctagct ttcttcctac ttcccttct tcccaatcct acacacccca    49140
aaaatgaaca ttagaaatat atatgattta agtcattatt atcatatatt aaaatctgat    49200
tcctagatga ttctaattaa ttacatttt atcacctgta agcaaatcga gcaactcgat    49260
tttgtttgat gttctgaacg gttgtagaac atcgggatgt tctgaataga gctcttcgat    49320 agtcccttt tttcatgatt gaaatcgtat aagtttgaac tctccatgta acttgtatcc    49380
aatgctatta tctgcatttt gtattataat attaccggag ttaaaatttt gtaaaatata    49440
cttagtttaa cgcttttttgt tatggttctg attttacgtt agaaaatatc gtgttcttgt    49500
caaataaaaa gacgtagttg aaaaaaagtc agaagaacaa aaagaatgga gagtacttac    49560
ttgccattga tatgctttga gaacaaaagg tctaaccaat cccataatgg ctttcccatt    49620
cactactctc ctgagtaaag ccacctgcca ctcttttcat attttgtca ccaaactatt      49680 gttaccataa catcatcttt tattcagata actagttact agaataccat tcattttag     49740 ctagctttct taattacagg accactccca ctatttaact agaaacatat ggttgtttag    49800
tgatttattt tttagattct agggttatat gtagagtcac aatcaccta gacaaaggtt     49860 gatcactatg tagcaccggt ccaaagagtt ggaccgcagt gataactcca gccaccactc    49920
caagcacact acccttgaaga aatccgatgt cagtggtgtg accttcgatg gctcctacaa    49980
tggcggctac cacaacacta gctacattca aaattaatga catttcgtga tcttataaaa    50040
ttgtttaaca tggaatgtgg aatgaaaaca atgcaatgtg atatgttaaa atgatacata    50100
ccaaaaagaa agtatatttt tctaagaatt tggatgaaga tattgttgac aaaaagatat    50160
```

```
acttttctta aagaatgaga atttaagggt agagaatcca tacataagat aagttattaa    50220
attcaattaa ggaatgcata gacaacaagt aattcaggtt aaaggaaaaa actaagaaaa    50280
tggaaaagaa gatcccacat cagactctta tggtaagtag aagttgcttg acacatcgca    50340
tccattcaag aattttctct ttatctttt  gttaatatgt tttagttctt ttatcaaaca    50400
ctcatgtcaa gttgtcaact atatatagta tacatatgtg tggattcata tatgagaggt    50460
aagtacatgt caatgaagta catatatcca aaaccaatga gatggcgtct caagtttcat    50520
cttaaaagt  acgttagttt agcaagcatc tatagaattc aaaaaaaaaa aggggaacaa    50580
acagcattaa atgataagaa aatgaagata acttgtaaat ttaccggaag caagaatgaa    50640
gatgaatgag cccaacaaag ctcgttttat cgttcttgac atttgaaga tcacgcaagt     50700
aatccagaaa gaaacaacat atgtgaattt cagaagaatc atcttagaaa tgcccatgaa    50760
gaaagatgg  aagactaatt gattttttt  ctttctctta aagatatttt tgaatttgtc    50820
tatttatggg gtgagagctt gaattggaga gtggtgtgga gtgtgagaaa agagcaattt    50880
ataaggaaa  aaagagagaa aggaggagga gttgcattta agaagctgaa ctacccatac    50940
ctctaatcta cattgcattg gcgactctat tggcgcatgc atgaacttgc gcccacagaa    51000
gaatctaaat gttttataaa ataaaataaa agcaagaaaa ttgaatggag aaattaatgc    51060
agttttgaaa tatgaaaatg ggaagggatg ggataagctt gagattgaaa tatatccaat    51120
ttacattcca ctacgatctg aatgagttgt ttattgccat ttacattcta gtcattatag    51180
tggtagcagt aaacttccaa tcttggattc ttaatctagc aaaaagaagc tcttcattaa    51240
ccaatgttta tcaatgagtt tggatagact aattttacc  gcatttgttt gttagctcaa    51300
ctagatttat gtttcatata ggctatgaca cagacttgta tagtaagaag actagcatac    51360
attagaaatg gagatctggg ttacaactaa gattgagccc aacatgttgt cgtggggcag    51420
caaggtcttc ttatcagtgg atatgacacc actcactggc aacgatttta tgttttcgtt    51480
tatggctaca agtttcttca ttgatgaaga gaagaaaatc gctgtggttt ttaatcaaag    51540
caaagacagg aagcacaaca cagctttcat cattggacag gatggatcct tgaaagaagt    51600
ggatcttgga gaagttcgaa acagagatct caaaccactt gtgtcctctt atgttccaag    51660
ttcaatgcaa cttgaatagt gcattttaca aaacccataa tctatttctt gcactttac    51720
ttgtttcttt ttctcttttg tcatcttctt ctttgaacaa tatatagaaa tttaattcgt    51780
ctctcatact tcttttttgtt tgccatattt gacttcgttt tgttgccttt agttgtttaa    51840
tttacttctt ctgttgtagt agactcattg ctaaatctct gtttctcttc taacatttgt    51900
tatgtttgtg ttcttgcaaa taggcagctc tgctgttgta atttatgtag aacagacaac    51960
agagtaagct gcgtttaact ttgaaatttg caagtacgca tgcttagatt tgagtttccc    52020
atttttaactt ttgtccttgt cagttttaca aagtgcaagt ggctgctagg ctgacacgta    52080
gaagattgaa tgatttctcg gagttaagtt ttgtcctttg atactccctg gtcttaaagc    52140
atacttacag agtaaccgta gctgaatatc aacctcaagc aagtcatgga accatacacc    52200
ttccttcaat ccaccagttt tgggctggtt agcgctctcc tagatttatg tttcatataa    52260
gctaaccatt aaaagtttaa gagaagcttg tgtagtaaga agacaagcta atgagttct    52320
cagtagcctt aattcttctt ctttttttga ctaaatatga gcacttatag atgaagacta    52380
gtaatgcatt gattatgaga atactaaaaa gttaagatga ataatcaaaa aaattatttg    52440
gttagtatta aaatcttcaa atgaaactta gtcttaagat ttgttgagat ctttcatact    52500
atcgaagtca tgtagagtgg aggtacgtag ccaggcctag gagaagagaa gagaagagaa    52560
```

```
ggagaagcaa gctaagaaac tgaaagccta aaaacttttg aatgttgatg attaaaaaag   52620
aatagataca tgctaacagc ttatgcattt ttgaaatagt ttttgttaac tgtcgtgtag   52680
cttgtgtgta aatatgtcga cgacaagtca atgatgtcac acacactaca caaaacaaaa   52740
cactgcttca aactaccttc aacttcgagt ccattactat aagcaaaagt cccaaatcaa   52800
aacatcaatt ttcttgttct tgtcagctac tcaaacctca acatgttaca tatatttttt   52860
cagataaaac aaatcattct catcgttctt atctgaccag gaataattca atggaagtat   52920
gagtttgact cggtttcctt ttgatattag tcgtactttt caacatttta cctagataga   52980
gccgtcctct tataattatt catcatttca tgcttctcat gttacatttc tgcaattttt   53040
caactctttg attttatata atcatttgtt tcctttctta atcaaatcca tctggctaac   53100
attatttagc ttgatgcaat taaggtatat tatctaatga ggtgatgctt ccacgtcttt   53160
atattattat aatccctcaa caatttttaaa aaaagatcct gactttcaat tttctctctt   53220
gtttcttctt ttgatcatct tcaacaaaaa aaagttacga tctttctctc cgggtcatcg   53280
gaatttgagc tagcttagct aaagttccga tctttcctct ctgggtcgtc ggaatttgag   53340 cttttttaaaa tcatgggaaa ttgttttgcc aagaaccatg gattgatgaa gccacagcaa   53400
aatggtaata ccactagatc agttgaagta ggagtaacca accaagatcc accgtcgtat   53460
actccacaag cgagaaccac tcagcagccg gagaaaccag gttccgtgaa tagtcaacca   53520
ccaccgtgga gggcggcggc tgcagcacca ggactaagtc ccaagaccac cactaagagc   53580
aattcaatac tagagaacgc tttcgaagac gtgaagctct tttacacatt gggtaaagag   53640
ctaggtcgtg gtcaatttgg ggtaacgtat ctgtgcacag agaattccac ggggaagaag   53700
tacgcttgca aatcgatctc gaagaagaag ctggtgacta aagctgataa ggatgatatg   53760
aggagagaga ttcagataat gcagcatttg agtgggcagc ctaatattgt ggagtttaaa   53820
ggagcttatg aggatgagaa agctgtgaat ttggtgatgg agctttgtgc tggtggtgaa   53880
ttgtttgata gaatcattgc taagggacat tacactgaga gagctgctgc ttctgtttgt   53940
agacagattg tgaatgttgt caagatttgt catttcatgg gtgtgttgca tagagacttg   54000
aagcctgaga atttcttgct ctctagcaaa gatgagaagg ctttgatcaa ggctactgat   54060
ttcggattgt ctgtctttat tgaagagggt aaaataatca gactttctctt tagggtttag   54120 tacattttga tgaagttggt tgtctctagg acatagatag gatacgtatc aaggttctgg   54180
ttatattggt atcttgtgtc tcttggttcc gtgaattgca tgaagaagtt cagacctttc   54240
ttgatatacg gactaggcta gagaccgctg tttttgttct ctgatagagt ttgatgtttc   54300
ttactcttca tcatttggtg tttcttcttc ttgtctttgc aggaaaagta tatagagata   54360
ttgttgggag tgcatactat gttgctccag aagtcttacg tcgcagatat gggaagaag   54420 ttgatatctg gagtgctgga atcatcttat acattctact cagcggtgtg cccccgtttt   54480
gggctggtaa cgcgatattc tctcttcttt gttcctttcc cttttgagat ttatatgttg   54540
tgaataaaaa gctgaaaaca gaacattgga tatgcagaga ctgagaaagg aatatttgat   54600
gctatattgg aaggccatat cgactttgag agccaaccat ggccgtcaat ctccagcagt   54660
gccaaagatt tggtacgtag aatgttgact gcggatccaa aaaggcggat ttctgctgct   54720
gatgttcttc gtaagtacct tttgaagaca ttttacggag ccacaacaca atgcaaagtt   54780
ctggaagatt ccattatcgg ttccttcttg attctgagat ttgctctact gttttgtgca   54840
gagcatccat ggcttagaga aggtggagaa gcatcagaca agccaattga cagtgctgtt   54900
ctctcaagga tgaaacaatt tagagcaatg aataagctaa agaaacttgc tttaaaggtg   54960
```

```
aagtcaagat ttttcacata tgcaatgtga ttctgtggtt gtggtcctct ttttcgttat    55020
actcatgatg agattctaac aggtcatagc ggagaatatt gacacggaag aaatccaagg    55080
attgaaggca atgtttgcta acatagacac tgacaacagt ggcacaatca cttatgaaga    55140
actgaaagaa ggattagcca aattgggatc taaactcaca gaggcagaag tgaaacagct    55200
catggatgct gtaagttggt caaaaactat attttccccc attccgttcc tttactttaa    55260
gaactcagat tctcgggttt gtgattaggc tgatgttgat gggaacgggt ccatcgacta    55320
catagagttt attacagcaa caatgcatag gcacaggctt gaaagtaatg agaatcttta    55380
caaagctttc cagcattttg acaaagacag cagcgggtaa gtgacctgtt tcttctcgat    55440
gttattcatt cttaaccggt atatatataa gcaagatggt gagccttttc ttgggatcaa    55500
aatgtgtaca cagatacatt acaatagacg aactggaatc tgcattgaag gaatatggaa    55560
tgggagatga tgcaacaatc aaagaggttt tgtcagatgt cgactccgat aacgtaagtt    55620
aaaataattc atctcctctc tttatcttct tcttcttctt cttataagga aactgaactc    55680
tgtccataac ggtttgcctc tcttgcagga tggtagaatc aactatgaag agttctgcgc    55740
aatgatgaga agtggaaatc cacaacaaca acaacctcgg ctgttctagt ggacattgtt    55800
gctggattaa aagtcttttt gtttgtatct aatccagaaa aatcaggagc tgaattaatg    55860
tttgttcaga caaaaaccac gtaaagagga agatactcaa aactctgatt gcttgtgttt    55920
tgtattttgt tcttcacttc ttctgttttg tcctttgtgt tctgtactca ggctgttgtg    55980
atatgagaga aagagaggtt tcatttttac cgttaagatt ttgatcctga ctgtgttaac    56040
attttacctc agttcctcca ctttttaatgt gattctccat tccatcaaat gtcaaatcaa    56100
cgaaacaact gctaaagcag agcttttccta tattttaaca tattccggag gcgcaagtat    56160 cttttggcaaa tggcttggtt cgcctacaaa ttctccgtag tgggggtaca agagactaat    56220 taacccagg ctagtaggtt caaagaaaaa cataaaattc gaaagtgatt cattagaggg    56280 tgttttggt tcaagggtaa atacaatttt taatttaca aatgatacaa gaccattaga    56340
gataatgaga ttttctcaag gctctaatca tgtgatacgc cgaggagctt tctgcttttct    56400 ttatcttgga ctgttcatct cccttcatat ataatgttttt ttcttctgtt atcttaatct    56460
tagcagagca aacaaatctc tttccctgta ccgagcttct atcttcctca acgctgaaaa    56520
aatgtgaaaa acaataacaa aatgttttta acaatggct tatcaaatgt gttctgcttc    56580
ttgagattat aagactttag actactcaag tatgtgaatg cttccaagat gtaggagtag    56640
gatatacctg tagataggct taggccactt tttcttaag caaatctcgt tcaacttcgt    56700
tttagcatgt gtaagttgaa tctctacact atcttcatca ataaccatttt caacgggaaa    56760 aacttctgac aacttccgta acgcttcttt agcagcgatc agccttgcga tatctttatt    56820
ctcagctcgg cctgaagcca aaagctcatc atcaagatat ataacagcaa tactgacatt    56880
accatctttc caattcttga tgtcgattcg cttcttatgt ttatgacata atttaaaaag    56940
catagacaca ggttgaggtt gcttctgcaa atcgtccaat gtaactatcg gttccaaaag    57000
acccctaaag atctgcaaaa tcgacaataa gaaagaagcc cttaacttc agtaacaaag    57060 acaaaacaca caagagtaga tctaaagaag aagtagacac agaccaccca tagtctttgt    57120
agatcaaagt tgacatcaac atacacagct ccagctaaag actcaaaaag atcagctaga    57180
actttagggg ctttgactaa tccaccatat gacactgaca aatcatcttc tttccccacc    57240
gcctctgaga actcttttaac ctatcaaacg acatcaacac acacaacttg gtggtgaaga    57300
tatcacaaga atcactctgt ttcacataaa gaatcactct gtttccaggg ttcttcaatg    57360
```

```
caaagacaag ttttatggat tacctttca tctaaagaag gagcattgcg tcgaagaaat    57420
gaatagagac catgattaag agagacacga gcgagtttct cagtactaac attagctgct    57480
ctcaacagag acaagtcgtg tggctcaagg ctagggtacg ttaggtatag gtaatttgag    57540
attgctaaac caatagcact atcgcctatg aactctagcc gctcgtaaga aggaaagtct    57600
gtacacgagg tgtgtgtaat cgcttccttg agaagactct tgttactgaa tttgtagttg    57660
agtatcttct ctactgcttc catagactcc atctccgacg aaaccggaac gcttggtgct    57720
gatggggaaa gagaattgta gaagcggtgg atatcggccg aagacggcag tggtgatggt    57780
ggacggtgag gaagtgaatt ggataaaacta cagcgagtga tggccgggaa attgtactcc    57840
ggtgagatag agtgatccat ggtagagaga atctaaagag acgccaagtc ttctctgttt    57900
caattttcct tttaattctt tttgttttcc taattctatt agttttgact ttttcattga    57960
ctatagtcct caggacaaat aaggaaagta tatatatata atttattata ttggggcaaa    58020
atataattaa aaactttat ataaaggaaa tggattaagc ttttttctta aagggcaaaa    58080
attgcctaaa ccctaaagct gagattttc ttgctcagta ttgggtcgat gacgatgaag    58140
tgtgtgtttt gttgataatc tcgagtgtgg gtgatcgaag agcaaaggaa gtcccaaggt    58200
tagcttctta ttttgtttat ttcgcgattc taattgatct actttgtatt gagcaatttt    58260
ttgagagatt catgttttg aaatcgtgtt attggatgtt cttgtgagat tatcgttgta    58320
aatgtaaatg gtttcgaagt ttttgtttga atggattggg attttgtgc gagtgttgtt    58380 ttgttatgtg ttacattttg aagttgtgtt tggtttttgg ttgggatttt aggttttga    58440 tctcatggag ggagaagaga gtttgttgga tgctataaat gaagaagacg gatttgaaaa    58500
cttggaggat gttgaaatgg ttgatgttga agaaggggag attgttgtgg atcatgattt    58560
agattctgga gagaggcaaa atgatgatgg tgatggagtc aaagataaag aggcgatttt    58620
gggtgagaag aatggactgc aacagacaaa caagaacaag aggaagaaga agaagaaaaa    58680
gagaaaaggc cctgtgatgg acaaacccat gagtgtagac tggtaagtgt tctttttcta    58740
tatgctaata ttgttgtgta aattcttggt atagctgcct gatcttggct atggttgaaa    58800
cgttgctcat tgtttgatgt tttgttatgg caggtttgtt agggatactt gtagacgcct    58860
taaggagaag aagtcttaca tgatatacac agctgttggg tgtctcggaa ttgctgcctt    58920
aagtgatctt gtcaatgagg tatacactac ttcaagatgt tttctgtgtt attccagtta    58980
aaaccttgtt tgatctgtgt gtgaccagca gtggcaatct tgtttagctg tattgtttca    59040
cctgcagttc aagatattcc tagtggagcc tttttttgctg cttgtgcctt ttgctgagat    59100
gtagatggta aaacttcata ttttaggttg attttttttt cccttctctt gtgcacatct    59160 gtctttctc tgttttatt gatctagaca atttgtatga aaccataagt ggatagatga    59220 agttttatg atcaacagtg tcaaccatat tttcatgatc gagaccataa gtggtttgag    59280
tgagaccaac agtgtcaacc ttattttcat gatcgagaaa tgactgtcca catattcact    59340
actgctttgt ggattgatcc ttctgttact cccactgtat gcttttaagt tggttaagaa    59400
tatttctatt ccacttcgca agattcttgc caaagatatg attgatgatg gcaagaaata    59460
ttttttctta ggtggtagca attgagacct gtggaggtca ggtgactgct gatggcacta    59520
ggaaacggac aagtggtggt gtattgtgga acatcatcaa agcgagacag cctgaagctt    59580
atagagagat aatgaaaaag accaaggagt ttgaggtttg tacttgccta tcatatcaca    59640
acattcgtaa atatatcctg ctttcttagc ttaaatgtga aatagcagtc atgaagatgt    59700
tatatcactg ttttctatct tacacctctt tctctcttgc tctttgtctt acgctttcaa    59760
```

```
actttgcaga aacaatttag gcaaccaaac acgagaccaa aatcagggcc taaaagagat    59820
cagggtagct cctccgaagg acttgcctct ggaaatgtat ctgctgatga agctctggtg    59880
agcgagatgt gtgttatgcc ggtagctgag caaactgaat ccaaaccgga aaaggaaagg    59940
aaatctgttc atgagaggat cagggtacct gtttcatatg atgacctttt cagagatgca    60000
cctttggatg attcactagc acatcatcct tctgcttaag ctcatttata caccgtttac    60060
cttggacttt ttttaactag gtaaacaata tatctaagct actggatgac ttctcttgtg    60120
gaaagcaatt gttttgtcga gaaatggaaa gcattgattt tgtcgagaaa tgcattaaca    60180
aaactatata taccaactac caaagatttc ttaaatacac aaacttgagc acctcctaga    60240
aatttactac ataacatcag tcggcctaca ccattaagag gttcatgtgt taacttctcg    60300
ttacatgatg cagctgattt gatacaaaac atttgtttgc ttgaactaca ccacgagatg    60360
aattggtctt cctgggattc tctttatgaa ctgcttgttc ttttattgca cctctgtgaa    60420
ggcgtgattg ataatcttct taactgccat catcgcttgg acgagccatg ttaatattac    60480
atcacctctt gtagtgacct tgggttcata cctagcctct cagacaaaca tgcttggtgt    60540
ttgtatgtgg catacaaaga gagaggatca tattcggagg atccgggtca acttgtaaac    60600
ctgagaatat aaaaatggag tttgaatcaa catatgacag gttgaatgca tctatgaatc    60660
aattctcatg gcagtagata gcatagagag agagcaaaag aaggagagag agagagagag    60720
ctgacttggg cagtccggct aggcaaaaac acctctaagc aatttctttg accatcaatt    60780
ctgcacaaat gtggattcgg ttcaaaatga tgaacagata acatccttat atctttgcta    60840
agtaggatac tataacatta aactaaaatt acaaacctct tgctaattga ccgttgaaga    60900
tagtggtctt ctgttacaat cccttgaccc ccatacttta cttcatcgga gttcagtatc    60960
atctgcaaaa tccaggtaat attctcaggt gaaacgcatt gaacaacctt atagtggagt    61020
tcattgttct atcaacgagt aaaaacgcgg tagcaactgt gtttcatgga gagcaaagca    61080
gtggtttcat tgacagacac ttattaaaga tgatagatga tgggtgcaat atctaaacag    61140
agaatggaaa aaacttacgg tatattcacc agcttcctct acaccgacat catacttttc    61200
atatgaattt gatgggtgga agttaaagat aaataggaaa ggaccccttg agaaagaaat    61260
cacctgtaga gaacaattag ttgactagta agcaggctca ttgtacaaac tctttcattt    61320
ctgatgctta ctttaggtag tctcattttg ctcaggttta cactgttatt ttataattct    61380
ataaatgtat ttggagaatt cccaaatgtt gcaggaagac agttggttta tttatttttcc   61440 gcattagctg aataatatcg tatataaagg catatacaaa cactagcatg ccaaagaatg    61500
ccaggaactc attttttcaga ccctgaaccc aatcaatttt cagtggaaaa taaaagagaa   61560
aaaggattca attaccatat ttgcatcatt cacatggtgg atgctgggca gacctcttga    61620 aaggatacccc ttgctttat ccaagtccat tagctcctac aaataaagaa cgagatcagt    61680
agctaaaaag catctcttct gatacaagag gatatatgct tggaacattt tctagtcctt    61740
acatttaaaa gatatacaat taaaacttca ataagaaatc aagcatttag tttcttctga    61800
tatgatatcg gcagtaaagt tttttaagtt cgagttctga caactttctc ggcttgataa    61860
catttatttg ccgccttcat agactaatac agtattaaat tgctaggaaa tttaaggaag    61920
aaaattttca gagatgctaa caaaatcatg gatatgaag ctgcactttt gtaaacaggt     61980
ggtaatggta agactgatac cttgtcaaag gaaacaagt gatgatgcac tccactttcc     62040
agcaggtccc agcggcggtt agcaagtgaa aacgagaagt tattgctctg cgttggaaac    62100
tcaaccctct gacacaagga tgaaacgtca gaatcagaaa catgaagatg atgtctttag    62160
```

```
aacagtggga gtttgtagat ttacctcagg atgtccaaat tcatttccca tgaaattgag   62220
gtatgcacgg ccaccacttg taaaagtaat cagtctaatc atctggtcgt ccaagcaatg   62280
acaagaaacg ttagctttca gaatataagt gaaacaatat agataaaaga caacagaggg   62340
caataattag acaatcttcc agatttcata ttttcacttt tcaatgcaaa atcaaaata    62400 atatcaaatc ttattctaca gttgtgttct catcaggata gaggtatgct aagttcggga   62460
agtagtgcgt aaaggactaa gaaagggata ccttatgtag tgaaattccc ctgtctagca   62520
attcttttcc tccaggagaa ccattatcga ctccaccgaa taagatttca gcaaatgaac   62580
gccctcctga tatggactgg tggaaaggaa aagtagaata acaacaatg tcaatgcaac    62640 ataaaagttt agttgtgtag tagaaatgaa aaactaaagt tacaacgtag atacttggtt   62700
gtgattttcg gcatagctga gcatcttgtc tgcatactct ttgttagcca ccaatgtact   62760
gacaatctgt agcactggct gaacatcaga caacaggaca aaagtcttgt tctgccatat   62820
ataacaatga aaacgtaaaa gctataacct tgctcatgct ccattcatta tccggtacat   62880
tgtcgaggag agaaacccac atttctgacg cagaaagatt cacataataa tcaaatccaa   62940
gtccaccttg agaaactggc tcacacaacc cagggtaata tgttgcctaa agcaaaagg    63000 aaaccttgtt aagttctata agtgggtaga tagtgaaacc caacgagcaa cgattcagat   63060
catcgacaga aaaattaatg caattttct gtcaataaga atcttaaact ttttaccac    63120 tgatatacat ctaacattcg taaaagataa ttcgtcaaga acttcttttc ctgcgtatgg   63180
ccagtttaaa ttggcttaca caagccagtc gacactatgg ttaccgtcat gtgttgtaca   63240
tgagaaagca tatatataca tgttacatgt tactctctta cacaactttt tatctacata   63300
tagcatattt ggaaaaagca tgaaaagttt tcactaactg gcagtaacag tactaattct   63360
actaaccaac acttgcaaga ctaaaaacta gagataattt agaagcaatt atgcccagaa   63420
atatacttca gagacttagt gatattctat gatgaaagca gtgtcagtag ctagtccccc   63480
tcaatactat caattaagac aaagcaattc aataaggatg aatatttaat agctttaaac   63540
aaaagcatga ccaaaaaaaa gtgatgtgta gcttacatcc tcagcaattg ttattatatt   63600
tggatgttga acgtgcagga tttcattggc caaaatgagg tacatcagag catctcggtc   63660
aacatactga ttgcaatagc tgccaacagg aaagacgtca acagtttgac caactgtaat   63720
caaaattata caaagaggtg tgtagtctca tagatgcctt actcatccaa atcgttgtta   63780
aatgaagcaa acccattgtg cgtgtaaatc atcgaggcaa gcgagtgaaa ttggtaacca   63840
tcaacttgat actctgtaat ccacctgcaa aagccaaatg caacagcatc agattcctat   63900
aaccaaaaag tgtgcaacac tttcctacta taccaaaaga gtgagtacaa ccaatacatt   63960
attaacaaac cacttaataa tgtagctgcc tttaccagtt caaatttgat attagaaaat   64020
gaagaacatc caaatcaccg tatttgaaca tccgggtgcc ccagtgtttg tgatgccccc   64080
ttttacctat ttccacgatg aagaaaatgg aacattgtgt ttttagacag gcccatattc   64140
aactatgtca gacatgtttg acgtcatctt tggacgtaca caagattatg aacaacattg   64200
gttgtaacac gaaaattatg gtgcatactt tctagttaca taccaatgac ttggacatca   64260
acacgttaga ataaaggcat gcaagaagtc ttttattcat gcaagaactc atgaaataaa   64320
taaaaagtga actactatta tggaaattac cataatgaaa atagcaatca tttgaaccat   64380
cgaagagaga aagcccaacc atctgatcag ctgctgcata agaatgcacg atgtccaaaa   64440
agacaagaag tcctaggcct gtatatcatg tgccttcgtca ctacatggtt atacaacatc   64500
aagaaaacaa gaaagacgag aaataattac catgtgcctc atcaaccaac cgtttgaaat   64560
```

```
catctggcgt gccatatcgg ctactggcag caaagaagtt cgtaacctga aatggtgatg    64620
gataccaatt atgacaaatg aggtaaaaaa taattttcat aaatccattc attcggttta    64680
aagataagtg acagtagttt ccttaataat ttgtaaaatc tgccatatta tgtactagga    64740
attctggtta ttagcttgag tgtagttcca tagctgttat ttttttcaaa tgtaactagt    64800
aaaaggacct gatcaggact aaatgacata tgcaatgccc actaatcaaa attgtttctt    64860
tccactttat ttctatcaag ttgttctctt cttgttccat attttcatc aattctctct    64920 attctacact attgtctatt ttttactaat cattcggcaa agaccttcag aacctttcat    64980
gcacagtgga cagcaaagcc aaagacgata taatcataag aactggaggt aacataagac    65040
tatgaataac agctatgctg accctataac cagactaaga agtagtaaaa aagaaagttt    65100
aagtgctaga agtttagctt gctgacccta taaccaacag taaaataatc cttgtgctca    65160
gggacaccaa tcaactggat tgcattgtat ccagctcttt tcacatgagg aaggacctga    65220
tgtttgatag gccacagaaa aactgagatg tgtgcataat aagattgcaa gtaagaatac    65280
aatgaataca ttaggaggta ccttcttagt aaattcttcg aaagttgaaa cttttggctc    65340
ggacccactg attccaacat gacattcgta tatgcgcaag gactctggaa cttttggctt    65400
ggaatatttc cacttgtatg cagcttcagg agaaggttcc caatgaattg cgtaagcttg    65460 cttttccttca tcctctattt tagagaaaaa tgaatacatt aataataaac aagatacatt    65520
atcgtggaaa tattaacatg acacatacaa aaacgttatt ttaaaagcat ctctgcatag    65580
aaacatcaag cagtagcgta tagaaacaag aaaggtttta cagcttctct gaaaaatgtt    65640
gttcagtaag actgttaatt tagtgcttac aaagttctag taactctgga catgaaaagc    65700
agagagtaaa aaaaatggaa aaaaactcct tccgtttgtt caattcgtgc aaatacttct    65760
aagcatgtgt catcagatga aagaaaaact gaatgcttgc ttccatatat ttatgaatgt    65820
tatgaaattt gttaaatttc atgtgctact cctaaccata gaaataccaa acgctgtcat    65880
acctggttgc acatatgtag cccaagcagg cactcgttca agcggtccat caggagtatt    65940
gaaatacaat ctatacttgc ttccatgtgg aacagctgga atatattttt gcaaccatgc    66000 cttttcttcct ttacgtgtct ctaaccaata tggaatcgga ggttctttct cataaaattt    66060
ctttgtccat tctggagatg tcacgacatt aaaaatatca tatggctttc cttgaccttt    66120
atcaatgatg tcgcatggag gtagattact tggcgggtca tctttatgct cctctttcca    66180
ctgtttatat ctcgtttctg catctggtat atctccaagc tcttctaacg tttgtggact    66240
gttcgggcca aacatctgct cgtatagttt ggcaggaact tcaaagcggt ttttaataaa    66300
ccgatcctca ccaggttccc aatactcatc attagctttc tggaagattt cttcagctga    66360
tacaccacta tcacccttat catagtcatc gacatagtta tactgctgaa agtatagttc    66420
atctggttct tcaccctctc ttaacttatc ttcaagaata atgaaccaat acccataatc    66480
atcatggcca aataggccct ctctagctgc attttctgta ggcgaccatc cattgaaatc    66540
tccgattata gccccataac gagaacctga atttaggatt ggttagtatt ctcaaacttc    66600
ccaacataca tatcaagttt ctgaacatca ttcattctgt ttcagaacca aatgtaagta    66660
atgaactgac taatgaaatt ttaagattag agcaagagac agaacctgga ccccagtcca    66720
taaagtcaac ccggtgttcc atatgtcgat gcatccccaa taactcaaat ctacaatgaa    66780
aagaaggcta ttcattagac aaagcatttt ggatacacat cagtcactaa tccaggatca    66840
aaatcttctc ttgaaagaaa ctgggaccaa gaggatacat accctgaagc aaaatctctg    66900
aaatcgaaat ggcgtttgaa aatctcatct ttaaggtctt tcaaagcttt atgcctacag    66960
```

```
aaaaacgaac aggcttatta tacacagctg taatcaaaat tgatcctttt ttgttgccca   67020 tttttttcaaa atcaaagttg atacatttttt atacctttcc cggagaaatt gagcaaagat   67080
tctgtcagca attccgagtc tggtgagaaa cccaacaggg tcaactccag cctcagcgtc   67140
gctagtgctc tggctctgac tcttcttttt ctgtttctcc tggcgtggtc tctcggcggc   67200
gaagcaagtg attttcaact tgatcttcct gggaaaattg actcctgaga ttcccaggcg   67260
ccgtttctcg gaaacgacaa gattgtttgg gtggaaagag aatctggttt gattagagag   67320
ggacaccatt tttgttggtg ctacgaagaa gatttgttca tactctcact cacactcagg   67380
gttttagtct ttttttaaga taagagaggt ttttgagtcg actcgttata agaacgacg   67440 acgagttcac tcggtattcg gatattttc tcaatttgaa atttgaacca aaccgagcgt   67500
aatttaaacc ggttcaatcc cgaaccgatt gataagaact acatggattt gtgatcttga   67560
aagtgagatt tctcgttttt tatttacttt taattaaatt caacacgagt atggttttct   67620
tttgataaat ttttaacatt cacatatttt tacagattta attgaatttt ggatgccaat   67680
ttttggttta agcaccggtt ttgcccttct ttacagcaat ctccaagttt cttcttgtga   67740
tttgaagctc tcttgtgtag taatgcattc tatctataac catggccaag aacaagacag   67800
tcccttttca cacacataaa aataaaaata aattaagaat tagatccaaa aaaaacacat   67860
aaaaatggtg tgtgaaataa aatggtgttt taatgtcact atttacccat gaggaaagct   67920
tcgaggaggc gattggcaaa catgacttga tcggtcgagt tagctacacc accagattca   67980
gagacccttg tgtggattg aatagtgctg aacataaccg agccaaacaa cacaagcata   68040
gtggctgcga ccgttttcgc aaccagtggt gctcgacctt gctttgatag gtctagcagt   68100
ttcaccacca ctcttctcgc tggagtcccg aacccgagtg ttaatatcag gacggcttcg   68160
attgtcacga ttgtgaatag aagttgaaac atctctacga acatttttta ttagtacatg   68220
gagaagttta gagtggatca atccaaaaat gggttcaagt tgttataaaa agtgttgatg   68280
agtagaaaga ataagaagtt tgcttggtgc gatggtaact gataatatat aactaaggat   68340
ttggaatgga atactagctc atatgctttg tgtgctctca tgattcaagg aacggatgat   68400
tttactctct cttttttttt tttgtagttt aattatttcg agatttagtt tgttttatta   68460
aaagaagtat taattttgtg aagaaaaaaa atataacaag gaaataacaa tcggaacaaa   68520
atatgcaaaa ctctttatac attatttgaa actctttaac aaaaaagtat gcaaaactct   68580
tgaatttgag atcactgaat tcaaaatcct tgtcaaaatt ttgtgttatt catatagtat   68640
tttaaaatgt tagttaaaat tcatttttta tccaacatat tgttttttaa tgttcaagta   68700
tattcaaatt aaacatacaa agactcaaat acaaaaaaaa actttattat tctaaataaa   68760
ctttattatt tctaagtaaa attcattttt aatcaacata ttgttcttca ctatgttgca   68820
tgaaaacgga aacggaaacg cggaaacgaa acgtttcaaa actgaaaaac gatttttttc   68880
taaaattagg gtatggaaac gttttgaaaa cgtatacaca cacatattgt atatatatat   68940
atatatactt taaataacaa aaatctaaaa cataaatatc aaatagttta actaaaattc   69000 taaaagtaa agattaaaaa gcttaatctc aaatatttag accatcatct tcattagttc   69060
catcaaaaat catatgaagc atatgaaatt tgattcgtcg ggagaaaaat cttaaaactc   69120
gcgtctccca aaattaatta aatcttgata ttttcaaact ttttaattat taagttttca   69180
aagtaaaaag acaagatttt tcgacgtgag tttccattga gtttccgaga gttttcgttt   69240
ccgaaacatt tcagaaacga gaaacgcatt gtggagagag tttccatgca acatagtgtc   69300
caagtatatt caaattaaaa atacaaagat aaactttatt attctaaata cattttaat   69360
```

```
aaaaatcgaa atcgacaaga tcgattttga aatcagtgaa ttctacgaca ctaagatttg   69420
aaatctatgt agattttta aattaaaata gaaaaactat taaaccttct ttacttttgt   69480
tttttctcca tatatactac aaactaataa tataaacaaa aatactagct gtgaaattga   69540
atgtttctgg tgtgtcatga gtttctcatt caacgatcac ttgatcaaag aatacaaaat   69600
tttgttaatg ccaatgattt gcgtaatcta tatattaaat tctatttgaa cattcaaaca   69660
atcgctgtat atagattcca ttgataagat gcaaacatat atgacattga cattttatct   69720
gtctgtgatg ttgatccggt catcttcatg ctgttcaggg atcttatgac acatatgtat   69780
gtacatgaac atcgatctga tttagcatat taatatatat aattacaaaa tactaaaatt   69840
atgaaatcat caaatactca attaacaaaa aatatatttt tcaacaaaat caactagttg   69900
tgattataac tttattttat gtttataaaa agactataag cagatatata tataaaaaaa   69960
aaaatgataa atcacactat atatgaattt actgcggata tatcaatcca cctaagaatt   70020
aatgaattat gatctccaaa actttgttag aaaaaaatat attatggaaa aggaacgtgc   70080
accatcttta tcagttacaa atcaaattcc aaattttagc taaaaataat tgattttctt   70140
ttaatattcc attcgtatta tgtggaaacg taatgtgtct atatggactc catgtctagc   70200
atgattaaat gaaatgaact tttgccattt taagtcgtgt ctcccaaatt gtctttcttt   70260
gtttgctttt ttatatgcat cgttcttcca caaatcctac gcaaaagttt gattgaatgc   70320
aattctaaca aattcagttg tttgttacaa ataaatgaaa taagaacaat caatatttgt   70380
tgacaaatat tgattgttta ctgaaagtat tcaagtaaat caaataaaca gtaaattata   70440
aaaacacgtt attcatgtgg gttcactttt tttttttaat cttttttaag tttggtcaac   70500
taggggtgtt accgtgttat ttatatgttt ttcagtggga tatcccacac taaaattat   70560 tgtcattttt ataagttttc aacagctata gaaatttggc aatagcaaaa aatgaaaggg   70620
attattgttt gaaatgcatt ttttgggaaa caagcttacc aaaataccat tttgaatagt   70680
ttatggattt tttcattttt atacatttaa caatatactt atttcaaatt ttccctgca   70740 aaaacatgta ctttatatca aatactaatt tttaaaaatt aaaaaaaaaa acgaataaac   70800
tcaaaaataa cgagtaaaaa tgtatgttaa attataattt ttttgcctg ataaatgata   70860 aaattcacaa aatagtttaa gaaggggcaa atttaacgaa tgtcactcta caaagaggca   70920
tacccgcaaa agtcgatcat tggtcaatac tcaaacataa aaaattacaa ctagatgttg   70980
acagcaagaa aattactcac tagcttaacg tcatcgaagt agttttttcca taccactgac   71040 tcaaatgtga accggtttct taactggtgt atatatatct agaattttc tttcttattt   71100 ttcgaccgaa aattgtaagt gctatgtttt tatgtaacat atattggctt tcacttgccg   71160 attttttttat ttatctttta cttctgtaaa acctagttta cgtttcttgc ttaaatcttt   71220
tatttatttt aaacatattt ctcatttaaa tcactggaat tgatgcgtca aaaatcacta   71280
taattaattg aaatcacata atcgcttagt caaacttgag tatcattcaa aagcttata   71340 ttatatttag ctttatatac aatttgttcc aggctcttgt cacccatgta aaaagcttca   71400
tatacaactg tatgtatata tatatatata cacatataac aaaatgtata tattatatag   71460
tatatgtctc ttcgttcaca tgtacgatat tgtttttag aataatgta aggttaacgt   71520 atatataaaa aatggaatca agtgatgagg caccagttaa gaaatacgg taaaaaacca   71580 attgacgatt tttatcatga actgtttgaa aaaacaata caaaaaccta gcctaaata   71640 attccaaatt gtttgctcca acagtccaac tgtttgaaat taattaatta cacacagtta   71700
gactactgtc taaaataatt tattactaat caatcttgta aaataaattt aaatatttcc   71760
```

```
ctaggcattc taaacctgac aaattggctg tagaaaatac cataaataag aatggttcaa    71820
atgaaaaagt attaaatgtt taaacaaaca aaaaaatctt ttttgttgag acttgcacgt    71880
catactctgt tgtttcttaa tctttatccc acatataatg gaattagccc cacgaaactt    71940
agtctatctc attaatcttt ctttccttca atctgtctgt tgctctctct ctctctcaca    72000
cacactgatc agccatggga gacgaaccac ttcttcagaa agtcaagatt caagaagaca    72060
ttgaatccgt accacttctt cagaaagtca agattcaaga agacattgaa tccgttaaag    72120
gaattcgtgt aaataatgac ggcgaagagg acggtcccgt tactttaatt ctactcttca    72180
caaccttcac tgctctctgc ggcaccttct cctatggcac tgccgtaatt ttcttcatct    72240
tctcttcttt ttttcttttc tctatgtttt ttctagggta aacacagaat ctaatcccat    72300
aattaattag ttaccataag atttaaccaa aattgtaagt tatagctaat tcgttatcta    72360
tttgaaaaag ggtccaaatc aaagagaatg atgtatcaac aaggattatg ccgtcgcaga    72420
aaaagcaaca tttttcaaat gattgataac gacatgaata ttataggttt atgttatttt    72480
tgtgtaggcc ggctttacat caccagctca aaccgggatt atggcaggac tgaacctttc    72540
tttggctgag gtcagtgctg agttgttaat tttatttcca ttttttattg attagttta     72600 ttaatttgtt aatcgttgtc ttaaaaatat atagatggat tgtcacaaaa aaaaaaagta    72660
tatatgagat agaagtatat ataaaaagta tatattagtg acttagtgtg gtagaaaaaa    72720
aaaatgcaaa gaatcattta tctaaaaagt aattagtctt caaaatccaa tatttgcata    72780
taaaaattgt ctatttatta gagttcaaat tttctactta aaagtatatg attgttttg     72840 gtaatggcgt aagagtgtgc gctagtgtca ttgttaaaca cttttgcaga ttttgatcat    72900
cttttaattt aaatattagt tataaccact ttaatgtgta ttactgtatt agaagaaaag    72960
gtactcaagt cattgttcgt tcatggatgt agttctcatt ctttgggct gtcttaacaa     73020 ttggtggact tgtgggagcc gcgatgtcgg gaaaacttgc tgatgtcttt ggtcgaagag    73080
gcgtaagctc tcttttttat attttttaat ctcttttat catcatgact aaaattacaa     73140
ttccattaag gagtttcttt acacatatat tccaaacaaa agatatatag cggtttcatg    73200
aatgactata cgcaggcttt gggggtttca aactcgtttt gcatggccgg ctggcttatg    73260
attgccttct ctcaggtttc taacgatcat tttatatatc tcaatactta tttaaatagt    73320
gtttgtttgt cacgtatgac ataagcttaa gcgtttgaat gtttcaagtt ttaccaaga    73380 aaaactctgg tttagagttc cctcgactat tattctagac aaaaaaagat ctttcaaaat    73440
caaaagttta tacgaatagt taattgtttg ctgtttctta agtattgttt atcatatata    73500
ggcgacttgg tcccttgata tcggaagact ttttctcggg gtcgcagctg gcgtagcttc    73560
ttatgtggta cgtagttaaa taggtcgcct ggtaattact gttattgac ttttactcca     73620 agcaaccaat ttaagtattt tttgtcatta actccacgca tctaatctca ggtaccagtc    73680
tatattgttg aaatcgctcc caaaaaagtt cgtggcacat tctctgcgat taactcggta    73740
atacactgga aaaaaaaatt taagagaaat tttaatttta ttagtttgaa atcattcatt    73800
tttttttttt ttggttgata gcttgtgatg tgtgctagcg tcgccgtcac atacctcctt    73860
ggatcagtca tttcatggca aaaattagct ctcataagta aatactggac tctgcctatg    73920
aactaattat aatatttaaa ttattttta actatgttaa attaatcaag ttgacaaaat     73980
atttacttgg tgttgtttgg agttgtgcag gtacggttcc ttgtgttttt gaattcgtcg    74040
gtttattctt cataccggag tctcctaggt ggctggtaat tagttaatta gtcttgttac    74100
tttttagtaa ctaacatata caaataaaac atattaaaaa ttgttactac aagtaaatca    74160
```

```
aaccattatt aacagtttgg tatctttgta atttatagtc tagaaacggt agggtgaaag   74220
aatcggaagt ttcactccaa cgcctacgag gaaacaacac tgatatcact aaagaggctg   74280
cagaaatcaa agtaaaacaa aaaagagtt cgaaaagtg acactatacg taaatttgac    74340
aaaaacttat tttgattgtt cttttttttt cttcagaaat atatggataa tcttcaagaa   74400
ttcaaagaag atggtttttt cgatctcttc aacccacgat attctcgtgt cgttactgta   74460
agaattttat taattgaaat ttgaatgtct ttttgagtaa aaatgcgtta atactcttgt   74520
aaattttgta ggttggaatt ggattgctag tactacaaca actgggaggt ctcagtggct   74580
atacatttta ccttagctcg atattcaaaa aatcgggtaa attaaaactc aaatgactta   74640
ctgaaagaga attattttgt ctaatataat gaccaaaact atactattta atatgcaatt   74700
taattatttt gtagggtttc ctaacaacgt aggagtaatg atggcgagcg tggtgcagtc   74760
tgtgacaagc gttttaggaa tagtaatcgt ggataaatat ggaagacgat ccctttaac   74820 ggttataatt tgttttatat ccttttaatc agtgaaactg tataatatat agtgggtaac   74880
cagaagttaa ttaacgttgt ttctttgttc tttctgtgaa ttacttattt acaggttgcg   74940
acgatcatga tgtgtttggg ctcattaatt acaggactat cgttttgtt tcaggttttt    75000 tttttcctga aataaaatta cttattagtt aaataaaaag ttatatgatt tatgtacatt   75060
ctactctctt tttttagttt gttttcttg aaatgagttt tattactatt ttttttcttt    75120
tcaatataac taatacaatc aaaactaata tgcagagcta tggtttactt gaacattaca   75180 ccccaattc aacatttatg ggagtgttgg tacgtactac tacataatga tttcattctg     75240
tcctcctttt ttcttttata aataaaatca tgtcctcctt cttatataaa cataatgata   75300
tatgaatatt tcgttcctcc ttttttatat gattacatag acataatcat ataaaatcat   75360
gtcctcctcc tttttttttt tctttagac aaaaagata aaaattaata tttcttaaga     75420 taaatttac cgactcttgt tacaggtttt tctaacttcg attacaatcg gaataggagg     75480
tattccatgg gttatgatat ctgaggtaat catttgtctt cagtttgatc gtaaccagat   75540
gaatagttca acaatatatt tatgttcgac aaaaatattt tgtatatagt caaattcaaa   75600
agcatatata aagattatga atatctatga ccaggttaga tgaataatga aacaatctga   75660
tacacagaaa aaagaagtag atctgatcat ctgataagaa aatgttagaa taaattattt   75720
ttcgtataat ttaaaatag accccttttgg tatgataaca taatacaatt tattattttt    75780
aaaataaagt ataacataat gacttataaa ccataataac ttgataaatg aagtggttat   75840
aaattgtttt aaaacgtggc tacatttaaa aaacaagaac tcgattttat ttttatgtca   75900
ataaaaaatg ttccttattg gtctgagcca gtgaaaaata ttactaagtg ttctgcttct   75960
gtatgcagca tgcaaatagt tattacactt gagaatatta gttgggtgct aacattaatt   76020
taagataaca ttaatttagg atataatcta gataaaaact aactagtagt tttcaatata   76080
tctaattatt atatttgtgg gataattaga tgacaccgat caatataaaa ggatcagcag   76140
ggacgctatg caatttaact agctggtcca gcaattggtt cgtctcttac acattcaact   76200
tcctcttcca gtggagctct tctggtaatt tacttcattt tacaattgtc tctaagtaaa   76260
taatgcattt actaactttt gatcaaattt taatcatttg ttgatattta aatcataggt   76320 gtgttttca tatatacaat gatatcgggt gtgggcatcc tgtttgtgat gaagatggta    76380
cccgagactc gaggtcgttc gctcgaagaa attcaagctg ccattacccg ataactttgt   76440
aaaatatcat ttacttggtg tcaaaattca tataattgta tacatggcct ccctcactta   76500
tcaatgaatt cagaattgtt tgtcccagtt tttaaatgct tgattttgac atcattcacc   76560
```

```
aaacaattgg ctctttttatt tttaaggtt ggttggttca tgttttgaga tacatttcca   76620
tacaagatat aaatttaaag cttgaacaaa tatgtactat ttgagtttaa attttttggat  76680
ggtaacatat caacatcact aacacgaaat cattaccgct ttttgccatg atcagtaata   76740
atttcaatga aacaaaagtt aatttaccaa gtatatatat acagtttaga gtacgaacat   76800
tggaccatcg gagttattgc tatatatcca accatggcca gttaataaat agtccagata   76860
tatgtggtat tctatgttat tataaaaata ttttttacca ctgtcaaata atgttgttgt   76920
tcctttggt tacgatccga aaaattaaac agatctaaaa tcctaagaaa aatcgttcac    76980
gtcagtgaaa tagtcaaata taaagcccta tttagatgtt caatgttctt tttttctctc   77040
atatttagag aattagaggt attaatttct tgttcatttt tagtttatat ttgggttgta   77100
cggtattaat acctcattaa gaaagttgca tttagagttt gattccattc aatgtagacg   77160
gtacgtttca aattcatcta agaatccacc taaaatttat tgatttcaaa ttatataaat   77220
ttacttggag gatgcatctt tatatttctg catgcttttg gaaatagggc tttatttacg   77280
tgtttatggt tataaattaa atggtcaagt atttctcttc gtgtttacgt tgagtaacag   77340
tcaaatcgaa ttgaacatgt caaagaaaca ctgaagaaga tatagactgg ccgggtcacc   77400
aagtagagct cgattatttt ttctaattca ttcatttatt tcctcaaagg ccgataataa   77460
cacaaaatca tggaccgaat cactttagat gaataatata ttaatctttt ttcataagac   77520
tttggtacgt aaaacccatt gccatgcatt ccattccatg gtttaacgtc aagatcttat   77580
agcttctcat caatgatgtc caccaccgaa accacctccg gcaccggctc ccccaccgaa   77640
accaccacca ataccgcttc cgcctcctcc tccaaaccca ccaccgccac cagctccacc   77700
tcctcctccg agtccacccc cagcaccagc tcctcctcca aaccctccac ctgaaccacc   77760
accagcccca ccgccaaatc ctccaccagc accaccaccc ccaccaagac caccaccgct   77820
cccagctcct ccaccaaatc ctcctccagc tccaccacca gctcctcctc ctaaaccgcc   77880
accgcctcca gctcctccgc caagaccgcc tcctccacca aagccgcctc ctccaccaag   77940
accactgcct ccaccaatac cgcctcctcc accgagacct ccgcctggat ggtggaagaa   78000
tgtctttttgg tcctcgagac cactcttcag cttcctgtta gcgacactgg caaatgaagt   78060
gaaagcaaaa gagccgacaa gtaaggcaac aagaaagagt gacttggaag ccatgtcgat   78120
ttttgtgttt tgcgtatgtg atgatgagga actctatcag ccaataaggt gtttatatag   78180
accatttggc atgagctgaa gaatcaaaca attgaataaa aagagggaga gagtaaagtt   78240
ttagagtgag taattatcat taattcatct gcccatctaa ttcatgttgg caaatttaat   78300
gcaatcccta actaccagtg ttgacaaaca tgttactcat ccacatgtag tagacccctt   78360
ctttattctt tgtgttagta ctacttaata gtactcattt tcttgccttt cacatttaaa   78420
tttggctgca gtatttgatg aatctgagat tttagattat tcttatgtcc ggagaccgga   78480
gttatttaat gttttttgtta atgtgttttt tagtacattt tggtgtccac cattattaaa   78540
gaaaacaaca acaaggtatc tatattttca tgtttacgat aaataaactt tacacattac   78600
attggaagag aataataagt atgaaataat ttgttttcac tacatttctt gacttggaca   78660
aggttaattt aaattcggga tctgcctcgc actggcccat ggtataaaca atctcgttgt   78720
ttaatgcatt tacgcgagta aaatattcat catggtgact gtttgtgatt tttataggaa   78780
agagaataat tatgcaacaa gccgatatgt tttcaaaact tggttctctt cttggattga   78840
atgctctctt cttaattacg ttctcatcca taatttgaac atctaattaa taataaaatt   78900
gtcaaagttc cgtggtccca gtagactatt ggcaataagt taatatatga aaataactta   78960
```

```
aaaccaactt taagtcaaaa tttgatctta atacgattta attagatgtc tgaaaaaagt   79020
ttgcgtaatc aatagattgt aaatctagct atgattagaa ttgttaacac attgttctat   79080
aactcaaatt actaatataa agtaatcgaa tgttacctat tacttaagat aaaattttac   79140
ggggttaaaa gtctgaaaag ttatcattta aatgtggcta atagttatac atgaagacat   79200
gatacatggt acaatactac aattacaatg accttggatc tatataccat agtttgtctc   79260
ttgaaaccaa aattatggag attttttattg gtgatctcat gtgttttact aatcatcctt   79320
ttttcttaca caaatcaatt atccgaatat ttacttacga tataaaaaaa gtcacgattt   79380
caaataagtt ttagttagga tatttaatat ctatggatgt tttaaattat cgaataacaa   79440
agaaattatt taataatgat tgattttcca tattgtatat atatatatat atatatatat   79500
atatatatat caatattggt tatgtatgat atatacataa ttttattaac gacttcattt   79560
tatacagata tttatgcatt ttttccttta ggacatactc cacatgtaaa ttttatattt   79620
cacaattatt tgaaatttag tgaatttacc aatcgaatga atatattctg taaaattggt   79680
tgctgatgga aattcgaaga aaacaaggcc gttcaaaatt gattgaaagt gttaattaaa   79740
ggatgtttca tattggtcac aaatgattgt acaatcaaat tattagtctt catgatataa   79800
tagaaattct ataaattaat atttttaaaa ttaataattt ttgtcggtcc caaatcagaa   79860
caatgtaaaa attaaccaaa atcgataaga taataaaata ataatttttt ttcaaatctc   79920
tatataaaat tatggtctaa ataatatcat aaatattaaa catacattct aagacaattt   79980
aatataatat aaatctagtg ttgtttgtct ccgcttaagt gtttacggta atgtcgtaga   80040
tataaagaca taatatcttg caaaaagaaa gttaataaag taaaaaataa aaatttagta   80100
ttgtgtcttc cataaatatt tttaaaatta atattttata ggataatata actataaatt   80160
aataaatttt atgatcgaac attattaatt tatagagctt ccactatata aatatattcg   80220
atgaaaagaa aataaataaa tagaaattct aatttctgca atcggacggt gagaaaacgt   80280
ggaaatttaa ttcgacggtg acaacgtttg ttcgataatt agtttttttt tttttgtcga   80340
ttgtttttct ttttcttaaa cgcgatattt aacttatcta tataaaaaac aaattcccat   80400
caaattcgga gactttggat tctctgtttc gcgcgcttcg cagttcatct tccccaacga   80460
ctctgctcct tccccttctc tccatctctc tctcgttcta atcttcgaca atggaggaaa   80520
tggaagacac tgaaaccgaa ccacaggtat cttcgattac atattctctc taaattcgct   80580
ttctcttctg attttgccgt tcgtcgtcac tagagagaga gcgatttat gccgattgtg   80640 atcgatgtgt aaaaatttga tatctagtta gggattattg aataaaaacc tcggatctat   80700
tgttgaatcg atctcaatag tacagacatt gataaaccct agctgtttcc ccttttcaac   80760
ctcaaatttg attaatcgga agtagttgtt ccgccgattt gatcccagaa acactaatat   80820
ctgaggcact gtgcattaac acagaaccaa tcctacttt actctcttgc ttcgtatgtg   80880
aaattgtgaa tgtaccaatc tgttttcaat gcaatgcagg tttacatggc ttgtattcag   80940
cacggtcgga ggttagcaat tgaattcaac ttctgtgcac aattttttgag aaactttaac   81000 aatttctcaa ttacaagtgg acaagaaaga gcatatgagt gaatgcttat gctcatattc   81060
ttctctttat gttgttttag taaggatcag tgtctcactt aaacattctc ttctcagagt   81120
tggagtttct tactacgact gtagtgtacg ccagcttcat gtgctagaat tttgggaaga   81180
agattgctca gattttacat tgatcaatat gggtataact tttcaacttc aaacagaatt   81240
gatatcattg catgtcgagt cttgccattc cttactatct gtaccctact ctaaatgaag   81300
tttggtgaag caatttcttg attaacatct actttgcagc acttttgttc tgctacactg   81360
```

```
tccctataac atttgttttt tgatcgcttc atttgtcttg gttatatatc ttcagtaaaa   81420
tatcaagcga agccatcgat catttacgca agcacgaaaa gtgaagaatc ctttgtagct   81480
gctttgcagc agaatggtat ggtgctatct attttgttga aatatgagtc cttaagttta   81540
tggtcttgca taattacatt gtttctgcag acggaactga cgagactacc atggtaaagc   81600
tggtaaagag ctcaacattc agctacgagc aagcgtggca caggtacaga agtttaatc   81660 aactccattt ttcaccttat ttatgtggtt ctggttagtc ctattacatg atgaattccc   81720
catgaaaaat ggtctagtag gaaactggtt cctgcagttt cagtttcttg actcaaatgt   81780
aatagcttac ttggcttatg atattttat gatacctgct gttttacact gattgttatc   81840
ccaatattgt gtagactggt atatcttcga gtaactggaa tggatgatgg attgaacatc   81900
aaagaaagga tttgttatgt aagtttcagc gagggaaatg ttaatcccct tttactaagg   81960
attttgatca tttggttatt gtattctcca gttggaatct caatcataat gttgaattaa   82020
ttgatatttt cgatgtcaca atgaaataat ttgacattgt agctaactag ttttatggtc   82080
cttatctatc tacaattgta tgaagtttct tcattttgct tgtaaatttc agctgagttc   82140
catgatggat gtgggcagtg aagtccaagt tcgtgttagt ggtggtcttc ttgctatatt   82200
agaaagcgaa cgaattgtag aaaccctgga acaaaacgaa tctgggagtg catcaatcgc   82260
aattgattca gtcatggaag taccattgta tcctttactt tttctgttct gtttcttatg   82320
tcttgatgat ctatactttc ctgaattatt gggatgataa tgctgcatgc aaatccttta   82380
caaaatttat aacaggaaca agtttcttaa acttgatgct gctgctcacg aggctctgca   82440
gatatttcag acagataaac atccaagcca tatgggcatt ggccgggcca agaagggta   82500 aatgactaaa tgccttagtt aatctgtgga atcttatatc tccttttcct actttgactt   82560
gtaatcttca ctgaaacttt gaaatgaagg ttctcggtat ttggaatgat gaataaggtt   82620
tgctttcctt gcattggttc attctgggtt atgctgcttg catatatgat ttaacttacc   82680
ttggcctatt tcagtgtgcc acgccaatgg gtagacgcct tttaaggtaa taaatgaaaa   82740
ttatagatat atgcaaactg ttctgaagct gatgtagtct tacgacattg gtttccttct   82800
ctctatttca gaagctggtt tatgagacca atttagatc ttgaagtgtt agatcgccgt   82860
ctcaatgctg tatcctttga tctcttgtga aggagtttgc cttatgtcaa gcagaatagg   82920
agttaacaat caacatcaaa taagagaaac caatagatta aactttatgt ctgctttctg   82980
tagccttatc agcatagttt taaccgatcg tcatttgttc tgaacgaaaa aaaaaattgt   83040
tcgaccacta attgacaggg gtgccttca ctgatgttct gagaggtttc ttttgactgt   83100
actagatttc cttttcatt tcttcagtag agctgatggc atcattgcgg gagacactga   83160
aatcagtgaa ggacatttca catctactca aggtatgtag gtaccattat tctatataat   83220
atagttttag catgcctatc tcttttagcc ataagagcct gtgaaggaga attaaaatta   83280
ctaactaatg gtacagagaa aactttccac aaagtttgcg gtgaatatgt taattgttaa   83340
tctgttggta gaaatagtgt tatatgagca tattctgccc agacagagga cgtggatata   83400
ttgcatgcca aatatcttct tgtatgccaa ttctgtagat tccatttag ttttgataac   83460 acttttttt tttttttctg gcattcttat gttaaaacaa gaaattcaac tctccgacgt   83520
ccctctgtac cagtaacgac tggacagctt tcttgaaggt aaattccatt ttcttgacta   83580
tcatctttca tttagtctat aaaactagtc ttccaagccc caatataatg ctatcttatt   83640
gtgtgcatta gagcataagt gcgctcctgc acgtgaataa gatatttgaa gttggagttt   83700
cagaaagtct cagagagcat atgagacgct tcaacttgga cattattgag aaggttactt   83760
```

```
atgttttatc aattgttatt ctcccactct tcaatccact ttcgtggttg ttgctaagtt   83820
ctcttttcat gttgcaggcc ggcttatgta tcagcacaga gctagattat gtctatgaac   83880
tggtcagttg attttacgtt ctgtttcttc aattccatta taatccatac tctccttttc   83940
aaaagaacag atcttgaatt cttgatgctt tcaaaattgg ggtcttaaca tctctctata   84000
ccttttcctc ctttgataca tttcttattc ctatatcatc cttagaaatt ttaaacctta   84060
atggagttat attgttaaaa aaacgggaaa gtcacaattt tttgagtggc taagaaaagg   84120
tcagctaaga tttattctga aaaagtcaca attttaaggc tattcagaag ttggataccc   84180
caagatttga gaaactgggt taaacaaatt cagcaggcct tagtgagaga taattatgac   84240
tacagttagt aacaacagac aataactcca caggtcattg gagtcattga tgttactaga   84300
agcaaagaga ggggatatca aactttggtt aaagaaggat tctgtgctga ggttatcata   84360
gaagttcatt ttgttcaggt tgtcatacca ctaatctttt gttttttgca agtaactcat   84420
ttcttatttt accagttgga tgagctcagg caaatatatg aggagttgcc agaatttctg   84480
caggaggttt gttctatgtg ataagttcct ttaattgata aatgaaggta aactggaatc   84540
tctcctaaat gattctaatt actgacaggt tcagcgatg gagttagaac actttcctca   84600
tttgcataag gaaaagcttc ctccttgtat cgtctatatt caacaaattg gtgggtctga   84660
agtttcacgt tttaagtttg acataagttc tatacagtgt tatatcctca aaggtttatc   84720
tgcgctgatt ttttaacata attcctttt agaatttcac ctcatcccta agaaaggtga   84780
aatctagctg cacgaattca ttttttggaa ccaccatgtc ctggaattat cagctcaact   84840
atggtgtcta tgcttcttga ttgctcaata gcctttcact ttatgatgcg tctttaacaa   84900
atcgcgacca catgtatttc ttcacacatt gaaaacagtt atttcgtttc tgtaaatgaa   84960
tatatagttt atctgttctg cagggtacct catgtgtatc tttggagaaa agcttgatga   85020
aactgctctt aataggctta ctgaatttga atttgcggta cagtttgttt gtgttcaaaa   85080
tcttaatccc atactttggg cactatgcat atatgtcatt atgaaacaga gttttaatc   85140
atatctatct tgtgattagt tttctgatat ggatggagag actcagcgat tcttttacca   85200
tacctcgaag acacgagagt tagacaacct tcttggagat atctaccaca aaattttagg   85260
tatgttcttc ttgctggttt atattttcca tggcgtattc ttcttgagta caatgacgtt   85320
gtttcttgtt ttacaaaatt ttgctgacag atatggaaag gcaattatt agggacttgc   85380
tgtcacacac acttttgttc tcggctcacc tgctgaaggc agttaacttt gttgcagaac   85440
ttgattggta atcaatattc aagagctacg gatatcccat atcatttcta gtctctcctc   85500
ttgaagaaaa gcaacacatt ttcacgtacc tattatctaa ttagctactt atgagaaatg   85560
actaatgact tatccattat tcttggcttt tctagcattt tatcgttggc ttgtgtagcc   85620
catcagaata actacgtaag gcctgtcctg acagtagaat cattgcttga tattcgaaat   85680
ggaaggtgaa gttgactcta tcagctgcac ttatgtcttg ttgttgcatt tatacataaa   85740
ctccttacga aaaattatat ctgaatatca atactggtgg gcaggcatgt tttgcaggaa   85800
atggctgtag atacttttat cccaaacgac actgaaatca atgataatgg tgagctgaat   85860
gttgataaag ttgttttgac tatttaggca tgcattacaa cttaaacttg tgaactagtt   85920
tttgtccatc acctgattgc aagcttgtct gtcgcaggac gaattcatat aattaccggg   85980
cctaattact caggaaagag catatatgta aagcaggtcg gctttacttt tctaagtctt   86040
atttctcttc gttcaaccaa agtgtactgc atcatcatga attgacaact caagttctga   86100
cttgctattt gtaggtggcg ttaattgttt tcctatccca tattggaagc tttgtaccag   86160
```

```
cagatgcagc aactgttggt ttaactgaca ggtctaacgt catacattct ttttgatctt   86220
tttacaatcg cttttatgt atattttcgt tactaagatt agtcgtacta caacaggatc   86280
ttttgtgcaa tgggaagcaa gttcatgacc gcggagcaat ctacattcat gatagatctg   86340
catcaagtag gaatgatgct caggtattcc aaactgcttc tattttaac ttgatttcaa   86400
ttagctccac tactgatagg ccttgtgagc cggtctcagt ctcttcagtc agttagtgac   86460
ttctagttca cgaggtccat tatttaagtt catgggacc caagaatgaa gatatcaatc   86520
aaaattcaac tgtgcattgc tcatgactta tgatcgtgtt cctaatcatt gtgaccgatc   86580
caaattctcc aggcaggcaa cttcaagatc tctgtgtctc ttagacgagt ttggtaaagg   86640
cactcttaca gaaggtatgg atttctccgc cctctgcatt ggcataaaag gcatgtgttt   86700
gtgaaaactt ctgccttacc cacactcttt tttaagtaca gatggtattg gcttgcttgg   86760
tgggacaatt agtcactttg ctacatgtgc tgagccacca agggtaccgt atagcgttct   86820
cttgtctgtc tctaagcttg tagattcttt tagaaccccta acatgacatt gcctattgct   86880
gcatgctttc aggttgtagt atgtacgcac ttgactgagc tacttaacga gagctgcttg   86940
cctgttgtat gtactccgac tcaatttcag atagataact cagcagattt tgaagtggtt   87000
ccttgcttat agtgagagtc tatcttttt tacttttca tttcagtctg agaagattaa   87060
gttctacaca atgagcgttc ttaggccaga cacagaatct gcaaacatgg aagagattgt   87120
ttttctttat aggtatggag tctcattgac tagcattcta cctaaactgc ctacattctt   87180
aagacttcca tgttttgacc aatgattttg ccggcaggtt aattccggga caaactttgc   87240
tgagctatgg tgagcatttt tgtcctttgc gttattgtct acatgatctt cttgtgtata   87300
caccgagctt catcaaacct atttatgtaa tgcaggcctt cactgtgcgc tactcgctgg   87360
tacatttagg aagattacta atatctttaa tgaattgaat acaattttg atggatctat   87420
ttacgactgt ggattataga gtaacaaaag gaaattttca ctattgttga tgcaaggtgt   87480
cccggaggaa gtcgtgaaga gagcagccat cgtgttggac gcctttgaga gtaacaacaa   87540
cgtcgataaa ctaagccttg acaaaatatc gtctcaagat caagcattca aggtcttttt   87600
gctctctctc acttacacaa gcttttaccc cctttatctt cttctgtcct ctcaggcctt   87660
accaaacttt tactgatttc gaatgaaatt tgcaggatgc tgttgacaag tttgcggagc   87720
ttgacatcag taaaggtgac atccatgcct tctttcaaga tatcttcact tcctaaaccc   87780
ttacttaaaa gtcaagatc                                              87799
```

COMPOSITIONS AND METHODS OF A PHOSPHATIDIC ACID BINDING PROTEIN

STATEMENT OF GOVERNMENT INTEREST

This invention was made with government support under MCB 0453858 awarded by The National Science Foundation. The government has certain rights in the invention.

FIELD OF THE INVENTION

The present invention is related to the field of phospholipid detection. In particular, certain embodiments provide the detection of phosphatidic acid. For example, certain proteins are capable of binding phosphatidic acid and can be used as a diagnostic and/or research tool to identify and quantitate phosphatidic acid. For example, a TGD2 protein may be fused with a fluorescent probe to monitor and measure phosphatidic acid in vitro as well as in vitro.

BACKGROUND

The biogenesis of the photosynthetic thylakoid membranes inside plant chloroplasts requires enzymes at the plastid envelope and the endoplasmic reticulum (ER). Extensive lipid trafficking is required for thylakoid lipid biosynthesis. Trigalactosyldiacylglycerol (TGD) proteins are believed to be permease-like components of an ABC transporter located in the chloroplast inner envelope membrane.

TGD proteins have been suggested to have a phosphatidic acid-binding protein with a predicted mycobacterial cell entry domain such that they may be tethered to the inner chloroplast envelope membrane facing the outer envelope membrane. However, these specific phosphatidic acid binding sites had not been identified, purified and/or isolated.

This lack of knowledge has hampered the development of specific diagnostic and detection methods designed to detect and quantify phosphatidic acid in plants. What is needed in the art is a reliable, quantitatively sensitive, and routine laboratory assay to detect plant phosphatidic acid for the purposes of botanical diagnostics and as a laboratory research tool.

SUMMARY OF THE INVENTION

The present invention is related to the field of phospholipid detection. In particular, certain embodiments provide the detection of phosphatidic acid. For example, certain proteins are capable of binding phosphatidic acid and can be used as a diagnostic and/or research tool to identify and quantitate phosphatidic acid. For example, a TGD2 protein may be fused with a fluorescent probe to monitor and measure phosphatidic acid in vitro as well as in vitro.

In one embodiment, the present invention contemplates a TGD2 protein comprising a phosphatidic acid binding domain, wherein said domain encompasses amino acid residues 201-225 (SEQ ID NO: 12), wherein at least one of said residues is a proline. In one embodiment, the protein lacks a transit peptide domain and a transmembrane domain. In one embodiment, the domain further comprises at least one accessory binding domain. In one embodiment, the accessory binding domain comprises amino acid residues 251-300 (SEQ ID NO: 103). In one embodiment, the accessory binding domain comprises amino acid residues 161-204 (SEQ ID NO: 104). In one embodiment, the accessory binding domain comprises amino acid residues 291-340 (SEQ ID NO: 105). In one embodiment, the domain comprises a phosphatidic acid binding motif. In one embodiment, an N-terminal β-strand and a C-terminal α-helix create the binding motif In one embodiment, the binding motif comprises a $^{221}$Lysine. In one embodiment, the protein further comprises a label.

In one embodiment, the present invention contemplates a method, comprising: a) providing: i) a TDG2 protein comprising a phosphatidic acid binding domain, wherein said domain encompasses amino acid residues 201-225 (SEQ ID NO: 12), wherein at least one of said residues is a proline; ii) a sample suspected of containing phosphatidic acid capable of binding to said domain; b) contacting said sample with said protein under conditions such that said phosphatidic acid binds to said domain; c) determining an amount of said phosphatidic acid-domain binding. In one embodiment, the sample comprises a plant sample. In one embodiment, the method further comprises identifying a plant disease with said phosphatidic acid-domain binding amount. In one embodiment, the method further comprises identifying a plant wound with said phosphatidic acid-domain binding amount. In one embodiment, the method further comprises identifying a plant stress with said phosphatidic acid-domain binding amount. In one embodiment, the plant stress is selected from the group consisting of biotic stress, abiotic stress, pathogen infection, drought, salinity, and cold.

In one embodiment, the present invention contemplates a kit, comprising: a) a first container comprising a TDG2 protein comprising a phosphatidic acid binding domain, wherein said domain encompasses amino acid residues 201-225 (SEQ ID NO: 12), wherein at least one of said residues is a proline; b) a second container comprising a plurality of buffers and a plurality of reagents, wherein said protein is soluble; and c) a set of instructions for determining a phosphatidic acid. In one embodiment, the protein further comprises a label. In one embodiment, the phosphatidic acid is derived from a sample. In one embodiment, the protein further comprises at least one accessory binding protein. In one embodiment, the kit further comprises a test strip, capable of binding the TDG2 protein.

In one embodiment, the present invention contemplates a test strip comprising a phosphatidic acid binding protein and a test sample. In one embodiment, the test sample comprises a phospholipid. In one embodiment, the phospholipid comprises phosphatidylinositol. In one embodiment, the phosphatidylinositol comprises phosphatidic acid. In one embodiment, the test strip further comprises a phosphatidic acid binding protein/phosphatidic acid complex. In one embodiment, the test strip is Strip lot #JJ-032108-47. In one embodiment, the test strip is Strip lot #KB15011-47.

In one embodiment, the present invention contemplates a method comprising; a) providing i) a test strip comprising a phosphatidic acid binding protein; ii) a test sample, wherein the sample comprises a phospholipid; b) treating the phospholipid under conditions that release a phosphatidic acid; c) placing the phosphatidic acid on the test strip under conditions such that the phosphatidic acid is captured by the phosphatidic acid binding protein. In one embodiment, the method further comprises step (d) detecting said phosphatidic acid binding protein/phosphatidic acid complex. In one embodiment, the phospholipid comprises phosphatidylinositol. In one embodiment, the test strip is Strip lot #JJ-032108-47. In one embodiment, the test strip is Strip lot #KB15011-47.

Definitions

The term "phosphatidic acid" as used herein, refers to any one of several acids $(RCOO)_2C_3H_5OPO_3H_2$ that are formed from phosphatides by partial hydrolysis and that yield on hydrolysis two fatty-acid molecules RCOOH and one molecule each of glycerol and phosphoric acid The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to "apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The terms "specific binding" or "specifically binding" when used in reference to the interaction of a lipid (i.e., for example, PA) and a protein or peptide (i.e., for example, TGD2 protein and/or a truncated TGD2 peptide) means that the interaction is dependent upon the presence of a particular structure (i.e., for example, a tertiary amino acid structure) on a protein; in other words a lipid is recognizing and binding to a specific protein structure rather than to proteins in general. For example, if a lipid is specific for tertiary structure "A", the presence of a protein containing tertiary structure A (or free, unlabelled A) in a reaction containing labeled "A", the lipid will reduce the amount of labeled A bound to the lipid.

A "variant" of a protein is defined as an amino acid sequence which differs by one or more amino acids from a polypeptide sequence or any ortholog and/or homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide is defined as a novel nucleotide sequence which differs from a reference oligonucleotide by having deletions, insertions and substitutions. These may be detected using a variety of methods (e.g., sequencing, hybridization assays etc.). Included within this definition are alterations to the genomic DNA sequence which encodes TGD2 (i.e., for example, SEQ ID NO:1), the inability of a selected fragment of SEQ ID NO:1 to hybridize under high stringency conditions to a sample of genomic DNA (e.g., using allele-specific oligonucleotide probes), and improper or unexpected hybridization, such as hybridization to a locus other than a wild type chromosomal locus (e.g., using fluorescent in situ hybridization (FISH)).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring protein.

A "substitution" results from the replacement of one or more nucleotides or amino acids by different nucleotides or amino acids, respectively.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

Transcriptional control signals in eukaryotes comprise "promoter" and "enhancer" elements. Promoters and enhancers consist of short arrays of DNA sequences that interact specifically with cellular proteins involved in transcription. Maniatis, T. et al., *Science* 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: *Molecular Cloning: A Laboratory Manual*, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonucleotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "binding" as used herein, refers to any interaction between an infection control composition and a surface. Such as surface is defined as a "binding surface". Binding may be reversible or irreversible. Such binding may be, but is not limited to, non-covalent binding, covalent bonding, ionic bonding, Van de Waal forces or friction, and the like. An infection control composition is bound to a surface if it is impregnated, incorporated, coated, in suspension with, in solution with, mixed with, etc.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term, "test strip" as used herein, refers to any material capable of binding a protein, wherein the protein may capture a ligand without releasing from the material. For example, a test strip may comprises a glass slide coated with a polymer matrix, a silica material, absorbent fiber (i.e., for example, cloth or paper).

The term, "phosphatidic acid binding protein" as used herein, refers to any protein and/or enzyme that is capable of forming a complex with phosphatidic acid.

The term "test sample" or "sample" as used herein, refers to any material comprising phosphatidic acid that may be placed on a test strip, or may be treated for placement on a test strip such that the phosphatidic acid may be detected.

The term "complex" as used herein, refers to any stable interaction between two compounds such that a close association is formed. The complex may be stabilized by atomic interactions including, but not limited to, covalent bonding, non-covalent bonding, electrostatic interactions, hydrophobic interactions, or Van der Waals forces.

The term "capture" as used herein, refers to any compound having a stereospecific affinity for a second compound. For example, an antibody may capture a ligand wherein the antibody has been raised by an antigen to the ligand. Alternatively, a protein or enzyme may have a tertiary structure such that a ligand finds multiple points of interaction such that a stable complex is formed.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1A:
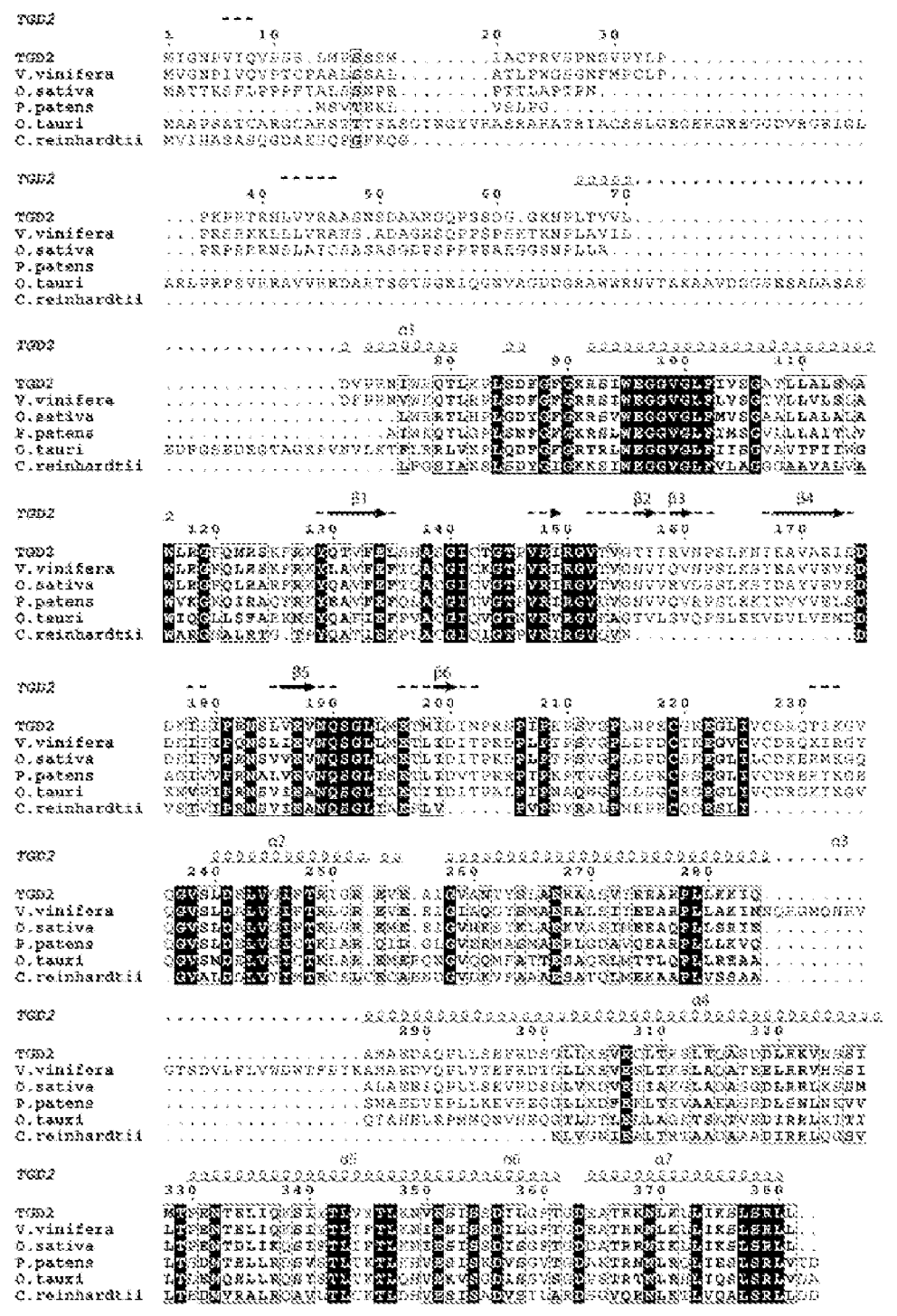

FIG. 1 illustrates various embodiments and relationships of TGD2 amino acid sequences. Gene bank accession numbers for disclosed sequences: *Arabidopsis thaliana*, NP_566659.1 (SEQ ID NO: 5); *Vitis vinifera*, CAN71395.1 (SEQ ID NO: 6); *Oryza sativa*, EAY77419.1 (SEQ ID NO: 7); *Physcomitrella patens*, XP_001778862.1 (SEQ ID NO: 8); *Ostreococcus tauri*, CAL53419.1 (SEQ ID NO: 9); *Chlamydomonas reinhardtii*, XP_001699315.1 (SEQ ID NO: 10); *Prochlorococcus marinus* str. NATL2A, YP_292846.1 (SEQ ID NO: 115); *Prochlorococcus marinus* str. MIT 9301, YP_001090537.1 (SEQ ID NO: 116); *Synechococcus* sp. WH 5701, ZP_01083418.1 (SEQ ID NO: 117); *Synechococcus* sp. CC9902, YP_376253.1 (SEQ ID NO: 118); *Synechococcus* sp. JA-2-3B'a(2-13), YP_477327.1 (SEQ ID NO: 119); *Anabaena variabilis*, YP_323182.1 (SEQ ID NO: 120); *Nodularia spumigena*, ZP_01630545.1 (SEQ ID NO: 121); *Crocosphaera watsonii*, ZP_00516249.1 (SEQ ID NO: 122); *Cyanothece* sp. PCC 8801, ZP_02940544.1 (SEQ ID NO: 123); *Microcystis aeruginosa*, CAO90615.1 (SEQ ID NO: 124); *Acaryochloris marina*, YP_001516641.1 (SEQ ID NO: 125); *Thermosynechococcus elongatus*, NP_683197.1 (SEQ ID NO: 126).

FIG. 1A: Alignments of the TGD2 sequence with various orthologs in plants and green algae. Predicted TGD2 secondary structure is shown on the top. Open boxes mark conserved residues, and black boxes indicate identical residues.

FIG. 2 presents exemplary data showing binding of DsRed-TGD2C WT fusion protein to PA as a function of weight percent of PA in PA/PC mixture.

FIG. 3 presents one embodiment of a phosphatidic acid (PA) binding domain on TGD2C by deletion and truncation mutagenesis.

FIG. 4 presents exemplary data showing the binding of a TGD2 minimal domain to PA.

FIG. 5A: PA binding for DsRed-TGD2C WT (DR-WT).

FIG. 5B: PA binding for DsRed-TGD2C minimal domain (DR-25).

FIG. 5C: Quantification of relative binding of PA for DR-WT and R-25.

FIG. 5D: PA binding for DsRed-TGD2C minimal domain (DR-25).

FIG. 5E: PA binding for DsRed-TGD2C with deletion of minimal domain (DR-Δ25).

FIG. 5F: Quantification of relative binding of PA for DR-25 and DR-Δ25.

FIG. 6A: A schematic of TGD2 domains indicating a predicted transit peptide domain (TP), a transmembrane domain (TMD), a conservative mammalian cell entry (MCE) domain, and a PA binding minimal domain (MBD).

FIG. 6B: Deletion and truncation mutants were generated on TGD2C and C-terminally fused to the DsRed open reading frame. Liposome-association assays were performed to assess binding of various mutants to PA liposomes (chromatographic plate, bottom).

FIG. 7A schematically illustrates a TGD2 protein that is N-terminally truncated lacking a TMD and is C-terminally fused to the *Discosoma* sp. red fluorescent protein (DsRed, DR) open reading frame.

FIG. 7B presents exemplary data from the expressed fusion protein using an protein-lipid overlay assay with a commercially available phospholipid-containing membrane strip. LPA, lysophosphatidic acid; LPC, lysophosphatidylcholine; Ptdlns, phosphatidylinositol; Ptdlns(3)P, phosphatidylinositol 3-phosphate; Ptdlns(4)P, phosphatidylinositol 4-phosphate; Ptdlns(5)P, phosphatidylinositol 5-phosphate; PE, phosphatidylethanolamine; PC, phosphatidylcholine; SIP, sphingosine 1-phosphate; Ptdlns(3,4)P2, phosphatidylinositol 3,4-bisphosphate; Ptdlns(3,5)P2, phosphatidylinositol 3,5-bisphosphate; Ptdlns(4,5)P2, phosphatidylinositol 4,5-bisphosphate; Ptdlns(3,4,5)P3, phosphatidylinositol 3,4,5-bisphosphate; PA, phosphatidic acid; PS, phosphatidylserine TGD2

FIG. 8A: Membrane binding assay with commercial phospholipid-containing membrane.

FIG. 8B: Membrane binding assay with a plant lipid-containing membrane.

FIG. 8C: Liposome binding assay. Liposomes consisted of phosphatidylcholine only (PC, first lane) or PC (60% wt/wt, second through fourth lanes) mixed with different molecular species of PA (40% wt/wt). PA molecular species tested were dioleoyl-PA (18:1), sn1-oleoyl, sn2-palmitoyl PA (18:1/16:0), and dipalmitoyl-PA (16:0). DGDG, prokaryotic digalactosyldiacylglycerol; DGDGe, eukaryotic digalactosyldiacylglycerol; L-PA, lysophosphatidic acid; L-PC, lysophosphatidylcholine; MGDG, prokaryotic monogalactosyldiacylglycerol; MGDGe, eukaryotic monogalactosyldiacylglycerol; PC, phosphatidylcholine; PE, phosphatidylethanolamine; PG, phosphatidylglycerol; PI, phosphatidylinositol; PIP(3), phosphatidylinositol 3-phosphate; PIP(4), phosphatidylinositol 4-phosphate; PIP(5), phosphatidylinositol 5-phosphate; PIP2(3,4), phosphatidylinositol 3,4-bisphosphate; PIP2(3,5), phosphatidylinositol 3,5-bisphosphate; PIP2(4,5), phosphatidylinositol 4,5-bisphosphate; PIP3(3,4,5), phosphatidylinositol 3,4,5-bisphosphate; PS, phosphatidylserine; SIP, sphingosine 1-phosphate; SQDG, sulfoquinovosyldiacylglycerol; TGDG, trigalactosyldiacylglycerol.

FIG. 10A: Thin-layer chromatogram of polar lipids. Lipids were visualized by α-naphthol staining.

FIG. 10B: Thin-layer chromatogram of neutral lipids. Lipids were visualized by exposure to iodine vapor.

FIG. 10C: Polar lipid composition (relative mol %) determined by quantification of fatty acid methylesters derived from individual lipids.

FIG. 10D: Fatty acid composition of the two galactolipids MGDG and DGDG.

FIG. 11A: Map position of the tgd2-1 mutation on chromosome 3 and structure of the TGD2 gene (At3g20320). Markers used for mapping and the respective number of recombinations are indicated. The TGD2 gene is indicated by a black box and expanded on the lowest line. The coding region of At3g20320 is shown as a shaded box. The darker shading indicates the predicted TMD. A region encoding an MCE domain is shown hashed. Introns are indicated by a line. Noncoding regions of the gene deduced from the cDNA are shown as open boxes.

FIG. 11C: Genotyping at the DGD1 locus. Point mutation-specific dCAPS markers were used, and ethidium bromide stained DNA diagnostic DNA fragments are shown with their respective lengths in base pairs.

FIG. 11D: Genotyping at the TGD2 locus. Point mutation-specific dCAPS markers were used, and ethidium bromidestained DNA diagnostic DNA fragments are shown with their respective lengths in base pairs.

FIG. 11E: Lipid phenotype of the six different plant lines. A section of thin-layer chromatogram stained for glycolipids is shown. DGDG, digalactosyldiacylglycerol; TGDG, trigalactosyldiacylglycerol.

FIG. 12A: Semiquantitative RT-PCR of mRNA levels derived from the TGD2 wild-type gene (top), the TGD2 wild-type gene and the tgd2-1 transgene (middle), and the ubiquitin (UBQ10) control (bottom). Negative images of ethidium bromide-stained gels are shown.

FIG. 12B: Polar lipid phenotype of the indicated plants. A section of the thin-layer chromatogram stained for glycolipids is shown. DGDG, digalactosyldiacylglycerol; SQDG, sulfoquinovosyldiacylglycerol; TGDG, trigalactosyldiacylglycerol.

FIG. 13A: Localization of full-length TGD2 protein fused to GFP (TGD2-GFP). The insertion of the respective protein into the membrane is schematically shown on the left. GFP, green fluorescence specific for GFP; Ch1, red fluorescence of chloroplasts; the overlay of the two images is shown on the right. Confocal images are shown. (Scale bars: 10 µm)

FIG. 13B: Topology of the TGD2 protein. The wild-type TGD2 protein, the tgd2-1 mutant protein, and the GFP fusion were transiently produced in tobacco leaves, and isolated chloroplasts were analyzed. The TGD2 and tgd2-1 proteins were detected by using a TGD2-specific antibody. The GFP fusion was detected by using a GFP-specific antibody. Samples were untreated with protease (−) or treated with thermolysin (+, Th) or with trypsin (+, Tr). Immunoblots are shown.

FIG. 15A: Primary structure of TGD2 indicating a predicted transit peptide (TP), transmembrane domain (TMD) and a conservative mammalian cell entry (MCE) domain.

FIGS. 15B & 15C: A series of deletion and truncation mutants were generated on TGD2C and C-terminally fused to dsRed protein the same manner as WT TGD2C. Black ball represents dsRed protein, black bars represent deletion fragment. Liposome-association assays were performed to assess binding of various mutants to PC, PA/PC or PA liposomes. PA-specific binding data were summarized on the right. +++++, ++++, +++, ++, +, indicate a qualitative assessment of PA-specific binding in decreasing intensity, and − indicate no binding.

FIG. 17 presents TGD2 ortholog sequences and phylogenetic organization in plants and Cyanobacteria.

DETAILED DESCRIPTION OF THE INVENTION

Figure 1B:
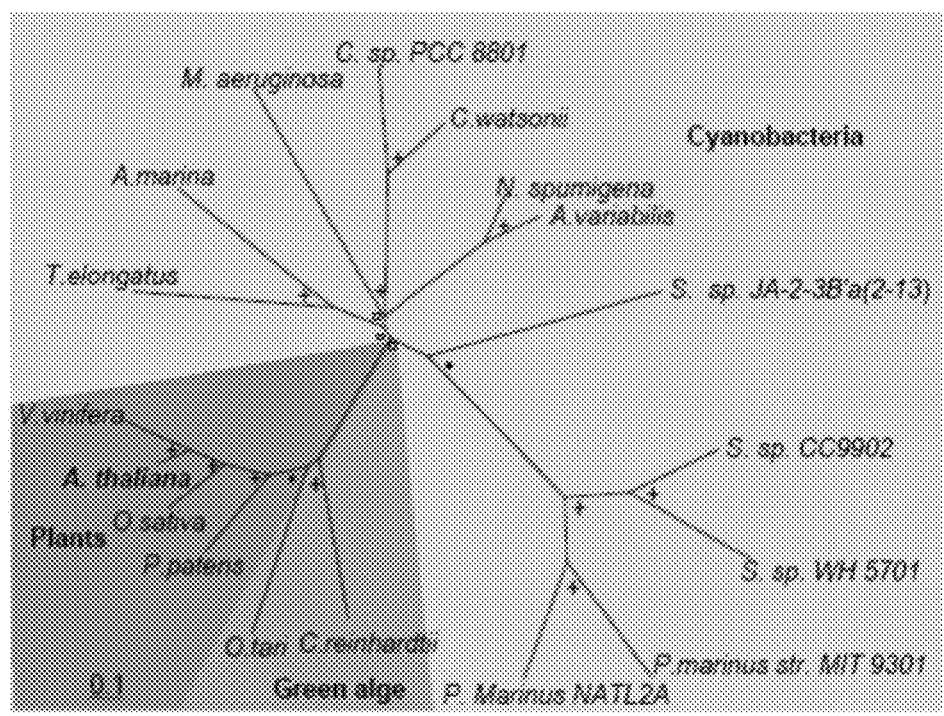
FIG. 1B: An 'unrooted tree' diagram showing the apparent relatedness of predicted TGD2 orthologs in plants, green algae and Cyanobacteria. Boot strapping values >950 are marked by +, those between 500 and 950 are marked with a solid circle, and those under 500 are marked by open square.

The present invention is related to the field of phospholipid detection. In particular, certain embodiments provide the detection of phosphatidic acid. For example, certain proteins are capable of binding phosphatidic acid and can be used as a diagnostic and/or research tool to identify and quantitate phosphatidic acid. For example, a TGD2 protein may be fused with a fluorescent probe to monitor and measure phosphatidic acid in vitro as well as in vitro.

The TGD2 protein of *Arabidopsis* is proposed to be the substrate binding component of a lipid transfer complex in the inner chloroplast envelope membrane. Loss of function of this protein or other components of this complex may disrupt the endoplasmic reticulum (ER)-pathway of thylakoid lipid biosynthesis.

In one embodiment, the present invention contemplates a method comprising fusing an open reading frame encoding the TGD2C truncated protein wherein the transit peptide and transmembrane domain are removed. In one embodiment, the protein is attached to the C-terminal of the *Discosoma* sp. red (DsRed) fluorescent protein open reading frame. In one embodiment, the fusion protein is in operable combination with a T7 promoter.

In one embodiment, the present invention contemplates a method comprising expressing a labeled TGD2C truncated fusion protein. In one embodiment, the label is a fluorescent label. In one embodiment, the fluorescent label comprises a *Discosoma* s. red fluorescent protein (DsRed). Although it is not necessary to understand the mechanism of an invention, it is believed that the DsRed-TGD2C fusion protein specifically binds phosphatidic acid (PA). The data presented herein, demonstrates that the binding of DsRed-TGD2C to PA displays positive cooperativity with a Hill number of 5.8 and the apparent $K_d$ of 39.81 mol % PA (wt/wt). Further data presented herein, utilized deletion and truncation mutagenesis to identify a 25 amino acid TGD2C segment as a specific PA minimal binding domain.

The task of studying lipid-protein interactions is difficult due to the hydrophobicity property of the interacting molecules. Moreover, there are few reliable quantitative techniques available to assess specific binding kinetics and each method has its own limitations. Therefore, the present invention overcame these limitations by utilizing: (1) a protein-lipid overlay assay for rapid detection and qualitative assessment of binding; and (2) a liposome-association assay combined with densitometry quantification to evaluate relative binding between proteins. Together, these methods allow us to identify a specific binding domain and evaluate it semi-quantitatively.

I. Plant Lipid Biosynthesis

As plant leaves expand, the demand on the lipid biosynthetic machinery is high because leaf cells contain one of the most extensive membrane systems found in Nature, for example, a chloroplast photosynthetic thylakoid membrane. Chloroplast thylakoid lipids include, but are not limited to, nonphosphorous galactolipids.

Galactolipid biosynthesis involves the formation of phosphatidic acid (PA) in the plastid and at the endoplasmic reticulum (ER) in many plants, including *Arabidopsis*. Browse et al., (1991) Annu. Rev. Plant Physiol. Plant Mol. Biol. 42:467-506; and Roughan et al., (1982) Annu. Rev. Plant Physiol. 33:97-132. Fatty acids derived from de novo synthesis in the plastid are assembled into PA in the plastid or at the ER. In *Arabidopsis*, diacylglycerols derived from the plastid pathway or the ER pathway are present in galactolipids in approximately equal proportion. Browse et al., (1986) Biochem. J. 235:25-31. The *Arabidopsis* lipid galactosyltransferases MGD1 and DGD1, which successively galactosylate diacylglycerol, are associated with the inner and the outer chloroplast envelope membranes, respectively. Benning et al., (2005) J. Biol. Chem. 280:2397-2400. The topology of the galactolipid biosynthetic machinery and the involvement of the ER pathway require extensive subcellular lipid trafficking, most of which is mechanistically not understood.

To date, two mutants of *Arabidopsis* have been described that affect lipid trafficking from the ER to the plastid. The act1(ats1) mutant is deficient in the plastidic glycerol 3-phosphate acyltransferase, and most of the galactolipids in this mutant are derived from the ER pathway. Kunst et al., (1988) Proc. Natl. Acad. Sci. USA 85:4143-4147. In contrast, galactolipids in the tgd1 mutant are primarily derived from the plastid pathway. Xu et al., (2003) EMBO J. 22:2370-2379. This mutant presents a complex lipid phenotype comprising: i) the accumulation of oligogalactolipids (i.e., for example, trigalactosyldiacylglycerol) and triacylglycerols in the leaves; ii) a 5-fold increase in PA content; and iii) an increase of 16-carbon fatty acids in the galactolipids. Xu et al., (2005) Plant Cell 17:3094-3110.

Such observations are believed indicative of a change in molecular species toward those formed de novo in the plastid. Xu et al., (2003) *EMBO J.* 22:2370-2379; and Xu et al., (2005) *Plant Cell* 17:3094-3110. These observations comprised pulse-chase labeling of leaves that were consistent with a disruption of the transfer of lipid molecular species from the ER to the plastid in the tgd1 mutant. Isolated tgd1 chloroplasts showed a decreased rate of conversion of labeled PA into galactolipids. The TGD1 protein resembles the permease component of bacterial ABC transporters and was shown to be an integral component of the inner chloroplast envelope membrane. Such data supports a proposed that TGD1 is a component of a PA transporter in the inner chloroplast envelope and may play a role in the biosynthesis of ER-derived molecular species of galactolipids. Stronger alleles of tgd1 led to increased embryo arrest and seed abortion, suggesting that the affected biological process is essential.

In one embodiment, the present invention contemplates a composition comprising a trigalactosyldiacylglycerol 2 (tgd2) mutant of *Arabidopsis*. In one embodiment, the composition comprises a TGD2 gene. In one embodiment, the composition comprises a TGD2 protein.

Pulse-chase labeling of leaves also indicates a disruption of the transfer of lipid molecular species from the ER to the plastid in the tgd1 mutant. For example, isolated tgd1 chloroplasts show a decreased rate of conversion of labeled PA into galactolipids. The TGD1 protein resembles the permease component of bacterial ABC transporters and was shown to be an integral component of the inner chloroplast envelope membrane. Such observations lead to the proposal that TGD1 is a component of a PA transporter in the inner chloroplast envelope and that may be involved in biosynthesis of ER-derived molecular species of galactolipids. A second *Arabidopsis* TGD, trigalactosyldiacylglycerol 2 (tgd2), has been identified and characterized.

Protein importation into chloroplasts is believed to involve an interaction of protein complexes spanning the inner and outer chloroplast envelope membranes. Gutensohn et al., (2006) J. Plant Physiol. 163:333-347; and Jarvis et al., (2004) Curr. Biol. 14:R1064-R1077. Currently, knowledge about lipid importation into the plastid is extremely limited. Like protein importation into the plastid, ER-derived lipid importation during chloroplast biogenesis is extensive and presumably requires transporters mediating the transfer of lipids between and through the involved membranes.

As discussed above, TGD1 and TGD2 proteins may comprise components of a lipid transporter of the inner chloroplast envelope membrane. Although the analysis of the tgd1-1 mutant to date is far more extensive, it is apparent that the tgd2-1 mutation causes identical biochemical and physiological phenotypes: i) the accumulation of oligogalactolipids and triacylglycerols; ii) the increase of 16-carbon fatty acids in plastid lipids indicative of reduced presence of ER-derived molecular species; and iii) the increase in growth in the dgd1 background. Until the presently disclosed invention, a difference in phenotypes between TGD1 and TGD2 had not been identified, thereby suggesting that the products of the two genes are involved in the same biological process, thylakoid lipid biosynthesis from ER-derived precursors.

Currently available molecular analysis supported this interpretation because: i) TGD1 and TGD2 proteins are localized in the inner chloroplast envelope membrane; and ii) expression of green fluorescent protein (GFP) fusions for both proteins cause punctate fluorescence patterns in the periphery of plastids. Moreover, the *Arabidopsis* TGD1 and TGD2 proteins were reported as similar permeases and substrate-binding proteins of bacterial ABC transporters, respectively. Their corresponding bacterial orthologs are found in clusters, which is usually interpreted as meaning that the function of the gene products are in the same pathway or process. Overbeek et al., (2005) Nucleic Acids Res. 33:5691-5702.

Nonetheless, past research was unable to identify unambiguous evidence for any direct similarities in TGD1 and TGD2 function. Two findings suggest that TGD2 is active in a protein-lipid complex in *Arabidopsis* because: i) ectopic expression of the tgd2-1 mutant cDNA gives rise to the mutant phenotype, i.e., a dominant-negative mutation; and ii) the wild-type TGD2 protein is protected in isolated chloroplasts against trypsin whereas the TGD2 fusion protein is not. Both results can be interpreted as the association of the TGD2 protein with other proteins and/or specific lipid domains inaccessible to proteolytic activity.

Figure 8:
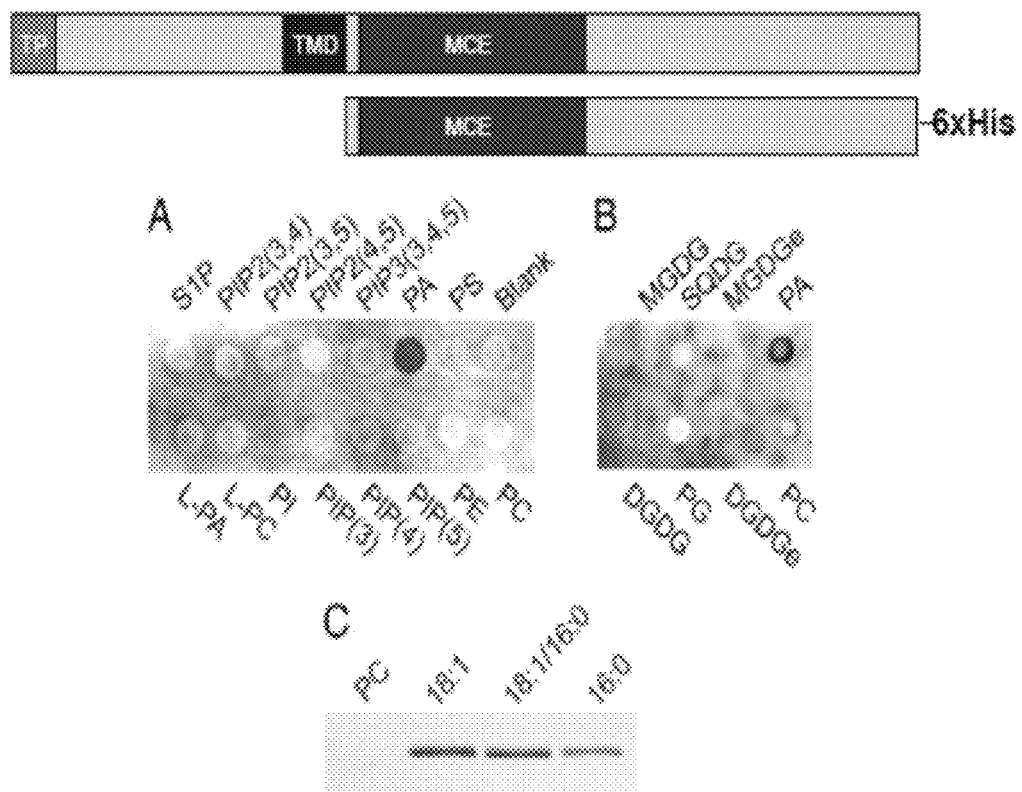
FIG. 8 presents exemplary data showing specific phosphidate binding to a recombinant TGD2C-His protein. Upper bars show the relative overlapping of a 6×His MCE binding fragment to a TGD2 protein. The 6×His TGD2 protein variant is N-terminally truncated lacking the TMD to exclude lipid binding to this region of the protein.
Figure 9:
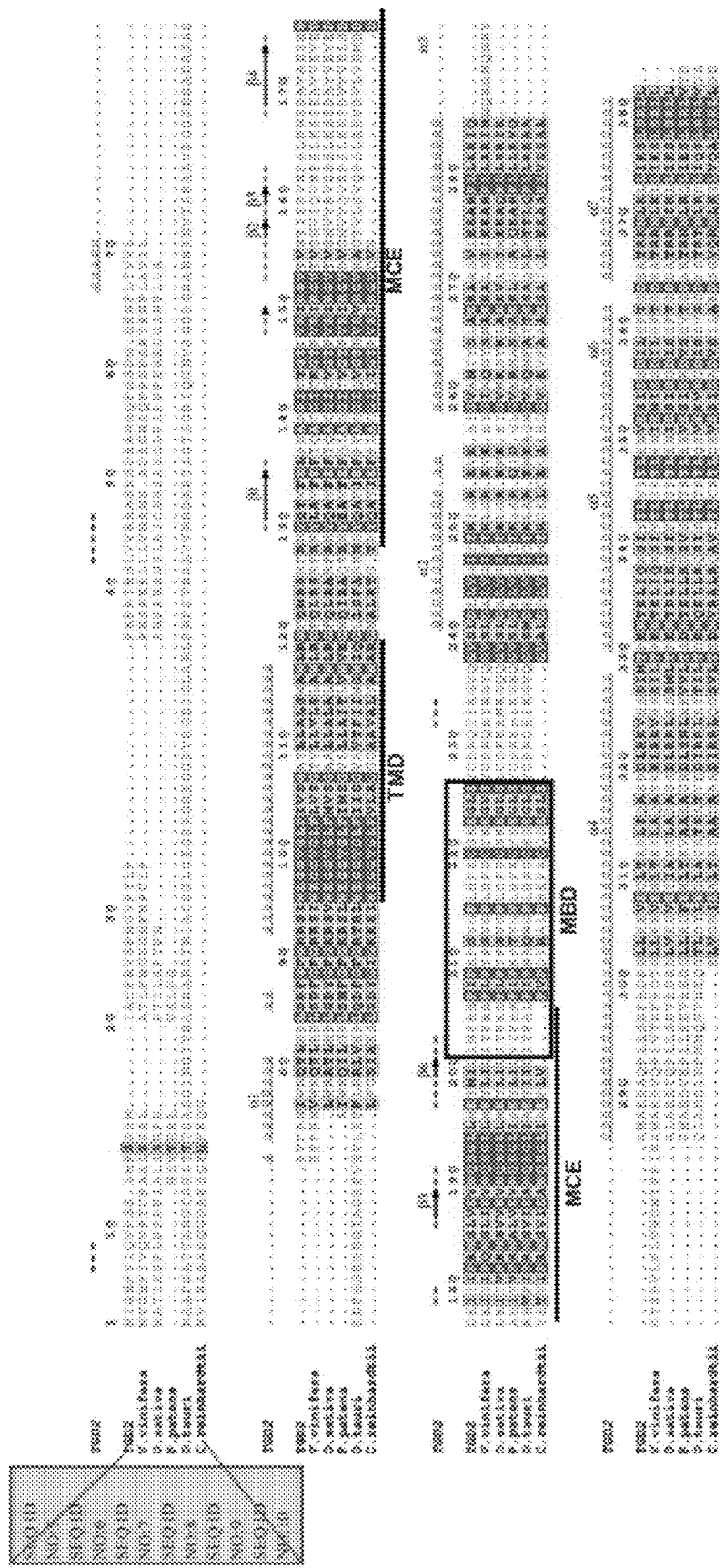
FIG. 9 demonstrates one embodiment of alignment comparisons showing that the TGD2 minimal PA binding domain is adjacent to the MCE domain.

Previous investigation of the tgd1-1 mutant indicated the accumulation of PA, and the reduced incorporation of PA into glycolipids of isolated plastids, led to the suggestion that the TGD1 protein is a component of a PA transporter. Xu et al., (2005) *Plant Cell* 17:3094-3110. Consistent with the proposed interaction of TGD1 and TGD2 in a PA-transporting complex, the recombinant TGD2 protein lacking the membrane-spanning domain was found to specifically bind PA. See, FIG. 8. An alternative interpretation would be that TGD2 binds PA as an effector molecule modulating the activity of TGD1. Further, TGD2 could remove a PA molecule from the outer envelope membrane and make it available to TGD1 for import into the plastid and conversion by the plastidic PA phosphatase. Because TGD2 appears to be tethered with its membrane-spanning domain to the inner envelope membrane, the PA binding domain might reach out to the inside of the outer envelope membrane either locally fusing the two membranes or extracting an ER-derived PA. Although, to date, there is no direct evidence for this hypothesis, one intriguing observation in support is derived from mycobacterial orthologs of TGD2 required for cell entry of the bacterium. Chitale et al., (2001) *Cell. Microbiol.* 3:247-254. Recombinant bacterial orthologs can mediate the uptake of latex beads into mammalian cells, a process requiring an interaction of the protein on the bacterial surface with the mammalian cell membrane. The MCE domains present in the MCE proteins or bacterial substrate binding proteins associated with ABC transporters have been delineated based on sequence. The finding that TGD2 specifically binds PA, possibly through its MCE domain, might also be relevant to the possibility that these bacterial proteins interact with membrane lipids.

II. Phosphatidic Acid and Plant Diseases

Phosphatidic acid (PA) has only recently been identified as a putative signaling molecule in both plants and animals. Nonetheless, PA already appears to be equivalent to the classic second messengers $Ca^{2+}$ and/or cAMP. In plants, PA's formation may be triggered in response to various biotic and abiotic stress factors, including pathogen infection, drought, salinity, wounding and cold. In general, PA signal production is fast (i.e., for example, in minutes) and transient. Recently, reports indicated that PA formation in stress responses may be a result of phospholipases C and D activity. Moreover, some protein targets of PA have been identified. Testerink et al., "Phosphatidic acid: a multifunctional stress signaling lipid in plants" Trends Plant Sci. 2005 August; 10(8):368-375.

Phospholipid-derived molecules maybe involved as second messengers in plant defense signaling. Recent research has begun to reveal PA signals produced by the enzymes phospholipase C, phospholipase D and phospholipase A2 in relationship to their putative downstream targets. These include, but are not limited to, the activation of a MAP kinase cascade and triggering of an oxidative burst by phosphatidic acid; the regulation of ion channels and proton pumps by lysophospholipids and free fatty acids; and the conversion of free fatty acids into bioactive octadecanoids such as jasmonic acid. Laxalt et al., "Phospholipid signalling in plant defence" Curr Opin Plant Biol. 2002 August; 5(4):332-338.

PA may also be a positive regulator of RPM1- or RPS2-mediated disease resistance signalling, and that an observed biphasic PA production may be a conserved feature of signalling induced by the coiled-coil nucleotide binding domain leucine-rich repeat class of resistance proteins. Bacterial pathogens are believed to deliver type III effector proteins into plant cells during an infection. On susceptible host plants, type III effectors contribute to virulence, but on resistant hosts they betray the pathogen to the plant's immune system and are functionally termed avirulence (Avr) proteins. Recognition induces a complex suite of cellular and molecular events comprising the plant's inducible defence response. As recognition of type III effector proteins occurs inside host cells, defence responses can be elicited by in planta expression of bacterial type III effectors. Andersson et al., "Phospholipase-dependent signalling during the AvrRpm1- and AvrRpt2-induced disease resistance responses in *Arabidopsis thaliana*" Plant J. 2006 September; 47(6):947-59. Recognition of either of two type III effectors, AvrRpm1 or AvrRpt2 from *Pseudomonas syringae*, induced a biphasic accumulation of phosphatidic acid (PA). The first wave of PA accumulation correlated with disappearance of monophosphatidylinosotol (PIP) and is thus tentatively attributed to activation of a PIP specific phospholipase C (PLC) in concert with diacylglycerol kinase (DAGK) activity. Subsequent activation of phospholipase D (PLD) produced large amounts of PA from structural phospholipids. This later wave of PA accumulation was several orders of magnitude higher than the PLC-dependent first wave. Inhibition of phospholipases blocked the response, and feeding PA directly to leaf tissue caused cell death and defence-gene activation. Inhibitor studies ordered these events relative to other known signalling events during the plant defense response. Influx of extracellular $Ca^{2+}$ occurred downstream of PIP-degradation, but upstream of PLD activation. Production of reactive oxygen species occurred downstream of the phospholipases.

The involvement of phospholipase C/diacylglycerol kinase (PLC/DGK)-mediated signalling in oxidative burst and hypersensitive cell death was studied in rice suspension-cultured cells treated with benzothiadiazole (BTH) and infected by *Xanthomonas oryza* pv. *oryza* (Xoo), believed to be a causative factor of rice leaf blight disease. Treatment of rice suspension cells with BTH resulted in a significant oxidative burst, as indicated by accumulation of superoxide anion and $H_2O_2$, and hypersensitive cell death, as determined by Evans blue staining. A peak in oxidative burst was detected 3-4 h after BTH treatment and hypersensitive cell death was observed 8 h after treatment. In addition, significant oxidative burst and hypersensitive cell death were detected in BTH-treated suspension cells, but not in untreated control cells, after Xoo infection. Scavengers and antioxidants of active oxygen species, e.g., superoxide dismutase, catalase, N-acetylcysteine, and flavone, reduced significantly the BTH-induced oxidative burst and hypersensitive cell death, indicating that oxidative burst is required for BTH-induced hypersensitive cell death. Expression of the PLC/DGK pathway genes, a diacylglycerol kinase gene, OsDAGK1, and a phosphoinositide-specific phospholipase C gene, OsPI-PLC1, and a defense-related EREBP transcriptional factor gene, OsBIERF3, was activated in rice cells after BTH treatment and in the BTH-treated cells after Xoo infection. Treatment of rice cells with phosphatidic acid, a phospholipid signalling molecule, resulted in the production of oxidative burst and hypersensitive cell death. However, neomycin, a PLC inhibitor, inhibited partially but not completely the production of oxidative burst, hypersensitive cell death, and expression of OsBIERF3 and OsDAGK1 induced by BTH in rice cells. These results suggest that PLC/DGK-mediated signalling plays an important role in BTH-induced oxidative burst, hypersensitive response, and activation of defense response in rice. Chen et al., "Phospholipase C/diacylglycerol kinase-mediated signalling is required for benzothiadiazole-induced oxidative burst and hypersensitive cell death in rice suspension-cultured cells" Protoplasma. 2007; 230(1-2):13-21.

Phospholipase D (PLD) has been implicated in multiple plant stress responses. Its gene transcription and activity increase upon exposure to various stresses, and manipulation of PLD protein levels leads to altered stress tolerance. The plant PLD family is relatively large and heterogeneous, and different PLD isoforms are involved in separate stress responses. PLD and its product, phosphatidic acid, exert their effects by functioning in signal transduction cascades and by influencing the biophysical state of lipid membranes. Bargmann et al., "The role of phospholipase D in plant stress responses" Curr Opin Plant Biol. 2006 October; 9(5):515-22.

Metabolomic approaches were used to elucidate some key metabolite changes occurring during interactions of *Magnaporthe grisea*—a causative factor of rice blast disease—with an alternate host, *Brachypodium distachyon*. Fourier-transform infrared (FT-IR) spectroscopy provided a high-throughput metabolic fingerprint of *M. grisea* interacting with the *B. distachyon* accessions ABR1 (susceptible) and ABR5 (resistant). Principal component-discriminant function analysis (PC-DFA) allowed the differentiation between developing disease symptoms and host resistance. Examination of PC-DFA loading plots indicated that fatty acids were one chemical group that discriminated between responses by ABR1 and ABR5 to *M. grisea*. To identify these, non-polar extracts of *M. grisea*-challenged *B. distachyon* were directly infused into an electrospray ionization mass spectrometer (ESI-MS). PC-DFA indicated that *M. grisea*-challenged ABR1 and ABR5 were differentially clustered away from healthy material. Subtraction spectra and PC-DFA loadings plots revealed discriminatory analytes (m/z) between each interaction and seven metabolites were subsequently identified as phospholipids (PLs) by ESI-MS-MS. Phosphatidyl glycerol (PG) PLs were suppressed during both resistant and susceptible responses. By contrast, different phosphatidic acid PLs either increased or were reduced during resistance or during disease development. This suggests considerable and differential PL processing of membrane lipids during each interaction which may be associated with the elaboration/suppression of defence mechanisms or developing disease symptoms. Allwood et al., "Metabolomic approaches reveal that phosphatidic and phosphatidyl glycerol phospholipids are major discriminatory non-polar metabolites in responses by *Brachypodium distachyon* to challenge by *Magnaporthe grisea*" Plant J. 2006 May; 46(3):351-68.

Multiple forms of phospholipase D (PLD) were activated in response to wounding, and the expressions of PLDα, PLDβ, and PLDγ differed in wounded *Arabidopsis* leaves. Antisense abrogation of PLDα decreased post-wounding phosphatidic acid induction, jasmonic acid (JA), and a JA-regulated gene for vegetative storage protein. Examination of the genes involved in the initial steps of oxylipin synthesis revealed that abrogation of the PLDα attenuated the wound-induced expression of lipoxygenase 2 (LOX2) but had no effect on allene oxide synthase (AOS) or hydroperoxide lyase in wounded leaves. The systemic induction of LOX2, AOS, and vegetative storage protein was lower in the PLDα-suppressed plants than in wild-type plants, with AOS exhibiting a distinct pattern. These results indicate that activation of PLD mediates wound induction of JA and that LOX2 is probably a downstream target through which PLD promotes the production of JA. Wang et al., "Involvement of phospholipase D in wound-induced accumulation of jasmonic acid in *arabidopsis*" Plant Cell. 2000 November; 12(11):2237-2246.

III. Phosphatidic Acid as a Signaling Lipid

Over the years, several signaling lipids have been identified in plants (1, 2). Among those are various important sphingolipids, glycerol lipids and fatty acid metabolites (3-6). Phosphatidic acid (PA), was found to be one representative signaling lipid. PA may represent a lipid second messenger that transiently accumulates in plants within minutes after a pathogen attack and/or a variety of stress conditions (i.e., for example, osmotic and temperature stress) (7-9). PA may be generated via two distinct pathways: i) by phosphalipase D (PLD), which is believed to hydrolyze structural phospholipids to generate PA; or ii) by sequential action of phospholipase C (PLC) and diacylglycerol (DAG) kinase (DGK), wherein PLC can hydrolyze phosphatidylinositol-4,5-bisphosphate [Ptdlns(4,5)P2, PIP2] into inositol-1,4,5-trisphosphate [Ins(1,4,5)P3] and DAG, which may be immediately converted to PA by DGK (10).

A. Phosphatidic Acid Targets

Despite ongoing efforts, the identification of PA targets has remained elusive. A few cellular targets of PA have been described but no clear lipid binding motif has been found. Although it is not necessary to understand the mechanism of an invention, it is believed that predicting biochemical interactions with PA may be difficult because since the putative targets may not share sequence similarity. For example, in mammalian cells, protein kinases Raf-1 (11; 12), protein phosphatases SHP-1(13) and PP1(14), and protein kinase C$\epsilon$ (15) have been reported as PA targets. In yeast, the SNARE protein Spo20p (16) and the inositol-regulated transcriptional repressor Opi1p(17) are putative PA targets.

Similarly, a limited number of PA targets have so far been identified in plants, for example, ABI1 (ABA insensitive 1) (18) and PDK1 (phosphoinositide-dependent kinase 1) (19). In one embodiment, the present invention contemplates that PA may be a positive regulator of the ABA signaling pathway. Although it is not necessary to understand the mechanism of an invention, it is believed that ABI1 may be a protein phosphatase 2C that negatively regulates ABA signaling, whereupon the ABA response, PA becomes induced and binds to ABI1, thereby reducing its phosphatase activity and resulting in translocation to the plasma membrane. Alternatively, *Arabidopsis* PDK1 is believed to be a protein kinase that binds both PA and phosphoinositides, whose activation is limited to PA and not by polyphosphoinositides (19, 20). Additional PA targets were isolated using a PA-affinity matrix, consisting of a PA analogue covalently linked to Affi-Gel 10, which is incubated with suspension-cultured tomato or *Arabidopsis* cell lysates (21). Mass spectrometry has shown that phosphoenolpyruvate carboxylase (PEPC) preferentially binds to PA over other phospholipids (21).

B. TGD2 as a PA Carrier

PA is also believed to act as a substrate that may be directly transported across the membranes by phospholipids and thus play a role in membrane biogenesis. For instance, it is believed that TGD2 comprises a PA target involved in lipid trafficking between the ER and chloroplast. On study has suggested that TGD2C (i.e., the C-terminal 6×-His tag-fused protein of TGD2 having both the N-terminal transit peptide and transmembrane domain removed) interacts selectively with PA (22). Further, an *Arabidopsis* TGD2 protein is proposed to be the substrate binding component of a lipid transfer complex in the inner chloroplast envelope membrane. Supporting this mechanism is the observation that the lipid transfer complex also comprises TGD1, a permease, wherein loss of function of TGD1 results in accumulation of PA in *Arabidopsis* plants (23, 24). Loss of function of other lipid transfer complex components also disrupt the endoplasmic reticulum (ER)-pathway of thylakoid lipid biosynthesis. Thus, TGD proteins, in general, play an active role in PA transport between the ER and the chloroplast, and possibly thylakoid lipid biosynthesis pathway as well.

In some embodiments, the present invention overcomes the known problems in the art in identifying PA-binding domains of TGD2 proteins because they do not share sequence homology to any other known PA-binding domains including, but not limited to, PX (25), pleckstrin homology (20) and some C2 domains (26). In one embodiment, the present invention contemplates a method for characterizing PA-binding domains in TGD2. In one embodiment, the TGD2 PA-binding domain is characterized using a protein-lipid overlay. In one embodiment, the TGD2 PA-binding domain is characterized using a liposome-association assay. In one embodiment, the TGD2 PA-binding domain is characterized using a mutagenesis.

1. TGD2 Orthologs

In one embodiment, a TGD2 gene encodes a 381 amino acid protein with a calculated molecular mass of 41.6 kDa (i.e., for example, Accession Number At3g20320; SEQ ID NO: 1). TGD2 proteins may contain a conserved mycobacterial cell entry domain (MCE, amino acids 127-204; SEQ ID NO: 2) expressed as a surface protein of some pathogenic mycobacteria. MCE proteins are believed to be virulence factors proposed to facilitate the bacterial entry into mammalian host cells (32).

In one embodiment, the present invention contemplates an MCE domain comprising a TGD2 PA-binding site and/or complex. For example, a TGD2 transmembrane domain (amino acids 96-118; SEQ ID NO: 3) and a TGD2 chloroplast targeting peptide (amino acids 1-45; SEQ ID NO: 4) were predicted. See, FIG. 3A. Orthologs to these sequences were found in plants, green algae and Cyanobacteria. (29); See, FIG. 1B. Further, a multiple sequence alignment of TGD2 to these orthologs demonstrates their relatedness. See, FIG. 1A.

2. PA Binding to a dsRed-TGD2C Wild Type Fusion Protein

TGD2C-His has been hypothesized to specifically bind to PA, possibly through its predicted mammalian cell entry (MCE) domain. (22) The present invention found that a DsRed fusion protein system provided a fusion protein having improved solubility in order to perform quantitative binding assays to validate this hypothesis.

Figure 15:
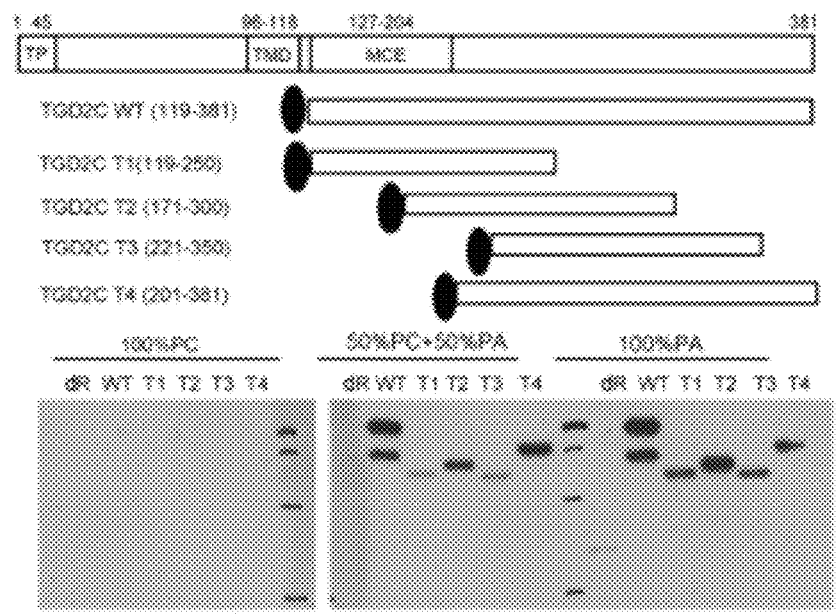
FIG. 15 presents exemplary data identifying a PA-binding minimal domain on TGD2C by deletion and truncation mutagenesis. Identification of a PA binding minimal domain on TGD2C by deletion and truncation mutagenesis.
Figure 15:
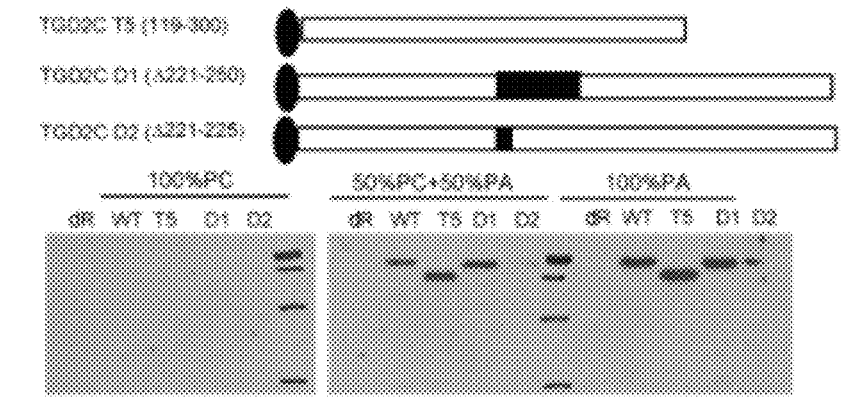
Figure 15:
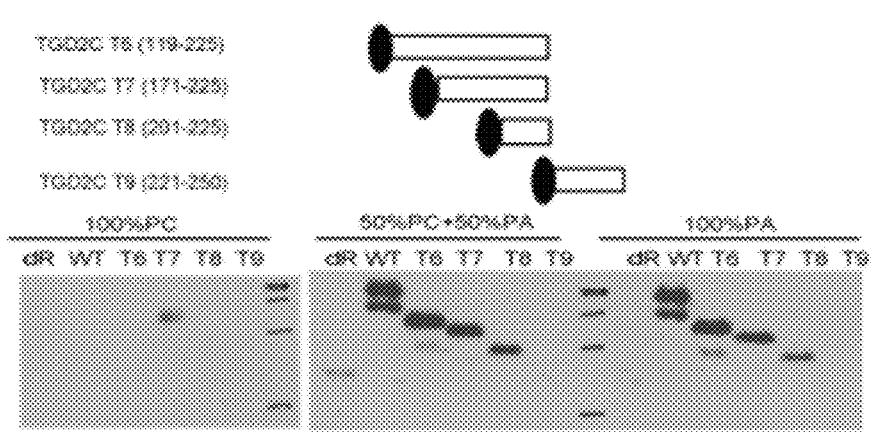
Figure 16:
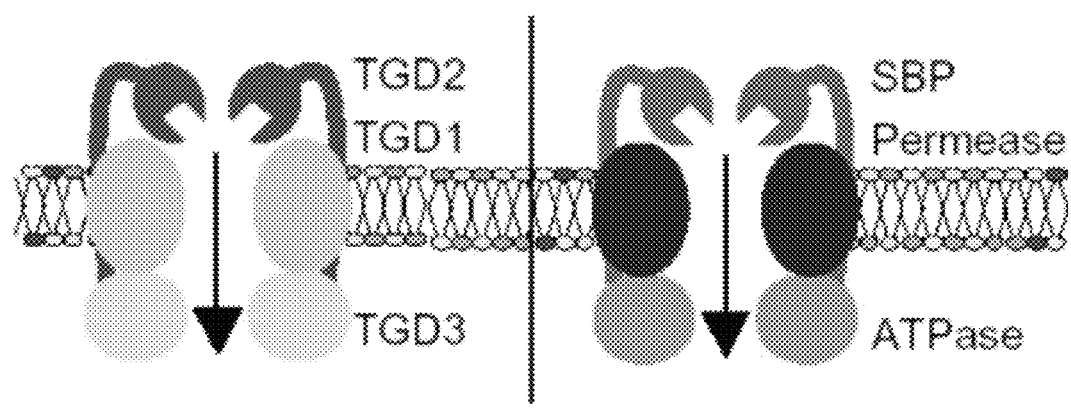
FIG. 16 presents an illustration showing the similarity between TGD proteins and bacterial ABC transporters.

For example, a commercial membrane strip pre-spotted with different phospholipids was used in a protein-lipid overlay assay with a DsRed-TGD2C WT fusion protein performed in accordance with Example II. The results suggested that, like TGD2C-His, a DsRed-TGD2C WT protein also shows specificity for PA over other lipids. FIG. 15, right. To verify that the binding was not due to non-specific PA interactions with DsRed, DsRed protein itself was also assayed for binding. No binding to any lipid for DsRed control was detected, indicating the specificity of this PA binding due to TGD2C protein moiety. FIG. 15, left.

Figure 2A:
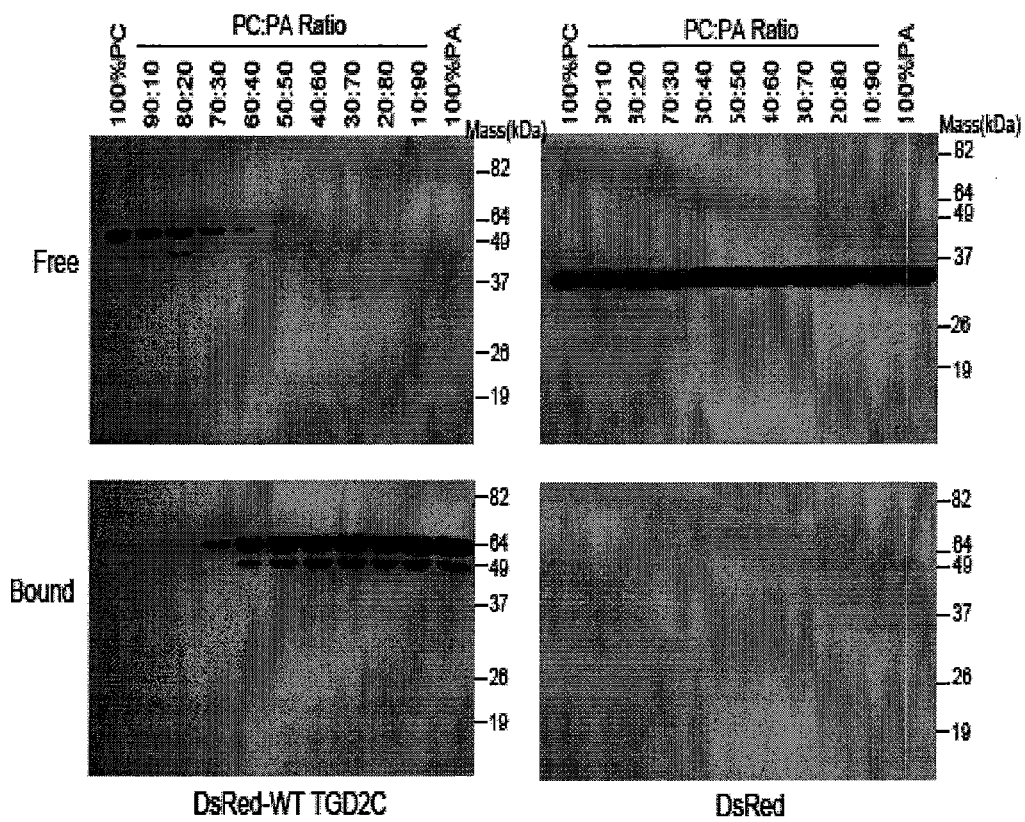
FIG. 2A: Analysis by liposome-association assay. A mixture of dioleoyl-PA and dioleoyl-PC was used where the weight percent of PA was varied from 0-100% (wt/wt), maintaining the total lipid invariant at 250 μg protein was used. P, protein recovered in the absence of lipids.

This result was further supported by lipsome association assay in accordance with Example III. In this assay, purified recombinant proteins were incubated with liposomes for 30 min at 30° C. before centrifugation at 20,000 g for 10 min to pellet the liposomes. Proteins bound to the liposomes were found associated with the lipid pellet, whereas non-binding proteins remained in the supernatant. In an effort to determine the optimal concentration of PA required for high specificity binding, a PA/PC liposome mixture containing varying weight fractions of PA was prepared and incubated with DsRed-TGD2CWT or DsRed alone. The DsRed-TGD2CWT fusion proteins were found to bind PC/PA liposome mixtures, as most of the proteins remained in the pellet/bound fraction. FIG. 2A, left panel, bottom. On the contrary, DsRed alone is almost exclusively present in the supernatant as a free form. FIG. 2A, right panel, top.

Figure 2B:
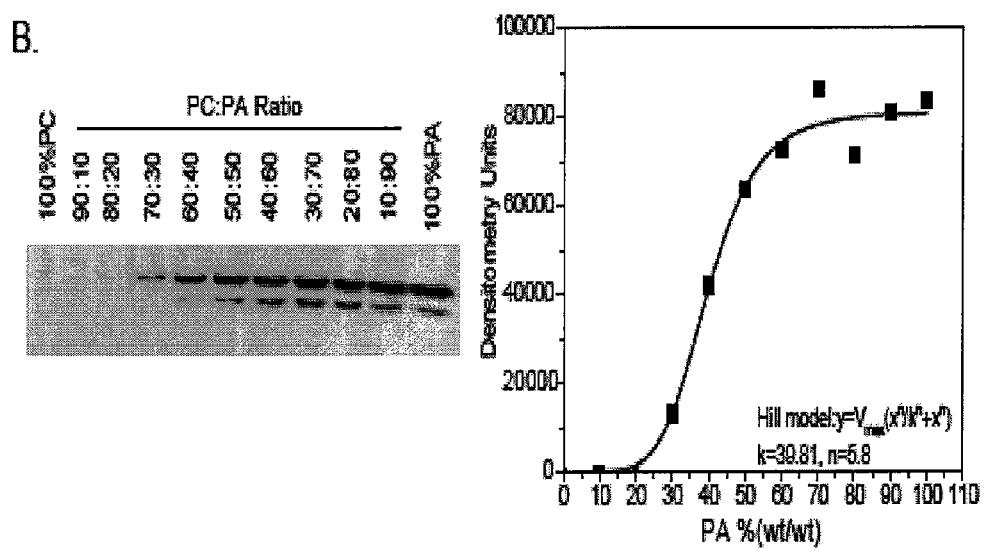
FIG. 2B: Association of DsRed-WT TGD2C to PA/PC liposomes as determined by scanning densitometry (left), and the values are plotted as a function of PA concentration in the liposomes (right). The data were fit to the modified Hill equation for receptor-ligand binding. A Hill number of 5.8 was obtained, suggestive of positive cooperativity.

At the tested protein concentration (1 µg total protein), a significant increase in binding occurred when the liposomes contained between approximately 30-40% PA. These blot were scanned, each individual band was quantified, and the resulted data was plotted and fit to the Hill equation for receptor-ligand binding. FIG. 2B. The data revealed that liposomes made with 100% PA bound the greatest amount of the protein. Moreover, from the Sigmoidal fit, the half maximal binding affinity ($K_d$) of DsRed-TGD2C WT for PA was estimated to be 39.8 mol % PA (wt/wt), which is comparable to the results obtained for RafC-PA association (20 mol % PA) (11). From the binding plot, a Hill number of 5.8 was obtained, suggestive of positive cooperativity. FIG. 2B. Again, this value is similar to that obtained for RafC-PA interaction (Hill number between 3.3 and 6.2) (11). The results may reflect that there is a cooperative sequestering of a domain of PA surrounding the C-terminal part of the TGD2 protein.

3. Identification of TGD2C PA Binding Regions

It has been reported that various reported PA-binding regions share no significant homology in primary structures (10). Consequently, attempting to identify any TGD2 PA binding domain was not intuitively obvious. In one embodiment, the present invention contemplates a method to identify TGD2 PA-binding regions by using a liposome-association assay. In one embodiment, the liposome association assay comprised incubating liposomes with purified mutant proteins. In one embodiment, the mutant proteins comprised amino acid sequences generated using a TGD2C nucleic acid template. In one embodiment, the TGD2C nucleic acid template generated deletion or truncation nucleic acid sequence mutants encoding a mutant TDG2C protein. In one embodiment, the nucleic acid sequence mutants were fused to a C-terminal end of a DsRed nucleic acid open reading frame. Although it is not necessary to understand the mechanism of an invention, it is believed that because the liposome association assay relies on a nonquantitative assessment of binding to identify regions of lipid interaction within the protein, maximizing the binding of TGD2 proteins was highly desired. The present data show that liposomes made with 100% PA bind the greatest amount of the TGD2 protein. FIG. 2. Hence, the binding reactions reported herein included liposomes comprised of 100% PA to achieve the highest lipid binding specificity. As a specificity control, liposomes comprised of 100% phosphatidylcholine (PC) and/or 50% PC+50% PA were included for comparison. Insolubility problems due to the deletion of large portions of the protein (i.e., for example, possibly exposing hydrophobic domain) were solved by using the DsRed protein as a solubilizing and stabling partner. As a result, all the generated mutant proteins disclosed herein were obtained at a satisfactory amount and purity. PA binding data for these representative TGD2 protein mutants are presented. FIG. 3.

Figure 3A:
FIG. 3A: A schematic of TGD2 domains indicating a predicted transit peptide domain (TP), a transmembrane domain (TMD) and a conservative mammalian cell entry (MCE) domain. Upper number represent linear order of amino acid residues.
Figure 3B:
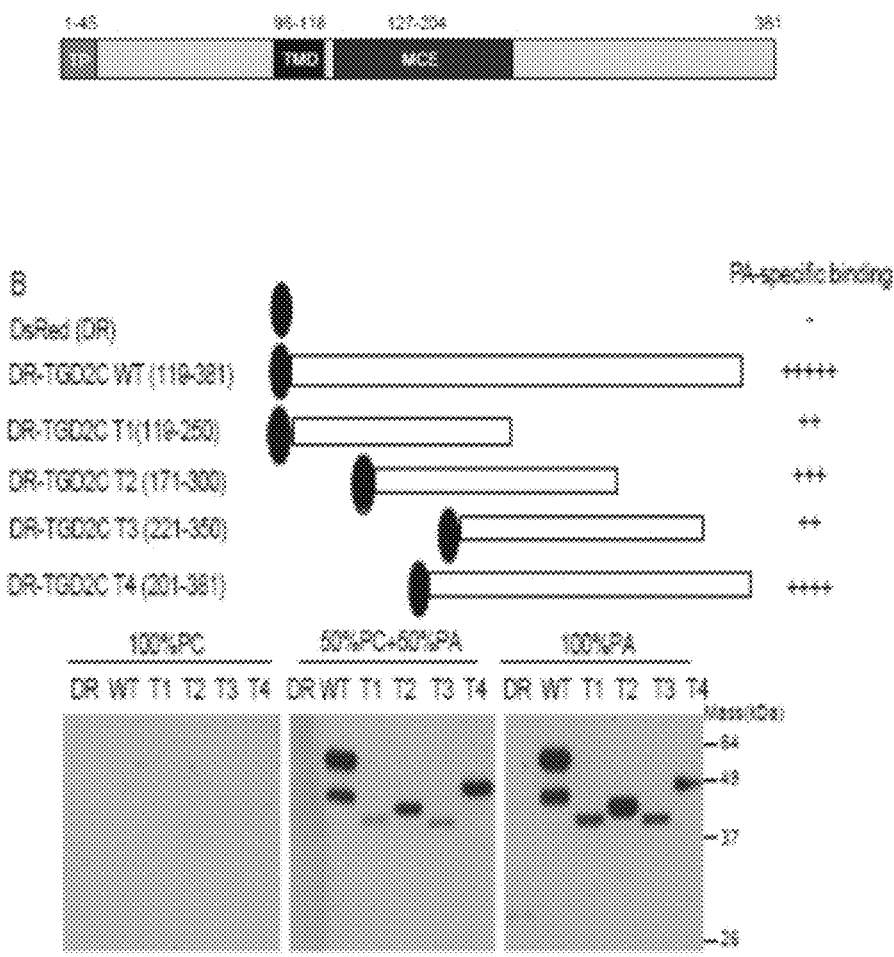
FIGS. 3B and 3C: Deletion and truncation mutants generated on TGD2C and C-terminally fused to the DsRed open reading frame the same manner as WT TGD2C. Black ball represents DsRed protein, grey bars represent deletion fragment. Liposome-association assays were performed to assess binding of various mutants to PC, PA/PC or PA liposomes. PA-specific binding data were summarized on the right. +++++, ++++, +++, ++, +, indicate a qualitative assessment of PA-specific binding in decreasing intensity, and – indicate no binding.

These data show binding characteristics of representative truncated TGD2 mutants ranging in length from between approximately 130 to 180 amino acids. FIG. 3A. DRWT (119-381) (SEQ ID NO: 107) and four mutants displayed significant binding to PA, while having no interaction with the PC control lipid. DsRed itself does not display binding to either PC or PA, confirming the specificity of PA binding by TGD2. FIG. 3B. Although it is not necessary to understand the mechanism of an invention, it is believed that these data suggest that the PA-specific binding domain might reside in the TGD2 region comprising 221-250 amino acid residues (SEQ ID NO: 40), since this region overlaps between the tested mutants.

Figure 3C:
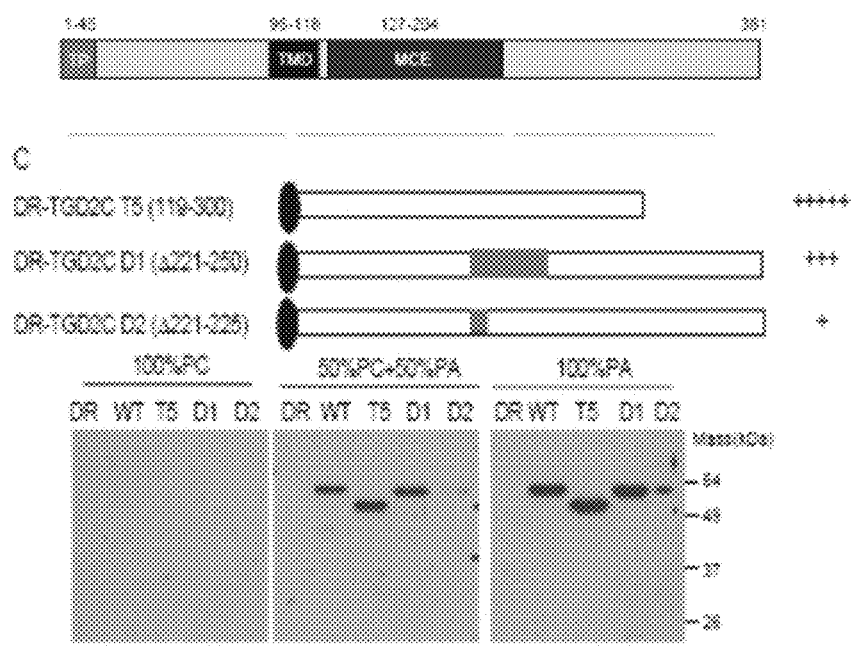

Two internal deletion mutants within the 221-250 amino acid residues (SEQ ID NO: 40) were then generated and tested for PA binding. Surprisingly, the deletion of entire 221-250 region (SEQ ID NO: 40) did not seem to affect PA binding, while the deletion of a smaller 221-225 region (SEQ ID NO: 108) decreases binding activity dramatically. FIG. 3C.

This data was completely counterintuitive and required considerable analysis before proceeding with further evaluation. Although it is not necessary to understand the mechanism of an invention, it is believed that protein folding effects may mediate this observation, wherein a deletion could potentially disrupt or reconstitute the protein structure and thus affect protein function depending on the realistic location of the function domain.

In one embodiment, the present invention contemplates a PA binding domain that is in or close to a TGD2 region comprising amino acid residues 221-250 (SEQ ID NO: 40). Observations that a fifth mutant (i.e., comprising, amino acid residues 119-300 (SEQ ID NO: 28)) also shows strong binding to PA provide corroborating data. FIG. 3C.

These initial deletion studies indicate that a region between residues 201 and 225 (SEQ ID NO: 12) may be sufficient for PA specific binding, even when fused with DsRed. Furthermore, it was observed that this short fusion segment has much less overall binding, suggesting the presence of a minimal PA binding domain (infra).

4. Minimal TGD2 PA Binding Domain

In one embodiment, the present invention contemplates a minimum TGD2 PA binding domain. In one embodiment, the binding domain was identified by fragmenting a TGD2 region comprising amino acid residues 119-250 (SEQ ID NO: 11). In one embodiment, the fragments were fused to DsRed, and assayed using liposome association.

Figure 4A:
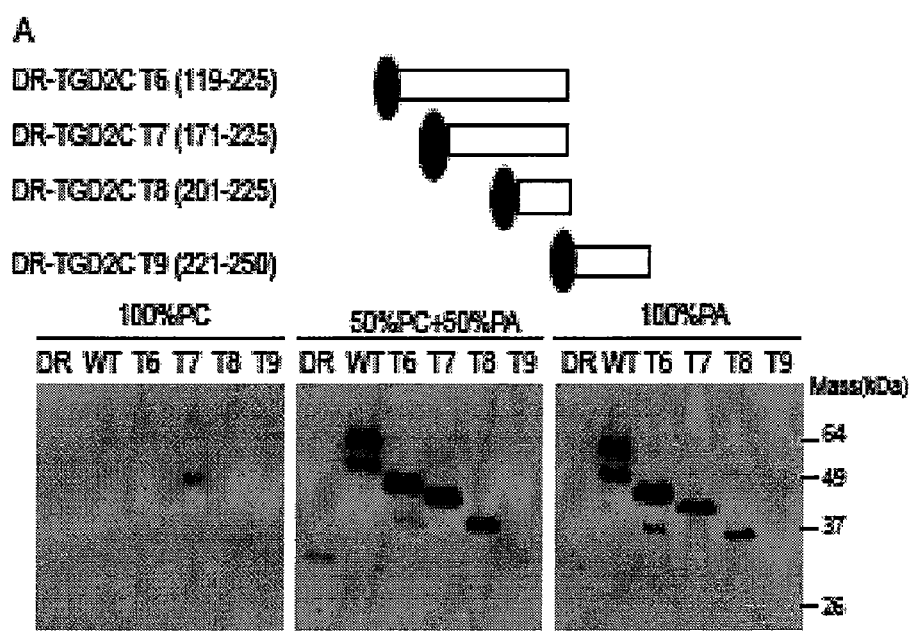
FIG. 4A: Truncation mutants generated to localize a PA binding domain. PA binding activity were assessed by liposome-association assay.
Figure 4B:
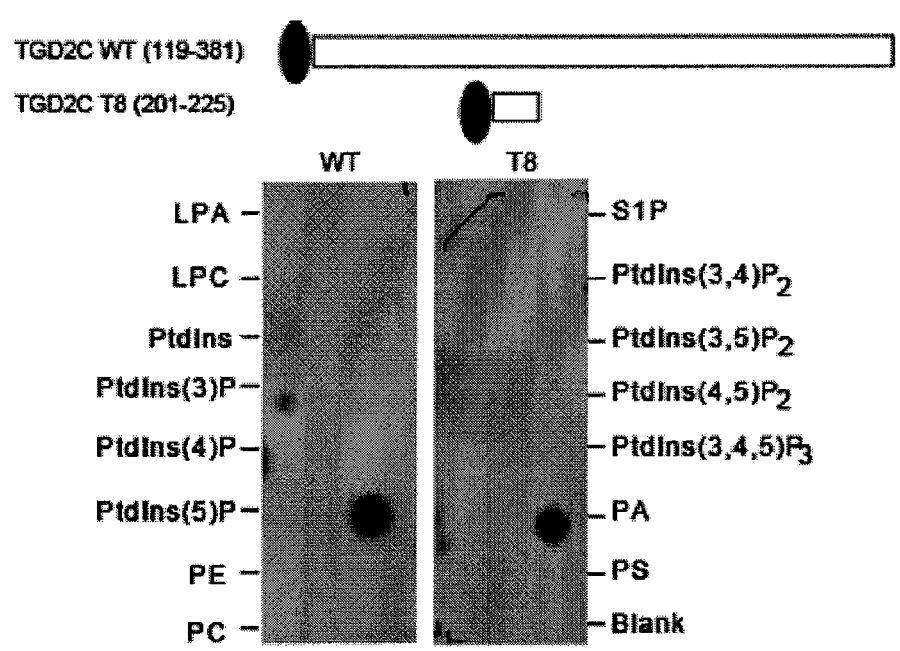
FIG. 4B: Verification of PA binding to a minimal domain (TGD2C T8 (201-225) (SEQ ID NO: 12)) as compared to wild type (TGD2C WT (119-381) (SEQ ID NO: 107)) by protein-lipid overlay assay conducted with commercial phospholipid-containing membrane strip. LPA, lysophosphatidic acid; LPC, lysophosphatidylcholine; Ptdlns, phosphatidylinositol; Ptdlns(3)P, phosphatidylinositol 3-phosphate; Ptdlns(4)P, phosphatidylinositol 4-phosphate; Ptdlns(5)P, phosphatidylinositol 5-phosphate; PE, phosphatidylethanolamine; PC, phosphatidylcholine; SIP, sphingosine 1-phosphate; Ptdlns(3,4)P2, phosphatidylinositol 3,4-bisphosphate; Ptdlns(3,5)P2, phosphatidylinositol 3,5-bisphosphate; Ptdlns(4,5)P2, phosphatidylinositol 4,5-bisphosphate; Ptdlns(3,4,5)P3, phosphatidylinositol 3,4,5-bisphosphate; PA, phosphatidic acid; PS, phosphatidylserine.

In brief, amino acids were removed from the N-terminal of TGD2C down to the middle of a TGD2C region comprising amino acid residues 221-250 (SEQ ID NO: 40) (i.e., for example, amino acid residue 225). See, FIG. 4A. The data indicated that a 25 amino acid sequence (i.e., for example, amino acid residues 201-225; SEQ ID NO: 12) is sufficient to mediate specific binding to PA. FIG. 4A. A TGD2C region comprising amino acid residues 221-250 (SEQ ID NO: 40) was also tested; however, no interaction to PA was detected. These data indicate that this TGD2C region may play a lesser role in PA binding, and partially explains why deletion of this region does not appreciably affect PA binding (supra). A protein-lipid overlay in accordance with Example II verified PA binding by the 25 amino acid sequence (SEQ ID NO: 12). FIG. 4B. Similar to DR-WT, this mutant itself binds PA on the membrane strip, with apparent lower affinity.

Figure 4C:
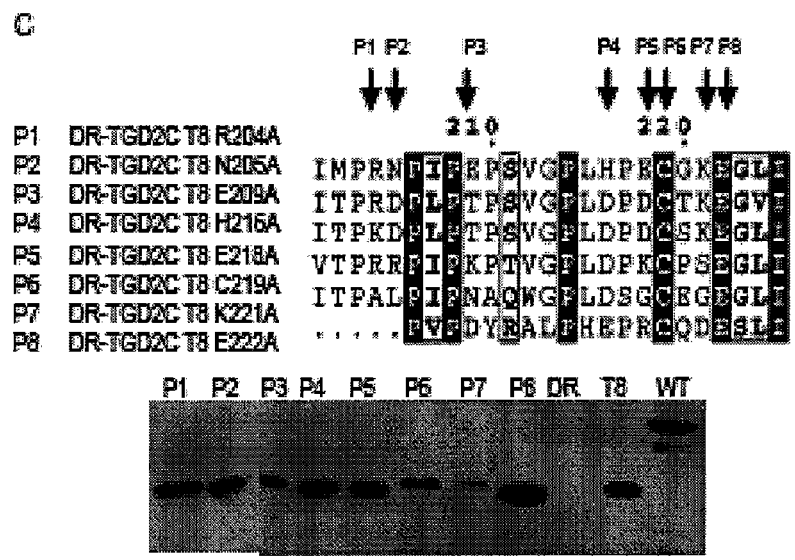
FIG. 4C: PA binding of point mutations on the minimal domain shown by liposome association assay with 100% PA liposomes. Point mutations are indicated by arrows.

Some reports have identified that TGD2 PA-binding regions involve basic amino acids and/or tryptophan residues (10). In particular, one recent study shows that electrostatic interactions of PA with basic amino acids (i.e., for example, lysine and/or arginine) combined with hydrogen bond interactions, may form a basis for specific binding of PA to PA targets (33). Based on sequence similarity of TGD2 to its closely related homologs in plants and green algae, several charged and/or conserved amino acids were picked as potential interesting residues in the 25-mer minimal domain for possibly mediating interactions with PA. An alanine screen was then performed to evaluate these residues within a minimal PA binding region of TGD2 (i.e., for example, SEQ ID NO:12). Point mutations were generated in the 25-mer minimal domain and fused with DsRed to test PA binding by liposome-association assay using 100% PA liposomes. The data demonstrate that, all point mutations have little or no effect on PA-liposome binding except K221A. FIG. 4C. This lysine-to-alanine mutation significantly reduced the amount of interaction with PA-liposomes. No detectable PC-liposome binding was observed for any of the constructs (data not shown).

In one embodiment, the present invention contemplates a TGD2 PA binding domain comprising amino acid residues 201-225 (SEQ ID NO: 12). In one embodiment, the binding domain is adjacent to a MCE domain. Although it is not necessary to understand the mechanism of an invention, it is believed that mutation of $^{221}$Lys to $^{221}$Ala significantly diminishes PA binding. Further, upon generation of a point mutant (K221A) within a minimal domain, PA binding was diminished, thereby identifying $^{221}$Lys as an amino acid residue involved in PA binding. This discovery is consistent with previous hypotheses that basic amino acids and/or tryptophan might be involved in lipid PA binding (10; 33).

Figure 5:
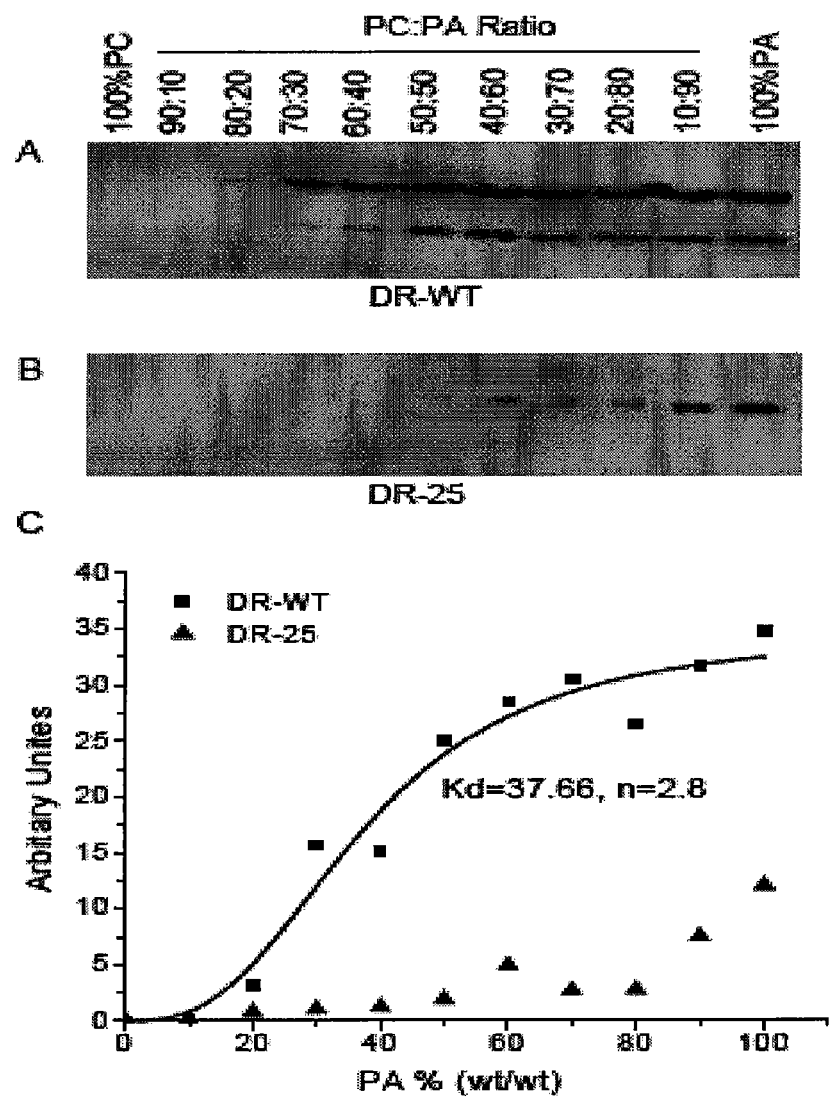
FIG. 5 presents exemplary data showing loss of positive cooperativity by a minimal binding domain.
Figure 5:
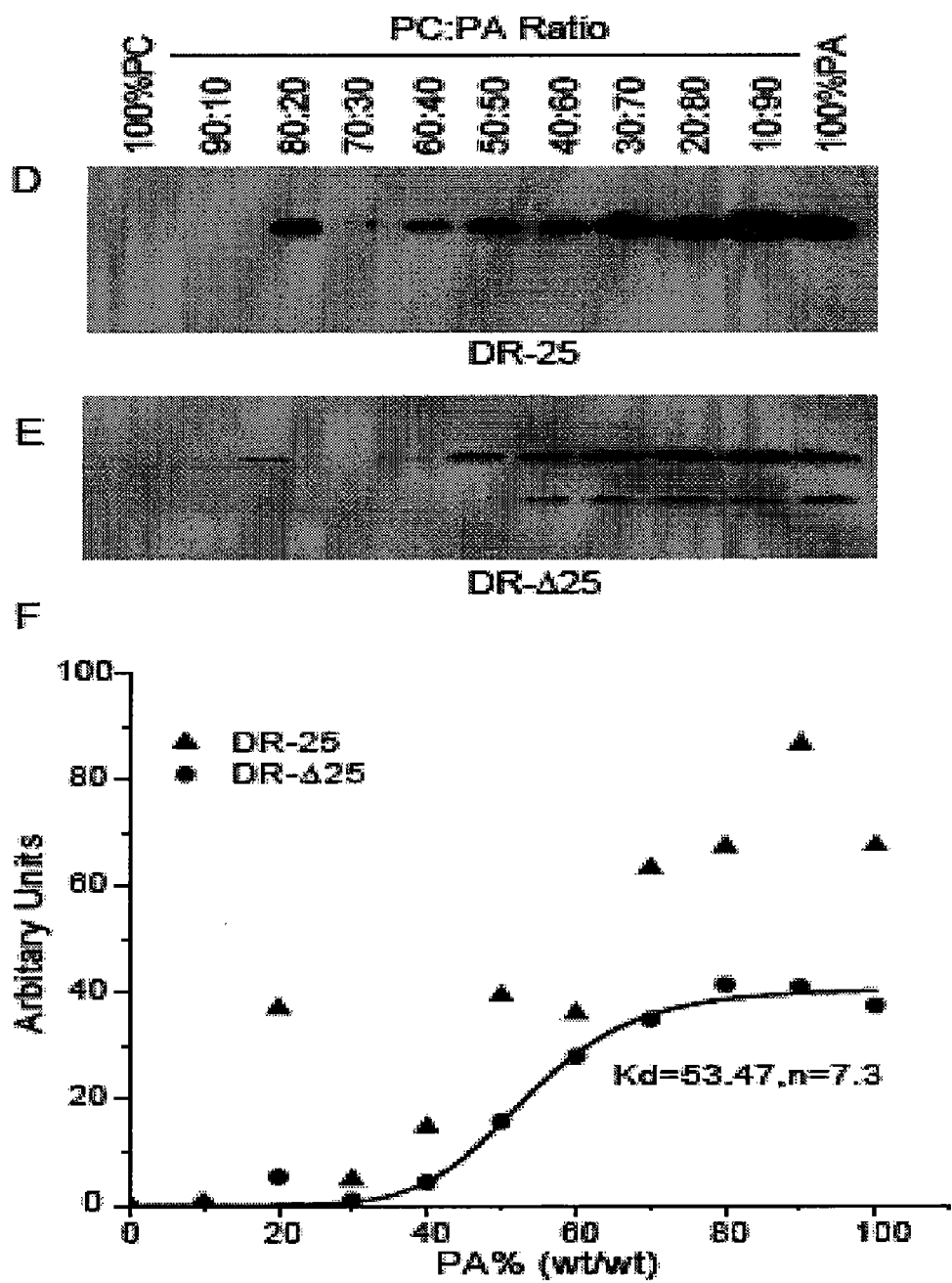

Surprisingly, a PA binding TGD2 minimal domain is sufficient, but not necessary, to mediate interactions between TGD2 and PA liposomes. For example, a TGD2 fragment wherein a minimal domain was deleted still retains residual binding activity, albeit with significantly lower affinity. Moreover, a TGD2 protein having a minimal domain deletion still displays positive cooperativity to PA binding. FIGS. 5E and 5F. These data suggested the presence of accessory PA binding domains or segments that also play a role in cooperating PA binding by the minimal domain.

5. Accessory TGD2 PA Binding Components

The above data showing that DR-WT protein displayed positive cooperativity upon PA binding suggested that a 25 amino acid sequence comprising a minimal PA binding domain may not be acting independently. Although it is not necessary to understand the mechanism of an invention, it is believed that the minimal binding domain may comprise accessory biochemical properties involved in PA binding. Liposome-association assay was performed with mixed PA/PC liposomes using DR-WT as a quantification control. The data show DR-25 binding to PA loses positive cooperativity, while DR-WT binding to PA still obeys the Hill equation, with a modified $K_d$ of 37.66 mol % and a Hill number of 2.8. FIGS. 5A-5C.

A 25-mer deletion mutant (designated as DR-Δ25) was generated that retained some residual PA binding activity. But moreover, the binding of this deletion mutant to PA also displayed positive cooperativity. An increased Kd of 53.47 mol % and a Hill number of 7.3 were identified from the fitting curve. FIGS. 5E and 5F. In contrast, the data show that DR-25 is not cooperative. FIGS. 5D and 5F. Apparently, a 25-mer minimal domain, alone, is sufficient to facilitate PA binding, but might also involve accessory components. In one embodiment, the present invention contemplates PA binding accessory components capable of modulating PA binding of TGD2 protein.

This hypothesis is consistent with observations that some deletions of the TDG2 region comprising amino acid residues 221-250 (SEQ ID NO: 40) do not affect PA binding, while some deletions of the TDG2 region comprising amino acid residues 221-225 (SEQ ID NO: 108) significantly decrease PA binding activity. Although it is not necessary to understand the mechanism of an invention, it is believed that these observations also suggest that there are accessory PA binding components flanking the TGD2 region comprising amino acid residues 201-225 (SEQ ID NO: 12), wherein different deletions differentially affect protein folding and, ultimately, functionality. This semi-quantitative analysis demonstrated that PA binding by a minimal domain lost positive cooperativity, which was also a property of wild type TGD2C protein.

Figure 6:
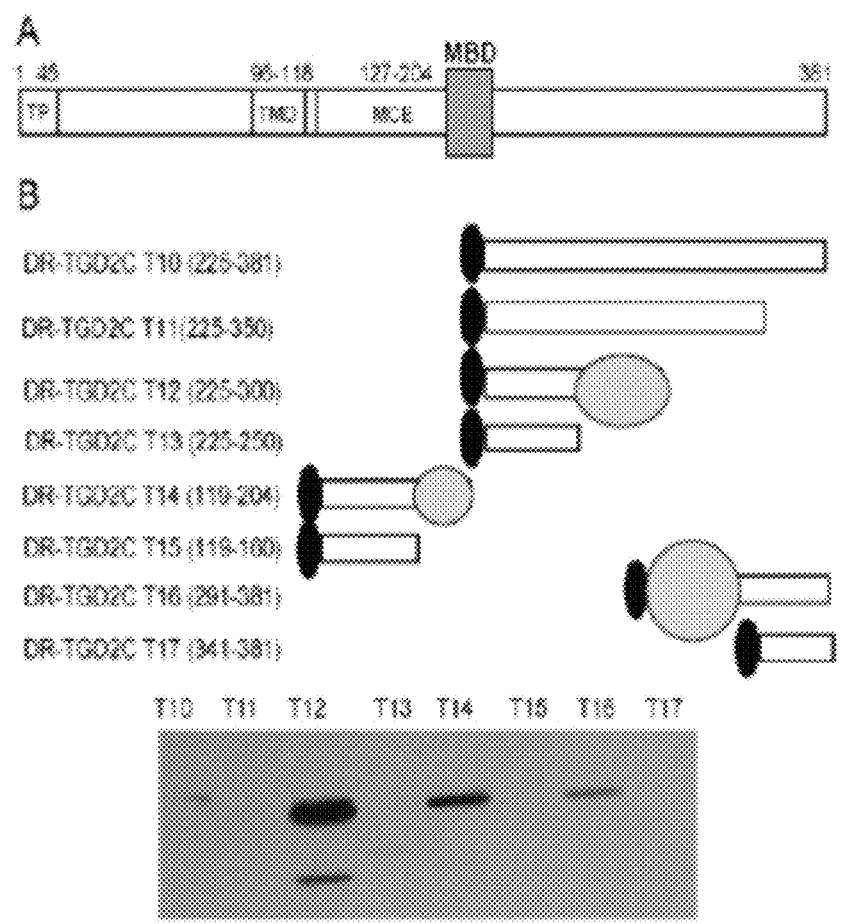
FIG. 6 illustrates additional embodiments of PA binding sites.

In one embodiment, the present invention contemplates a plurality of TGD2 accessory PA binding segments. For example, TGD2 mutants were generated with truncated sequences from either the C-terminus (i.e., for example, amino acid residue 381) or within the middle of TGD2 (i.e., for example, amino acid residue 204) and fused to an DsRed open reading frame. (FIG. 6B). These mutated TGD2 proteins were tested for PA binding by using the liposome association assay using 100% PA liposomes. The data show that, at least four mutants were found to have various PA binding activity. FIG. 6B.

In one embodiment, a TGD2 accessory PA binding site comprises amino acid residues 251-300 (SEQ ID NO: 103). In one embodiment, a TGD2 accessory PA binding site comprises amino acid residues 161-204 (SEQ ID NO: 104). In one embodiment, a TGD2 accessory PA binding site comprises amino acid residues 291-340 (SEQ ID NO: 105).

6. A TDG2 PA Binding Motif

In one embodiment, the present invention contemplates a TGD2 minimal PA binding region comprising a PA binding motif. In one embodiment, a PA binding motif further comprises at least three other regions in proximity with, or adjacent to, a TGD2 minimal PA binding domain.

In one embodiment, the TGD2 minimal PA binding domain comprises amino acid residues 201-225 (SEQ ID NO: 12), wherein at least one amino acid residue is a proline. In one embodiment, at least two amino acids are prolines. In one embodiment, at least three amino acids are prolines. In one embodiment, at least four amino acids are proline. In one embodiment, at least five amino acids are prolines. In one embodiment, at least six amino acids are prolines.

Although it is not necessary to understand the mechanism of an invention, it is believed that proline residues within the TGD2 region comprising amino acid residues 201-225 (SEQ ID NO: 12) may induce folding alongside an N-terminal β-strand and a C-terminal α-helix to form a PA binding site.

This proline-induced folding hypothesis is supported by a secondary structure prediction showing that residues 201-225 (SEQ ID NO: 12) is a loop-strand fold lacks helical or β-strand structure. FIG. 1A. Therefore, a full PA binding domain on TGD2 likely comprises amino acid residues comprising a minimal PA binding domain (i.e., for example, TGD2 amino acid residues 201-225 (SEQ ID NO: 12)) as well as amino acid residues present in both sides of a minimal PA binding domain (i.e., for example, amino acid residues 161-204 (SEQ ID NO: 104) and/or amino acid residues 251-300 (SEQ ID NO: 103)). Such a combination of a minimal PA binding domain with at least one accessory PA binding domain is believed to generate a complete PA binding domain having a complicated tertiary binding structure.

Because the TGD2 protein resembles substrate binding proteins of bacterial ABC transporters, and because the tgd2-1 phenotype was consistent with a defect in lipid transfer into the chloroplast, the TGD2 protein was tested for the specific binding of different lipids. To distinguish lipid binding to the TMD from lipid binding to a possible substrate site in the C-terminal domain, an N-terminally truncated version, TGD2-dTMD-His, was produced in Escherichia tag was used for purification and detection of TGD2-dTMD-His by an anti-His tag antibody. A commercial membrane with different phospholipids and membranes with plant-specific lipids were used. Of all of the lipids tested, including diacylglycerol (data not shown), only PA bound to TGD2-dTMD-His. See, FIG. 8A.

By employing an independent approach, the TGD2-dTMD-His protein bound phosphatidylcholine liposomes containing different molecular species of PA. See, FIG. 8B. Liposomes consisting of phosphatidylcholine alone did not bind. Binding was independent of the molecular species of PA at least at the semiquantitative immunoblot level. The results suggested that TGD2 contains a PA-specific binding domain in the C-terminal part of the protein.

7. Expression of TGD2 Fusion Proteins

Proteins containing different fragments of Arabidopsis TGD2 were C-terminally fused to DsRed protein (i.e., for example, a Discosoma sp. reef coral protein) and expressed in E. coli BL-21 (DE3) strain using a DsRed-plw01-His vector in accordance with Example I. The quality of the expressed fusion protein was routinely monitored by SDS-PAGE followed by Coomassie Brilliant Blue staining. Typically, the purity of the DsRed-TGD2 fusion proteins was greater than 90%. A variety of DsRed-TGD2 mutated fusion proteins have been evaluated. Table 2.

TABLE 2

PCR primers used to create dsRed-TGD2 mutated fusion proteins.

| dsRed-TGD2 protein | mutation | 5' primer | 3' primer |
|---|---|---|---|
| TGD2C WT (SEQ ID NO: 13) (119-391) | WT | 5'-CCG GAG CTC GGT TTT CAA ATG CCG TC-3' (SEQ ID NO: 14) | 5'-CGG CTC GAG TAG TAG CCT GCT-TAG GG-3' (SEQ ID NO: 15) |
| TGD2C T1 (SEQ ID NO: 11) (119-250) | 119-250 | 5'-CCG GAG CTC GGT TTT CAA ATG CGG TC-3' (SEQ ID NO: 14) | 5'-GCG CTC GAG AAT ACG AGT-GAA AAT TCC-3' (SEQ ID NO: 18) |
| TGD2C T2 (SEQ ID NO: 19) (171-300) | 171-300 | 5'-CCG GAG CTC GCT GAG ATA GAA GAT G-3' (SEQ ID NO: 20) | 5'-CGA CTC GAG GCT ATC AC-G AAA CTC AG-3' (SEQ ID NO: 21) |
| TGD2C T3 (SEQ ID NO: 22) (221-350) | 221-350 | 5'-CAG GAG CTC AAG GAA GGT CTG ATC G-3' (SEQ ID NO: 23) | 5'-CGG CTC GAG GAC GTT CT-T CAA AGT AT-3' (SEQ ID NO: 24) |
| TGD2C T4 | 201-381 | 5'-CCG GAG CTC ATT ATG CCT AGG AAT CCG-3' | 5'-CGG CTC GAG TAG TAG CCT GCT-TAG |

TABLE 2-continued

PCR primers used to create dsRed-TGD2 mutated fusion proteins.

| dsRed-TGD2 protein | mutation | 5' primer | 3' primer |
|---|---|---|---|
| (SEQ ID NO: 25) (201-381) | | (SEQ ID NO: 26) | GG-3' (SEQ ID NO: 27) |
| TGD2C T5 (SEQ ID NO: 28) (119-300) | 119-300 | 5'-CCG GAG CTC GGT TTT CAA ATG CGG TC-3' (SEQ ID NO: 14) | 5'-CGA CTC GAG GCT ATC ACG AAA CTC AG-3' (SEQ ID NO: 21) |
| TGD2C T6 (SEQ ID NO: 31) (119-225) | 119-225 | 5'-CCG GAG CTC GGT TTT CAA ATG CGG TC-3' (SEQ ID NO: 14) | 5'-CGG CTC GAG GAT CAG ACC TTC-CTT AC-3' (SEQ ID NO: 33) |
| TGD2C T7 (SEQ ID NO: 34 (171-225) | 171-225 | 5'-CCG GAG CTC GCT GAG ATA GAA GAT G-3' (SEQ ID NO: 35) | 5'-CGG CTC GAG GAT CAG ACC TTC-CTT AC-3' (SEQ ID NO: 33) |
| TGD2C T8 (SEQ ID NO: 12 (201-225) | 201-225 | 5'-CCG GAG CTC ATT ATG CCT AGG AAT CCG-3' (SEQ ID NO: 26) | 5'-CGG CTC GAG GAT CAG ACC TTC-CTT AC-3' (SEQ ID NO: 33) |
| TGD2C T9 (SEQ ID NO: 40) (221-250) | 221-250 | 5'-CAG GAG CTC AAG GAA GGT CTG ATC G-3' (SEQ ID NO: 23) | 5'-GCG CTC GAG AAT ACG AGT-GAA AAT TCC-3' (SEQ ID NO: 18) |
| TGD2C D1 (SEQ ID NO: 43) (Δ221-250) | 221-250 deleted (SEQ ID NO: 44) | 5'-CTG CAT CCT GAA TGT GGT GGA CGC GAA GTT GAG GCC-3' (SEQ ID NO: 45) | 5'-GGC CTC AAC TTC GCG TCC ACC ACA TTC AGG ATG CAG-3' |
| TGD2C D2 (SEQ ID NO: 46) (Δ221-225) | 221-225 deleted (SEQ ID NO: 47) | 5'-CTG CAT CCT GAA TGT GGT GTT TGT GAT AGG CAG ACA-3' (SEQ ID NO: 48) | 5'-TGT CTG CCT ATC ACA AAC ACC ACA TTC AGG ATG CAG-3' |

One previous study suggested that the C-terminus of TGD2 protein lacking a transit peptide domain and transmembrane domain (TGD2C) could bind to PA when fused with 6×His tag. (22) However, a major drawback of using this reported His-tag-fused-TGD2C protein is bad solubility, which brings significant technical difficulties when attempting mutagenesis and other in vitro studies. In fact, most reports in the lipid binding field use GST-fusion techniques to create a better solubilized protein. However, GST-TGD2 fusion proteins also resulted in unsatisfactory results. While expression and purification of the GST-TGD2 fusion protein was possible, GST alone resulted in non-specific PA binding to the tested lipid substrates, leading to controversial conclusions (data not shown).

Among several other expression systems tested, DsRed-fusion provided an optimized assay system and is described herein. The DsRed-monomer is an engineered mutant of the red fluorescent protein from *Discosoma* sp. reef coral, and has specific advantages of being extremely stable and highly soluble. These properties allow expression of soluble DsRed-TGD2 fusion proteins in order to monitor 'real time' fluorescence during recombinant protein production and purification.

Figure 7:
FIG. 7 presents exemplary data showing the binding of DsRed-TGD2C WT fusion protein to PA.
Figure 7:
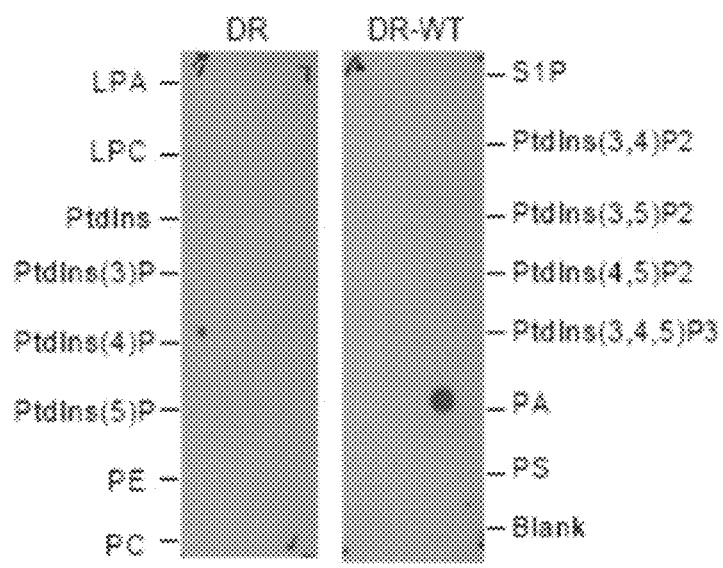

The data presented herein utilizes the same C-terminus of TGD2 protein as reported in the GST fusions, but were fused to DsRed instead. As discussed above, these DsRed-TGD2 fusion proteins demonstrated specific PA binding using protein-lipid overlay assay. See, FIG. 7. Furthermore, a minimal PA binding domain in TGD2 was identified that is sufficient to mediate the interaction between the protein and lipid. These data: i) demonstrate that TGD2 specifically binds PA and is a possible substrate for transportation by the proposed TGD123 complex; and (2) define a specific TGD2 PA binding domain that does not show any sequence or structure homology with known PA targets.

8. TGD2 Crystallography

As discussed above, it is generally known that PA-binding regions reveal no significant homology in primary protein structure (i.e., linear amino acid sequence). (10). None of the previously reported PA targets were predicted by common amino acid sequences.

Attempts to identify other PA binding proteins using a TGD2-minimal PA binding domain sequence (i.e., for example, amino acid residues 201-225 (SEQ ID NO: 12)) yielded no results when searching a non-redundant protein database. FIG. 1A. Hence, homology modeling of TGD2 failed to find other possible PA binding sites in order to generate a working model. Therefore, further analysis will focus on crystallization PA with the full-length TGD2 in an effort to circumvent these difficulties.

IV. Isolation of a tgd2-1 Mutant

The tgd2-1 mutant was initially identified during a suppressor screen in the dgd1 mutant background using a chemically induced mutant population. Xu et al., (2003) *EMBO J.* 22:2370-2379. The dgd1 mutant was reported to be deficient in DGD1, the protein believed responsible for the bulk of digalactolipid biosynthesis. Dormann et al., (1999) *Science* 284:2181-2184. Presence of the tgd2-1 mutation in the dgd1 background partially alleviated the digalactolipid deficiency and caused the accumulation of a lipid co-chromatographing with trigalactosyldiacylglycerol diagnostic for all tgd mutants. Crossing the double-homozygous dgd1/tgd1-1 and dgd1/tgd2 mutants gave rise to uniform plants in the F1 generation with a homozygous dgd1-like phenotype, suggesting that tgd1-1 and tgd2-1 are not allelic. The tgd2-1/dgd1 homozygous double mutant was crossed to *Arabidopsis* wild-type, ecotype Columbia-2 (Col-2). The F1 plants showed a wild-type lipid phenotype confirming that the tgd2-1 mutant allele is recessive. After selfing and lipid analysis, F2 plants homozygous at the tgd2-1 locus were genotyped at the DGD1 locus by using a derived cut amplified polymorphic sequence (dCAPS) marker to test for loss of the dgd1 mutation. A homozygous tgd2-1 mutant line was back-crossed with wild type (Col-2) three times to reduce the chance of secondary mutations. Unless indicated otherwise, further analysis was done with this tgd2-1 mutant in the wild-type background.

Figure 10:
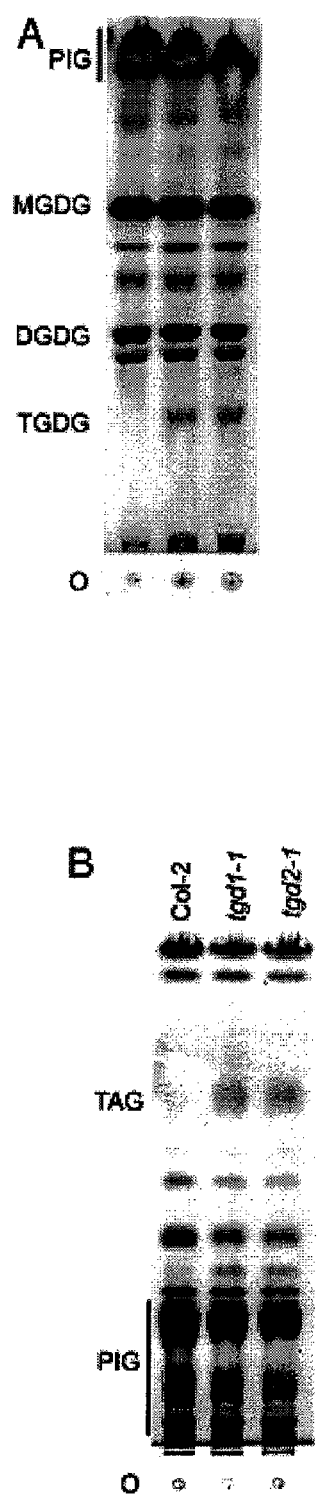
FIG. 10 presents exemplary data showing a lipid phenotype of the tgd2-1 mutant as compared with the tgd1-1 mutant and the Col-2 wild type. Fatty acids are indicated with number of carbons:number of double bonds. DGDG, digalactosyldiacylglycerol; MGDG, monogalactosyldiacylglycerol; O, origin; PC, phosphatidylcholine; PE, phosphatidylethanolamine; PG, phosphatidylglycerol; PI, phosphatidylinositol; PIG, pigments; SQDG, sulfoquinovosyldiacylglycerol; TAG, triacylglycerol; TGDG, trigalactosyldiacylglycerol.
Figure 10:
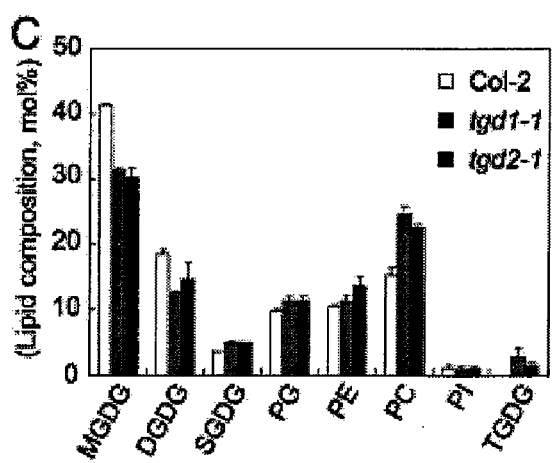
Figure 10:
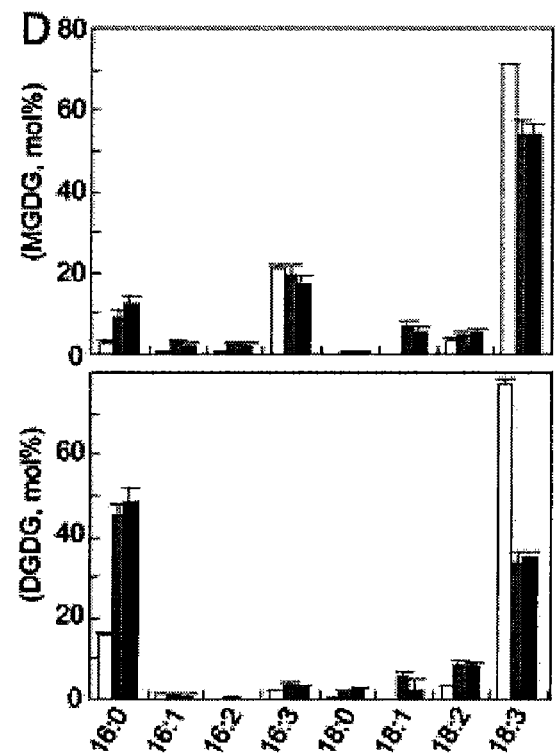

Compared to the wild type, tgd2-1 plants were consistently smaller and slightly pale, as was observed for the tgd1-1 mutants. Xu et al., (2005) *Plant Cell* 17:3094-3110. Chlorophyll contents were reduced to a similar extent in the tgd1-1 and tgd2-1 mutants [chlorophyll (Chl) per gram of fresh weight (FW) ±SD, n=4: wild type, 1,136±138 $\mu g_{Chl} \cdot g^{-1}$ FW; tgd1-1, 553±115 $\mu g_{Chl} \cdot g^{-1}$ FW; tgd2-1, 656±145 $\mu g_{Chl} \cdot g^{-1}$ FW]. Leaf lipid extracts of the wild type and the tgd1-1 and tgd2-1 mutants were compared by TLC. In the tgd2-1 sample a lipid staining positive for sugar and cochromatographing with authentic trigalactolipid of tgd1-1 is present. See, FIG. 10A. A lipid co-chromatographing with authentic triacylglycerol accumulating in tgd1-1 leaves was present in the tgd2-1 sample as well. See, FIG. 10B. Quantitative analysis of the polar lipids indicated similar changes in the two mutants with relative amounts of the monogalactolipid and digalactolipid reduced and relative amounts of phosphatidylcholine increased. See, FIG. 10C. In addition, trigalactolipid was present to a similar extent in both mutants (tgd1-1, 2.7±1.4 mol %; tgd2-1, 1.6±0.4 mol %; n=4; data are ±SD) but was not detectable in the wild type. Analyzing the fatty acid composition of the two galactolipids indicated a reduction of 18-carbon fatty acids and an increase in 16-carbon fatty acids to the same extent in both mutants. See, FIG. 10D. These overall fatty acid compositions for the tgd2-1 mutant imply a change in molecular species distribution in the two galactolipids consistent with a reduction of molecular species derived from the ER pathway. In addition, similar to the tgd1-1 mutant carrying a weak chemically-induced mutant allele, the tgd2-1 mutant produced a fraction (~43%, 281 of 651 in a representative sample) of aborted seeds.

Figure 11:
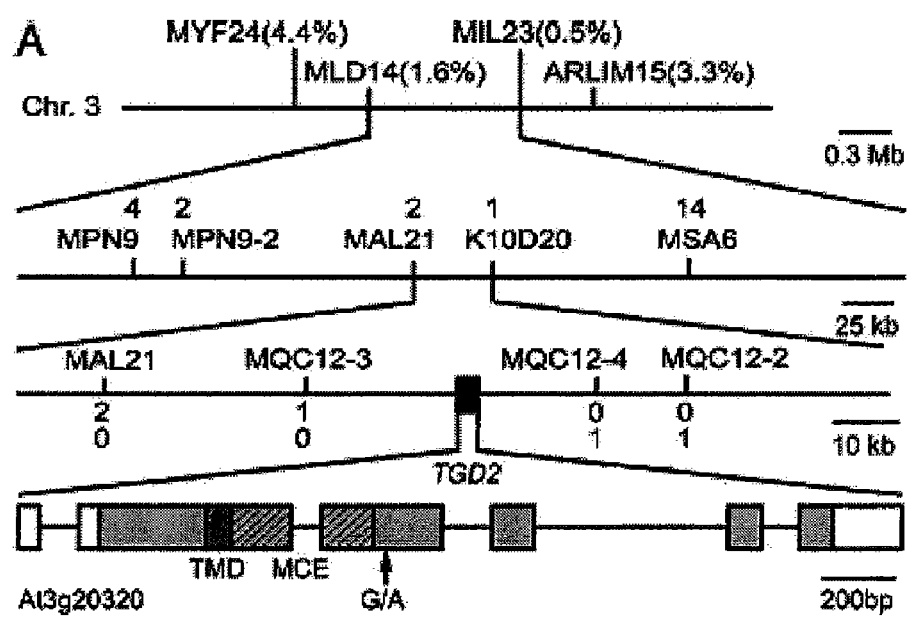
FIG. 11 presents exemplary data showing an identification of a TGD2 locus.

In a mapping population of 93 homozygous tgd2-1 F2 mutant plants (186 chromosomes) from a cross between the homozygous tgd2-1 mutant in the dgd1(Col-2) background and a plant from the ecotype Landsberg erecta the tgd2-1 mutant locus was mapped close to cut amplified polymorphic sequence (CAPS) marker ARLIM15.1 (arabidopsis.org) at ~30 cM on chromosome 3. See, FIG. 11A. In an enlarged F2 mapping population from the same cross (3,506 chromosomes) the tgd2-1 mutant locus was mapped to an ~45-kb fragment flanked by CAPS marker MQC12-3 and dCAPS marker MQC12-4. See, FIG. 11A.

This region falls onto the *Arabidopsis* bacterial artificial chromosome clone MQC12 (Gen-Bank accession no. AB024036; SEQ ID NO: 129) and encompasses 14 predicted or confirmed genes (At3g20270-At3g20390). Notably, the translation product of At3g20320 (SEQ ID NO: 1) was similar to the ttg2C protein (GenBank accession no. AAD17959 (SEQ ID NO: 128); 25.0% identity over >100 aa) of *Pseudomonas putida*. This protein is predicted to be the substrate-binding protein of an ABC transporter, and its ORF is flanked by one encoding the ABC transporter permease ttg2B (GenBank accession no. AAD17958; SEQ ID NO: 127). Most notably, the *Arabidopsis* TGD1 protein is similar to ttg2B (29.6% identity over >100 aa) of *P. putida*. The predicted bacterial ABC transporter encoded by the ttg2 operon in *P. putida* has been genetically implicated in toluene resistance. Kim et al., (1998) *J. Bacteriol.* 180:3692-3696. The At3g20320 cDNA sequence obtained by RT-PCR from the *Arabidopsis* tgd2-1 mutant contained a G-to-A mutation (See, FIG. 2A) corresponding to position 7,088,870 of the assembled chromosome 3 sequence (GenBank accession no. NC_003074) and leading to a glycine-to-arginine change in the amino acid sequence. See, FIG. 11A. This mutation was confirmed by designing a tgd2-1 allele-specific dCAPS marker that was later used for genotyping. See, FIG. 11D.

The TGD2 ORF of 1,146 by encodes a protein of 41.6 kDa. In addition to the similarity to bacterial substrate binding proteins, the TGD2 protein contains a MCE domain (amino acids 99-216 (SEQ ID NO: 109)). See, FIG. 11A, bottom. This domain is found in surface proteins of pathogenic mycobacteria. These proteins may comprise virulence factors proposed to facilitate the bacterial entry into mammalian host cells. Chitale et. al., (2001) *Cell. Microbiol.* 3:247-254. The mutation in tgd2-1 affects amino acid 234 just outside this MCE domain. A transmembranespanning domain (TMD) in TGD2 (amino acids 96-118) (SEQ ID NO: 3) was predicted by using SOSUI software. Hirokawa et al., (1998) *Bioinformatics* 14:378-379. A chloroplast targeting peptide of 45 N-terminal amino acids was predicted (score 0.545) by using CHLOROP with default settings. Emanuelsson et al., (1999) *Protein Sci.* 8:978-984.

V. TGD2 cDNA Expression

Figure 11B:
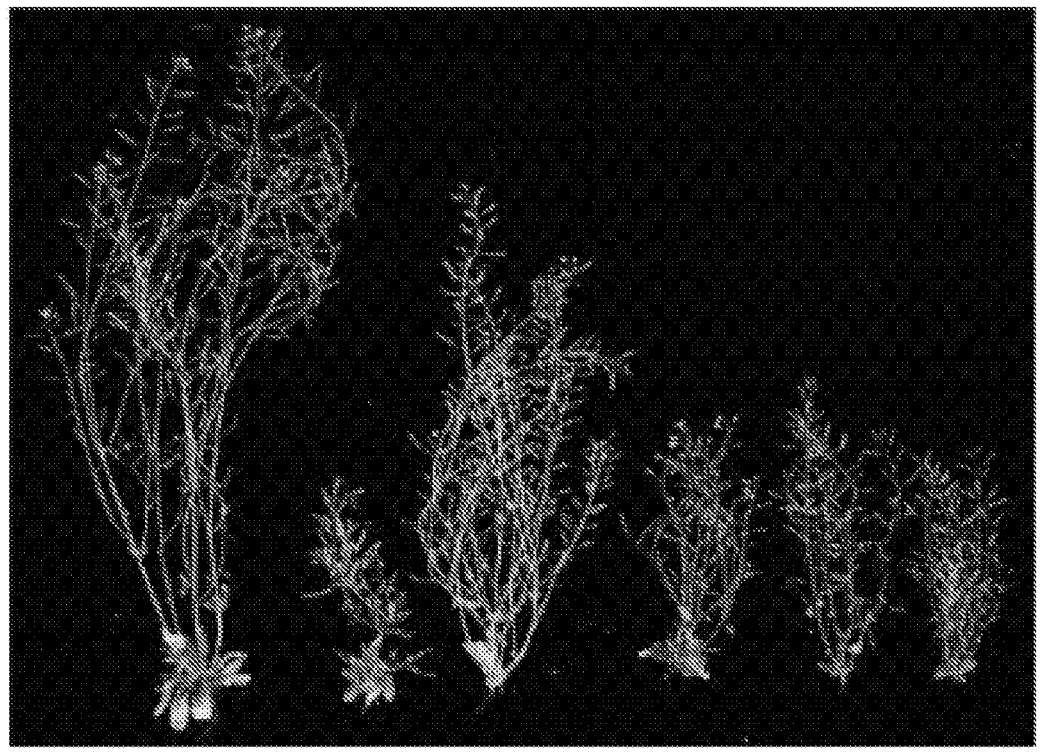
FIG. 11B: Growth of different plants on soil (8 weeks old) with a genotype as indicated below the panel. Mutants were homozygous at all indicated loci. Three plants from independent transformation events expressing the TGD2 cDNA are indicated by "(c)."
Figure 11:
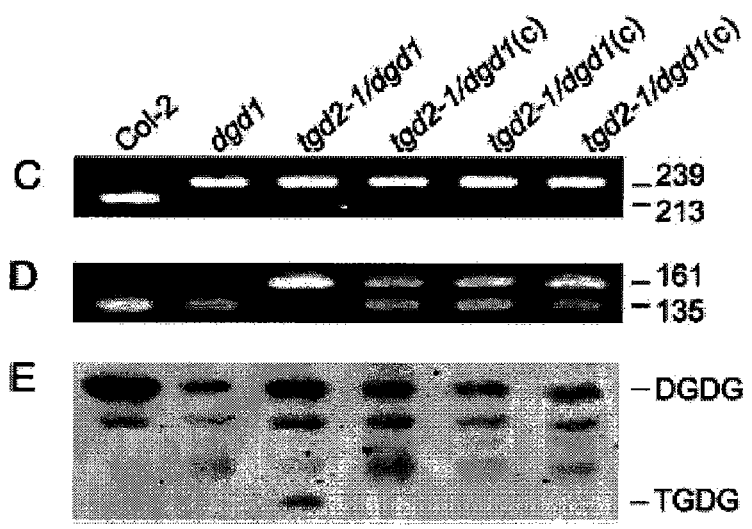

The tgd2-1 mutation in the dgd1 mutant background led to increased growth compared with the homozygous dgd1 mutant. This phenotype was reversed by expression of the wild-type TGD2 cDNA under the control of the 35S-CMV (cauliflower mosaic virus) promoter in the tgd2-1/dgd1 homozygous double mutant. See, FIG. 11B. The genotypes were confirmed by using mutant allele-specific dCAPS markers. See, FIGS. 11C and 11D. In both transgenic lines two bands were present, a first band corresponding to a wild-type cDNA and a second band corresponding the a tgd2-1 genomic mutant locus. See, FIG. 11D. Reversion of the digalactolipid and the trigalactolipid phenotype of the tgd2-1/dgd1 double mutant to the homozygous dgd1 phenotype was observed as well. See, FIG. 11E. This complementation analysis confirmed the identity of the TGD2 gene as At3g20320.

Figure 12:
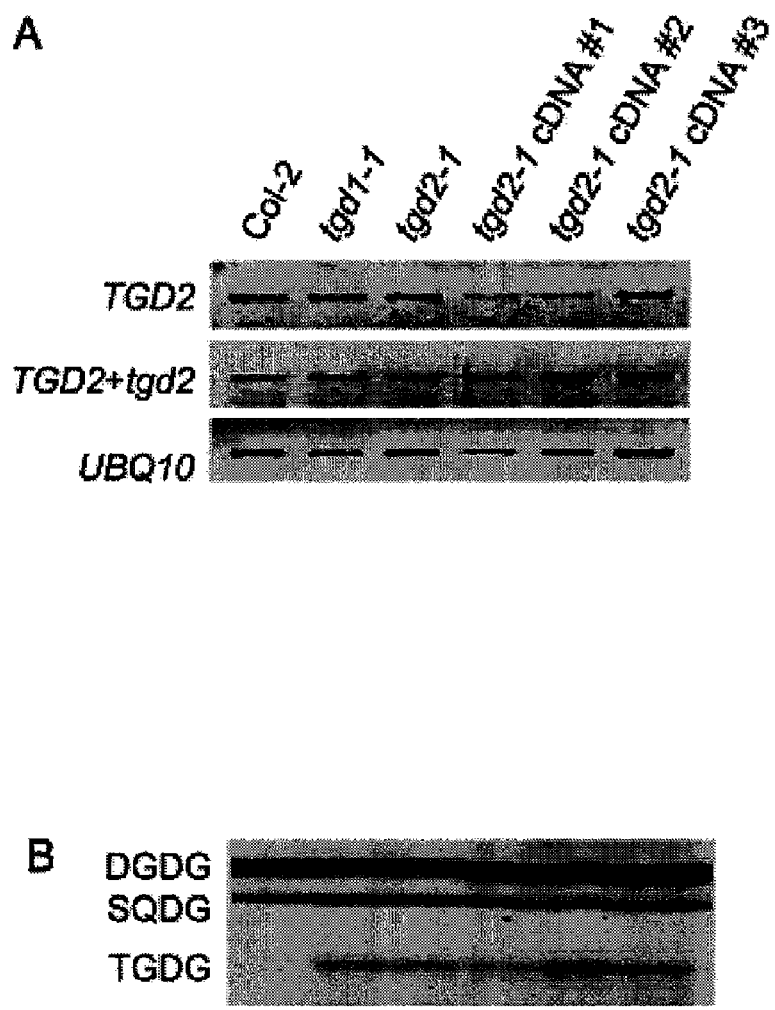
FIG. 12 presents exemplary data showing an expression of the tgd2-1 mutant cDNA in the Col-2 wild type. The untransformed wild type (Col-2) and the untransformed tgd1-1 and tgd2-1 mutants are included for comparison. Three independent transformants are shown.

The similarity of tgd1-1 and tgd2-1 mutant phenotypes and the organization of predicted bacterial orthologs of these two *Arabidopsis* genes in operons suggested that TGD1 and TGD2 act together in the same cellular process possibly as part of a larger lipid transfer complex. Expression of the tgd2-1 mutant cDNA under the control of the 35S-CMV promoter in the wild type led to the accumulation of a lipid cochromatographing with the trigalactolipid accumulating in the tgd1-1 and tgd2-1 mutants. See, FIG. 12B.

Semiquantitative RT-PCR confirmed that this effect was not due to cosuppression of the genomic wild-type TGD2 gene and the tgd2-1 cDNA expression construct, because RNA derived from both genes was abundant in the transgenic lines. See, FIG. 12A. One interpretation of this dominant negative effect is that the tgd2-1-encoded mutant protein is impaired in its activity but can still become part of its native protein complex, thereby disrupting overall function of the process involving the complex. In addition, this result provided independent corroboration for the identity of TGD2 with At3g20320.

VI. TGD2 Intracellular Localization

Figure 13:
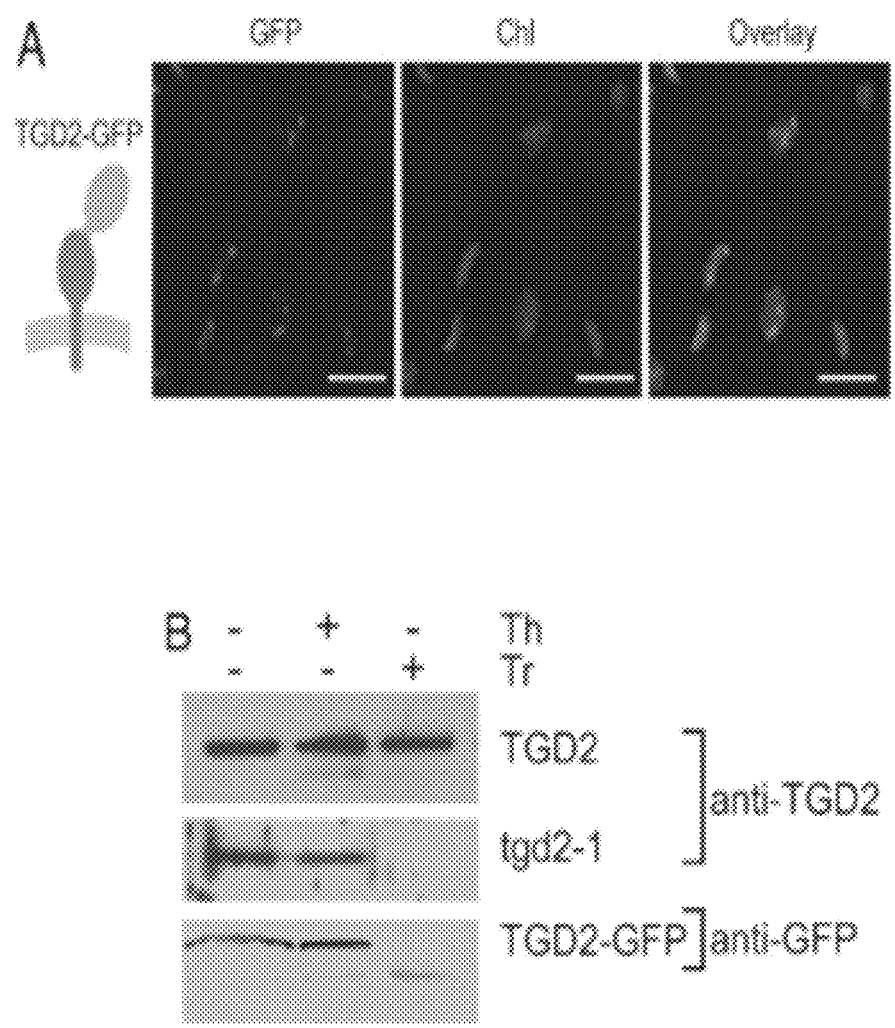
FIG. 13 presents exemplary data showing a subcellular localization and topology of TGD2 after transient expression in tobacco leaves.
Figure 14:
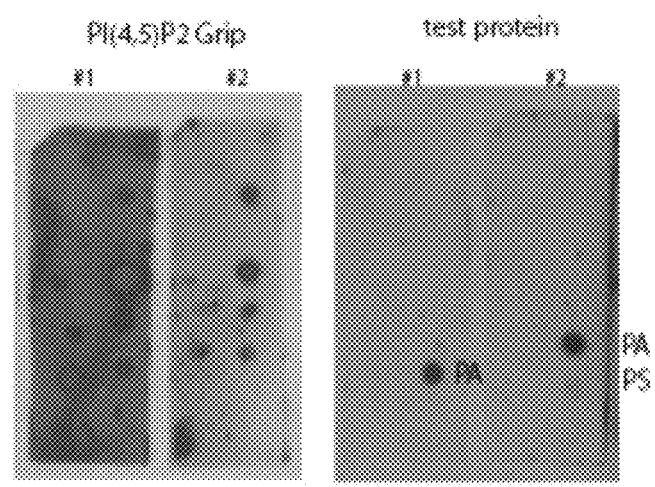
FIG. 14 presents one embodiment of a test strip that identifies a phosphatidic acid. Phosphatidylinositol 4,5 bis phosphate was chromatographed and compared to standard chromatograms of phosphatidic acid (PA) and phosphatidylserine (PS). Slides #1=Strip lot #JJ-032108-47 (#1 Left slide pair); Slides #2=Strip lot #KB15011-47 (#2 Left slide pair).

To determine the subcellular localization of the TGD2 protein, a construct encoding a full-length C-terminal fusion between the TGD2 protein and a GFP was transiently expressed in tobacco the periphery of chloroplasts. See, FIG. 13A. It should be noted that the equivalent experiment for the TGD1-GFP fusion construct showed a similar punctate fluorescence pattern at the chloroplast surface. Xu et al., (2005) *Plant Cell* 17:3094-3110.

To further explore the association of the TGD2 protein with one of the two chloroplast envelope membranes and to determine its topology, chloroplasts were isolated from tobacco leaves expressing a wild-type TGD2 cDNA or the tgd2-1 mutant cDNA. See, FIG. 13B. The TGD2 wild type and the tgd2-1 mutant proteins were detected with a polyclonal antibody against TGD2. The chloroplasts were either untreated or treated with thermolysin, a protease unable to penetrate the outer envelope membrane, or trypsin, a protease able to penetrate the outer envelope but not the inner envelope membrane. Interestingly, the wild-type TGD2 protein was resistant to both proteases, whereas the mutant protein tgd2-1 was resistant to thermolysin but not trypsin. See, FIG. 13B, top and middle.

When the full-length wild-type TGD2 protein C-terminally fused to GFP was tested, the GFP tag detected by a GFP-specific antibody was resistant to thermolysin but not to trypsin. See, FIG. 13B, bottom. With the exception of the TGD2 wild-type protein, the result suggests that the TGD2 protein is associated with the inner envelope membrane with the C terminus facing the intermembrane space. The wild-type TGD2 is trypsin-resistant either because it is inside the plastid or, more likely, because it is in a complex or a membrane domain inaccessible to trypsin.

VII. Kits

In one embodiment, the present invention contemplates a kit, comprising: a) a first container comprising a test strip comprising a phosphatidic acid binding protein; b) a second container comprising a plurality of buffers and a plurality of reagents, wherein said protein is soluble; and c) a set of instructions for determining a phosphatidic acid. In one embodiment, the protein further comprises a label. In one embodiment, the phosphatidic acid is derived from a sample. In one embodiment, the protein further comprises at least one accessory binding protein.

In another embodiment, the present invention contemplates kits for the practice of the methods of this invention. The kits preferably include one or more containers containing a phosphatidic acid determination method of this invention.

The kit can optionally include a a TDG2 protein comprising a phosphatidic acid binding domain, wherein said domain encompasses amino acid residues 201-225 (SEQ ID NO: 12), wherein at least one of said residues is a proline. The kit can optionally include a plurality of buffers as described herein. The kit can optionally include a plurality of reagents as described herein. The kit can optionally include enzymes as described herein. The kit can optionally include enzymes capable of performing PCR (i.e., for example, DNA polymerase, Taq polymerase and/or restriction enzymes). The kit can optionally include a pharmaceutically acceptable excipient and/or a delivery vehicle (e.g., a liposome). The reagents may be provided suspended in the excipient and/or delivery vehicle or may be provided as a separate component which can be later combined with the excipient and/or delivery vehicle.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in the determination of phosphatidic acid for one of many plant disorders. In particular a plant disease, wounding and/or stress can include any one or more of the disorders described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VIII. Phosphatidic Acid-Binding Protein

The TGD2 protein of *Arabidopsis* is proposed to be the substrate binding component of a lipid transfer complex in the inner chloroplast envelope. Loss of function of this protein or other components of this complex disrupts the ER-pathway of thylakoid lipid biosynthesis. Previous studies demonstrated that the C-terminal 6×-His tag-fused protein of TGD2 (TGD2C, with removal of the N-terminal transit peptide and transmembrane domain) interacts selectively with phosphatidic acid (PtdOH). Awai et al., (2006) "A phosphatidic acid-binding protein of the chloroplast inner envelope membrane involved in lipid trafficking" *Proc Natl Acad Sci USA* 103: 10817-10822) To improve expression and solubilization of this protein, we fused the open reading frame encoding the TGD2C truncated protein C-terminally to the *Discosoma* sp. red fluorescent protein (DsRed) open reading frame and expressed the fused open reading frame under the control of the T7 promoter. Like its predecessor, the DsRed-TGD2C fusion protein was shown to specifically bind PtdOH. By deletion and truncation mutagenesis, the PtdOH binding site within TGD2C was further narrowed down to a 25-amino-acid segment. Our data suggest that this segment is necessary and sufficient for PtdOH binding. Crystallization of the DsRed-fusion protein will provide a stereochemical analysis.

Various TGD2 fusion proteins may be made by polymerase chain reaction (PCR) using primers identified in Table 1:

TABLE 1

PCR primers used for generation of dsRed-TGD2 fusion proteins

| dsRed fusion protein | mutation | 5' primer | 3' primer |
|---|---|---|---|
| TGD2C WT (SEQ ID NO: 13) (119-381) | WT | 5'-CCG GAG CTC GGT TTT CAA ATG CGG TC-3' (SEQ ID NO: 14) | 5'-CGG CTC GAG TAG TAG CCT GCT TAG GG-3' (SEQ ID NO: 15) |
| TGD2C T1 (SEQ ID NO: 11) (119-250) | 119-250 | 5'-CCG GAG CTC GGT TTT CAA ATG CGG TC-3' (SEQ ID NO: 14) | 5'-GCG CTC GAG AAT ACG AGT GAA AAT TCC-3' (SEQ ID NO: 18) |

TABLE 1-continued

PCR primers used for generation of dsRed-TGD2 fusion proteins

| dsRed fusion protein | mutation | 5' primer | 3' primer |
|---|---|---|---|
| TGD2C T2 (SEQ ID NO: 19) (171-300) | 171-300 | 5'-CCG GAG CTC GCT GAG ATA GAA GAT G-3' (SEQ ID NO: 20) | 5'-CGA CTC GAG GCT ATC ACG AAA CTC AG-3' (SEQ ID NO: 21) |
| TGD2C T3 (SEQ ID NO: 22) (221-350) | 221-350 | 5'-CAG GAG CTC AAG GAA GGT CTG ATC G-3' (SEQ ID NO: 23) | 5'-CGG CTC GAG GAC GTT CTT CAA AGT AT-3' (SEQ ID NO: 24) |
| TGD2C T4 (SEQ ID NO: 25) (201-381) | 201-381 | 5'-CCG GAG CTC ATT ATG CCT AGG AAT CCG-3' (SEQ ID NO: 26) | 5'-CGG CTC GAG TAG TAG CCT GCT TAG GG-3' (SEQ ID NO: 27) |
| TGD2C T5 (SEQ ID NO: 28) (119-300) | 119-300 | 5'-CCG GAG CTC GGT TTT CAA ATG CGG TC-3' (SEQ ID NO: 17) | 5'-CGA CTC GAG GCT ATC ACG AAA CTC AG-3' (SEQ ID NO: 21) |
| TGD2C T6 (SEQ ID NO: 31) (119-225) | 119-225 | 5'-CCG GAG CTC GGT TTT CAA ATG CGG TC-3' (SEQ ID NO: 17) | 5'-CGG CTC GAG GAT CAG ACC TTC CTT AC-3' (SEQ ID NO: 33) |
| TGD2C T7 (SEQ ID NO: 34) (171-225) | 171-225 | 5'-CCG GAG CTC GCT GAG ATA GAA GAT G-3' (SEQ ID NO: 35) | 5'-CGG CTC GAG GAT CAG ACC TTC CTT AC-3' (SEQ ID NO: 33) |
| TGD2C T8 (SEQ ID NO: 12) (201-225) | 201-225 | 5'-CCG GAG CTC ATT ATG CCT AGG AAT CCG-3' (SEQ ID NO: 26) | 5'-CGG CTC GAG GAT CAG ACC TTC CTT AC-3' (SEQ ID NO: 33) |
| TGD2C T9 (SEQ ID NO: 40) (221-250) | 221-250 | 5'-CAG GAG CTC AAG GAA GGT CTG ATC G-3' (SEQ ID NO: 23) | 5'-GCG CTC GAG AAT ACG AGT GAA AAT TCC-3' (SEQ ID NO: 18) |
| TGD2C D1 (SEQ ID NO: 43) (Δ221-250) | 221-250 deleted | 5'-CTG CAT CCT GAA TGT GGT GGA CGC GAA GTT GAG GCC-3' (SEQ ID NO: 44) | 5'-GGC CTC AAC TTC GCG TCC ACC ACA TTC AGG ATG CAG-3' (SEQ ID NO: 45) |
| TGD2C D2 (SEQ ID NO: 46) (Δ221-225) | 221-225 deleted | 5'-CTG CAT CCT GAA TGT GGT GTT TGT GAT AGG CAG ACA-3' (SEQ ID NO: 47) | 5'-TGT CTG CCT ATC ACA AAC ACC ACA TTC AGG ATG CAG-3' (SEQ ID NO: 48) |

The TGD2 protein is N-terminally truncated lacking the TMD and C-terminally fused to the *Discosoma* sp. red fluorescent protein (DsRed, dR) open reading frame. Fusion protein was expressed and protein-lipid overlay assay was conducted with commercial phospholipid-containing membrane strip. LPA, lysophosphatidic acid; LPC, lysophosphatidylcholine; PtdIns, phosphatidylinositol; PtdIns(3)P, phosphatidylinositol 3-phosphate; PtdIns(4)P, phosphatidylinositol 4-phosphate; PtdIns(5)P, phosphatidylinositol 5-phosphate; PE, phosphatidylethanolamine; PC, phosphatidylcholine; S1P, sphingosine 1-phosphate; PtdIns(3,4)P2, phosphatidylinositol 3,4-bisphosphate; PtdIns(3,5)P2, phosphatidylinositol 3,5-bisphosphate; PtdIns(4,5)P2, phosphatidylinositol 4,5-bisphosphate; PtdIns(3,4,5)P3, phosphatidylinositol 3,4,5-bisphosphate; PA, phosphatidic acid; PS, phosphatidylserine. See FIG. 7.

Figure 17A:
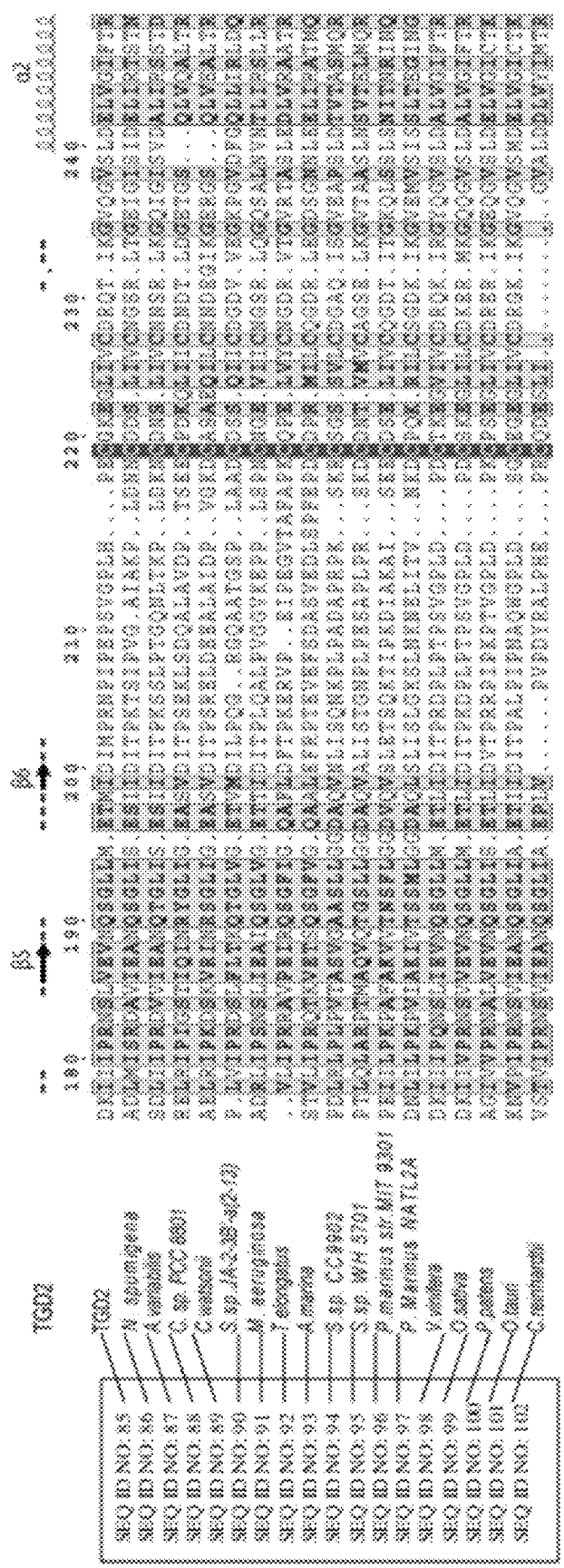
FIG. 17A: A partial sequence alignment of TGD2 orthologs showing the region of minimal PA binding domain. Conserved residues are highlighted in red, similar residues are boxed in yellow.
Figure 17B:
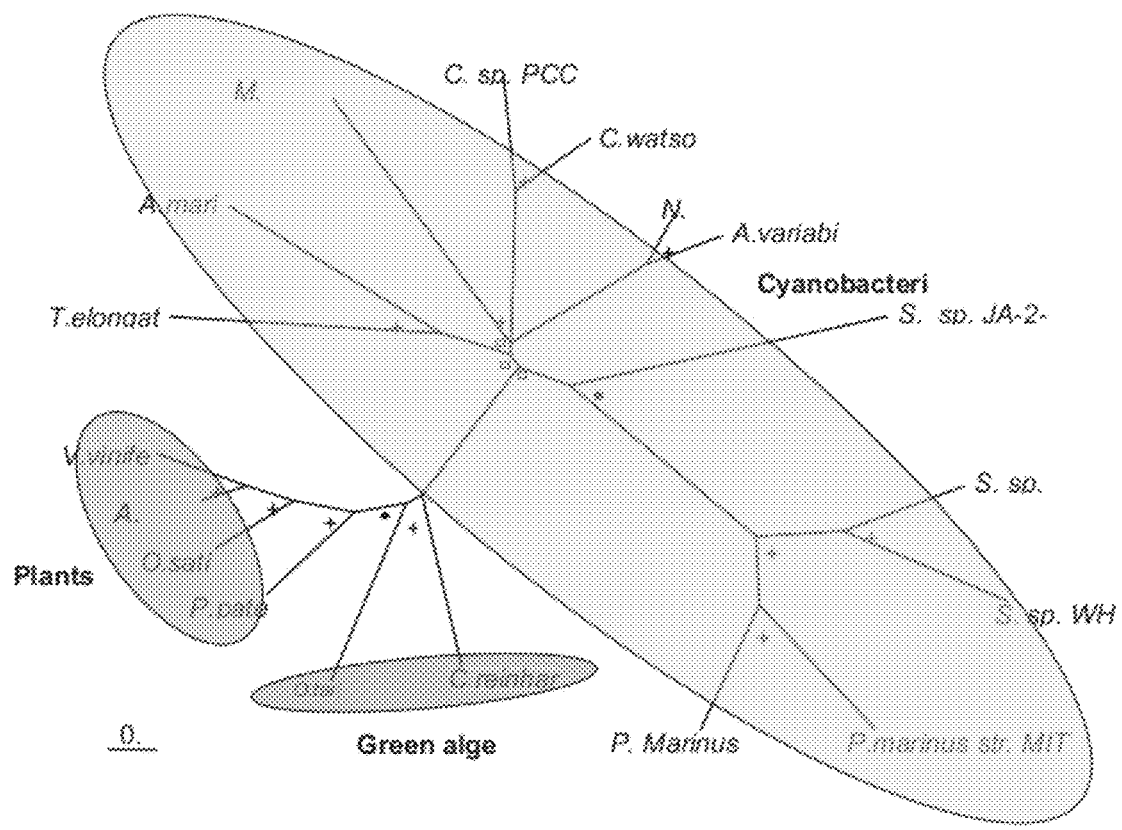
FIG. 17B: An unrooted phylogenetic tree showing the relatedness of predicted TGD2 orthologs in plants and Cyanobacteria. Boot strapping values>950 are marked by +, those between 500 and 950 are marked with a solid circle, and those under 500 are marked by open square.

Gene bank accession numbers for representative TGD2 ortholog sequences include, but are not limited to: *Arabidopsis thaliana*, NP_566659.1 (SEQ ID NO: 5); *Vitis vinifera*, CAN71395.1 (SEQ ID NO: 6); *Oryza sativa*, EAY77419.1 (SEQ ID NO: 7); *Physcomitrella patens*, XP_001778862.1 (SEQ ID NO: 8); *Ostreococcus tauri*, CAL53419.1 (SEQ ID NO: 9); *Chlamydomonas reinhardtii*, XP_001699315.1 (SEQ ID NO: 10); *Prochlorococcus marinus* str. NATL2A, YP_292846.1 (SEQ ID NO: 115); *Prochlorococcus marinus* str. MIT 9301, YP_001090537.1 (SEQ ID NO: 116); *Synechococcus* sp. WH 5701, ZP_01083418.1 (SEQ ID NO: 117); *Synechococcus* sp. CC9902, YP_376253.1 (SEQ ID NO: 118); *Synechococcus* sp. JA-2-3B'a(2-13), YP_477327.1 (SEQ ID NO: 119); *Anabaena variabilis*, YP_323182.1 (SEQ ID NO: 120); *Nodularia spumigena*, ZP_01630545.1 (SEQ ID NO: 121); *Crocosphaera watsonii*, ZP_00516249.1 (SEQ ID NO: 122); *Cyanothece* sp. PCC 8801, ZP_02940544.1 (SEQ ID NO: 123); *Microcystis aeruginosa*, CAO90615.1 (SEQ ID NO: 124); *Acaryochloris marina*, YP_001516641.1 (SEQ ID NO: 125); *Thermosynechococcus elongatus*, NP_683197.1 (SEQ ID NO: 126). See, FIG. 17.

EXPERIMENTAL

Example I

Expression and Purification of DsRed-TGD2 Fusion Proteins

All the TGD2 truncated proteins used in this example were obtained from DNA generated by PCR using a TGD2-dTMD-pQE31 (also known as TGD2C-pQE31) plasmid template (22). Following digestion with NcoI and XhoI, the fragment was ligated into DsRed-plw01-His (a gift from Dr. Michael Garavito, Michigan State University, East Lansing, Mich.). Internal deletion mutants and/or point mutants were generated by site-directed mutagenesis approach on TGD2CDsRed-plw01 via PCR, with the primers and mutation sites listed in Table 1 (supra).

All fusion proteins were expressed in the *Escherichia coli* strain, BL21 (DE3) (Novagen, Madison, Wis.). An overnight pre-culture of LB medium (5 mL) was used to start a 200 mL culture in LB medium. The protein was induced with 50 μM IPTG (isopropyl-β-D-thiogalactopyranoside) at OD600 0.6-0.8, 16° C. and growth was continued overnight. Cultures were cooled to 4° C., washed twice and resuspended in lysis buffer (50 mM Tris-HCl, pH7.5, 300 mM NaCl, 10 mM imidazole). The suspensions were lysed by sonication, followed by centrifugation at 18,000 g.

The resultant supernatant was applied to Ni-NTA agarose column (Qiagen, Valencia, Calif.). Non-specific binding proteins were washed off the column by lysis buffer containing 20 mM imidazole. The His-tagged protein was then eluted with lysis buffer containing 250 mM imidazole.

Samples were concentrated and dialyzed into assay buffer (10 mM $KH_2PO_4$, pH ~7.4), using Amicon centrifugal filter devices (Millipore, Billerica, Mass.). Protein concentration was determined according to Bradford (27) using bovine serum albumin as a standard. The fusion proteins were analyzed for purity by SDS-PAGE (28) and stored at 4° C. for a few weeks without significant loss of activity.

Phylogenetic Analysis of TGD2-full-length TGD2 amino acid sequences were BLASTed against non-redundant protein database (29) and the resulted sequences with high similarities and identities were aligned using Clustalx® software (version 1.81). Generation of the bootstrapped phylogenetic tree was performed using the PHYLIP software package as previously described (30).

Example II

Protein-lipid Overlay Assay

Membrane lipid strips were purchased from Echelon Biosciences (Salt Lake City, Utah). The strips were first blocked with 3% bovine serum albumin in TBST (10 mM Tris-HCl, pH 8.0, 150 mM NaCl, and 0.25% Tween-20) for two hours and incubated in 0.5 μg/mL DsRed-TGD2 fusion protein solution in the blocking buffer at 4° C. overnight. The strips were washed 10 min for 3 times with TBST the next day and soaked in 3% bovine serum albumin in TBST with a Penta-His mouse monoclonal antibody (Sigma-Aldrich, St. Louis, Mo.) at 1:2,000 dilution at 4° C. overnight. The strips were washed twice with TBST and soaked in 3% bovine serum albumin in TBST with horseradish peroxidase-conjugated anti mouse antibody (Bio-Rad, Hercules, Calif.) at 1:20,000 dilution for an hour at room temperature. Following washing with TBST for 1 hour, the protein was detected by using the chemiluminescent detection system (Sigma-Aldrich).

Example III

Liposome-Association Assay

The liposome association assay was performed as previously reported. (31). Briefly, lipids (dioleoyl-phosphatidyl-choline, DOPC or dioleoyl-PA, DOPA) were incubated in TBS (50 mM Tris-HCl, pH 7; 0.1 M NaCl) at 37° C. for an hour followed by vigorous vortexing for 5 min. The liposomes were precipitated at 20,000 g and washed twice with ice-cold TBS.

Liposomes (200 μg) were mixed with purified DsRed-TGD2 fusion protein and TBS to make a final 100 μL solution. The mixture was incubated at 30° C. for 30 min and washed twice with ice-cold TBS by centrifugation at 20,000 g at 4° C. The liposome pellet mixed with sample buffer was analyzed by SDS-PAGE (28). Immuno-detection of the His-tagged protein was accomplished using the above mentioned Penta-His antibody at 1:15,000 and the anti mouse antibody at 1:75,000 dilution.

The protein band was visualized by chemiluminescent detection kit from Sigma. The autoradiography film was scanned, distinct protein bands were quantified using computer software Multi Gauge V3.0 (Fujifilm USA, Valhalla, N.Y.) and resulted data were plotted and analyzed by Origin-Pro8 (Origin lab corporation, Northampton, Mass.).

Example IV

Plant Material

*Arabidopsis thaliana* plants were of the ecotypes Columbia-2 (Col-2) or Landsberg erecta (Ler). The tgd1-1 and dgd1 mutants were previously isolated. Xu et al., (2003) *EMBO J.* 22:2370-2379; and Dormann et al., (1995) *Plant Cell* 7:1801-1810. Standard growth conditions were used for surface-sterilized seeds on agar-solidified MS medium supplemented with 1% (wt/vol) sucrose or for plants grown on soil. Murashige et al., (1962) *Physiol. Plant.* 15, 473-497; and Xu et al., (2002) *Plant Physiol.* 129:594-604.

Example V

Lipid Analysis

Lipids were extracted, and fatty acid methylesters were prepared and quantified by gas chromatography as previously Mallinckrodt, Baker, N.J.) by using a solvent system of acetone/toluene/water (90/30/7, vol/vol). Neutral lipids were separated on untreated TLC plates and developed with petroleum ether/ether/acetic acid (70/30/1, vol/vol). Polar lipids were analyzed on activated ammonium sulfate-impregnated silica gel TLC plates (Si250PA; Mallinckrodt, Baker, N.J.) by using a solvent system of acetone/toluene/water (90/30/7, vol/vol). Neutral lipids were separated on untreated TLC plates and developed with petroleum ether/ether/acetic acid (70/30/1, vol/vol). Lipids were visualized by brief exposure to iodine vapor or staining with α-naphthol to detect glycolipids. Benning et al., (1995) *Arch. Biochem. Biophys.* 317:103-111.

Example VI

Markers for Genetic Mapping and Genotyping

For fine mapping, 10 CAPS markers (Konieczny et al., (1993) *Plant J.* 4, 403-410) and 1 dCAPS (MQC12-4) marker (Neff et al., (1998) *Plant J.* 14:387-392) were generated, taking advantage of the Monsanto Polymorphism and Ler Sequence Collection (arabidopsis.org/Cereon/index.jsp). Primers and restriction enzymes were as follows:

```
MYF24:
5'-GACAGCCCACAAATTGATGG-3'        (SEQ ID NO: 49)
and
5'-ACCAACGCTCAATGCCTAC-3'         (SEQ ID NO: 50)
cut with HinfI.

MLD14:
5'-GGGGTCCTTAAAATAGAGAC-3'        (SEQ ID NO: 51)
and
5'-GGCCTTTTGAGTTGGGAAAAG-3'       (SEQ ID NO: 52)
cut with HindIII.
```

```
MIL23:
5'-GGGGGTGATATCTATCGTAG-3'       (SEQ ID NO: 53)
and
5'-GCACCCTGGATATTCTTTCG-3'       (SEQ ID NO: 54)
cut with HinfI.

MPN9:
5'-CGGTCATATGCTGGCTGAAG-3'       (SEQ ID NO: 55)
and
5'-GACAGCACACAAGTTCCAGG-3'       (SEQ ID NO: 56)
cut with AluI.

MPN9-2:
5'-GTGCTATGGTTCAGGAGTTC-3'       (SEQ ID NO: 57)
and
5'-CTTACCAGCCATGACGATTC-3'       (SEQ ID NO: 58)
cut with AccI.

MAL21:
5'-GAGAAGAAACACCGATTCCG-3'       (SEQ ID NO: 59)
and
5'-GTTGTGATACGAATGGTGGC-3'       (SEQ ID NO: 60)
cut with RsaI.

K10D20:
5'-GGACCTGCCTTTCCCATATC-3'       (SEQ ID NO: 61)
and
5'-GCCCAAGCCTCAAGATGTTG-3'       (SEQ ID NO: 62)
cut with HindIII.

MSA6:
5'-GGAAGAGGGAGGTTTTGTTC-3'       (SEQ ID NO: 63)
and
5'-CCAATTCGTCTCCTTTTCACC-3'      (SEQ ID NO: 64)
cut with SpeI.

MQC12-2:
5'-GTGAGACCAACAGTGTCAAC-3'       (SEQ ID NO: 65)
and
5'-CCACAATACACCACCACTTG-3'       (SEQ ID NO: 66)
cut with HinfI.

MQC12-3:
5'-CCTCCGTCTCATACATCTAC-3'       (SEQ ID NO: 67)
and
5'-CCAATTCGGTTTCATCCAATCCTCT-3'  (SEQ ID NO: 68)
cut with BfaI.

MQC12-4:
5'-CATATGCATTGATGATAACTGAAATCGA-3' (SEQ ID NO: 69)
and
5'-CTTCTAGATCTCCTCCTTTC-3'       (SEQ ID NO: 70)
cut with EcoRI.
```

For genotyping of the tgd2-1 mutant, a dCAPS marker was generated:

```
5'-TGATCGTTTGTGATAGGCAGCCTATAAA  (SEQ ID NO: 71)
A-3'
and

5'-CCTTGCTTCCTCAATAACCG-3',      (SEQ ID NO: 72)
cut with EcoNI.
```

The dgd1 dCAPS marker was made as previously described. Xu et al., (2003) *EMBO J.* 22:2370-2379.

Example VII

Complementation and Dominant-Negative Mutation Analysis

The ORFs for TGD2 and tgd2-1 were isolated by RT-PCR from mRNA preparations by using RNeasy and Omniscript kits (Qiagen, Valencia, Calif.) and standard PCR conditions. The following primers were used:

```
5'-GTCGACATGATTGGGAATCCAGTAATTCAA  (SEQ ID NO: 73)
G-3'
and

5'-GTCGACTCATAGTAGCCTGCTTAGGG-3'.  (SEQ ID NO: 74)
```

The fragments were ligated into pGEM-T Easy (Promega) and sequenced at the Michigan State University Genomics and Technology Facility. The resulting plasmids were digested with SalI and inserted into pCAMBIAmcs1300 followed by transformation into *Agrobacterium*. Plants were transformed by the floral-dip method (22) and screened by resistance to hygromycin (25 µg/ml) on agarsolidified MS medium. Clough et al., (1998) *Plant J.* 16:735-743. For semi-quantitative PCR of TGD2 and tgd2 transcripts the following primers were used: TGD2-specific:

```
5'-CGGCTTGCTCAAGGAAGTTG-3'       (SEQ ID NO: 75)
and

5'-CCAGTCTAAAATCTACAGGCTG-3';    (SEQ ID NO: 76)
```

TGD2 and tgd2-1:

```
5'-TGATCGTTTGTGATAGGCAGCCTATAAA  (SEQ ID NO: 77)
A-3'
and

5'-CCTTGCTTCCTCAATAACCG-3';      (SEQ ID NO: 78)
```

UBQ10:

```
5'-TCAATTCTCTCTACCGTGATCAAGATGC  (SEQ ID NO: 79)
A-3'
and

5'-GTGTCAGAACTCTCCACCTCAAGAGTA-3'. (SEQ ID NO: 80)
```

Isolation of RNA and reverse transcription were done as described above. Amplification conditions were as follows: 94° C. for 3 min followed by 25 cycles at 94° C. for 0.5 min, 55° C. for 0.5 min, and 72° C. for 0.5 min followed by 3 min at 72° C.

Example VIII

TGD2GFP Fusion and In Vivo Chloroplast Import Assay

The sequence encoding the full-length TGD2 protein was amplified from the pCAMBIAmcs1300 plasmid derivative mentioned above by PCR using the following primers: forward, 5'-GTCGACATGATTGGGAATCCAGTAATTCAAG-3' (SEQ ID NO: 81); reverse, 5'-GTCGACTAGTAGCCTGCTTAGGGATTTG-3' (SEQ ID NO: 82). The fragment was inserted into the pGEM-T Easy vector, sequenced and digested with SalI, and inserted into pCAMBIAmcsGFP. In vivo analysis of the GFP-tagged protein was done by confocal fluorescence microscopy.

In vivo chloroplast import analysis was performed using transient expression of the constructs in tobacco leaves. Xu et al., (2005) *Plant Cell* 17:3094-3110. For immunodetection of the TGD2 or tgd2-1 proteins, a polyclonal antibody was raised in rabbits (Cocalico Biologicals, Reamstown, Pa.) against the truncated TGD2 protein used also for the lipid binding assay. The anti-serum was purified with a Melon Gel IgG Purification Kit (Pierce). For TGD2 immunodetection, the purified anti-TGD2 antibody was used at a 1:2,000 dilution. For GFP immunodetection, a rabbit anti-GFP antibody (Molecular Probes) was used at a 1:3,000 dilution. The antibodies were detected with an anti-rabbit horseradish peroxidase-coupled antibody (Bio-Rad) at a dilution of 1:60,000 followed by development with Chemiluminescent Peroxidase Substrate (Sigma).

Example IX

Recombinant TGD2 Protein Production and Purification

The sequence encoding N-terminally truncated TGD2-dTMD protein (from Gly-119 to stop codon) lacking the targeting peptide and the TMD was PCR-amplified by using primers:

5'-GTCGACGGTTTTCAAATGCGGTCGAAG-3'   (SEQ ID NO: 83)
and

5'-GTCGACTCATAGTAGCCTGCTTAGGG-3'.   (SEQ ID NO: 84)

This fragment was inserted into pPICT2 plasmid and sequenced. Kawaguchi et al., (2001) *J. Bone Miner. Res.* 16, 260-269. After digestion with SalI, the insert was ligated into pQE31 (Qiagen). An overnight preculture of LB medium (1 ml) was used to start a 500-ml culture in M9 medium. Duffieux et al., (2000) *Eur. J. Biochem.* 267:5306-5312. The protein was induced with 0.1 mM isopropyl-β-D-thiogalactopyranoside at an $OD_{600}$ of 0.4 at 22° C., and growth was continued overnight. Cultures were cooled to 4° C., washed twice, and resuspended in lysis buffer (50 mM Tris.HCl, pH 7.5/600 mM NaCl/20 mM imidazole). The suspensions were lysed by sonication followed by brief centrifugation at 1,500×g to eliminate cell debris. The supernatants were centrifuged at 20,000×g and applied to a Ni-NTA agarose column (Qiagen). The His-tagged protein was eluted with lysis buffer containing 250 mM imidazole. Samples were dialyzed in the lysis buffer lacking imidazole. Protein concentration was determined by using BSA as a standard. Bradford, M. M. (1976) *Anal. Biochem.* 72, 248-254.

Example X

Lipid Binding Assays

Commercially available membrane strips prespotted with lipids were purchased. (Echelon Biosciences, Salt Lake City, Utah). Prokaryotic phosphatidylcholine and PA were also purchased (Avanti Polar Lipids). Prokaryotic monogalactolipid, digalactolipid, sulfolipid, and phosphatidylglycerol were purified from *Synechocystis* PCC6803 by TLC of lipid extracts. Eukaryotic monogalactolipid and digalactolipid was isolated from pea leaves.

Approximately 5 μg of lipids were spotted onto a Hybond-C membrane (Amersham Pharmacia Biosciences). The membranes were first blocked with 3% BSA in TBST (10 mM Tris.HCl, pH 8.0/150 mM NaCl/0.1% Tween 20) for 1 h and incubated in 0.5 μg/ml TGD2 protein solution in the blocking buffer at 4° C. overnight. The blots were washed five times with TBST and soaked in 3% BSA in TBST with a Penta-His mouse monoclonal antibody (Qiagen) at a 1:1,000 dilution at room temperature overnight. The membranes were washed twice with TBST and soaked in 3% BSA in TBST with alkaline phosphatase-conjugated anti-mouse antibody (Jackson ImmunoResearch) at a 1:5,000 dilution for 1 hour at room temperature. After washing with TBST twice, the protein was detected by using the Immun-Star AP detection system (Bio-Rad).

The liposome binding assay was performed as previously reported. Sano et al., (1998) *J. Biol. Chem.* 273:4783-4789. Lipids (i.e., for example, phosphatidylcholine or a mixture of phosphatidylcholine and PA at 6:4 wt/wt) were incubated in TBS (50 mM Tris/HCl, pH 7/0.1M NaCl) at 37° C. for 1 hour followed by vigorous vortexing for 5 min. The liposomes were precipitated at 20,000×g and washed twice with ice-cold TBS.

Liposomes (200 μg) were mixed with purified TGD2 protein lacking the TMD (10 μg/ml) and TBS to make 100 μl of solution. The mixture was incubated at 30° C. for 30 min and washed twice with ice-cold TBS by centrifugation at 20,000×g at 4° C. The liposome pellet mixed with sample buffer was analyzed by SDS/PAGE. Laemmli, U. K. (1970) *Nature* 227, 680-685. Immunodetection of the His-tagged protein was accomplished by using the above-mentioned Penta-His antibody at 1:6,000 and the anti-mouse antibody at 1:10,000 dilution. The BCIP/NBT Kit from Bio-Rad was used for color detection.

REFERENCES

1. Meijer, H. J. G. and Munnik T. Phospholipid-based signaling in plants. Annu. Rev. Plant Biol. 54, 265-306.2003.
2. Wang, X. Lipid signaling. Curr. Opin. Plant Biol. 7, 329-336. 2004.
3. Mueller-Roeber, B. and Pical C. Inositol phospholipids metabolism in *Arabidopsis*. Characterized and putative isoforms of inositol phospholipids kinase and phosphaonioositide-specific phospholipase C. Plant Physiol. 130, 22-46. 2002.
4. Ryu, S. B. Phospholipid-derived signaling mediated by phospholipase A in plants. 9, 229-235. Trends Plant Sci. 9, 229-235. 2004.
5. van Leeuwen, W. et al. Learning the lipid language of plant signaling. Trends Plant Sci. 9, 378-384. 2004.
6. Zonia, L. and Munnik T. Cracking the green paradigm: functional coding of phosphoinositide signals in plant stress responses. In Subcellular Biochemistry: Biology of Inositols and Phosphoinositides (Vol. 39) (Majunder, A. and Biswas, B., eds), Kluwer/Plenum Publishers (in press). 2008.
7. Laxalt, A. M. and Munnik T. Phospholipid signaling in plant defense. Curr. Opin. Plant Biol. 5, 332-338. 2002.
8. Munnik, T. Phosphatidic acid: an emerging plant lipid second messenger. Trends Plant Sci. 6, 227-233.2001.
9. Wang, X. Phospholipase D in hormonal and stress signaling. Curr. Opin. Plant Biol. 5, 408-414. 2002.
10. Munnik T, Testerink C. Phosphotidic acid: a multifunctional stress signaling lipid in plants. Trends Plant Sci. 10, 368-375. 2005.
11. Ghosh, S. et al. Raf-1 kinase possesses distinct binding domains for phosphatidylserine and phosphatidic acid. J. Biol. Chem. 271, 8472-8480. 1996.
12. Ghosh, S. et al. Functional analysis of a phosphatidic acid binding domain in human Raf-1 kinase. J. Biol. Chem. 278, 45690-45696. 2003.
13. Frank, C. et al. Binding of phosphatidic acid to the protein-tyrosine phosphatase SHP-1 as a basis for activity modulation. Biochemisty 38, 11993-12002. 1999.
14. Jones, J. A. and Hannun Y. A. Tight binding inhibition of protein phosphatase-1 by phosphatidic acid. J. Biol. Chem. 277, 15530-15538. 2002.

15. Jose Lopez-Andreo, M. et al. The simultaneous production of phosphatidic acid and diacylglycerol is essential for the translocation of protein kinase Cα to the plasma membrane in RBL-2H3 cells. Mol. Biol. Cell 14, 4885-4895. 2003.
16. Nakanishi, H. et al. Positive and negative regulation of a SNARE protein by control of intracellular localization. Mol. Biol. Cell 15, 1802-1815. 2004.
17. Loewen, C. J. R. et al. Phospholipid metabolism regulated by a transcription factor sensing phosphatidic acid. Science 204, 1644-1647. 2004.
18. Zhang, W. et al. Phospholipase Dα1-derived phosphatidic acid interacts with ABI1 phosphatase 2C and regulates abscisic acid signaling. Proc. Natl. Acad. Sci. U.S.A. 101, 9508-9513. 2004.
19. Anthony, R. G. et al. A protein kinase target of a PDK1 signaling pathway is involved in root hair growth in *Arabidopsis*. EMBO J. 23, 572-581. 2004.
20. Deak, M. et al. Characterization of a plant 3-phosphoinositide-dependent protein kinae-1 homologue which contains a pleckstrin homology domain. FEBS Lett. 451, 220-226. 1999
21. Testerink C. et al. Isolation and identification of phosphatidic acid targets from plants. Plant J. 39, 527-536. 2004.
22. Awai K, Xu C Tamot B Benning C. A phosphatidic acid-binding protein of the chloroplast inner envelope membrane involved in lipid trafficking. Proc Natl Acad Sci USA 103, 10817-10822. 2006.
23. Xu C, Fan J Froehlich J Awai K Benning C. Mutation of the TGD1 chloroplast envelope protein affects phosphatidate metabolism in *Arabidopsis*. Plant Cell 17, 3094-3110. 2005.
24. Xu C, Fan J Riekhof W Froehlich J E Benning C. A permease-like protein involved in ER to thylakoid lipid transfer in *Arabidopsis*. EMBO J 22, 2370-2379. 2003.
25. Karathanassis, D. et al. Binding of the PX domain of P47phox to phosphatidylinositol 3, 4-bisphosphate and phosphatidic acid is masked by an intramolecular interactions. EMBO J. 21, 5057-5068. 2002.
26. Lindsay, A. J. and McCaffrey M. W. The C2 domains of the class I Rab11 family of interacting proteins target recycling vesicles to the plasma membrane. J. Cell Sci. 117, 4365-4375. 2004.
27. Bradford, M. M. Anal. Biochem. 72, 248-254. 1976. Ref Type: Generic 28. Laemmli, U. K. Nature 227, 680-685. 1970.
29. Stephen F. Altschul, Thomas L. Madden Alejandro A. Schäffer Jinghui Zhang Zheng Zhang Webb Miller and David J. Lipman. Gapped BLAST and PSI-BLAST: a new generation of protein database search programs. Nucleic Acids Res 25, 3389-3402. 1997.
30. Mamedov, T. G. Moellering E. R. and Chollet R. Identification and expression analysis of two inorganic C- and N-responsive genes encoding novel and distinct molecular forms of eukaryotic phosphoenolpyruvate carboxylase in the green microalga *Chlamydomonas reinhardtii*. Plant J. 42, 832-843. 2005.
31. Sano, H. Kuroki Y. Honma T. Ogasawara Y. Sohma H. Voelker D. R. & Akino T. J. Biol. Chem. 273, 4783-4789. 1998.
32. Chitale, S. Ehrt S. Kawamura I. Fujimura T. Shimono N. Anand N. Lu S. Cohen-Gould L. & Riley L. W. Cell. Microbiol. 3, 247-254. 2001.
33. Kooijman E, Tieleman D Testerink C Munnik T Rijkers D Burger K and Kruijff B. An electrostatic/hydrogen bond switch as the basis for the specific interaction of phosphatidic acid with proteins. J. Biol. Chem. 282(15), 11356-11364. 2007.

We claim:

1. A truncated TDG2 protein consisting of a phosphatidic acid binding domain, at least one accessory binding domain, and a C-terminally attached label, wherein said binding domain is selected from the group consisting of amino acid residues 119-225 (SEQ ID NO: 31), amino acid residues 171-225 (SEQ ID NO:34), and amino acid residues 201-225 (SEQ ID NO: 12).

2. The protein of claim 1, wherein said truncated TDG2 protein lacks a transit peptide domain and a transmembrane domain.

3. The protein of claim 1, wherein said accessory binding domain comprises amino acid residues 251-300 (SEQ ID NO: 103).

4. The protein of claim 1, wherein said accessory binding domain comprises amino acid residues 161-204 (SEQ ID NO: 104).

5. The protein of claim 1, wherein said accessory binding domain comprises amino acid residues 291-340 (SEQ ID NO: 105).

6. The protein of claim 1, wherein said binding domain comprises a phosphatidic acid binding motif.

7. The protein of claim 6, wherein an N-terminal β-strand and a C-terminal α-helix create said phosphatidic acid binding motif.

8. The protein of claim 6, wherein said phosphatidic acid binding motif comprises a $^{221}$Lysine.

9. A method, comprising:
 a) providing:
  i) a truncated TDG2 protein consisting of a phosphatidic acid binding domain, at least one accessory binding domain, and a C-terminally attached label, wherein said binding domain is selected from the group consisting of amino acid residues 119-225 (SEQ ID NO: 31), amino acid residues 171-225 (SEQ ID NO: 34), and amino acid residues 201-225 (SEQ ID NO: 12);

ii) a sample suspected of containing phosphatidic acid capable of binding to said domain;

b) contacting said sample with said truncated TDG2 protein under conditions such that said phosphatidic acid binds to said phosphatidic acid binding domain;

c) determining an amount of said bound phosphatidic acid.

10. The method of claim 9, wherein said sample comprises a plant sample.

11. The method of claim 9, further comprising identifying a plant disease with said amount of said bound phosphatidic acid.

12. The method of claim 9, further comprising identifying a plant wound with said amount of said bound phosphatidic acid.

13. The method of claim 9, further comprising identifying a plant stress with said amount of said bound phosphatidic acid.

14. The method of claim 13, wherein said plant stress is selected from the group consisting of biotic stress, abiotic stress, pathogen infection, drought, salinity, and cold.

* * * * *